US010513739B2

(12) United States Patent
Zhang et al.

(10) Patent No.: US 10,513,739 B2
(45) Date of Patent: Dec. 24, 2019

(54) METHYLATION MARKERS FOR DIAGNOSING HEPATOCELLULAR CARCINOMA AND LUNG CANCER

(71) Applicants: YouHealth Oncotech, Limited, Grand Cayman, Cayman Islands (KY); The Regents of the University of California, Oakland, CA (US)

(72) Inventors: Kang Zhang, San Diego, CA (US); Rui Hou, Shenyang (CN); Lianghong Zheng, Shenyang (CN)

(73) Assignees: YouHealth Oncotech, Limited (KY); The Regents of the University of California, Oakland, CA (US)

(*) Notice: Subject to any disclaimer, the term of this patent is extended or adjusted under 35 U.S.C. 154(b) by 0 days.

(21) Appl. No.: 15/910,857

(22) Filed: Mar. 2, 2018

(65) Prior Publication Data

US 2018/0274039 A1    Sep. 27, 2018

Related U.S. Application Data

(60) Provisional application No. 62/466,328, filed on Mar. 2, 2017, provisional application No. 62/466,329, filed on Mar. 2, 2017, provisional application No. 62/569,462, filed on Oct. 6, 2017.

(51) Int. Cl.
*C12Q 1/68* (2018.01)
*C12Q 1/6886* (2018.01)

(52) U.S. Cl.
CPC ...... *C12Q 1/6886* (2013.01); *C12Q 2600/118* (2013.01); *C12Q 2600/154* (2013.01)

(58) Field of Classification Search
None
See application file for complete search history.

(56) References Cited

U.S. PATENT DOCUMENTS

| | | |
|---|---|---|
| 4,683,202 A | 7/1987 | Mullis |
| 5,525,462 A | 6/1996 | Takarada et al. |
| 5,786,146 A | 7/1998 | Herman et al. |
| 5,972,602 A | 10/1999 | Hyland et al. |
| 6,017,704 A | 1/2000 | Herman et al. |
| 6,033,854 A | 3/2000 | Kurnit et al. |
| 6,114,117 A | 9/2000 | Hepp et al. |
| 6,127,120 A | 10/2000 | Graham et al. |
| 6,180,349 B1 | 1/2001 | Ginzinger et al. |
| 6,200,756 B1 | 3/2001 | Herman et al. |
| 6,265,171 B1 | 7/2001 | Herman et al. |
| 6,306,597 B1 | 10/2001 | Macevicz |
| 6,331,393 B1 | 12/2001 | Laird et al. |
| 6,344,317 B2 | 2/2002 | Urnovitz |
| 6,448,001 B2 | 9/2002 | Oku et al. |
| 6,528,632 B1 | 3/2003 | Catanzariti et al. |
| 6,797,470 B2 | 9/2004 | Barany et al. |
| 7,011,944 B2 | 3/2006 | Prudent et al. |
| 7,037,687 B2 | 5/2006 | Williams et al. |
| 7,083,917 B2 | 8/2006 | Barany et al. |
| 7,166,434 B2 | 1/2007 | Barany et al. |
| 7,169,560 B2 | 1/2007 | Lapidus et al. |
| 7,186,512 B2 | 3/2007 | Martienssen et al. |
| 7,232,656 B2 | 6/2007 | Balasubramanian et al. |
| 7,320,865 B2 | 1/2008 | Barany et al. |
| 7,332,285 B2 | 2/2008 | Barany et al. |
| 7,364,858 B2 | 4/2008 | Barany et al. |
| 7,429,453 B2 | 9/2008 | Barany et al. |
| 7,459,274 B2 | 12/2008 | Lakey et al. |
| 7,553,627 B2 | 6/2009 | Laird et al. |
| 7,598,035 B2 | 10/2009 | Macevicz |
| 7,611,869 B2 | 11/2009 | Fan |
| 7,645,596 B2 | 1/2010 | Williams et al. |
| 7,700,324 B1 | 4/2010 | Issa et al. |
| 7,769,400 B2 | 8/2010 | Backholm et al. |
| 7,901,880 B2 | 3/2011 | Jeddeloh et al. |
| 7,910,296 B2 | 3/2011 | Jeddeloh et al. |
| 8,323,890 B2 | 12/2012 | Laird et al. |
| 9,984,201 B2 | 5/2018 | Zhang et al. |
| 10,093,986 B2 | 10/2018 | Zhang et al. |
| 2005/0069879 A1 | 3/2005 | Berlin |
| 2008/0261217 A1 | 10/2008 | Melnikov et al. |
| 2009/0155791 A1 | 6/2009 | Wojdacz et al. |
| 2010/0144836 A1 | 6/2010 | Van et al. |
| 2013/0296183 A1 | 11/2013 | Eggan et al. |

(Continued)

FOREIGN PATENT DOCUMENTS

| | | |
|---|---|---|
| CN | 106947830 A | 7/2017 |
| TW | I454578 B | 10/2014 |

(Continued)

OTHER PUBLICATIONS

Xu et al Nature Materials. Oct. 9, 2017. p. 1155-1161 and Supplementary Information, p. 1-24.*
Ushijima et al. Nature Reviews. 2005. 5: 223-231.*
Song et al PLoS ONE 8(2): e55761.*
Feber et al. Eur Urol Suppl. 2013. 12: e51.*
Hernandez-Vargas et al. Hepatocellular carcinoma displays distinct DNA methylation signatures with potential as clinical predictors. PLoS One, 5(3):e9749 (2010).
PCT/US2018/020761 International Search Report and Written Opinion dated Jun. 15, 2018.
Villanueva et al. DNA methylation-based prognosis and epidrivers in hepatocellular carcinoma. Hepatology, 61(6):1945-1956 (2015).
Zhang et al. Predicting hepatocellular carcinoma by detection of aberrant promoter methylation in serum DNA. Clin Cancer Res. 13(8):2378-2384 (2007).

(Continued)

*Primary Examiner* — Carla J Myers
(74) *Attorney, Agent, or Firm* — Morrison & Foerster LLP

(57) ABSTRACT

Disclosed herein, in certain embodiments, are methods and kits for diagnosing a subject as having hepatocellular carcinoma (HCC) or lung cancer. In some instances, also described herein are methods of determining the prognosis of the subject having HCC or lung cancer. In additional instances, described herein are methods of determining the specific staging of HCC or lung cancer in a subject.

11 Claims, 66 Drawing Sheets
(64 of 66 Drawing Sheet(s) Filed in Color)
Specification includes a Sequence Listing.

(56) References Cited

U.S. PATENT DOCUMENTS

| | | |
|---|---|---|
| 2014/0080715 A1 | 3/2014 | Lo et al. |
| 2014/0094380 A1 | 4/2014 | Sherlock et al. |
| 2015/0031065 A1 | 1/2015 | Kearney et al. |
| 2016/0210403 A1 | 7/2016 | Zhang et al. |
| 2018/0094325 A1 | 4/2018 | Zhang et al. |
| 2018/0341745 A1 | 11/2018 | Zhang et al. |
| 2019/0136327 A1 | 5/2019 | Zhang et al. |

FOREIGN PATENT DOCUMENTS

| | | |
|---|---|---|
| WO | WO-03064701 A2 | 8/2003 |
| WO | WO-2005012578 A1 | 2/2005 |
| WO | WO-2005019477 A2 | 3/2005 |
| WO | WO-2005111209 A1 | 11/2005 |
| WO | WO-2006056480 A2 | 6/2006 |
| WO | WO-2009021141 A1 | 2/2009 |
| WO | WO-2009049916 A2 | 4/2009 |
| WO | WO-2012006181 A2 | 1/2012 |
| WO | WO-2012031329 A1 | 3/2012 |
| WO | WO-2012098215 A1 | 7/2012 |
| WO | WO-2012104642 A1 | 8/2012 |
| WO | WO-2012149171 A1 | 11/2012 |
| WO | WO-2013033380 A1 | 3/2013 |
| WO | WO-2016115530 A1 | 7/2016 |
| WO | WO-2018/009696 A1 | 1/2018 |
| WO | WO-2018/009703 A1 | 1/2018 |
| WO | WO-2018/009709 A1 | 1/2018 |
| WO | WO-2018009705 A1 | 1/2018 |

OTHER PUBLICATIONS

Abbruzzese et al. Analysis of a diagnostic strategy for patients with suspected tumors of unknown origin. J Clin Oncol 13:2094-2103 (1995).
Abdi et al. Principal component analysis. Wiley Interdisciplinary Reviews: Computational Statistics 2(4):433-459 (2010).
Acevedo et al. Analysis of the mechanisms mediating tumor-specific changes in gene expression in human liver tumors. Cancer Res. 68:2641-2651 (2008).
Akbani et al. A pan-cancer proteomic perspective on The Cancer Genome Atlas. Nat Commun 5:3887 (2014).
Alberg et al. Epidemiology of lung cancer: Diagnosis and management of lung cancer: American College of Chest Physicians evidence-based clinical practice guidelines. CHEST Journal 143:e1S-e29S (2013).
Alix-Panabieres et al. Clinical Applications of Circulating Tumor Cells and Circulating Tumor DNA as Liquid Biopsy. Cancer Discov 6:479-491 (2016).
Baldi et al. Neural networks and principal component analysis: Learning from examples without local minima. Neural networks 2(1):53-58 (1989).
Balic et al. High quality assessment of DNA methylation in archival tissues from colorectal cancer patients using quantitative high-resolution melting analysis. J. Mol. Diagn. 11:102-108 (2009).
Ball et al. Targeted and genome-scale methylomics reveals gene body signatures in human cell lines. Nat. Biotechnol 27:361-368 (2009).
Baylin et al. A decade of exploring the cancer epigenome—biological and translational implications. Nat Rev Cancer 11:726-734 (2011).
Baylin et al. Epigenetic Determinants of Cancer. Cold Spring Harb Perspect Biol 8:a019505 (2016).
Benjamini e al. Controlling the false discovery rate: a practical and powerful approach to multiple testing. Journal of the Royal Statistical Society. Series B (Methodological). pp. 289-300 (1995).
Benson et al. Hepatobiliary Cancers: Clinical Practice Guidelines in Oncology. J Natl Compr Canc Netw 7:350-391 (2015).
Best et al. RNA-Seq of Tumor-Educated Platelets Enables Blood-Based Pan-Cancer, Multiclass, and Molecular Pathway Cancer Diagnostics. Cancer cell 28:666-676 (2015).
Bettegowda et al. Detection of Circulating Tumor DNA in Early- and Late-Stage Human Malignancies. Sci. Transl. Med. 6(224):224ra24 (2014).
Bhardwaj et al. Kernel-based machine learning protocol for predicting DNA-binding proteins. Nucleic Acids Res 33(20):6486-6493 (2005).
Bibkova et al. High-throughput DNA methylation profiling using universal bead arrays. Genome Res. 16:383-393 (2006).
Bo et al. New feature subset selection procedures for classification of expression profiles. Genome Biology 3(4):research0017.1-0017.11 (2002).
Brat et al. Comprehensive, integrative genomic analysis of diffuse lower-grade gliomas. N Engl J Med 372(26):2481-2498 (2015).
Breiman. Random Forests. Machine Learning 45:5-32 (2001).
Bruix et al. Management of hepatocellular carcinoma. Hepatology 42:1208-1236 (2005).
Candiloro et al. Assessing combined methylation-sensitive high resolution melting and pyrosequencing for the analysis of heterogeneous DNA methylation. Epigenetics 6(4):500-507 (2011).
Carter et al. Interaction Landscape of Inherited Polymorphisms with Somatic Events in Cancer. Cancer Discov. 7(4):410-423 (2017).
Co-pending U.S. Appl. No. 15/865,152, filed Jan. 8, 2018.
Costello et al. Restriction landmark genome scanning. Meth. Mol Biol 200:53-70 (2002).
Cottrell et al. A real-time PCR assay for DNA-methylation using methylation-specific blockers. Nucleic Acids Res. 32:e10 (2004).
Cottrell et al. Discovery and validation of 3 novel DNA methylation markers of prostate cancer prognosis. J. Urology 177:1753-1758 (2007).
Dawson et al. Analysis of circulating tumor DNA to monitor metastatic breast cancer. N Engl J Med 368:1199-1209 (2013).
Dees et al. MuSiC: identifying mutational significance in cancer genomes. Genome Res 22(8):1589-1598 (2012).
Degraves et al. High-Sensitivity Quantitative PCR Platform. Biotechniques 34(1):106-115 (2003).
Deiman et al. Characteristics and applications of nucleic acid sequence-based amplification (NASBA). Mol. Biotechnol. 20(2):163-179 (2002).
Deng et al. Targeted bisulfite sequencing reveals changes in DNA methylation associated with nuclear reprogramming. Nat. Biotechnol 27:353-360 (2009).
Diaz et al. The molecular evolution of acquired resistance to targeted EGFR blockade in colorectal cancers. Nature 486:537-540 (2012).
Diehl et al. Circulating mutant DNA to assess tumor dynamics. Nat Med 14(9):985-990 (2008).
Diep et al. Library-free methylation sequencing with bisulfite padlock probes. Nature Methods 9(3):270-272 (2012).
Dudoit et al. Comparison of Discrimination Methods for the Classification of Tumors Using Gene Expression Data. Journal of the American Statistical Association 97:77-87 (2002).
Eads et al. MethyLight: a high-throughput assay to measure DNA methylation. Nucleic Acid Res. 28:e32 (2000).
Edge et al. The American Joint Committee on Cancer: the 7th edition of the AJCC cancer staging manual and the future of TNM. Annals of surgical oncology 17:1471-1474 (2010).
Egger et al. Epigenetics in human disease and prospects for epigenetic therapy. Nature 429:457-463 (2004).
Ehrlich. DNA methylation in cancer: too much, but also too little. Oncogene 21(35):5400-5413 (2002).
Eisenhauer et al. New response evaluation criteria in solid tumours: revised RECIST guideline (version 1.1). Euro J Cancer 45:228-247 (2009).
Esteller. Epigenetics in cancer. N Engl J Med 358:1148-1159 (2008).
Fackler et al. Quantitative multiplex methylation-specific PCR analysis doubles detection of tumor cells in breast ductal fluid. Clin. Cancer Res. 12(11 Pt 1):3306-3310 (2006).
Fackler et al. Quantitative multiplex methylation-specific PCR assay for the detection of promoter hypermethylation in multiple genes in breast cancer. Cancer Res. 64(13):4442-4452 (2004).
Feinberg et al. The history of cancer epigenetics. Nat Rev Cancer 4(2):143-153 (2004).

(56) References Cited

OTHER PUBLICATIONS

Friedman et al. Regularization Paths for Generalized Linear Models via Coordinate Descent. J Stat Softw 33:1-22 (2010).
Friedman. Regularized Discriminant Analysis. Journal of the American Statistical Association 84:165-175 (1989).
Frommer et al. A genomic sequencing protocol that yields a positive display of 5-methylcytosine residues in individual DNA strands. PNAS USA 89:1827-1831 (1992).
Gebhard et al. Genome-wide profiling of CpG methylation identifies novel targets of aberrant hypermethylation in myeloid leukemia. Cancer Res. 66:6118-6128 (2006).
Gebhard et al. Rapid and sensitive detection of CpG-methylation using methyl-binding (MB)-PCR. Nucleic Acids Res. 34:e82 (2006).
Gibson et al. A novel method for real time quantitative RT-PCR. Genome Research 6:995-1001 (1996).
Gonzalgo et al. Rapid quantitation of methylation differences at specific sites using methylation-sensitive single nucleotide primer extension (MS-SNuPE). Nucleic Acids Res. 25:2529-2531 (1997).
Grant et al. Molecular and genetic pathways in gliomas: the future of personalized therapeutics. CNS Oncology 3(2):123-136 (2014).
Greco et al. Cancer of unknown primary site. Cancer: Principles and Practice of Oncology. Ed 9. Chapter 137. (pp. 2033-2051) (2011).
Greco et al. Molecular profiling diagnosis in unknown primary cancer: accuracy and ability to complement standard pathology. J Natl Cancer Inst 105(11):782-790 (2013).
Grunnet et al. Carcinoembryonic antigen (CEA) as tumor marker in lung cancer. Lung Cancer 76:138-143 (2012).
Han et al. The Pan-Cancer analysis of pseudogene expression reveals biologically and clinically relevant tumour subtypes. Nat Commun 5:3963 (2014).
Hannum et al. Genome-wide methylation profiles reveal quantitative views of human aging rates. Mol Cell 49:359-367 (2013).
Hao et al. DNA methylation markers for diagnosis and prognosis of common cancers. PNAS USA 114(28):7414-7419 (w/Supplemental Information) (2017).
Harrell et al. Tutorial in Biostatistics: Multivariable Prognostic Models: Issues in Developing Models, Evaluating Assumptions and Adequacy, and Measuring and Reducing Errors. Stat Med 15:361-387 (1996).
Harris et al. Single-molecule DNA sequencing of a viral genome. Science 320:106-109 (2008).
Heagerty et al. Time-dependent ROC curves for censored survival data and a diagnostic marker. Biometrics 56:337-344 (2000).
Hearst et al. Support vector machines. Intelligent Systems and their Applications. IEEE 13(4):18-28 (1998).
Herman et al. Gene silencing in cancer in association with promoter hypermethylation. N Engl J Med 349(21):2042-2054 (2003).
Herman et al. Methylation-specific PCR: a novel PCR assay for methylation status of CpG islands. PNAS USA 93:9821-9826 (1996).
Heyn et al. DNA methylation profiling in the clinic: applications and challenges. Nature Reviews Genetics 13(10):679-692 (2012).
Horak et al. ChIP-chip: a genomic approach for identifying transcription factor binding sites. Methods Enzymol 350:469-483 (2002).
Hudson. A new statistic for detecting genetic differentiation. Genetics 155(4):2011-2014 (2000).
Irizarry et al. The human colon cancer methylome shows similar hypo- and hypermethylation at conserved tissue-specific CpG island shores. Nat Genet 41:178-186 (2009).
Itzkowitz et al. Improved fecal DNA test for colorectal cancer screening. Clin Gastroenterol. Hepatol. 5(1):111-117 (2007).
Jaenisch et al. Epigenetic regulation of gene expression: how the genome integrates intrinsic and environmental signals. Nat Genet 33 Suppl:245-254 (2003).
Johnson. Role of alpha- fetoprotein in the diagnosis and management of hepatocellular carcinoma. J Gastro Hepatol 14:S32-S36 (1999).
Kandoth et al. Mutational landscape and significance across 12 major cancer types. Nature 502(7471):333-339 (2013).
Koboldt et al. VarScan 2: somatic mutation and copy number alteration discovery in cancer by exome sequencing. Genome Res 22(3):568-576 (2012).
Koga et al. Genome-wide screen of promoter methylation identifies novel markers in melanoma. Genome Res. 19:1462-1470 (2009).
Kulis et al. DNA methylation and cancer. Adv Genet 70:27-56 (2010).
Laird. Early Detection: The power and the promise of DNA methylation markers. Nat Rev Cancer 3:253-266 (2003).
Langmead et al. Fast gapped-read alignment with Bowtie 2. Nature Methods 9:357-359 (2012).
Lehmann-Werman et al. Identification of tissue-specific cell death using methylation patterns of circulating DNA. PNAS USA 113:E1826-1834 (2016).
Li et al. Multiplex padlock targeted sequencing reveals human hypermutable CpG variations. Genome Res 19(9):1606-1615 (2009).
Lieb. Genome-wide mapping of protein-DNA interactions by chromatin immunoprecipitation and DNA microarray hybridization. Methods Mol Biol 224:99-109 (2003).
Liefers et al. Micrometastases and survival in stage II colorectal cancer. N Engl J Med 339(4):223-228 (1998).
Margulies et al. Genome sequencing in microfabricated high-density picolitre reactors. Nature 437:376-380 (2005).
Mazor et al. DNA Methylation and Somatic Mutations Converge on the Cell Cycle and Define Similar Evolutionary Histories in Brain Tumors. Cancer Cell 28(3):307-317 (2015).
McClelland et al. Effect of site-specific modification on restriction endonucleases and DNA modification methyltransferases. Nucleic Acids Res.22(17):3640-3659 (1994).
Meinshausen et al. Stability selection. Journal of the Royal Statistical Society. Series B Statistical Methodology 72:417-473 (2010).
Misale et al. Emergence of KRAS mutations and acquired resistance to anti EGFR therapy in colorectal cancer. Nature 486(7404):532-536 (Jun. 28, 2012).
Mok et al. Detection and Dynamic Changes of EGFR Mutations from Circulating Tumor DNA as a Predictor of Survival Outcomes in NSCLC Patients Treated with First-line Intercalated Erlotinib and Chemotherapy. Clin Cancer Res 21:3196-3203 (2015).
Morris et al. Who to treat with adjuvant therapy in Dukes B/stage II colorectal cancer? The need for high quality pathology. Gut 56(10):1419-1425 (2007).
Murphy et al. Patterns of Colorectal Cancer Care in the United States: 1990-2010. J Natl Cancer Inst 107(10):11 pgs. (2015).
Nakano et al. Single-molecule PCR using water-in-oil emulsion. J. Biotech. 102:117-124 (2003).
National Lung Screening Trial Research Team et al. Reduced lung-cancer mortality with low-dose computed tomographic screening. N Engl J Med 365:395-409 (2011).
Nolte. Branched DNA signal amplification for direct quantitation of nucleic acid sequences in clinical specimens. Adv. Clin. Chem. 33:201-235 (1998).
O'Geen et al. Comparison of sample preparation methods for ChIP-chip assays. BioTechniques 41(5):577-580 (2006).
Ogino et al. Predictive and prognostic analysis of PIK3CA mutation in stage III colon cancer intergroup trial. J Natl Cancer Inst 105(23):1789-1798 (2013).
O'Shea et al. Cytokine signaling in 2002: new surprises in the Jak/Stat pathway. Cell 109(2):S121-S131 (2002).
Olek et al. The pre-implantation ontogeny of the H19 methylation imprint Nat. Genet. 17(3):275-276 (1997).
O'Quigley et al. Explained randomness in proportional hazards models. Stat Med 24:479-489 (2005).
Paez et al. EGFR mutations in lung cancer: correlation with clinical response to gefitinib therapy. Science 304(5676):1497-1500 (2004).
PCT/US2016/013716 International Preliminary Report on Patentability dated Jul. 27, 2017.
PCT/US2016/013716 International Search Report and Written Opinion dated May 12, 2016.
Pelizzola et al. MEDME: an experimental and analytical methodology for the estimation of DNA methylation levels based on microarray derived MeDIP-enrichment. Genome Res. 18:1652-1659 (2008).

(56) References Cited

OTHER PUBLICATIONS

Pentheroudakis et al. Novel microRNA-based assay demonstrates 92% agreement with diagnosis based on clinicopathologic and management data in a cohort of patients with carcinoma of unknown primary. Mol Cancer 12:57 (2013).
Porreca et al. Multiplex amplification of large sets of human exons. Nature Methods 4(11):931-936 (2007).
Raab et al. Quality in cancer diagnosis. CA Cancer J Clin 60(3):139-165 (2010).
Radmacher et al. A paradigm for class prediction using gene expression profiles. Journal of Computational Biology 9:505-511 (2002).
Ramaswamy et al. Multiclass cancer diagnosis using tumor gene expression signatures. PNAS USA 98:15149-15154 (2001).
Rauch et al. High-resolution mapping of DNA hypermethylation and hypomethylation in lung cancer. PNAS USA 105:252-257 (2008).
Reich et al. Linkage disequilibrium in the human genome. Nature 411:199-204 (2001).
Rein et al. Identifying 5-methylcytosine and related modifications in DNA genomes. Nucleic Acids Res. 26(10):2255-2264 (1998).
Robin et al. pROC: an open-source package for R and S+ to analyze and compare ROC curves. BMC Bioinformatics 12:77 (2011).
Ross et al. Comprehensive Genomic Profiling of Carcinoma of Unknown Primary Site: New Routes to Targeted Therapies. JAMA Oncol 1(1):40-49 (2015).
Ruczinski et al. Logic Regression. Journal of Computational and Graphical Statistics 12:475-5111 (2003).
Sadri et al. Rapid analysis of DNA methylation using new restriction enzyme sites created by bisulfite modification. Nucleic Acids Res. 24:5058-5059 (1996).
Salazar et al. Gene expression signature to improve prognosis prediction of stage II and III colorectal cancer. J Clin Oncol 29(1):17-24 (2011).
Schmoll et al. Capecitabine Plus Oxaliplatin Compared With Fluorouracil/Folinic Acid as Adjuvant Therapy for Stage III Colon Cancer: Final Results of the No. 16968 Randomized Controlled Phase III Trial. J Clin Oncol 33(32):3733-3740 (2015).
Schroder et al. survcomp: an R/Bioconductor package for performance assessment and comparison of survival models. Bioinformatics 27:3206-3208 (2011).
Schwarzenbach et al. Cell-free nucleic acids as biomarkers in cancer patients. Nat Rev Cancer 11:426-437 (2011).
Shevade et al. A simple and efficient algorithm for gene selection using sparse logistic regression. Bioinformatics 19(17):2246-2253 (2003).
Shiraishi et al. Isolation of DNA fragments associated with methylated CpG islands in human adenocarcinomas of the lung using a methylated DNA binding column and denaturing gradient gel electrophoresis. PNAS USA 96(6):2913-2918 (1999).
Siegel et al. Cancer statistics, 2015. CA Cancer J Clin 65:5-29 (2015).
Simon et al. Pitfalls in the use of DNA microarray data for diagnostic and prognostic classification. Journal of the National Cancer Institute 95:14-18 (2003).
Singal et al. Meta-analysis: surveillance with ultrasound for early-stage hepatocellular carcinoma in patients with cirrhosis. Aliment Pharmacol Ther 30:37-47 (2009).
Smith et al. Cancer screening in the United States, 2015: a review of current American cancer society guidelines and current issues in cancer screening. CA Cancer J Clin 65(1):30-54 (2015).
Smyth. Chapter 23: Limma: linear models for microarray data. Bioinformatics and computational biology solutions using R and Bioconductor (Springer) (pp. 397-420) (2005).
Snyder et al. Cell-free DNA Comprises an In Vivo Nucleosome Footprint that Informs Its Tissues-of-Origin. Cell 164:57-68 (2016).
Soni et al. Progress toward ultrafast DNA sequencing using solid-state nanopores. Clin. Chem. 53:1996-2001 (2007).

Sorlie et al. Gene expression patterns of breast carcinomas distinguish tumor subclasses with clinical implications. PNAS USA 98:10869-10874 (2001).
Stroun et al. The origin and mechanism of circulating DNA. Ann N Y Acad Sci 906:161-168 (2000).
Sultan et al. Stat5 promotes homotypic adhesion and inhibits invasive characteristics of human breast cancer cells. Oncogene 24(5):746-760 (2005).
Sun et al. Plasma DNA tissue mapping by genome-wide methylation sequencing for noninvasive prenatal, cancer, and transplantation assessments. PNAS USA 112:E5503-5512 (2015).
Thomas et al. The role of JAK/STAT signalling in the pathogenesis, prognosis and treatment of solid tumours. British J Cancer 113(3):365-371 (2015).
Tibshirani. Regression shrinkage and selection via the lasso. Journal of the Royal Statistical Society Series B (Methodological) 58:267-288 (1996).
Torre et al. Global cancer statistics, 2012. CA Cancer J Clin 65:87-108 (2015).
Tost et al. DNA methylation analysis by pyrosequencing. Nature Protocols 2:2265-2275 (2007).
Toyota et al. Identification of differentially methylated sequences in colorectal cancer by methylated CpG island amplification. Cancer Res. 59:2307-2312 (1999).
Tran et al. Prolactin inhibits BCL6 expression in breast cancer through a Stat5a-dependent mechanism. Cancer Res 70(4):1711-1721 (2010).
Travis et al. Lung cancer. Cancer 75:191-202 (1995).
U.S. Appl. No. 14/986,520 Office Action dated Apr. 11, 2017.
U.S. Appl. No. 14/986,520 Office Action dated Jun. 30, 2017.
Ushijima et al. Methylation-Sensitive Representational Difference Analysis (MS-RDA). Methods Mol Biol 507:117-130 (2009).
Vaissiere et al. Epigenetic interplay between histone modifications and DNA methylation in gene silencing. Mutat Res 659(1-2):40-48 (2008).
Varadhachary. New strategies for carcinoma of unknown primary: the role of tissue-of-origin molecular profiling. Clin Cancer Res 19(15):4027-4033 (2013).
Vedeld et al. The novel colorectal cancer biomarkers CDO1, ZSCAN18 and ZNF331 are frequently methylated across gastrointestinal cancers. Int J Cancer 136:844-853 (2015).
Wall et al. Haplotype blocks and linkage disequilibrium in the human genome. Nat Rev Genetics 4:587-597 (2003).
Wang et al. Identification and characterization of essential genes in the human genome. Science 350(6264):1096-1101 (2015).
Wasserman et al. High dimensional variable selection. Annals of statistics 37:2178-2201 (2009).
Weber et al. Chromosome-wide and promoter-specific analyses identify sites of differential DNA methylation in normal and transformed human cells. Nat. Genet. 37:853-862 (2005).
Weinstein et al. The Cancer Genome Atlas Pan-Cancer analysis project. Nat Genet 45(10):1113-1120 (2013).
Wojdacz et al. Methylation-sensitive high resolution melting (MS-HRM): a new approach for sensitive and high-throughput assessment of methylation. Nucleic Acids Res. 35(6):e41 (2007).
Wojdacz et al. Methylation-sensitive high-resolution melting. Nature Protocols 3(12):1903-1908 (2008).
Wright et al. A random variance model for detection of differential gene expression in small microarray experiments. Bioinformatics 19(18):2448-2455 (2003).
Xiong et al COBRA: a sensitive and quantitative DNA methylation assay. Nucleic Acids Res. 25:2532-2534 (1997).
Xu et al. Circulating tumour DNA methylation markers for diagnosis and prognosis of hepatocellular carcinoma. Nat Mater 16(11):1155-1161 (2017).
Yan et al. IDH1 and IDH2 mutations in gliomas. N Engl J Med 360(8):765-773 (2009).
Yao et al. Inferring regulatory element landscapes and transcription factor networks from cancer methylomes. Genome Biol 16:105 (2015).
Zou et al. Association of Clinical Chemistry (AACC) poster presentation on Jul. 28, 2010. Sensitive Quantification of Methylated

(56) References Cited

OTHER PUBLICATIONS

Markers with a Novel Methylation Specific Technology. Available at www.exactsciences.com (10 pgs).
Bediaga et al. DNA methylation epigenotypes in breast cancer molecular subtype. Breast Cancer Res 12(5):R77 (2010).
Wilhelm-Benartzi et al. Review of processing and analysis methods for DNA methylation array data. Br J Cancer 109(6):1394-1402 (2013).
U.S. Appl. No. 16/315,610, filed Jul. 6, 2017, by Zhang et al. (U.S. Patent Application is not submitted herewith pursuant to the waiver of 37 C.F.R § 1.98(a)(2)(iii) issued by the Office on Sep. 21, 2004.)
U.S. Appl. No. 16/315,609, filed Jul. 6, 2017, by Zhang et al. (U.S. Patent Application is not submitted herewith pursuant to the waiver of 37 C.F.R § 1.98(a)(2)(iii) issued by the Office on Sep. 21, 2004.)
U.S. Appl. No. 16/315,608, filed Jul. 6, 2017, by Zhang et al. (U.S. Patent Application is not submitted herewith pursuant to the waiver of 37 C.F.R § 1.98(a)(2)(iii) issued by the Office on Sep. 21, 2004.)
U.S. Appl. No. 16/315,605, filed Jul. 6, 2017, by Zhang et al. (U.S. Patent Application is not submitted herewith pursuant to the waiver of 37 C.F.R § 1.98(a)(2)(iii) issued by the Office on Sep. 21, 2004.)

* cited by examiner

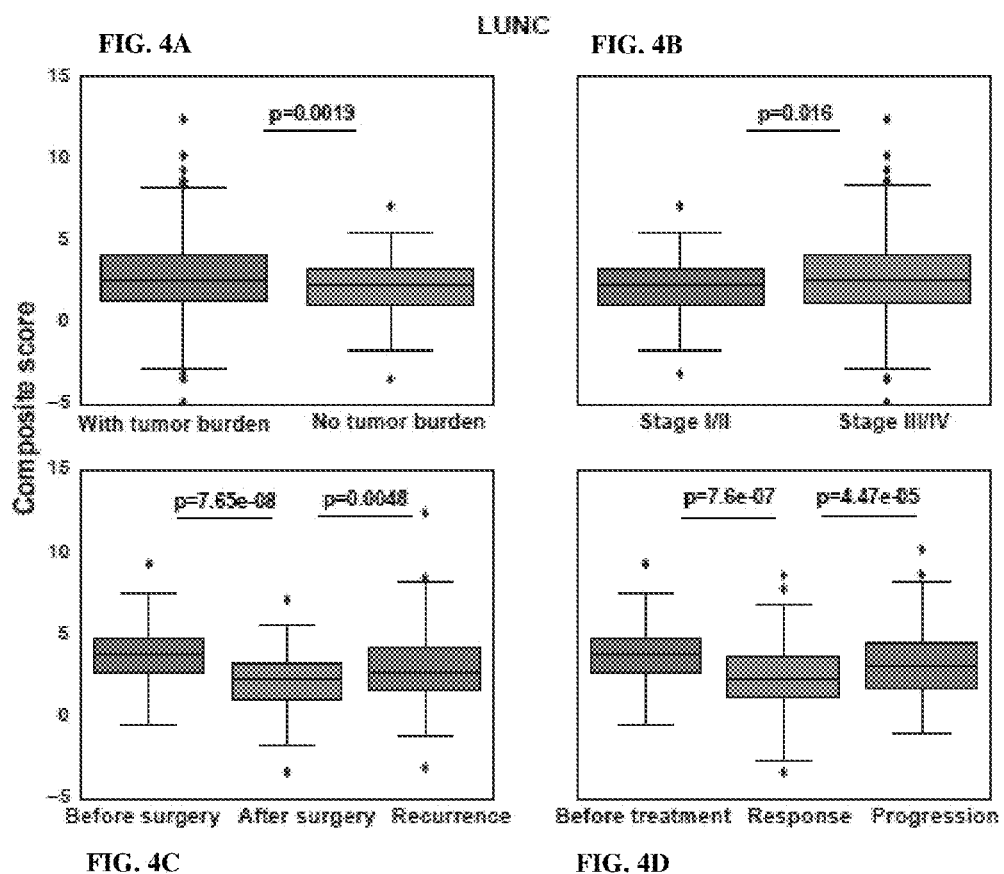

HCC FIG. 4F

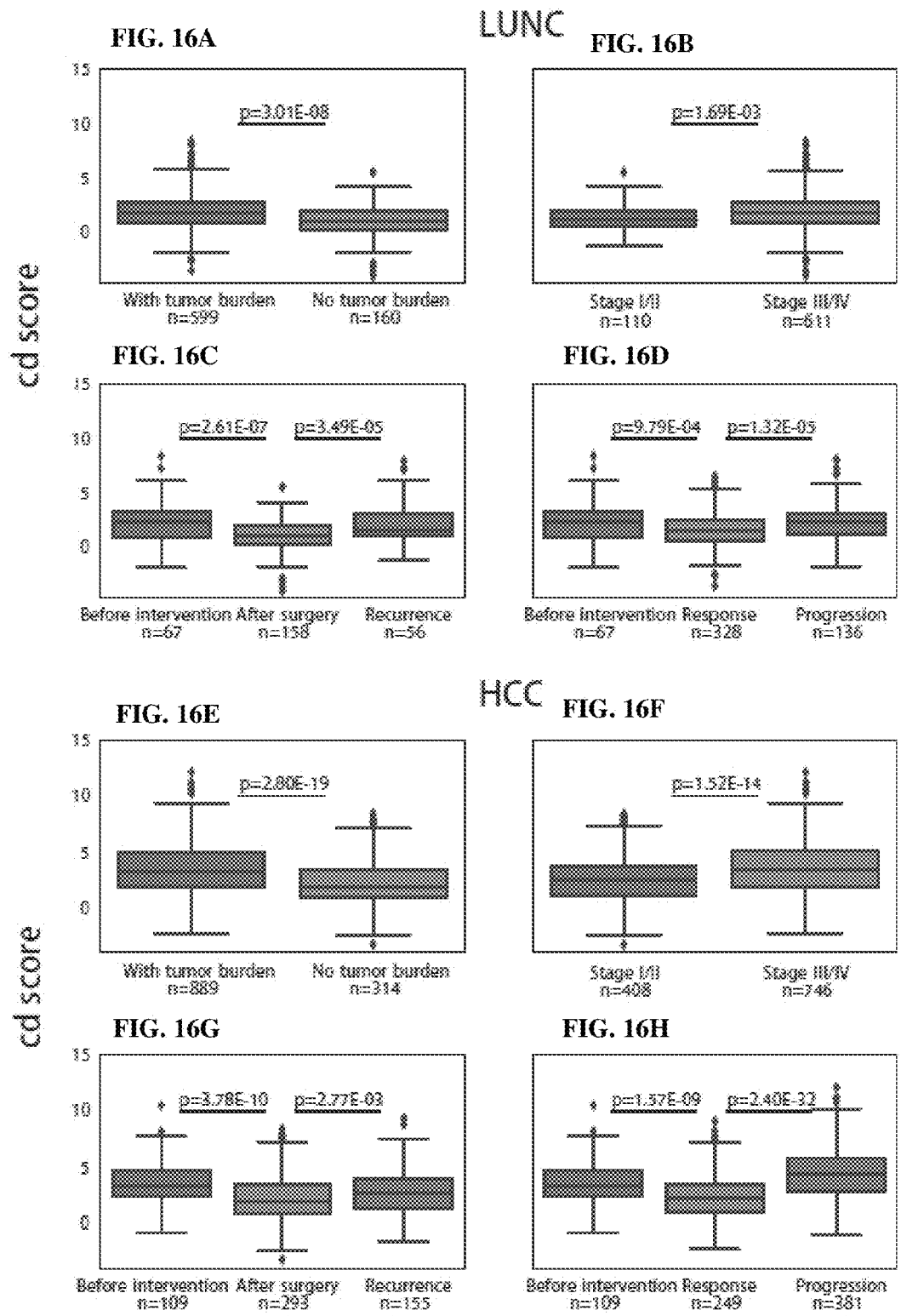

LUNC

HCC

FIG. 17A 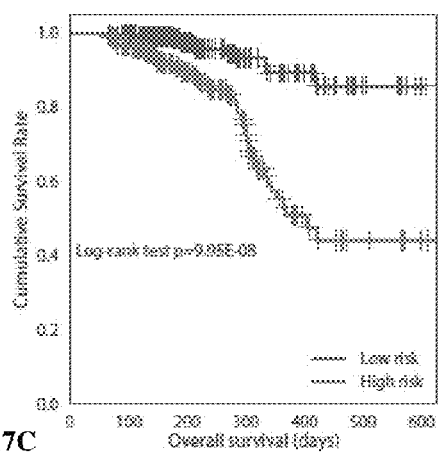 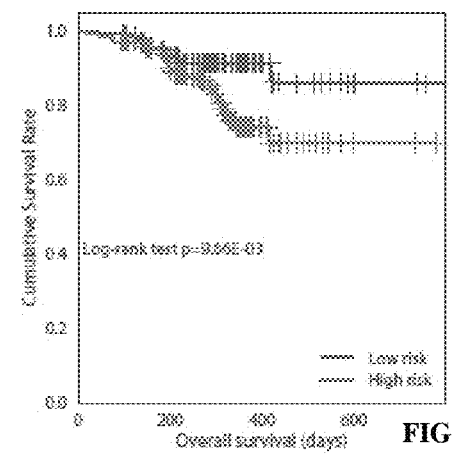 FIG. 17B
FIG. 17C 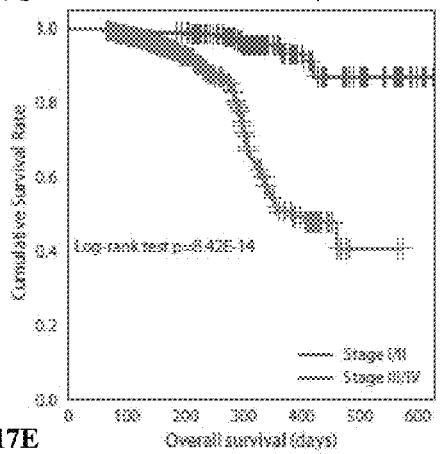 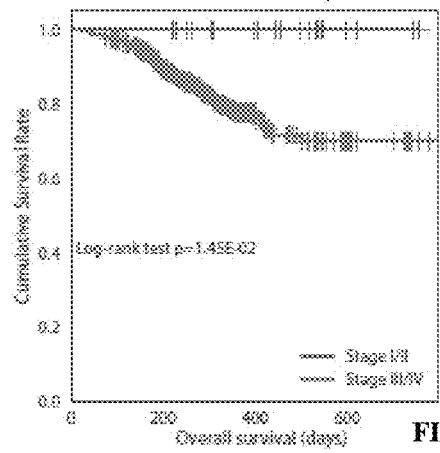 FIG. 17D
FIG. 17E 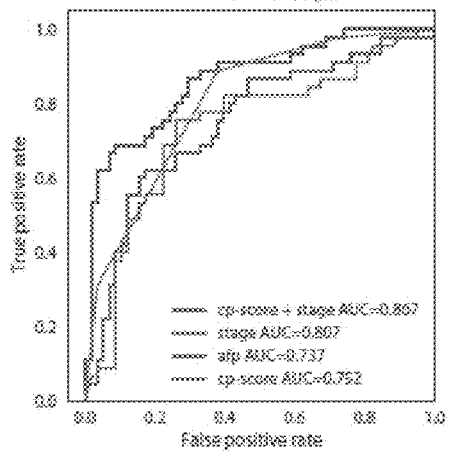 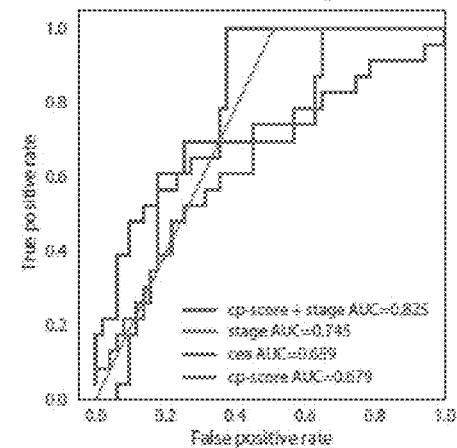 FIG. 17F Stage I LUNC: n=94
Benign nodules: n=126

| Validation Cohort | Stage I LUNC | Benign nodules | |
|---|---|---|---|
| Stage I LUNC | 77 | 22 | |
| Benign nodules | 17 | 104 | Totals |
| Totals | 94 | 126 | 220 |
| Correct | 77 | 104 | 181 |
| Sensitivity (%) | 81.9 | | |
| Specificity (%) | | 82.5 | |
| PPV (%) | 77.8 | | |
| NPV (%) | | 86.0 | |

FIG. 27C

| Training Dataset | HCC | Normal | |
|---|---|---|---|
| HCC | 613 | 32 | |
| Normal | 102 | 528 | Totals |
| Totals | 715 | 560 | 1275 |
| Correct | 613 | 528 | 1162 |
| False Positive | 102 | | 102 |
| False Negative | | 32 | 32 |
| Specificity (%) | 85.7 | | |
| Sensitivity (%) | | 94.3 | 89.5 |

FIG. 27D

| Validation Dataset | HCC | Normal | |
|---|---|---|---|
| HCC | 319 | 26 | |
| Normal | 64 | 249 | Totals |
| Totals | 383 | 275 | 658 |
| Correct | 319 | 249 | 568 |
| False Positive | 64 | | 65 |
| False Negative | | 26 | 26 |
| Specificity (%) | 83.2 | | |
| Sensitivity (%) | | 90.5 | 86.3 |

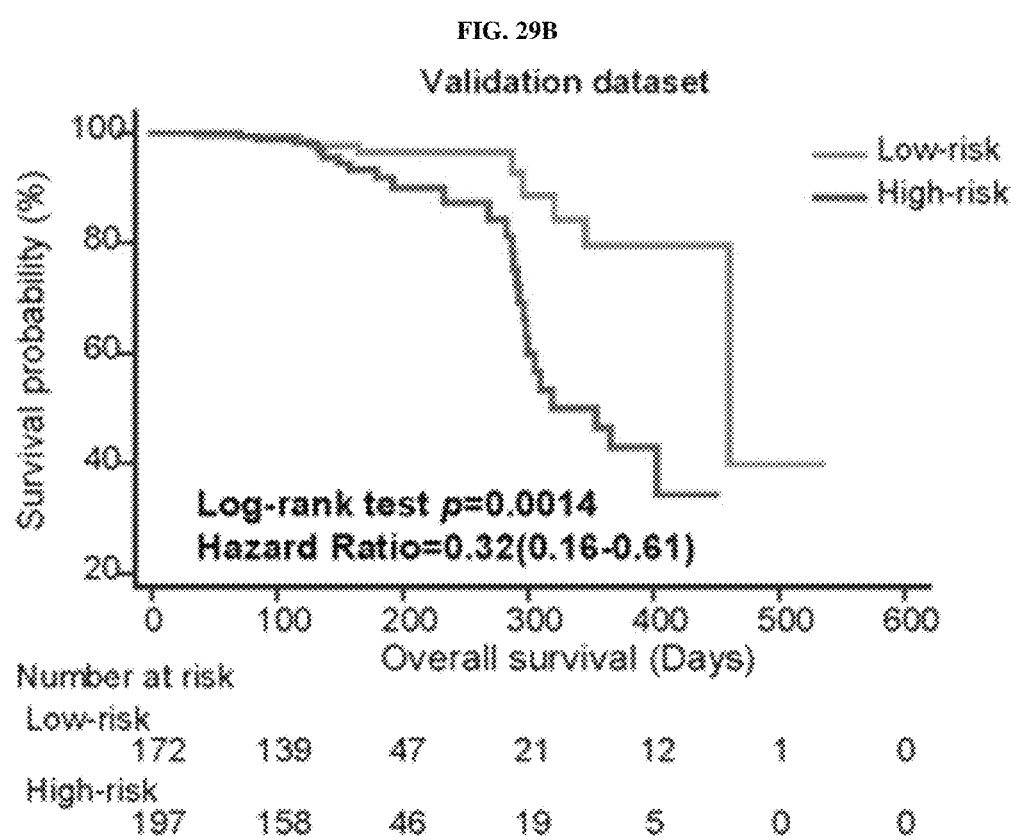

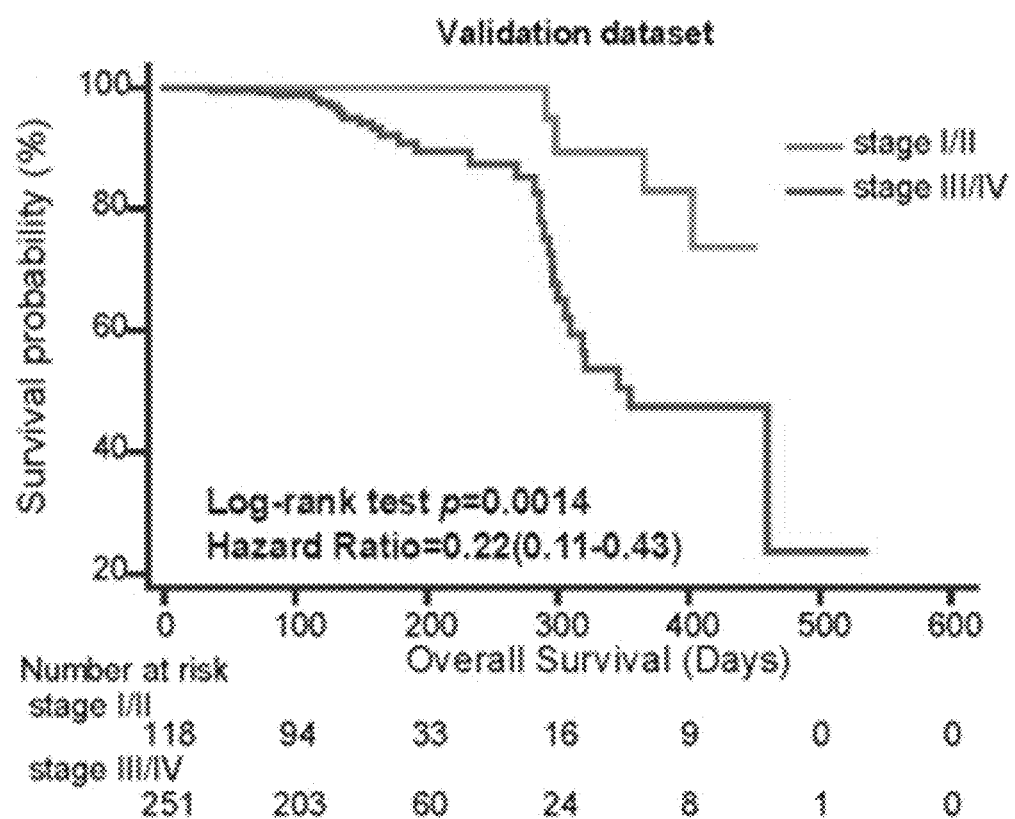

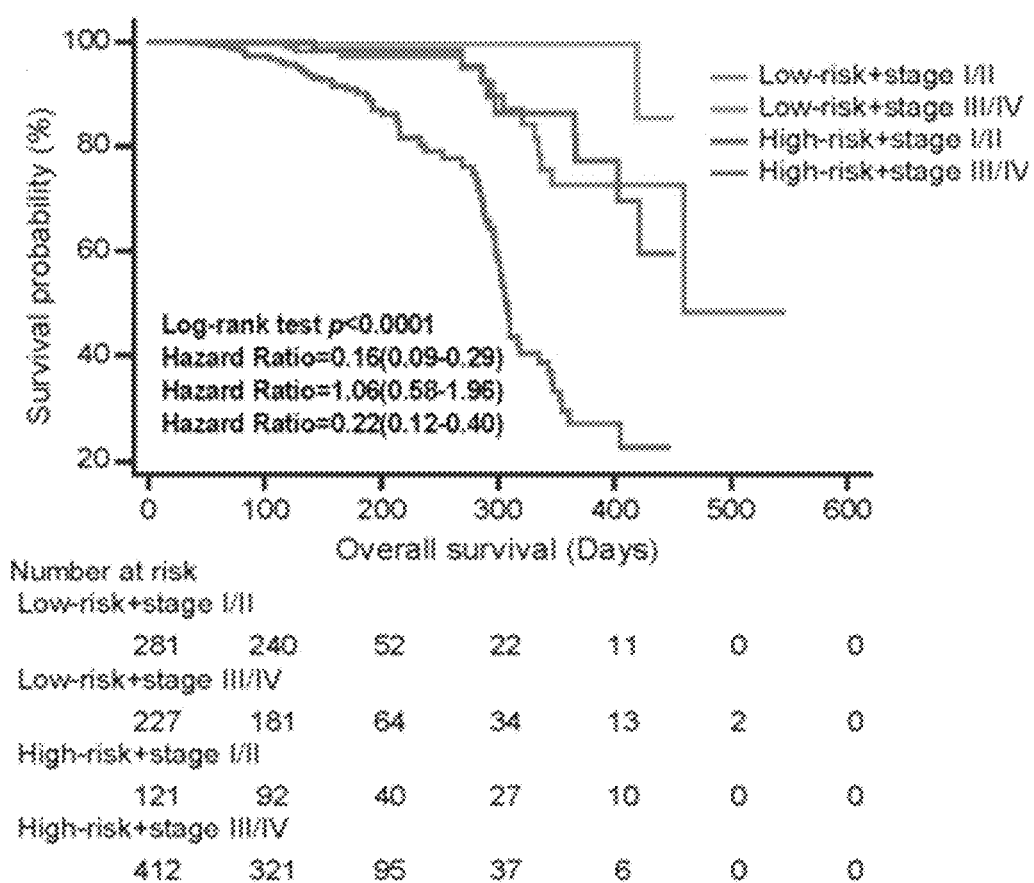

chr11: 68181288                                                                 71146211

FIG. 38B

| DNA type | Fraction of normal cfDNA | DNA type | Fraction of HCC gDNA | Methylated copy | Non-Methylated copy | M/(M+NM) | total copies |
|---|---|---|---|---|---|---|---|
| nor cfDNA | 100% | HCC gDNA | 0% | 58 | 924 | 5.90% | 982 |
| nor cfDNA | 90% | HCC gDNA | 10% | 134 | 784 | 14.60% | 918 |
| nor cfDNA | 70% | HCC gDNA | 30% | 266 | 654 | 28.90% | 920 |
| nor cfDNA | 40% | HCC gDNA | 60% | 420 | 532 | 44.10% | 952 |
| nor cfDNA | 0% | HCC gDNA | 100% | 694 | 334 | 67.50% | 1028 |

SEQUENCE LISTING

```
<160> NUMBER OF SEQ ID NOS: 22

<210> SEQ ID NO 1
<211> LENGTH: 137
<212> TYPE: DNA
```

```
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (108)..(113)
<223> OTHER INFORMATION: a, c, t, g, unknown or other

<400> SEQUENCE: 1
acaatatccc aaacacatca tcatctgtct cttatacaca tctccgagcc cacgagaccc      60
cccccccccc ccctcgtcg gcagcgtcag atgtgtataa gagacagnnn nnnaaattat     120
tttcttctaa ttcaaat                                                    137

<210> SEQ ID NO 2
<211> LENGTH: 137
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (105)..(110)
<223> OTHER INFORMATION: a, c, t, g, unknown or other

<400> SEQUENCE: 2
acaaccacat tcactaaaca ctgtctctta tacacatctc cgagcccacg agaccccccc      60
cccccccccc ctcgtcggca gcgtcagatg tgtataagag acagnnnnnn aaatataaaa    120
tattaaacaa ctaaaaa                                                    137

<210> SEQ ID NO 3
<211> LENGTH: 137
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (109)..(114)
<223> OTHER INFORMATION: a, c, t, g, unknown or other

<400> SEQUENCE: 3
accctcttct ctcacttcca ctgtctctta tacacatctc cgagcccacg agaccccccc      60
cccccccccc ccccctcgtc ggcagcgtca gatgtgtata agagacagnn nnnnacatcc    120
taaaaatata aaacata                                                    137

<210> SEQ ID NO 4
<211> LENGTH: 137
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (106)..(111)
<223> OTHER INFORMATION: a, c, t, g, unknown or other

<400> SEQUENCE: 4
acccctacta cccaccctat ctcctgtctc ttatacacat ctccgagccc acgagacccc      60
cccccccccc cctcgtcggc agcgtcagat gtgtataaga gacagnnnnn naccaacaat    120
aaatacataa taataat                                                    137
```

<210> SEQ ID NO 5
<211> LENGTH: 137
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (104)..(109)
<223> OTHER INFORMATION: a, c, t, g, unknown or other

<400> SEQUENCE: 5
acacaattac ctctcccctt ctgtctctta tacacatctc cgagcccacg agaccccccc      60
cccccccccc tcgtcggcag cgtcagatgt gtataagaga cagnnnnnna aaaatatatt     120
cattctccaa ataaaaa                                                    137

<210> SEQ ID NO 6
<211> LENGTH: 137
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (108)..(113)
<223> OTHER INFORMATION: a, c, t, g, unknown or other

<400> SEQUENCE: 6
tctttactct ctcaatccaa ccctgtctct tatacacatc tccgagccca cgagaccccc      60
cccccccccc ccctcgtcg gcagcgtcag atgtgtataa gagacagnnn nnnaaatccc      120
aaatacaatt tcaaaat                                                    137

<210> SEQ ID NO 7
<211> LENGTH: 137
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (110)..(115)
<223> OTHER INFORMATION: a, c, t, g, unknown or other

<400> SEQUENCE: 7
cccttaaaca ccaatcttcc aaccctgtct cttatacaca tctccgagcc cacgagaccc      60
cccccccccc cccccctcgt cggcagcgtc agatgtgtat aagagacagn nnnnnaataa     120
aacaaaaata accccaa                                                    137

<210> SEQ ID NO 8
<211> LENGTH: 137
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (104)..(109)
<223> OTHER INFORMATION: a, c, t, g, unknown or other

<400> SEQUENCE: 8

-continued atcttcccaa cactcaaaac aataccctgt ctcttataca catctccgag cccacgagac    60
cccccccccc tcgtcggcag cgtcagatgt gtataagaga cagnnnnnna tcccatacat   120
tcctaactcc tttaaat                                                  137

<210> SEQ ID NO 9
<211> LENGTH: 137
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (106)..(111)
<223> OTHER INFORMATION: a, c, t, g, unknown or other

<400> SEQUENCE: 9
tcttaaacca cttctaacta caccacaatc tgtctcttat acacatctcc gagcccacga    60 gaccccccccc cctcgtcggc agcgtcagat gtgtataaga gacagnnnnn naaccattat   120
atccttccca tcttttt                                                  137

<210> SEQ ID NO 10
<211> LENGTH: 137
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (107)..(112)
<223> OTHER INFORMATION: a, c, t, g, unknown or other

<400> SEQUENCE: 10
ctcctcctct taccacaccc ttttcctaaa cactgtctct tatacacatc tccgagccca    60
cgagaccccc cctcgtcgg cagcgtcaga tgtgtataag agacagnnnn nntaaatccc    120
catatatctt ttcttca                                                  137

<210> SEQ ID NO 11
<211> LENGTH: 137
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (110)..(115)
<223> OTHER INFORMATION: a, c, t, g, unknown or other

<400> SEQUENCE: 11
ataaaaacac taaaaccta aaacactgtc tcttatacac atctccgagc ccacgagacc    60
cccccccccc cccccctcgt cggcagcgtc agatgtgtat aagagacagn nnnnnaatac   120
cctctttaat acaaaaa                                                  137

<210> SEQ ID NO 12
<211> LENGTH: 137
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base

```
<222> LOCATION: (104)..(109)
<223> OTHER INFORMATION: a, c, t, g, unknown or other

<400> SEQUENCE: 12
atacaaccta aatacaaact tcccactgtc tcttatacac atctccgagc ccacgagacc      60 ccccccccc tcgtcggcag cgtcagatgt gtataagaga cagnnnnna aaaacctaac       120 cctacctcta aacaaat                                                    137

<210> SEQ ID NO 13
<211> LENGTH: 137
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (106)..(111)
<223> OTHER INFORMATION: a, c, t, g, unknown or other

<400> SEQUENCE: 13
cacaacctac actcctccca acctgtctct tatacacatc tccgagccca cgagaccccc     60 ccccccccc cctcgtcggc agcgtcagat gtgtataaga gacagnnnnn nttcccttac      120
cctaaatata attaata                                                    137

<210> SEQ ID NO 14
<211> LENGTH: 137
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (110)..(115)
<223> OTHER INFORMATION: a, c, t, g, unknown or other

<400> SEQUENCE: 14
tcatttcccc caacaaattc ttttctttct cctgtctctt atacacatct ccgagcccac     60 gagaccccc ccccctcgt cggcagcgtc agatgtgtat aagagacagn nnnntacca       120 aaacctttat attctaa                                                    137

<210> SEQ ID NO 15
<211> LENGTH: 137
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (106)..(111)
<223> OTHER INFORMATION: a, c, t, g, unknown or other

<400> SEQUENCE: 15
acatataact cacaacccct tcctacccct gtctcttata cacatctccg agcccacgag     60
accccccccc cctcgtcggc agcgtcagat gtgtataaga gacagnnnnn naaaaattta    120
taatattact atcatca                                                    137

<210> SEQ ID NO 16
<211> LENGTH: 137
<212> TYPE: DNA
<213> ORGANISM: Artificial Sequence
```

```
<220> FEATURE:
<223> OTHER INFORMATION: Description of Artificial Sequence: Synthetic
      polynucleotide
<220> FEATURE:
<221> NAME/KEY: modified_base
<222> LOCATION: (113)..(118)
<223> OTHER INFORMATION: a, c, t, g, unknown or other

<400> SEQUENCE: 16
actcaaacac tcatccacat cctgtctctt atacacatct ccgagcccac gagaccccc      60 cccccccccc ccccccccct cgtcggcagc gtcagatgtg tataagagac agnnnnnncc    120
cacctaaaac tacaatc                                                   137

<210> SEQ ID NO 17
<211> LENGTH: 137
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (105)..(110)
<223> OTHER INFORMATION: a, c, t, g, unknown or other

<400> SEQUENCE: 17
accaataaca actcacctaa actgtctctt atacacatct ccgagcccac gagaccccc      60 cccccccccc ctcgtcggca gcgtcagatg tgtataagag acagnnnnnn aaaactaacc    120
ctcaactctc acaaact                                                   137

<210> SEQ ID NO 18
<211> LENGTH: 137
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (104)..(109)
<223> OTHER INFORMATION: a, c, t, g, unknown or other

<400> SEQUENCE: 18 ctcccttaa atcaaaaact aaacatttaa atctgtctct tatacacatc tccgagccca      60
cgagaccccc tcgtcggcag cgtcagatgt gtataagaga cagnnnnnna tttacattcc    120
atccatctac attctat                                                   137

<210> SEQ ID NO 19
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
tgttagtttt tatggaagtt t                                              21

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
```

```
<220> FEATURE:
<221> NAME/KEY: modified_base
<222> LOCATION: (5)..(5)
<223> OTHER INFORMATION: Inosine

<400> SEQUENCE: 20
aaacnaacaa aatactcaaa                                                      20

<210> SEQ ID NO 21
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 21
tgggagagcg ggagat                                                          16

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 22
tttgggagag tgggagattt                                                      20
```

METHYLATION MARKERS FOR DIAGNOSING HEPATOCELLULAR CARCINOMA AND LUNG CANCER

CROSS-REFERENCE

This application claims the benefit of U.S. Provisional Application No. 62/466,328, filed on Mar. 2, 2017, U.S. Provisional Application No. 62/466,329, filed on Mar. 2, 2017, and U.S. Provisional Application No. 62/569,462, filed on Oct. 6, 2017, each of which are incorporated herein by reference in their entireties.

SEQUENCE LISTING

The instant application contains a Sequence Listing which has been submitted electronically in ASCII format and is hereby incorporated by reference in its entirety. Said ASCII copy, created on Apr. 18, 2018, is named 49697-715_201_SL.txt and is 10,022 bytes in size.

BACKGROUND OF THE DISCLOSURE

Cancer is a leading cause of deaths worldwide, with annual cases expected to increase from 14 million in 2012 to 22 million during the next two decades (WHO). Diagnostic procedures for liver cancer, in some cases, begin only after a patient is already present with symptoms, leading to costly, invasive, and sometimes time-consuming procedures. In addition, inaccessible areas sometimes prevent an accurate diagnosis. Further, high cancer morbidities and mortalities are associated with late diagnosis.

SUMMARY OF THE DISCLOSURE

Disclosed herein, in certain embodiments, are methods and kits for diagnosing a subject as having hepatocellular carcinoma (HCC) or lung cancer. In some instances, also described herein are methods of determining the prognosis of the subject having HCC or lung cancer. In additional instances, described herein are methods of determining the specific staging of HCC or lung cancer in a subject.

In certain embodiments, disclosed herein is a method of selecting a subject suspected of having hepatocellular carcinoma (HCC) or lung cancer for treatment, comprising: (a) contacting treated DNA with a probe that hybridizes under high stringency conditions to a target sequence of a gene selected from Tables 2, 6, 7, 9, or 10 to generate an amplified product, wherein the treated DNA is processed from a biological sample obtained from the subject; (b) analyzing the amplified product to generate a methylation profile of the gene; (c) applying the methylation profile to a model relating methylation profiles of genes from the gene panel to the presence to HCC or lung cancer; (d) evaluating an output from the model to determine whether the subject has HC or lung cancer; and (e) administering an effective amount of a therapeutic agent to the subject if the subject is determined to have HCC or lung cancer.

In certain embodiments, disclosed herein is a method of determining the prognosis of a subject having hepatocellular carcinoma (HCC) or monitoring the progression of HCC in the subject, comprising: (a) processing a biological sample obtained from the subject with a deaminating agent to generate treated DNA comprising deaminated nucleotides; (b) generating a methylation profile comprising one or more genes selected from SOCS2, EPSTI1, TIA1, Chromosome 4, Chromosome 6, ZNF323, FOXP4, and GRHL2 from the treated DNA; (c) obtaining a methylation score based on the methylation profile of the one or more genes; and (d) based on the methylation score, initiate a first treatment, decrease a dosage of a first therapeutic agent if the subject has experienced a remission, initiate a second treatment if the subject has experienced a relapse, or switch to a second therapeutic agent if the subject becomes refractory to the first therapeutic agent.

In certain embodiments, disclosed herein is a method of determining the prognosis of a subject having lung cancer or monitoring the progression of lung cancer in the subject, comprising: (a) processing a biological sample obtained from the subject with a deaminating agent to generate treated DNA comprising deaminated nucleotides; (b) generating a methylation profile comprising one or more genes selected from NPBWR1, Chromosome 2, AAK1, SIM1, C10orf46, C17orf101, DEPDC5, ZNF323, GABRA2, PLAC8, and ADRA2B from the treated DNA; (c) obtaining a methylation score based on the methylation profile of the one or more genes; and (d) based on the methylation score, initiate a first treatment, decrease a dosage of a first therapeutic agent if the subject has experienced a remission, initiate a second treatment if the subject has experienced a relapse, or switch to a second therapeutic agent if the subject becomes refractory to the first therapeutic agent.

In certain embodiments, disclosed herein is a kit comprising a set of nucleic acid probes that hybridizes to target sequences of SOCS2, EPSTI1, TIA1, Chromosome 4, Chromosome 6, ZNF323, FOXP4, GRHL2, NPBWR1, Chromosome 2, AAK1, SIM1, C10orf46, C17orf101, DEPDC5, ZNF323, GABRA2, PLAC8, and ADRA2B.

In certain embodiments, disclosed herein is a kit comprising a set of nucleic acid probes that hybridizes to one or more genes selected from Tables 2, 6, 7, 9, or 10.

In certain embodiments, disclosed herein is a method of selecting a subject suspected of having hepatocellular carcinoma (HCC) for treatment, comprising: (a) contacting treated DNA with a probe that hybridizes under high stringency conditions to a target sequence of a gene selected from a gene panel consisting of BMPR1A, PSD, ARHGAP25, KLF3, PLAC8, ATXN1, Chromosome 6:170, Chromosome 6:3, ATAD2 and Chromosome 8:20 to generate an amplified product, wherein the treated DNA is processed from a biological sample obtained from the subject; (b) analyzing the amplified product to generate a methylation profile of the gene; (c) applying the methylation profile to a model relating methylation profiles of genes from the gene panel to the presence to HCC; (d) evaluating an output from the model to determine whether the subject has HCC; and (e) administering an effective amount of a therapeutic agent to the subject if the subject is determined to have HCC.

In certain embodiments, disclosed herein is a method of selecting a subject suspected of having hepatocellular carcinoma (HCC) for treatment, comprising: (a) contacting treated DNA with a plurality of probes to generate amplified products, wherein each probe hybridizes under high stringency conditions to a target sequence of a gene selected from a gene panel consisting of BMPR1A, PSD, ARHGAP25, KLF3, PLAC8, ATXN1, Chromosome 6:170, Chromosome 6:3, ATAD2, and Chromosome 8:20, and each probe is different, and wherein the treated DNA is processed from a biological sample obtained from the subject; (b) analyzing the amplified products to generate a methylation profile of the genes from the gene panel; (c) applying the methylation profile to a model relating methylation profiles of genes from the gene panel to the presence to HCC; (d) evaluating an output from the model to determine whether the subject has HCC; and (e) administering an effective amount of a therapeutic agent to the subject if the subject is determined to have HCC.

In certain embodiments, disclosed herein is a method of determining the prognosis of a subject having hepatocellular carcinoma (HCC) or monitoring the progression of HCC in the subject, comprising: (a) processing a biological sample obtained from the subject with a deaminating agent to generate treated DNA comprising deaminated nucleotides; (b) generating a methylation profile comprising one or more genes selected from SH3PXD2A, C11orf9, PPFIA1, Chromosome 17:78, SERPINB5, NOTCH3, GRHL2, and TMEM8B from the treated DNA; (c) obtaining a methylation score based on the methylation profile of the one or more genes; and (d) based on the methylation score, initiate a first treatment, decrease a dosage of a first therapeutic agent if the subject has experienced a remission, initiate a second treatment if the subject has experienced a relapse, or switch to a second therapeutic agent if the subject becomes refractory to the first therapeutic agent.

In certain embodiments, disclosed herein is a method of detecting the methylation status of one or more genes of a gene panel in a subject, comprising: (a) processing a biological sample obtained from the subject with a deaminating agent to generate treated DNA comprising deaminated nucleotides; and (b) detecting the methylation status in a gene selected from the gene panel consisting of BMPR1A, PSD, ARHGAP25, KLF3, PLAC8, ATXN1, Chromosome 6:170, Chromosome 6:3, ATAD2, and Chromosome 8:20 by contacting the treated DNA with a probe that hybridizes under high stringency conditions to a target sequence of the gene to generate an amplified product; and analyzing the amplified product to determine the methylation status of the gene.

In certain embodiments, disclosed herein is a method of detecting the methylation status of one or more genes of a gene panel in a subject, comprising: (a) processing a biological sample obtained from the subject with a deaminating agent to generate treated DNA comprising deaminated nucleotides; and (b) detecting the methylation status in a gene selected from the gene panel consisting of SH3PXD2A, C11orf9, PPFIA1, Chromosome 17:78, SERPINB5, NOTCH3, GRHL2, and TMEM8B by contacting the treated DNA with a probe that hybridizes under high stringency conditions to a target sequence of the gene to generate an amplified product; and analyzing the amplified product to determine the methylation status in the gene.

In certain embodiments, disclosed herein is a kit comprising a set of nucleic acid probes that hybridizes to target sequences of BMPR1A, PSD, ARHGAP25, KLF3, PLAC8, ATXN1, Chromosome 6:170, Chromosome 6:3, ATAD2, Chromosome 8:20, SH3PXD2A, C11orf9, PPFIA1, Chromosome 17:78, SERPINB5, NOTCH3, GRHL2, and TMEM8B.

BRIEF DESCRIPTION OF THE DRAWINGS

Various aspects of the disclosure are set forth with particularity in the appended claims. The file of this patent contains at least one drawing/photograph executed in color. Copies of this patent with color drawing(s)/photograph(s) will be provided by the Office upon request and payment of the necessary fee. A better understanding of the features and advantages of the present disclosure will be obtained by reference to the following detailed description that sets forth illustrative embodiments, in which the principles of the disclosure are utilized, and the accompanying drawings of which:

FIG. 2A shows receiver operating characteristic (ROC) curves and the associated Area Under Curves (AUCs) of the diagnostic prediction model (cd-score) using cfDNA methylation analysis in the validation cohort.

FIG. 2B illustrates a box plot of composite scores used to classify normal, LUNC or HCC patients. The figure represents data from the validation cohort with scores derived from the multiclass classifier.

FIGS. 2C-FIG. 2D show unsupervised hierarchical clustering of methylation markers differentially methylated between cancer (HCC and LUNC) and normal (FIG. 2C) and between HCC and LUNC (FIG. 2D). Each row represents an individual patient and each column represents a CpG marker.

FIG. 3A shows that the methylation profiling differentiates HCC from high risk liver disease patients or normal controls. High risk liver diseases were defined as hepatitis, liver cirrhosis and fatty liver disease. FIG. 3B shows serum AFP differentiates HCC from high risk liver disease patients or normal controls. FIG. 3C shows methylation profiling differentiates LUNC from patients who smoke and normal controls.

FIG. 4A-FIG. 4L show cfDNA methylation analysis could predict tumor burden, staging, and treatment response using a composite diagnosis score in LUNC and HCC patients. (FIGS. 4A, 4E) cfDNA methylation analysis composite score (cd-score) in patients with and without detectable tumor burden; (FIGS. 4B, 4F) cd-score of patients with stage I/II and stage III/IV disease; (FIGS. 4C,4G) cd-score in patients before surgery, after surgery, and with recurrence; (FIGS. 4D, 4H) cd-score in patients before treatment, with treatment response, and with worsening progression; (FIG. 4I) The ROC curve and the AUC of cd-score and AFP for HCC diagnosis in the entire HCC cohort; (FIG. 4J) AFP in patients with stage I/II and stage III/IV HCC; (FIG. 4K) AFP in HCC patients before surgery, after surgery, and with recurrence; (FIG. 4L) AFP in HCC patients before treatment, with treatment response, and with worsening progression. Recurrence was defined as tumor initially disappeared after treatment/surgery but recurred after a defined period. Progression was defined as worsening disease despite treatment/surgery.

(FIG. 5A) Overall survival curves of LUNC patients with low or high risk of death, according to the combined prognosis score (cp-score) in the validation cohort. (FIG. 5B) Overall survival curves of HCC patients with low or high risk of death, according to the combined prognosis score (cp-score) in the validation dataset. (FIG. 5C) Survival curves of LUNC patients with stage I/II and stage III/IV in the validation cohort. (FIG. 5D) Survival curves of patients with stage I/II and stage III/IV HCC in the validation cohort. (FIGS. 5E, 5F) The ROC for 12 months survival predicted by cp-score, stage, and cp-score combined with stage of LUNC (FIG. 5E) and HCC (FIG. 5F) in the validation cohort.

FIG. 7A shows the genomic neighborhood of the BCM displayed within UCSC genome browser (genome.ucsc.edu. Pearson correlation track showed correlation data by summing r values for a marker within a BCM. Cg marker names below the Pearson correlation graph (cg14999168, cg14088196, cg25574765) were methylation markers from TCGA. Gene name and common SNPs were also listed. FIG. 7B shows a not-to-scale representation of a set of analyzed cg markers belonging to two BCMs in this region. Boundaries between blocks are indicated by a black rectangle, whereas red squares indicate correlated methylation (r>0.5) between two nearby markers. Correlation between any two markers is represented by a square at the intersection of (virtual) perpendicular lines originating from these two markers. White color indicates no significant correlation. 10 newly identified methylation markers in the left MCB anchored by marker cg14999168 or 11 newly identified methylation markers in the right MCB anchored by cg14088196/cg 25574765 were highly consistent and correlated among HCC ctDNA, normal cfDNA, and HCC tissue DNA. Using markers within the same MCB can significantly enhanced allele calling accuracy. Vertical lines at the bottom of panel b were genomic coordinates of boundaries of two MCBs.

FIG. 10A shows summary graphs of change in methylation value comparing patients after surgery, with clinical response (Partial Remission (PR) or Stable Disease (SD), or with disease progression/recurrent (PD). FIG. 10B shows methylation value trends in individual patients after complete surgical resection, with treatment response, and with disease progression. Delta methylation rate denotes the methylation value difference before treatment and after treatment. PRE: pre-treatment; POST: after-treatment.

(FIG. 14A) Receiver operating characteristic (ROC) curves and the associated Area Under Curves (AUCs) of the diagnostic prediction model (cd-score) using cfDNA methylation analysis in the validation cohort. (FIG. 14B) Box plot of composite scores used to classify normal and cancer patients (left), and LUNC and HCC patients (right). (FIG. 14C-FIG. 14D) Unsupervised hierarchical clustering of methylation markers differentially methylated between cancer (HCC and LUNC) and normal (FIG. 14C) and between HCC and LUNC (FIG. 14D). Each row represents an individual patient and each column represents a MCB marker.

(FIG. 15A) methylation profiling differentiates HCC from high risk liver disease patients or normal controls. High risk liver diseases were defined as hepatitis, liver cirrhosis and fatty liver disease. (FIG. 15B) Serum AFP differentiates HCC from high risk liver disease patients or normal controls. (FIG. 15C) methylation profiling differentiates LUNC from patients who smoke and normal controls. (FIG. 15D) Serum CEA differentiates LUNC from high risk (smoking) patients.

(FIG. 16R) The ROC curve and the AUC of cd-score and AFP for HCC diagnosis in the entire HCC cohort.

FIG. 17A-FIG. 17F illustrates prognostic prediction in HCC and LUNC survival based on cfDNA methylation profilingOverall survival curves of HCC patients with low or high risk of death, according to the combined prognosis score (cp-score) in the validation cohort (FIG. 17A). Overall survival curves of LUNC patients with low or high risk of death, according to the combined prognosis score (cp-score) in the validation dataset (FIG. 17B). Survival curves of HCC patients with stage I/II and stage III/IV in the validation cohort (FIG. 17C). Survival curves of patients with stage I/II and stage III/IV LUNC in the validation cohort (FIG. 17D). FIG. 17E and FIG. 17F illustrate the ROC for 12 months survival predicted by cp-score, CEA, AFP, stage, and cp-score combined with stage of HCC (FIG. 17E) and LUNC (FIG. 17F) in the validation cohort.

FIG. 27A-FIG. 27H illustrates cfDNA methylation analysis for diagnosis of HCC. FIG. 27A shows heatmap of methylation of 28 pairs of matched HCC tumor DNA and plasma cfDNA, with a mean methylation value threshold of 0.1 as a cutoff. FIG. 27B shows the methylation values and standard deviations often diagnostic markers in normal blood, HCC tumor DNA, and HCC patient cfDNA. FIG. 27C shows the confusion table of binary results of the diagnostic prediction model in the training dataset and FIG. 27D shows the confusion table of binary results of the diagnostic prediction model in the validation dataset. FIG. 27E and FIG. 27F show ROC of the diagnostic prediction model with methylation markers in the training (FIG. 27E) and validation datasets (FIG. 27F). FIG. 27G and FIG. 27H show unsupervised hierarchical clustering often methylation markers selected for use in the diagnostic prediction model in the training (FIG. 27G) and validation datasets (FIG. 27H).

FIG. 28A and FIG. 28B shows the combined diagnosis score (cd-score) (FIG. 28A) and AFP (FIG. 28B) in healthy controls, individuals with liver diseases (HBV/HCV infection, cirrhosis, and fatty liver) and HCC patients. FIG. 28C shows the cd-score in normal controls and HCC patients with and without detectable tumor burden. FIG. 28D shows the cd-score in normal controls, HCC patients before treatment, with treatment response, and with progression. FIG. 28E shows the cd-score in normal controls and HCC patients before surgery, after surgery, and with recurrence. FIG. 28F shows the cd-score in normal controls and HCC patients from stage I-IV. FIG. 28G illustrates the ROC of cd-score and AFP for HCC diagnosis in whole HCC cohort. FIG. 28H and FIG. 28I show the cd-score (FIG. 28H) and AFP (FIG. 28I) in HCC patients with initial diagnosis (before surgery or other treatment), with treatment response, with progression, and with recurrence. FIG. 28J and FIG. 28K show the cd-score (FIG. 28J) and AFP (FIG. 28K) in HCC patients from stages I-IV.

FIG. 29A-FIG. 29G show the cfDNA methylation analysis for prognostic prediction HCC survival. FIG. 29A and FIG. 29B show the overall survival curves of HCC patients with low or high risk of death at 6 months, according to the combined prognosis score (cp-score) in the training (FIG. 29A) and validation datasets (FIG. 29B). FIG. 29C and FIG. 29D show the survival curves of HCC patients with stage I/II and stage III/IV in the training (FIG. 29C) and validation datasets (FIG. 29D). FIG. 29E and FIG. 29F show the ROC for the cp-score, stage, and cp-score combined with stage in the training (FIG. 29E) and validation datasets (FIG. 29F). FIG. 29G shows the survival curves of HCC patients with combinations of cp-score risk and stage in the whole HCC cohort.

FIG. 31A shows a genomic neighborhood of the BCM displayed within UCSC genome browser (Pearson correlation track showed correlation data by summing r values for a marker within a BCM. Cg marker names below the Pearson correlation graph (cg14999168, cg14088196, cg25574765) were methylation markers from TCGA. Gene name and common SNPs were also listed. FIG. 31B shows a not-to-scale representation of a set of analyzed cg markers belonging to two BCMs in this region. Boundaries between blocks are indicated by a black rectangle, whereas red squares indicate correlated methylation (r>0.5) between two nearby markers. Correlation between any two markers is represented by a square at the intersection of (virtual) perpendicular lines originating from these two markers. White color indicates no significant correlation. 10 newly identified methylation markers in the left MCB anchored by marker cg14999168 or 11 newly identified methylation markers in the right MCB anchored by cg14088196/cg 25574765 were highly consistent and correlated among HCC ctDNA, normal cfDNA, and HCC tissue DNA. Using markers within the same MCB can significantly enhanced allele calling accuracy. Vertical lines at the bottom of panel b were genomic coordinates of boundaries of two MCBs.

FIG. 32A shows a change in cd-score comparing patients after surgery, with clinical response, and with disease progression (***p<0.001). FIG. 32B shows cd-score trends in individual patients after complete surgical resection with treatment response, and with disease progression. PRE: pre-treatment; POST: after-treatment.

FIG. 34A shows heatmap of methylation of 28 pairs of matched HCC tumor DNA and plasma cfDNA, with a mean methylation value threshold of 0.1 as a cutoff. FIG. 34B shows the methylation values and standard deviations often diagnostic markers in normal plasma, HCC tumor DNA, and HCC patient cfDNA.

FIG. 38A-FIG. 38C show mixing experiment to measure cfDNA fractions from tumor tissue genomic DNA (gDNA). FIG. 38A shows digital PCR (ddPCR) results. Upper panel, each blue dot represents a single PCR reaction and one methylated DNA molecule. Lower panel, each green dot represents a single PCR reaction and one unmethylated DNA molecule. A01 to A08 denoted a mixing experiment (A01, 100% normal cfDNA, 0% HCC gDNA; A02, 90% normal cfDNA, 10% HCC gDNA; A04, 70% normal cfDNA, 30% HCC gDNA; A07, 40% normal cfDNA, 60% HCC gDNA; A08, 0% normal cfDNA, 100% HCC gDNA. See b and c for a summary of the results. FIG. 38B shows mixing experiment results with different fraction of normal cfDNA and HCC (gDNA). FIG. 38C shows illustration of final methylation values of HCC cfDNA as a product of mixing normal cfDNA and pure HCC gDNA (ca_gDNA). Each vertical line represents a mixing experiment (from left to right, A01, A02, A04, A07, A08). Green dots and bars corresponding to the left Y axis (Ch1) represent mean values and standard error (S.E.) of unmethylated values; Blue dots and bars corresponding to the right Y axis (Ch2) represent mean values and S.E. of methylated values. The X axis denotes varying concentrations of normal cfDNA and HCC gDNA (see FIG. 38A for details).

FIG. 39A shows 11±4.7 ng cfDNA per 1 mL of normal plasma and 22±7.7 ng cfDNA per 1 mL of HCC plasma. The data were shown as mean±standard deviation (X±SD). P<0.001 (student t-test). FIG. 39B illustrates a plot demonstrating a linear relationship between amount of DNA and total copy numbers by digital droplet PCR (methylated plus unmethylated) (P<0.001). FIG. 39C shows comparison of cfDNA yields by different commercial extraction kits. Elitehealth and Qiagen kits gave higher and comparable yields (No significant difference in yield between Elitehealth and Qiagen, P>0.05; there was significant difference in yield between EliteHealth versus Thermo Fisher, P<0.05, or between Qiagen versus Thermo Fisher, P<0.05).

DETAILED DESCRIPTION OF THE DISCLOSURE

Figure 1A:
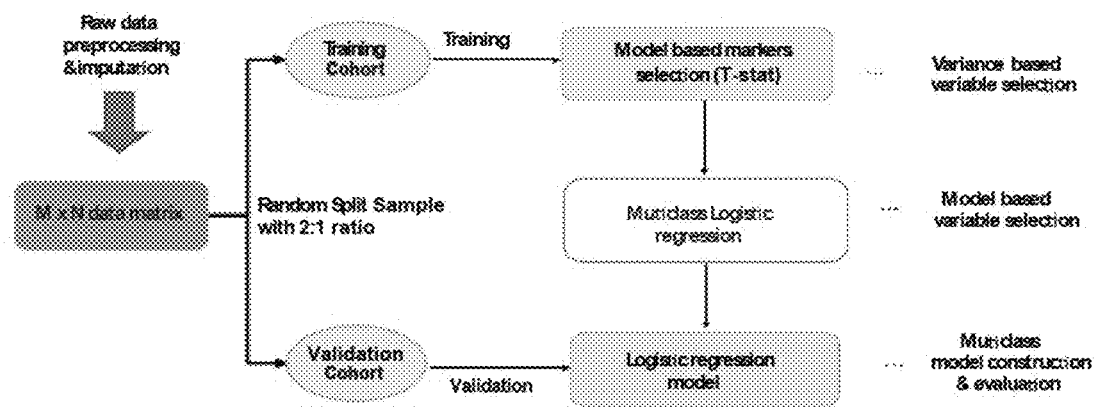
FIG. 1A-FIG. 1B illustrate exemplary workflows for building the diagnostic (FIG. 1A) and prognostic (FIG. 1B) models.

Cancer is characterized by an abnormal growth of a cell caused by one or more mutations or modifications of a gene leading to dysregulated balance of cell proliferation and cell death. DNA methylation silences expression of tumor suppression genes, and presents itself as one of the first neoplastic changes. Methylation patterns found in neoplastic tissue and plasma demonstrate homogeneity, and in some instances are utilized as a sensitive diagnostic marker. For example, cMethDNA assay has been shown in one study to be about 91% sensitive and about 96% specific when used to diagnose metastatic breast cancer. In another study, circulating tumor DNA (ctDNA) was about 87.2% sensitive and about 99.2% specific when it was used to identify KRAS gene mutation in a large cohort of patients with metastatic colon cancer (Bettegowda et al., Detection of Circulating Tumor DNA in Early- and Late-Stage Human Malignancies. Sci. Transl. Med, 6(224):ra24. 2014). The same study further demonstrated that ctDNA is detectable in >75% of patients with advanced pancreatic, ovarian, colorectal, bladder, gastroesophageal, breast, melanoma, hepatocellular, and head and neck cancers (Bettegowda et al).

Additional studies have demonstrated that CpG methylation pattern correlates with neoplastic progression. For example, in one study of breast cancer methylation patterns, P16 hypermethylation has been found to correlate with early stage breast cancer, while TIMP3 promoter hypermethylation has been correlated with late stage breast cancer. In addition, BMP6, CST6 and TIMP3 promoter hypermethylation have been shown to associate with metastasis into lymph nodes in breast cancer.

In some embodiments, DNA methylation profiling provides higher clinical sensitivity and dynamic range compared to somatic mutation analysis for cancer detection. In other instances, altered DNA methylation signature has been shown to correlate with the prognosis of treatment response for certain cancers. For example, one study illustrated that in a group of patients with advanced rectal cancer, ten differentially methylated regions were used to predict patients' prognosis. Likewise, RASSF1A DNA methylation measurement in serum was used to predict a poor outcome in patients undergoing adjuvant therapy in breast cancer patients in a different study. In addition, SRBC gene hypermethylation was associated with poor outcome in patients with colorectal cancer treated with oxaliplatin in a different study. Another study has demonstrated that ESR1 gene methylation correlate with clinical response in breast cancer patients receiving tamoxifen. Additionally, ARHI gene promoter hypermethylation was shown to be a predictor of long-term survival in breast cancer patients not treated with tamoxifen.

In some embodiments, disclosed herein are methods and kits of diagnosing lung cancer and hepatocellular carcinoma (HCC) based on DNA methylation profiling. In some instances, provided herein are methods and kits of distinguishing between lung cancer and HCC based on the DNA methylation profiling. In other instances, provided herein are methods and kits of identifying a subject has having lung cancer or HCC based on the DNA methylation profiling. In additional instances, provided herein are methods and kits of determining the prognosis of a subject having lung cancer or HCC and determining the progression of lung cancer or HCC in a subject based on the DNA methylation profilings.

Methods of Use

Methods of Diagnosis of a Subject

Disclosed herein, in certain embodiments, are methods of diagnosing hepatocellular carcinoma (HCC) and selecting subjects suspected of having liver cancer for treatment. In some instances, the methods comprise utilizing one or more biomarkers described herein. In some instances, a biomarker comprises a cytosine methylation site. In some instances, cytosine methylation comprises 5-methylcytosine (5-mCyt) and 5-hydroxymethylcytosine. In some cases, a cytosine methylation site occurs in a CpG dinucleotide motif. In other cases, a cytosine methylation site occurs in a CHG or CHH motif, in which H is adenine, cytosine or thymine. In some instances, one or more CpG dinucleotide motif or CpG site forms a CpG island, a short DNA sequence rich in CpG dinucleotide. In some instances, CpG islands are typically, but not always, between about 0.2 to about 1 kb in length. In some instances, a biomarker comprises a CpG island.

In some embodiments, disclosed herein is a method of selecting a subject suspected of having hepatocellular carcinoma (HCC) or lung cancer for treatment, comprising (a) contacting treated DNA with a probe that hybridizes under high stringency conditions to a target sequence of a gene selected from Tables 2, 6, 7, 9, or 10 to generate an amplified product, wherein the treated DNA is processed from a biological sample obtained from the subject; (b) analyzing the amplified product to generate a methylation profile of the gene; (c) applying the methylation profile to a model relating methylation profiles of genes from the gene panel to the presence to HCC or lung cancer; (d) evaluating an output from the model to determine whether the subject has HCC or lung cancer; and (e) administering an effective amount of a therapeutic agent to the subject if the subject is determined to have HCC or lung cancer.

In some embodiments, one or more genes in a gene panel described herein further comprises a methylation correlated block (MCB). In some cases, a MCB comprises about 2 to about 30, about 2 to about 25, about 2 to about 20, about 2 to about 15, about 2 to about 10, about 2 to about 8, or about 2 to about 5 genes. In some instances, a MCB comprises about 2, 3, 4, 5, 6, 7, 8, 9, 10, 11, 12, 13, 14, 15, 16, 17, 18, 19, 20, 21, 22, 23, 24, 25, 30, or more genes.

In some instances, MCB comprises one or more genes selected from Tables 2, 3, 6, 7, 9, or 10. In some instances, MCB comprises one or more genes selected from Table 2. In some instances, MCB comprises one or more genes selected from Table 3. In some instances, MCB comprises one or more genes selected from Table 6. In some instances, MCB comprises one or more genes selected from Table 7. In some instances, MCB comprises one or more genes selected from Table 9. In some instances, MCB comprises one or more genes selected from Table 10.

In some instances, MCB comprises one or more genes selected from SOCS2, EPSTI1, TIA1, Chromosome 4, Chromosome 6, ZNF323, FOXP4, GRHL2, NPBWR1, Chromosome 2, AAK1, SIM1, C10orf46, C17orf101, DEPDC5, ZNF323, GABRA2, PLAC8, and ADRA2B. In some instances, MCB comprises one or more genes selected from SOCS2, EPSTI1, TIA1, Chromosome 4, Chromosome 6, ZNF323, FOXP4, and GRHL2. In some instances, MCB comprises one or more genes selected from NPBWR1, Chromosome 2, AAK1, SIM1, C10orf46, C17orf101, DEPDC5, ZNF323, GABRA2, PLAC8, and ADRA2B. In some instances, MCB comprises SOCS2. In some instances, MCB comprises EPSTI1. In some instances, MCB comprises TIA1. In some instances, MCB comprises Chromosome 4. In some instances, MCB comprises Chromosome 6. In some instances, MCB comprises ZNF323. In some instances, MCB comprises FOXP4. In some instances, MCB comprises NPBWR1. In some instances, MCB comprises GRHL2. In some instances, MCB comprises Chromosome 2. In some instances, MCB comprises AAK1. In some instances, MCB comprises SIM1. In some instances, MCB comprises C10orf46. In some instances, MCB comprises C17orf101. In some instances, MCB comprises DEPDC5. In some instances, MCB comprises ZNF323. In some instances, MCB comprises GABRA2. In some instances, MCB comprises PLAC8. In some instances, MCB comprises ADRA2B.

In some instances, the method further comprises contacting the treated DNA with at least an additional probe that hybridizes under high stringency conditions to a target sequence of an additional gene selected from the gene panel to generated an additional amplified product, and analyze the additional amplified product to generate a methylation profile of the additional gene, thereby determining the presence of HCC or lung cancer in the subject.

In some cases, the biological sample is treated with a deaminating agent to generated the treated DNA.

In some cases, the model comprises methylation profiles of genes from the gene panel generated from an HCC positive sample or a lung cancer positive sample. In some instances, the HCC positive sample comprises cells from a metastatic HCC. In some cases, the lung cancer positive sample comprises cells from metastatic lung cancer.

In some cases, the model further comprises methylation profiles of genes from the gene panel generated from a normal sample.

In some cases, the model is developed based on the methylation profiles of biomarkers from Tables 3, 6 or 7.

In some cases, the model is developed based on the methylation profiles of biomarkers from Tables 9 or 10.

In some cases, the model is developed using an algorithm selected from one or more of the following: a principal component analysis, a logistic regression analysis, a nearest neighbor analysis, a support vector machine, and a neural network model.

In some cases, the method further comprises distinguishing between HCC and lung cancer.

Hepatocellular carcinoma (HCC or malignant hepatoma), in some instances, is the most common type of liver cancer. In some cases, HCC is the result of a viral hepatitis infection (e.g., by either Hepatitis B or C), metabolic toxins (e.g., alcohol or aflatoxin), non-alcoholic fatty liver disease (NASH), hemochromatosis, or alpha 1-antitrypsin deficiency.

In some embodiments, HCC is further classified by staging. In some instances, the staging takes into account tumor size, tumor number, presence of vascular invasion and extrahepatic spread, liver function (levels of serum bilirubin and albumin, presence of ascites and portal hypertension) and health of the patient. In some cases, the staging is the Barcelona Clinical Liver Cancer (BCLC) staging classification. In some cases, the staging of HCC comprises Stage I, Stage II, Stage III and Stage IV.

In some instances, one or more markers described herein is utilized to diagnose a subject as having HCC. In some cases, HCC is a metastized HCC. In some instances, one or more markers described herein is utilized to distinguish between HCC and lung cancer in a subject.

In some embodiments, a lung cancer is any type of lung cancer. In some instances, a lung cancer comprises non-small cell lung cancer (NSCLC), small cell lung cancer (SCLC), bronchial carcinoids or mesothelioma. In some instances, non-small cell lung cancer comprises adenocarcinoma, squamous cell carcinoma, large cell carcinoma or large cell neuroendocrine tumors. In some cases, the lung cancer is a metastized lung cancer. In other cases, the lung cancer is a relapsed or refractory lung cancer.

In some embodiments, a probe comprises a DNA probe, RNA probe, or a combination thereof. In some instances, a probe comprises natural nucleic acid molecules and non-natural nucleic acid molecules. In some cases, a probe comprises a labeled probe, such as for example, fluorescently labeled probe or radioactively labeled probe. In some instances, a probe correlates to a CpG site. In some instances, a probe is utilized in a next generation sequencing reaction to generate a CpG methylation data. In further instances, a probe is used in a solution-based next generation sequencing reaction to generate a CpG methylation data. In some cases, a probe comprises a molecular beacon probe, a TaqMan probe, locked nucleic acid probe, a padlock probe, or Scorpion probe. In some cases, a probe comprises a padlock probe.

In some instances, the treatment comprises transcatheter arterial chemoembolization, radiofrequency ablation, or brachytherapy.

In some instances, the treatment comprises a chemotherapeutic agent or an agent for a targeted therapy. In some cases, the chemotherapeutic agent comprises cisplatin, doxorubicin, fluoropyrimidine, gemcitabine, irinotecan, mitoxantrone, oxaliplatin, thalidomide, or a combination thereof. In some cases, the agent for the targeted therapy comprises axitinib, bevacizumab, cetuximab, erlotinib, ramucirumab, regorafenib, sorafenib, sunitinib, a thymidine kinase (TK) inhibitor, or a combination thereof.

In some embodiments, the treatment comprises surgery. In some cases, surgery comprises curative resection. In other cases, surgery comprises liver transplantation.

In some embodiments, the biological sample comprises a blood sample.

In some cases, the biological sample comprises a tissue biopsy sample.

In some cases, the biological sample comprises circulating tumor cells.

In some instances, the subject is a human.

HCC Gene Panel

In some embodiments, disclosed herein is a method of selecting a subject method of selecting a subject suspected of having hepatocellular carcinoma (HCC) for treatment, comprising: (a) contacting treated DNA with a probe that hybridizes under high stringency conditions to a target sequence of a gene selected from a gene panel consisting of gene selected from a gene panel consisting of bone morphogenetic protein receptor type 1A (BMPR1A), Pleckstrin Homology and SEC7 domain-containing protein 1 (PSD), Rho GTPase activating protein 25 (ARHGAP25), Kruppel like factor 3 (KLF3), placenta specific 8 (PLAC8), ataxin 1 (ATXN1), Chromosome 6:170, Chromosome 6:3, ATPase family AAA domain-containing protein 2 (ATAD2), and Chromosome 8:20 to generate an amplified product, wherein the treated DNA is processed from a biological sample obtained from the subject; (b) analyzing the amplified product to generate a methylation profile of the gene; (c) applying the methylation profile to a model relating methylation profiles of genes from the gene panel to the presence to HCC; (d) evaluating an output from the model to determine whether the subject has HCC; and (e) administering an effective amount of a therapeutic agent to the subject if the subject is determined to have HCC.

In some embodiments, also disclosed herein is a method of selecting a subject suspected of having hepatocellular carcinoma (HCC) for treatment, comprising: (a) contacting treated DNA with a plurality of probes to generate amplified products, wherein each probe hybridizes under high stringency conditions to a target sequence of a gene selected from a gene panel consisting of BMPR1A, PSD, ARHGAP25, KLF3, PLAC8, ATXN1, Chromosome 6:170, Chromosome 6:3, ATAD2, and Chromosome 8:20, and each probe is different, and wherein the treated DNA is processed from a biological sample obtained from the subject; (b) analyzing the amplified products to generate a methylation profile of the genes from the gene panel; (c) applying the methylation profile to a model relating methylation profiles of genes from the gene panel to the presence to HCC; (d) evaluating an output from the model to determine whether the subject has HCC; and (e) administering an effective amount of a therapeutic agent to the subject if the subject is determined to have HCC.

In additional embodiments, disclosed herein is a method of determining the prognosis of a subject having hepatocellular carcinoma (HCC) or monitoring the progression of HCC in the subject, comprising: (a) processing a biological sample obtained from the subject with a deaminating agent to generate treated DNA comprising deaminated nucleotides; (b) generating a methylation profile comprising one or more genes selected from SH3PXD2A, C11orf9, PPFIA1, Chromosome 17:78, SERPINB5, NOTCH3, GRHL2, and TMEM8B from the treated DNA; (c) obtaining a methylation score based on the methylation profile of the one or more genes; and (d) based on the methylation score, initiate a first treatment, decrease a dosage of a first therapeutic agent if the subject has experienced a remission, initiate a second treatment if the subject has experienced a relapse, or switch to a second therapeutic agent if the subject becomes refractory to the first therapeutic agent.

In additional embodiments, disclosed herein is a method of detecting the methylation status of one or more genes of a gene panel in a subject, comprising: (a) processing a biological sample obtained from the subject with a deaminating agent to generate treated DNA comprising deaminated nucleotides; and (b) detecting the methylation status in a gene selected from the gene panel consisting of BMPR1A, PSD, ARHGAP25, KLF3, PLAC8, ATXN1, Chromosome 6:170, Chromosome 6:3, ATAD2, and Chromosome 8:20 by contacting the treated DNA with a probe that hybridizes under high stringency conditions to a target sequence of the gene to generate an amplified product; and analyzing the amplified product to determine the methylation status of the gene.

In some embodiments, one or more genes in the gene panel further comprises a methylation correlated block (MCB). In some cases, a MCB comprises about 2 to about 30, about 2 to about 25, about 2 to about 20, about 2 to about 15, about 2 to about 10, about 2 to about 8, or about 2 to about 5 genes. In some instances, a MCB comprises about 2, 3, 4, 5, 6, 7, 8, 9, 10, 11, 12, 13, 14, 15, 16, 17, 18, 19, 20, 21, 22, 23, 24, 25, 30, or more genes.

In some instances, MCB comprises one or more genes selected from BMPR1A, PSD, ARHGAP25, KLF3, PLAC8, ATXN1, Chromosome 6:170, Chromosome 6:3, ATAD2, Chromosome 8:20, SH3PXD2A, C11orf9, PPFIA1, Chromosome 17:78, SERPINB5, NOTCH3, GRHL2, and TMEM8B. In some instances, a MCB comprises one or more genes selected from BMPR1A, PSD, ARHGAP25, KLF3, PLAC8, ATXN1, Chromosome 6:170, Chromosome 6:3, ATAD2, and Chromosome 8:20. In some instances, a MCB comprises one or more genes selected from SH3PXD2A, C11orf9, PPFIA1, Chromosome 17:78, SERPINB5, NOTCH3, GRHL2, and TMEM8B. In some instances, a MCB comprises BMPR1A. In some instances, a MCB comprises PSD. In some instances, a MCB comprises KLF3. In some instances, a MCB comprises PLAC8. In some instances, a MCB comprises ATXN1. In some instances, a MCB comprises Chromosome 6:170. In some instances, a MCB comprises Chromosome 6:3. In some instances, a MCB comprises ATAD2. In some instances, a MCB comprises Chromosome 8:20. In some instances, a MCB comprises SH3PXD2A. In some instances, a MCB comprises C11orf9. In some instances, a MCB comprises PPFIA1. In some instances, a MCB comprises Chromosome 17:78. In some instances, a MCB comprises ARHGAP25. In some instances, a MCB comprises SERPINB5. In some instances, a MCB comprises NOTCH3. In some instances, a MCB comprises GRHL2. In some instances, a MCB comprises TMEM8B.

In some instances, the method further comprises contacting the treated DNA with at least an additional probe that hybridizes under high stringency conditions to a target sequence of an additional gene selected from the gene panel to generated an additional amplified product, and analyze the additional amplified product to generate a methylation profile of the additional gene, thereby determining the presence of HCC in the subject.

In some cases, the biological sample is treated with a deaminating agent to generated the treated DNA.

In some cases, the model comprises methylation profiles of genes from the gene panel generated from an HCC positive sample. In some instances, the HCC positive sample comprises cells from a metastatic HCC.

In some cases, the model further comprises methylation profiles of genes from the gene panel generated from a normal sample.

In some cases, the model is developed based on the methylation profiles of biomarkers from Table 15 or Table 16.

In some cases, the model is developed using an algorithm selected from one or more of the following: a principal component analysis, a logistic regression analysis, a nearest neighbor analysis, a support vector machine, and a neural network model.

Hepatocellular carcinoma (HCC or malignant hepatoma), in some instances, is the most common type of liver cancer. In some cases, HCC is the result of a viral hepatitis infection (e.g., by either Hepatitis B or C), metabolic toxins (e.g., alcohol or aflatoxin), non-alcoholic fatty liver disease (NASH), hemochromatosis, or alpha 1-antitrypsin deficiency.

In some embodiments, HCC is further classified by staging. In some instances, the staging takes into account tumor size, tumor number, presence of vascular invasion and extrahepatic spread, liver function (levels of serum bilirubin and albumin, presence of ascites and portal hypertension) and health of the patient. In some cases, the staging is the Barcelona Clinical Liver Cancer (BCLC) staging classification. In some cases, the staging of HCC comprises Stage I, Stage II, Stage III and Stage IV.

In some embodiments, one or more biomarkers described herein distinguishes HCC from another type of liver cancer. In some cases, another type of liver cancer comprises cirrhosis of the liver or hepatic steatosis (or fatty liver disease).

In some embodiments, a probe comprises a DNA probe, RNA probe, or a combination thereof. In some instances, a probe comprises natural nucleic acid molecules and non-natural nucleic acid molecules. In some cases, a probe comprises a labeled probe, such as for example, fluorescently labeled probe or radioactively labeled probe. In some instances, a probe correlates to a CpG site. In some instances, a probe is utilized in a next generation sequencing reaction to generate a CpG methylation data. In further instances, a probe is used in a solution-based next generation sequencing reaction to generate a CpG methylation data. In some cases, a probe comprises a molecular beacon probe, a TaqMan probe, locked nucleic acid probe, a padlock probe, or Scorpion probe. In some cases, a probe comprises a padlock probe. In some cases, the probe is a padlock probe.

In some instances, the probe comprises about 80%, 85%, 90%, 95%, or 99% sequence identity to a probe selected from SEQ ID NOs: 1-18. In some instances, the probe comprises about 90%, 91%, 92%, 93%, 94%, 95%, 96%, 97%, 98%, or 99% sequence identity to a probe selected from SEQ ID NOs: 1-18. In some instances, the probe comprises about 90% sequence identity to a probe selected from SEQ ID NOs: 1-18. In some instances, the probe comprises about 91% sequence identity to a probe selected from SEQ ID NOs: 1-18. In some instances, the probe comprises about 92% sequence identity to a probe selected from SEQ ID NOs: 1-18. In some instances, the probe comprises about 93% sequence identity to a probe selected from SEQ ID NOs: 1-18. In some instances, the probe comprises about 94% sequence identity to a probe selected from SEQ ID NOs: 1-18. In some instances, the probe comprises about 95% sequence identity to a probe selected from SEQ ID NOs: 1-18. In some instances, the probe comprises about 96% sequence identity to a probe selected from SEQ ID NOs: 1-18. In some instances, the probe comprises about 97% sequence identity to a probe selected from SEQ ID NOs: 1-18. In some instances, the probe comprises about 98% sequence identity to a probe selected from SEQ ID NOs: 1-18. In some instances, the probe comprises about 99% sequence identity to a probe selected from SEQ ID NOs: 1-18.

In some instances, the probe comprises about 80%, 85%, 90%, 95%, or 99% sequence identity to a probe selected from SEQ ID NOs: 1-10. In some instances, the probe comprises about 90%, 91%, 92%, 93%, 94%, 95%, 96%, 97%, 98%, or 99% sequence identity to a probe selected from SEQ ID NOs: 1-10. In some instances, the probe comprises about 90% sequence identity to a probe selected from SEQ ID NOs: 1-10. In some instances, the probe comprises about 91% sequence identity to a probe selected from SEQ ID NOs: 1-10. In some instances, the probe comprises about 92% sequence identity to a probe selected from SEQ ID NOs: 1-10. In some instances, the probe comprises about 93% sequence identity to a probe selected from SEQ ID NOs: 1-10. In some instances, the probe comprises about 94% sequence identity to a probe selected from SEQ ID NOs: 1-10. In some instances, the probe comprises about 95% sequence identity to a probe selected from SEQ ID NOs: 1-10. In some instances, the probe comprises about 96% sequence identity to a probe selected from SEQ ID NOs: 1-10. In some instances, the probe comprises about 97% sequence identity to a probe selected from SEQ ID NOs: 1-10. In some instances, the probe comprises about 98% sequence identity to a probe selected from SEQ ID NOs: 1-10. In some instances, the probe comprises about 99% sequence identity to a probe selected from SEQ ID NOs: 1-10.

In some instances, the probe comprises about 80%, 85%, 90%, 95%, or 99% sequence identity to a probe selected from SEQ ID NOs: 11-18. In some instances, the probe comprises about 90%, 91%, 92%, 93%, 94%, 95%, 96%, 97%, 98%, or 99% sequence identity to a probe selected from SEQ ID NOs: 11-18. In some instances, the probe comprises about 90% sequence identity to a probe selected from SEQ ID NOs: 11-18. In some instances, the probe comprises about 91% sequence identity to a probe selected from SEQ ID NOs: 11-18. In some instances, the probe comprises about 92% sequence identity to a probe selected from SEQ ID NOs: 11-18. In some instances, the probe comprises about 93% sequence identity to a probe selected from SEQ ID NOs: 11-18. In some instances, the probe comprises about 94% sequence identity to a probe selected from SEQ ID NOs: 11-18. In some instances, the probe comprises about 95% sequence identity to a probe selected from SEQ ID NOs: 11-18. In some instances, the probe comprises about 96% sequence identity to a probe selected from SEQ ID NOs: 11-18. In some instances, the probe comprises about 97% sequence identity to a probe selected from SEQ ID NOs: 11-18. In some instances, the probe comprises about 98% sequence identity to a probe selected from SEQ ID NOs: 11-18. In some instances, the probe comprises about 99% sequence identity to a probe selected from SEQ ID NOs: 11-18.

In some instances, the treatment comprises transcatheter arterial chemoembolization, radiofrequency ablation, or brachytherapy.

In some instances, the treatment comprises a chemotherapeutic agent or an agent for a targeted therapy. In some cases, the chemotherapeutic agent comprises cisplatin, doxorubicin, fluoropyrimidine, gemcitabine, irinotecan, mitoxantrone, oxaliplatin, thalidomide, or a combination thereof. In some cases, the agent for the targeted therapy comprises axitinib, bevacizumab, cetuximab, erlotinib, ramucirumab, regorafenib, sorafenib, sunitinib, a thymidine kinase (TK) inhibitor, or a combination thereof.

In some embodiments, the treatment comprises surgery. In some cases, surgery comprises curative resection. In other cases, surgery comprises liver transplantation.

In some embodiments, the biological sample comprises a blood sample.

In some cases, the biological sample comprises a tissue biopsy sample.

In some cases, the biological sample comprises circulating tumor cells.

In some instances, the subject is a human.

Determining the Prognosis of a Subject or Monitoring the Progression of HCC or Lung Cancer in a Subject In some embodiments, disclosed herein include a method of determining the prognosis of a subject having HCC or lung cancer or monitoring the progression of HCC or lung cancer in a subject. In some embodiments, disclosed herein is a method of determining the prognosis of a subject having hepatocellular carcinoma (HCC) or monitoring the progression of HCC in the subject, comprising: (a) processing a biological sample obtained from the subject with a deaminating agent to generate treated DNA comprising deaminated nucleotides; (b) generating a methylation profile comprising one or more genes selected from suppressor of cytokine signaling 2 (SOCS2), epithelial stromal interaction protein 1 (EPSTI1), TIA1 cytotoxic granule associated RNA binding protein (TIA1), Chromosome 4, chromosome 6, zinc finger and SCAN domain containing 31 (ZNF323), forkhead box P4 (FOXP4), and grainyhead like transcription factor 2 (GRHL2) from the treated DNA; (c) obtaining a methylation score based on the methylation profile of the one or more genes; and (d) based on the methylation score, initiate a first treatment, decrease a dosage of a first therapeutic agent if the subject has experienced a remission, initiate a second treatment if the subject has experienced a relapse, or switch to a second therapeutic agent if the subject becomes refractory to the first therapeutic agent.

In some embodiments, disclosed herein is a method of determining the prognosis of a subject having lung cancer or monitoring the progression of lung cancer in the subject, comprising: (a) processing a biological sample obtained from the subject with a deaminating agent to generate treated DNA comprising deaminated nucleotides; (b) generating a methylation profile comprising one or more genes selected from neuropeptides B/W receptor 1 (NPBWR1), Chromosome 2, AP2 associated kinase 1 (AAK1), single-minded family BHLH transcription factor 1 (SIM1), C10orf46, C17orf101, DEP domain containing 5 (DEPDC5), zinc finger and SCAN domain containing 31 (ZNF323), gamma-aminobutyric acid type A receptor alpha2 subunit (GABRA2), placenta specific 8 (PLAC8), and adrenoceptor alpha 2B (ADRA2B) from the treated DNA; (c) obtaining a methylation score based on the methylation profile of the one or more genes; and (d) based on the methylation score, initiate a first treatment, decrease a dosage of a first therapeutic agent if the subject has experienced a remission, initiate a second treatment if the subject has experienced a relapse, or switch to a second therapeutic agent if the subject becomes refractory to the first therapeutic agent.

In additional embodiments, disclosed herein is a method of determining the prognosis of a subject having hepatocellular carcinoma (HCC) or monitoring the progression of HCC in the subject, comprising: (a) processing a biological sample obtained from the subject with a deaminating agent to generate treated DNA comprising deaminated nucleotides; (b) generating a methylation profile comprising one or more genes selected from SH3 and PX domains 2A (SH3PXD2A), C11orf9, PTPRF interacting protein alpha 1 (PPFIA1), Chromosome 17:78, Serpin family B member 5 (SERPINB5), neurogenic locus Notch homolog protein 3 (NOTCH3), grainyhead like transcription factor 2 (GRHL2), and transmembrane protein 8B (TMEM8B) from the treated DNA; (c) obtaining a methylation score based on the methylation profile of the one or more genes; and (d) based on the methylation score, initiate a first treatment, decrease a dosage of a first therapeutic agent if the subject has experienced a remission, initiate a second treatment if the subject has experienced a relapse, or switch to a second therapeutic agent if the subject becomes refractory to the first therapeutic agent.

In some instances, a methylation score is utilized to determine the prognosis of a subject. In some instances, the methylation score is further refers to herein as a combined prognosis score (cp-score). In some instances, prognosis refers to the prediction of the likelihood of cancer-attributable death or progression, including recurrence, metastatic spread, and drug resistance, of liver cancer. The term "prediction" is used herein to refer to the likelihood that a subject will respond either favorably or unfavorably to a drug or set of drugs, and also the extent of those responses, or that a subject will survive, following chemotherapy for a certain period of time without cancer recurrence and/or following surgery (e.g., removal of the spleen). In some instances, a methylation score is utilized to determine the prognosis of a subject having liver cancer.

In some embodiments, a methylation score (or cp-score) correlates with a "good" prognosis. In some instances, a "good" prognosis refers to the likelihood that a subject will likely respond favorably to a drug or set of drugs, leading to a complete or partial remission of liver cancer or a decrease and/or a stop in the progression of liver cancer. In some instances, a "good" prognosis refers to the survival of a subject of from at least 1 month to at least 90 years. In some instances, a "good" prognosis refers to the survival of a subject in which the survival of the subject upon treatment is from at least 1 month to at least 90 years. In some instances, the survival of a subject further refers to an extended survival rate of a subject receiving a treatment course relative to a subject without receiving the same course of treatment. In some cases, a "good" prognosis refers to an extended survival time of a subject receiving a treatment course relative to a subject without receiving the same course of treatment.

In some instances, a methylation score (or cp-score) correlates to a survival from at least 1 month to at least 90 years. In some instances, a methylation score of from about 1.5 to about 4 is indicative of a survival of at least 2 months, 4 months, 6 months, 8 months, 10 months, 1 year, 1.5 years, 2 years, 3 years, 4 years, 5 years, 10 years, 15 years, 20 years, 30 years, 50 years, or more.

In some embodiments, a methylation score (or cp-score) correlates with a "poor" prognosis. In some instances, a "poor" prognosis refers to the likelihood that a subject will likely respond unfavorably to a drug or set of drugs, leading to a progression of leukemia (e.g., progression to metastatic leukemia) and/or to refractory of one or more therapeutic agents. In some instances, a "poor" prognosis refers to the likelihood that a subject will not respond to a drug or set of drugs, leading to a progression of leukemia. In some instances, a "poor" prognosis refers to the survival of a subject of from less than 5 years to less than 1 month. In some instances, a "poor" prognosis refers to the survival of a subject in which the survival of the subject upon treatment is from less than 5 years to less than 1 month. In some instances, a "poor" prognosis further refers to the likelihood that a subject will develop a refractory leukemia toward one or more drugs.

In some instances, a methylation score (or cp-score) correlates with a survival of from less than 5 years to less than 1 month. In some instances, a methylation score of less than 1.5 is indicative of a survival of less than 5 years, 4 years, 3 years, 2 years, 1.5 years, 1 year, 10 months, 8 months, 6 months, 4 months, or 2 months.

In some embodiments, the methylation score is calculated, e.g., based on model for a survival analysis. In some instances, a survival analysis is a statistic analysis for analyzing the expected duration of time until one or more events of interest happen. In some instances, survival analysis comprises Cox proportional hazards (PH) regression analysis, log-rank test or a product limit estimator. In some instances, the methylation score is calculated based on Cox proportional hazards (PH) regression analysis, log-rank test or product limit estimator. In some instances, the methylation score is calculated based on Cox proportional hazards (PH) regression analysis. In some embodiments, the methylation score is further calculated based on a log-rank test. In some instances, the log-rank test is a hypothesis test to compare the survival distribution of two samples (e.g., a training set and a validation set). In some instances, the log-rank test is also referred to as a Mantel-Cox test or a time-stratified Cochran-Mantel-Haenszel test. In some instances, the methylation score is additionally calculated based on a product limit estimator. A product limit estimator (also known as Kaplan-Meier estimator) is a non-parametric statistic used to estimate the survival function from lifetime data. In some embodiments, the methylation score is initially calculated based on Cox proportional hazards (PH) regression analysis and then reprocessed with a log-rank test.

Detection Methods

In some embodiments, a number of methods are utilized to measure, detect, determine, identify, and characterize the methylation status/level of a gene or a biomarker (e.g., CpG island-containing region/fragment) in identifying a subject as having liver cancer, determining the liver cancer subtype, the prognosis of a subject having liver cancer, and the progression or regression of liver cancer in subject in the presence of a therapeutic agent.

In some instances, the methylation profile is generated from a biological sample isolated from an individual. In some embodiments, the biological sample is a biopsy. In some instances, the biological sample is a tissue sample. In some instances, the biological sample is a tissue biopsy sample. In some instances, the biological sample is a blood sample. In other instances, the biological sample is a cell-free biological sample. In other instances, the biological sample is a circulating tumor DNA sample. In one embodiment, the biological sample is a cell free biological sample containing circulating tumor DNA.

In some embodiments, a biomarker (or an epigenetic marker) is obtained from a liquid sample. In some embodiments, the liquid sample comprises blood and other liquid samples of biological origin (including, but not limited to, peripheral blood, sera, plasma, ascites, urine, cerebrospinal fluid (CSF), sputum, saliva, bone marrow, synovial fluid, aqueous humor, amniotic fluid, cerumen, breast milk, broncheoalveolar lavage fluid, semen, prostatic fluid, cowper's fluid or pre-ejaculatory fluid, female ejaculate, sweat, tears, cyst fluid, pleural and peritoneal fluid, pericardial fluid, ascites, lymph, chyme, chyle, bile, interstitial fluid, menses, pus, sebum, vomit, vaginal secretions/flushing, synovial fluid, mucosal secretion, stool water, pancreatic juice, lavage fluids from sinus cavities, bronchopulmonary aspirates, blastocyl cavity fluid, or umbilical cord blood. In some embodiments, the biological fluid is blood, a blood derivative or a blood fraction, e.g., serum or plasma. In a specific embodiment, a sample comprises a blood sample. In another embodiment, a serum sample is used. In another embodiment, a sample comprises urine. In some embodiments, the liquid sample also encompasses a sample that has been manipulated in any way after their procurement, such as by centrifugation, filtration, precipitation, dialysis, chromatography, treatment with reagents, washed, or enriched for certain cell populations.

In some embodiments, a biomarker (or an epigenetic marker) is obtained from a tissue sample. In some instances, a tissue corresponds to any cell(s). Different types of tissue correspond to different types of cells (e.g., liver, lung, blood, connective tissue, and the like), but also healthy cells vs. tumor cells or to tumor cells at various stages of neoplasia, or to displaced malignant tumor cells. In some embodiments, a tissue sample further encompasses a clinical sample, and also includes cells in culture, cell supernatants, organs, and the like. Samples also comprise fresh-frozen and/or formalin-fixed, paraffin-embedded tissue blocks, such as blocks prepared from clinical or pathological biopsies, prepared for pathological analysis or study by immunohistochemistry.

In some embodiments, a biomarker (or an epigenetic marker) is methylated or unmethylated in a normal sample (e.g., normal or control tissue without disease, or normal or control body fluid, stool, blood, serum, amniotic fluid), most importantly in healthy stool, blood, serum, amniotic fluid or other body fluid. In other embodiments, a biomarker (or an epigenetic marker) is hypomethylated or hypermethylated in a sample from a patient having or at risk of a disease (e.g., one or more indications described herein); for example, at a decreased or increased (respectively) methylation frequency of at least about 50%, at least about 60%, at least about 70%, at least about 75%, at least about 80%, at least about 85%, at least about 90%, at least about 95%, or about 100% in comparison to a normal sample. In one embodiment, a sample is also hypomethylated or hypermethylated in comparison to a previously obtained sample analysis of the same patient having or at risk of a disease (e.g., one or more indications described herein), particularly to compare progression of a disease.

In some embodiments, a methylome comprises a set of epigenetic markers or biomarkers, such as a biomarker described above. In some instances, a methylome that corresponds to the methylome of a tumor of an organism (e.g., a human) is classified as a tumor methylome. In some cases, a tumor methylome is determined using tumor tissue or cell-free (or protein-free) tumor DNA in a biological sample. Other examples of methylomes of interest include the methylomes of organs that contribute DNA into a bodily fluid (e.g. methylomes of tissue such as brain, breast, lung, the prostrate and the kidneys, plasma, etc.).

In some embodiments, a plasma methylome is the methylome determined from the plasma or serum of an animal (e.g., a human). In some instances, the plasma methylome is an example of a cell-free or protein-free methylome since plasma and serum include cell-free DNA. The plasma methylome is also an example of a mixed methylome since it is a mixture of tumor and other methylomes of interest. In some instances, the urine methylome is determined from the urine sample of a subject. In some cases, a cellular methylome corresponds to the methylome determined from cells (e.g., blood cells) of the patient. The methylome of the blood cells is called the blood cell methylome (or blood methylome).

In some embodiments, DNA (e.g., genomic DNA such as extracted genomic DNA or treated genomic DNA) is isolated by any means standard in the art, including the use of commercially available kits. Briefly, wherein the DNA of interest is encapsulated in by a cellular membrane the biological sample is disrupted and lysed by enzymatic, chemical or mechanical means. In some cases, the DNA solution is then cleared of proteins and other contaminants e.g. by digestion with proteinase K. The DNA is then recovered from the solution. In such cases, this is carried out by means of a variety of methods including salting out, organic extraction or binding of the DNA to a solid phase support. In some instances, the choice of method is affected by several factors including time, expense and required quantity of DNA.

Wherein the sample DNA is not enclosed in a membrane (e.g. circulating DNA from a cell free sample such as blood or urine) methods standard in the art for the isolation and/or purification of DNA are optionally employed (See, for example, Bettegowda et al. Detection of Circulating Tumor DNA in Early- and Late-Stage Human Malignancies. Sci. Transl. Med, 6(224): ra24. 2014). Such methods include the use of a protein degenerating reagent e.g. chaotropic salt e.g. guanidine hydrochloride or urea; or a detergent e.g. sodium dodecyl sulphate (SDS), cyanogen bromide. Alternative methods include but are not limited to ethanol precipitation or propanol precipitation, vacuum concentration amongst others by means of a centrifuge. In some cases, the person skilled in the art also make use of devices such as filter devices e.g. ultrafiltration, silica surfaces or membranes, magnetic particles, polystyrol particles, polystyrol surfaces, positively charged surfaces, and positively charged membranes, charged membranes, charged surfaces, charged switch membranes, charged switched surfaces.

In some instances, once the nucleic acids have been extracted, methylation analysis is carried out by any means known in the art. A variety of methylation analysis procedures are known in the art and may be used to practice the methods disclosed herein. These assays allow for determination of the methylation state of one or a plurality of CpG sites within a tissue sample. In addition, these methods may be used for absolute or relative quantification of methylated nucleic acids. Such methylation assays involve, among other techniques, two major steps. The first step is a methylation specific reaction or separation, such as (i) bisulfite treatment, (ii) methylation specific binding, or (iii) methylation specific restriction enzymes. The second major step involves (i) amplification and detection, or (ii) direct detection, by a variety of methods such as (a) PCR (sequence-specific amplification) such as Taqman®, (b) DNA sequencing of untreated and bisulfite-treated DNA, (c) sequencing by ligation of dye-modified probes (including cyclic ligation and cleavage), (d) pyrosequencing, (e) single-molecule sequencing, (f) mass spectroscopy, or (g) Southern blot analysis.

Additionally, restriction enzyme digestion of PCR products amplified from bisulfite-converted DNA may be used, e.g., the method described by Sadri and Hornsby (1996, Nucl. Acids Res. 24:5058-5059), or COBRA (Combined Bisulfite Restriction Analysis) (Xiong and Laird, 1997, Nucleic Acids Res. 25:2532-2534). COBRA analysis is a quantitative methylation assay useful for determining DNA methylation levels at specific gene loci in small amounts of genomic DNA. Briefly, restriction enzyme digestion is used to reveal methylation-dependent sequence differences in PCR products of sodium bisulfite-treated DNA. Methylation-dependent sequence differences are first introduced into the genomic DNA by standard bisulfite treatment according to the procedure described by Frommer et al. (Frommer et al, 1992, Proc. Nat. Acad. Sci. USA, 89, 1827-1831). PCR amplification of the bisulfite converted DNA is then performed using primers specific for the CpG sites of interest, followed by restriction endonuclease digestion, gel electrophoresis, and detection using specific, labeled hybridization probes. Methylation levels in the original DNA sample are represented by the relative amounts of digested and undigested PCR product in a linearly quantitative fashion across a wide spectrum of DNA methylation levels. In addition, this technique can be reliably applied to DNA obtained from micro-dissected paraffin-embedded tissue samples. Typical reagents (e.g., as might be found in a typical COBRA-based kit) for COBRA analysis may include, but are not limited to: PCR primers for specific gene (or methylation-altered DNA sequence or CpG island); restriction enzyme and appropriate buffer; gene-hybridization oligo; control hybridization oligo; kinase labeling kit for oligo probe; and radioactive nucleotides. Additionally, bisulfite conversion reagents may include: DNA denaturation buffer; sulfo nation buffer; DNA recovery reagents or kits (e.g., precipitation, ultrafiltration, affinity column); desulfonation buffer; and DNA recovery components.

In an embodiment, the methylation profile of selected CpG sites is determined using methylation-Specific PCR (MSP). MSP allows for assessing the methylation status of virtually any group of CpG sites within a CpG island, independent of the use of methylation-sensitive restriction enzymes (Herman et al, 1996, Proc. Nat. Acad. Sci. USA, 93, 9821-9826; U.S. Pat. Nos. 5,786,146, 6,017,704, 6,200, 756, 6,265,171 (Herman and Baylin); U.S. Pat. Pub. No. 2010/0144836 (Van Engeland et al); which are hereby incorporated by reference in their entirety). Briefly, DNA is modified by a deaminating agent such as sodium bisulfite to convert unmethylated, but not methylated cytosines to uracil, and subsequently amplified with primers specific for methylated versus unmethylated DNA. In some instances, typical reagents (e.g., as might be found in a typical MSP-based kit) for MSP analysis include, but are not limited to: methylated and unmethylated PCR primers for specific gene (or methylation-altered DNA sequence or CpG island), optimized PCR buffers and deoxynucleotides, and specific probes. One may use quantitative multiplexed methylation specific PCR (QM-PCR), as described by Fackler et al. Fackler et al, 2004, Cancer Res. 64(13) 4442-4452; or Fackler et al, 2006, Clin. Cancer Res. 12(11 Pt 1) 3306-3310.

In an embodiment, the methylation profile of selected CpG sites is determined using MethyLight and/or Heavy Methyl Methods. The MethyLight and Heavy Methyl assays are a high-throughput quantitative methylation assay that utilizes fluorescence-based real-time PCR (Taq Man®) technology that requires no further manipulations after the PCR step (Eads, C. A. et al, 2000, Nucleic Acid Res. 28, e 32; Cottrell et al, 2007, J. Urology 177, 1753, U.S. Pat. No. 6,331,393 (Laird et al), the contents of which are hereby incorporated by reference in their entirety). Briefly, the MethyLight process begins with a mixed sample of genomic DNA that is converted, in a sodium bisulfite reaction, to a mixed pool of methylation-dependent sequence differences according to standard procedures (the bisulfite process converts unmethylated cytosine residues to uracil). Fluorescence-based PCR is then performed either in an "unbiased" (with primers that do not overlap known CpG methylation sites) PCR reaction, or in a "biased" (with PCR primers that overlap known CpG dinucleotides) reaction. In some cases, sequence discrimination occurs either at the level of the amplification process or at the level of the fluorescence detection process, or both. In some cases, the MethyLight assay is used as a quantitative test for methylation patterns in the genomic DNA sample, wherein sequence discrimination occurs at the level of probe hybridization. In this quantitative version, the PCR reaction provides for unbiased amplification in the presence of a fluorescent probe that overlaps a particular putative methylation site. An unbiased control for the amount of input DNA is provided by a reaction in which neither the primers, nor the probe overlie any CpG dinucleotides. Alternatively, a qualitative test for genomic methylation is achieved by probing of the biased PCR pool with either control oligonucleotides that do not "cover" known methylation sites (a fluorescence-based version of the "MSP" technique), or with oligonucleotides covering potential methylation sites. Typical reagents (e.g., as might be found in a typical MethyLight-based kit) for MethyLight analysis may include, but are not limited to: PCR primers for specific gene (or methylation-altered DNA sequence or CpG island); TaqMan® probes; optimized PCR buffers and deoxynucleotides; and Taq polymerase.

Quantitative MethyLight uses bisulfite to convert genomic DNA and the methylated sites are amplified using PCR with methylation independent primers. Detection probes specific for the methylated and unmethylated sites with two different fluorophores provides simultaneous quantitative measurement of the methylation. The Heavy Methyl technique begins with bisulfate conversion of DNA. Next specific blockers prevent the amplification of unmethylated DNA. Methylated genomic DNA does not bind the blockers and their sequences will be amplified. The amplified sequences are detected with a methylation specific probe. (Cottrell et al, 2004, Nuc. Acids Res. 32:e10, the contents of which is hereby incorporated by reference in its entirety).

The Ms-SNuPE technique is a quantitative method for assessing methylation differences at specific CpG sites based on bisulfite treatment of DNA, followed by single-nucleotide primer extension (Gonzalgo and Jones, 1997, Nucleic Acids Res. 25, 2529-2531). Briefly, genomic DNA is reacted with sodium bisulfite to convert unmethylated cytosine to uracil while leaving 5-methylcytosine unchanged. Amplification of the desired target sequence is then performed using PCR primers specific for bisulfite-converted DNA, and the resulting product is isolated and used as a template for methylation analysis at the CpG site(s) of interest. In some cases, small amounts of DNA are analyzed (e.g., micro-dissected pathology sections), and the method avoids utilization of restriction enzymes for determining the methylation status at CpG sites. Typical reagents (e.g., as is found in a typical Ms-SNuPE-based kit) for Ms-SNuPE analysis include, but are not limited to: PCR primers for specific gene (or methylation-altered DNA sequence or CpG island); optimized PCR buffers and deoxynucleotides; gel extraction kit; positive control primers; Ms-SNuPE primers for specific gene; reaction buffer (for the Ms-SNuPE reaction); and radioactive nucleotides. Additionally, bisulfite conversion reagents may include: DNA denaturation buffer; sulfonation buffer; DNA recovery regents or kit (e.g., precipitation, ultrafiltration, affinity column); desulfonation buffer; and DNA recovery components.

In another embodiment, the methylation status of selected CpG sites is determined using differential Binding-based Methylation Detection Methods. For identification of differentially methylated regions, one approach is to capture methylated DNA. This approach uses a protein, in which the methyl binding domain of MBD2 is fused to the Fc fragment of an antibody (MBD-FC) (Gebhard et al, 2006, Cancer Res. 66:6118-6128; and PCT Pub. No. WO 2006/056480 A2 (Relhi), the contents of which are hereby incorporated by reference in their entirety). This fusion protein has several advantages over conventional methylation specific antibodies. The MBD FC has a higher affinity to methylated DNA and it binds double stranded DNA. Most importantly the two proteins differ in the way they bind DNA. Methylation specific antibodies bind DNA stochastically, which means that only a binary answer can be obtained. The methyl binding domain of MBD-FC, on the other hand, binds DNA molecules regardless of their methylation status. The strength of this protein—DNA interaction is defined by the level of DNA methylation. After binding genomic DNA, eluate solutions of increasing salt concentrations can be used to fractionate non-methylated and methylated DNA allowing for a more controlled separation (Gebhard et al, 2006, Nucleic Acids Res. 34: e82). Consequently this method, called Methyl-CpG immunoprecipitation (MCIP), not only enriches, but also fractionates genomic DNA according to methylation level, which is particularly helpful when the unmethylated DNA fraction should be investigated as well.

In an alternative embodiment, a 5-methyl cytidine antibody to bind and precipitate methylated DNA. Antibodies are available from Abeam (Cambridge, Mass.), Diagenode (Sparta, N.J.) or Eurogentec (c/o AnaSpec, Fremont, Calif.). Once the methylated fragments have been separated they may be sequenced using microarray based techniques such as methylated CpG-island recovery assay (MIRA) or methylated DNA immunoprecipitation (MeDIP) (Pelizzola et al, 2008, Genome Res. 18, 1652-1659; O'Geen et al, 2006, BioTechniques 41(5), 577-580, Weber et al, 2005, Nat. Genet. 37, 853-862; Horak and Snyder, 2002, Methods Enzymol, 350, 469-83; Lieb, 2003, Methods Mol Biol, 224, 99-109). Another technique is methyl-CpG binding domain column/segregation of partly melted molecules (MBD/SPM, Shiraishi et al, 1999, Proc. Natl. Acad. Sci. USA 96(6):2913-2918).

In some embodiments, methods for detecting methylation include randomly shearing or randomly fragmenting the genomic DNA, cutting the DNA with a methylation-dependent or methylation-sensitive restriction enzyme and subsequently selectively identifying and/or analyzing the cut or uncut DNA. Selective identification can include, for example, separating cut and uncut DNA (e.g., by size) and quantifying a sequence of interest that was cut or, alternatively, that was not cut. See, e.g., U.S. Pat. No. 7,186,512. Alternatively, the method can encompass amplifying intact DNA after restriction enzyme digestion, thereby only amplifying DNA that was not cleaved by the restriction enzyme in the area amplified. See, e.g., U.S. Pat. Nos. 7,910,296; 7,901,880; and 7,459,274. In some embodiments, amplification can be performed using primers that are gene specific.

For example, there are methyl-sensitive enzymes that preferentially or substantially cleave or digest at their DNA recognition sequence if it is non-methylated. Thus, an unmethylated DNA sample is cut into smaller fragments than a methylated DNA sample. Similarly, a hypermethylated DNA sample is not cleaved. In contrast, there are methyl-sensitive enzymes that cleave at their DNA recognition sequence only if it is methylated. Methyl-sensitive enzymes that digest unmethylated DNA suitable for use in methods of the technology include, but are not limited to, HpaII, HhaI, MaeII, BstUI and AciI. In some instances, an enzyme that is used is HpaII that cuts only the unmethylated sequence CCGG. In other instances, another enzyme that is used is HhaI that cuts only the unmethylated sequence GCGC. Both enzymes are available from New England BioLabs®, Inc. Combinations of two or more methyl-sensitive enzymes that digest only unmethylated DNA are also used. Suitable enzymes that digest only methylated DNA include, but are not limited to, DpnI, which only cuts at fully methylated 5'-GATC sequences, and McrBC, an endonuclease, which cuts DNA containing modified cytosines (5-methylcytosine or 5-hydroxymethylcytosine or N4-methylcytosine) and cuts at recognition site 5' . . . PumC(N4o-3ooo) PumC . . . 3' (New England BioLabs, Inc., Beverly, Mass.). Cleavage methods and procedures for selected restriction enzymes for cutting DNA at specific sites are well known to the skilled artisan. For example, many suppliers of restriction enzymes provide information on conditions and types of DNA sequences cut by specific restriction enzymes, including New England BioLabs, Pro-Mega Biochems, Boehringer-Mannheim, and the like. Sambrook et al. (See Sambrook et al. Molecular Biology: A Laboratory Approach, Cold Spring Harbor, N.Y. 1989) provide a general description of methods for using restriction enzymes and other enzymes.

In some instances, a methylation-dependent restriction enzyme is a restriction enzyme that cleaves or digests DNA at or in proximity to a methylated recognition sequence, but does not cleave DNA at or near the same sequence when the recognition sequence is not methylated. Methylation-dependent restriction enzymes include those that cut at a methylated recognition sequence (e.g., DpnI) and enzymes that cut at a sequence near but not at the recognition sequence (e.g., McrBC). For example, McrBC's recognition sequence is 5' RmC (N40-3000) RmC 3' where "R" is a purine and "mC" is a methylated cytosine and "N40-3000" indicates the distance between the two RmC half sites for which a restriction event has been observed. McrBC generally cuts close to one half-site or the other, but cleavage positions are typically distributed over several base pairs, approximately 30 base pairs from the methylated base. McrBC sometimes cuts 3' of both half sites, sometimes 5' of both half sites, and sometimes between the two sites. Exemplary methylation-dependent restriction enzymes include, e.g., McrBC, McrA, MrrA, BisI, GlaI and DpnI. One of skill in the art will appreciate that any methylation-dependent restriction enzyme, including homologs and orthologs of the restriction enzymes described herein, is also suitable for use with one or more methods described herein.

In some cases, a methylation-sensitive restriction enzyme is a restriction enzyme that cleaves DNA at or in proximity to an unmethylated recognition sequence but does not cleave at or in proximity to the same sequence when the recognition sequence is methylated. Exemplary methylation-sensitive restriction enzymes are described in, e.g., McClelland et al, 22(17) NUCLEIC ACIDS RES. 3640-59 (1994). Suitable methylation-sensitive restriction enzymes that do not cleave DNA at or near their recognition sequence when a cytosine within the recognition sequence is methylated at position C5 include, e.g., Aat II, Aci I, Acd I, Age I, Alu I, Asc I, Ase I, AsiS I, Bbe I, BsaA I, BsaH I, BsiE I, BsiW I, BsrF I, BssH II, BssK I, BstB I, BstN I, BstU I, Cla I, Eae I, Eag I, Fau I, Fse I, Hha I, HinPl I, HinC II, Hpa II, Hpy99 I, HpyCH4 IV, Kas I, Mbo I, Mlu I, MapAl I, Msp I, Nae I, Nar I, Not I, Pml I, Pst I, Pvu I, Rsr II, Sac II, Sap I, Sau3A I, Sfl I, Sfo I, SgrA I, Sma I, SnaB I, Tsc I, Xma I, and Zra I. Suitable methylation-sensitive restriction enzymes that do not cleave DNA at or near their recognition sequence when an adenosine within the recognition sequence is methylated at position N6 include, e.g., Mbo I. One of skill in the art will appreciate that any methylation-sensitive restriction enzyme, including homologs and orthologs of the restriction enzymes described herein, is also suitable for use with one or more of the methods described herein. One of skill in the art will further appreciate that a methylation-sensitive restriction enzyme that fails to cut in the presence of methylation of a cytosine at or near its recognition sequence may be insensitive to the presence of methylation of an adenosine at or near its recognition sequence. Likewise, a methylation-sensitive restriction enzyme that fails to cut in the presence of methylation of an adenosine at or near its recognition sequence may be insensitive to the presence of methylation of a cytosine at or near its recognition sequence. For example, Sau3AI is sensitive (i.e., fails to cut) to the presence of a methylated cytosine at or near its recognition sequence, but is insensitive (i.e., cuts) to the presence of a methylated adenosine at or near its recognition sequence. One of skill in the art will also appreciate that some methylation-sensitive restriction enzymes are blocked by methylation of bases on one or both strands of DNA encompassing of their recognition sequence, while other methylation-sensitive restriction enzymes are blocked only by methylation on both strands, but can cut if a recognition site is hemi-methylated.

In alternative embodiments, adaptors are optionally added to the ends of the randomly fragmented DNA, the DNA is then digested with a methylation-dependent or methylation-sensitive restriction enzyme, and intact DNA is subsequently amplified using primers that hybridize to the adaptor sequences. In this case, a second step is performed to determine the presence, absence or quantity of a particular gene in an amplified pool of DNA. In some embodiments, the DNA is amplified using real-time, quantitative PCR.

In other embodiments, the methods comprise quantifying the average methylation density in a target sequence within a population of genomic DNA. In some embodiments, the method comprises contacting genomic DNA with a methylation-dependent restriction enzyme or methylation-sensitive restriction enzyme under conditions that allow for at least some copies of potential restriction enzyme cleavage sites in the locus to remain uncleaved; quantifying intact copies of the locus; and comparing the quantity of amplified product to a control value representing the quantity of methylation of control DNA, thereby quantifying the average methylation density in the locus compared to the methylation density of the control DNA.

In some instances, the quantity of methylation of a locus of DNA is determined by providing a sample of genomic DNA comprising the locus, cleaving the DNA with a restriction enzyme that is either methylation-sensitive or methylation-dependent, and then quantifying the amount of intact DNA or quantifying the amount of cut DNA at the DNA locus of interest. The amount of intact or cut DNA will depend on the initial amount of genomic DNA containing the locus, the amount of methylation in the locus, and the number (i.e., the fraction) of nucleotides in the locus that are methylated in the genomic DNA. The amount of methylation in a DNA locus can be determined by comparing the quantity of intact DNA or cut DNA to a control value representing the quantity of intact DNA or cut DNA in a similarly-treated DNA sample. The control value can represent a known or predicted number of methylated nucleotides. Alternatively, the control value can represent the quantity of intact or cut DNA from the same locus in another (e.g., normal, non-diseased) cell or a second locus.

By using at least one methylation-sensitive or methylation-dependent restriction enzyme under conditions that allow for at least some copies of potential restriction enzyme cleavage sites in the locus to remain uncleaved and subsequently quantifying the remaining intact copies and comparing the quantity to a control, average methylation density of a locus can be determined. If the methylation-sensitive restriction enzyme is contacted to copies of a DNA locus under conditions that allow for at least some copies of potential restriction enzyme cleavage sites in the locus to remain uncleaved, then the remaining intact DNA will be directly proportional to the methylation density, and thus may be compared to a control to determine the relative methylation density of the locus in the sample. Similarly, if a methylation-dependent restriction enzyme is contacted to copies of a DNA locus under conditions that allow for at least some copies of potential restriction enzyme cleavage sites in the locus to remain uncleaved, then the remaining intact DNA will be inversely proportional to the methylation density, and thus may be compared to a control to determine the relative methylation density of the locus in the sample. Such assays are disclosed in, e.g., U.S. Pat. No. 7,910,296.

The methylated CpG island amplification (MCA) technique is a method that can be used to screen for altered methylation patterns in genomic DNA, and to isolate specific sequences associated with these changes (Toyota et al, 1999, Cancer Res. 59, 2307-2312, U.S. Pat. No. 7,700,324 (Issa et al), the contents of which are hereby incorporated by reference in their entirety). Briefly, restriction enzymes with different sensitivities to cytosine methylation in their recognition sites are used to digest genomic DNAs from primary tumors, cell lines, and normal tissues prior to arbitrarily primed PCR amplification. Fragments that show differential methylation are cloned and sequenced after resolving the PCR products on high-resolution polyacrylamide gels. The cloned fragments are then used as probes for Southern analysis to confirm differential methylation of these regions. Typical reagents (e.g., as might be found in a typical MCA-based kit) for MCA analysis may include, but are not limited to: PCR primers for arbitrary priming Genomic DNA; PCR buffers and nucleotides, restriction enzymes and appropriate buffers; gene-hybridization oligos or probes; control hybridization oligos or probes.

Additional methylation detection methods include those methods described in, e.g., U.S. Pat. Nos. 7,553,627; 6,331,393; U.S. patent Ser. No. 12/476,981; U.S. Patent Publication No. 2005/0069879; Rein, et al, 26(10) NUCLEIC ACIDS RES. 2255-64 (1998); and Olek et al, 17(3) NAT. GENET. 275-6 (1997).

In another embodiment, the methylation status of selected CpG sites is determined using Methylation-Sensitive High Resolution Melting (HRM). Recently, Wojdacz et al. reported methylation-sensitive high resolution melting as a technique to assess methylation. (Wojdacz and Dobrovic, 2007, Nuc. Acids Res. 35(6) e41; Wojdacz et al. 2008, Nat.

Prot. 3(12) 1903-1908; Balic et al, 2009 J. Mol. Diagn. 11 102-108; and US Pat. Pub. No. 2009/0155791 (Wojdacz et al), the contents of which are hereby incorporated by reference in their entirety). A variety of commercially available real time PCR machines have HRM systems including the Roche LightCycler480, Corbett Research RotorGene6000, and the Applied Biosystems 7500. HRM may also be combined with other amplification techniques such as pyrosequencing as described by Candiloro et al. (Candiloro et al, 2011, Epigenetics 6(4) 500-507).

In another embodiment, the methylation status of selected CpG locus is determined using a primer extension assay, including an optimized PCR amplification reaction that produces amplified targets for analysis using mass spectrometry. The assay can also be done in multiplex. Mass spectrometry is a particularly effective method for the detection of polynucleotides associated with the differentially methylated regulatory elements. The presence of the polynucleotide sequence is verified by comparing the mass of the detected signal with the expected mass of the polynucleotide of interest. The relative signal strength, e.g., mass peak on a spectra, for a particular polynucleotide sequence indicates the relative population of a specific allele, thus enabling calculation of the allele ratio directly from the data. This method is described in detail in PCT Pub. No. WO 2005/012578A1 (Beaulieu et al), which is hereby incorporated by reference in its entirety. For methylation analysis, the assay can be adopted to detect bisulfite introduced methylation dependent C to T sequence changes. These methods are particularly useful for performing multiplexed amplification reactions and multiplexed primer extension reactions (e.g., multiplexed homogeneous primer mass extension (hME) assays) in a single well to further increase the throughput and reduce the cost per reaction for primer extension reactions.

Other methods for DNA methylation analysis include restriction landmark genomic scanning (RLGS, Costello et al, 2002, Meth. Mol Biol, 200, 53-70), methylation-sensitive-representational difference analysis (MS-RDA, Ushijima and Yamashita, 2009, Methods Mol Biol 507, 1 17-130). Comprehensive high-throughput arrays for relative methylation (CHARM) techniques are described in WO 2009/021141 (Feinberg and Irizarry). The Roche® NimbleGen® microarrays including the Chromatin Immunoprecipitation-on-chip (ChIP-chip) or methylated DNA immunoprecipitation-on-chip (MeDIP-chip). These tools have been used for a variety of cancer applications including melanoma, liver cancer and lung cancer (Koga et al, 2009, Genome Res., 19, 1462-1470; Acevedo et al, 2008, Cancer Res., 68, 2641-2651; Rauch et al, 2008, Proc. Nat. Acad. Sci. USA, 105, 252-257). Others have reported bisulfate conversion, padlock probe hybridization, circularization, amplification and next generation or multiplexed sequencing for high throughput detection of methylation (Deng et al, 2009, Nat. Biotechnol 27, 353-360; Ball et al, 2009, Nat. Biotechnol 27, 361-368; U.S. Pat. No. 7,611,869 (Fan)). As an alternative to bisulfate oxidation, Bayeyt et al. have reported selective oxidants that oxidize 5-methylcytosine, without reacting with thymidine, which are followed by PCR or pyro sequencing (WO 2009/049916 (Bayeyt et al). These references for these techniques are hereby incorporated by reference in their entirety.

In some instances, quantitative amplification methods (e.g., quantitative PCR or quantitative linear amplification) are used to quantify the amount of intact DNA within a locus flanked by amplification primers following restriction digestion. Methods of quantitative amplification are disclosed in, e.g., U.S. Pat. Nos. 6,180,349; 6,033,854; and 5,972,602, as well as in, e.g., DeGraves, et al, 34(1) BIOTECHNIQUES 106-15 (2003); Deiman B, et al., 20(2) MOL. BIOTECHNOL. 163-79 (2002); and Gibson et al, 6 GENOME RESEARCH 995-1001 (1996).

Following reaction or separation of nucleic acid in a methylation specific manner, the nucleic acid in some cases are subjected to sequence-based analysis. For example, once it is determined that one particular genomic sequence from a sample is hypermethylated or hypomethylated compared to its counterpart, the amount of this genomic sequence can be determined. Subsequently, this amount can be compared to a standard control value and used to determine the present of liver cancer in the sample. In many instances, it is desirable to amplify a nucleic acid sequence using any of several nucleic acid amplification procedures which are well known in the art. Specifically, nucleic acid amplification is the chemical or enzymatic synthesis of nucleic acid copies which contain a sequence that is complementary to a nucleic acid sequence being amplified (template). The methods and kits may use any nucleic acid amplification or detection methods known to one skilled in the art, such as those described in U.S. Pat. No. 5,525,462 (Takarada et al); U.S. Pat. No. 6,114,117 (Hepp et al); U.S. Pat. No. 6,127,120 (Graham et al); U.S. Pat. No. 6,344,317 (Urnovitz); U.S. Pat. No. 6,448,001 (Oku); U.S. Pat. No. 6,528,632 (Catanzariti et al); and PCT Pub. No. WO 2005/111209 (Nakajima et al); all of which are incorporated herein by reference in their entirety.

In some embodiments, the nucleic acids are amplified by PCR amplification using methodologies known to one skilled in the art. One skilled in the art will recognize, however, that amplification can be accomplished by any known method, such as ligase chain reaction (LCR), Q-replicas amplification, rolling circle amplification, transcription amplification, self-sustained sequence replication, nucleic acid sequence-based amplification (NASBA), each of which provides sufficient amplification. Branched-DNA technology is also optionally used to qualitatively demonstrate the presence of a sequence of the technology, which represents a particular methylation pattern, or to quantitatively determine the amount of this particular genomic sequence in a sample. Nolte reviews branched-DNA signal amplification for direct quantitation of nucleic acid sequences in clinical samples (Nolte, 1998, Adv. Clin. Chem. 33:201-235).

The PCR process is well known in the art and include, for example, reverse transcription PCR, ligation mediated PCR, digital PCR (dPCR), or droplet digital PCR (ddPCR). For a review of PCR methods and protocols, see, e.g., Innis et al, eds., PCR Protocols, A Guide to Methods and Application, Academic Press, Inc., San Diego, Calif. 1990; U.S. Pat. No. 4,683,202 (Mullis). PCR reagents and protocols are also available from commercial vendors, such as Roche Molecular Systems. In some instances, PCR is carried out as an automated process with a thermostable enzyme. In this process, the temperature of the reaction mixture is cycled through a denaturing region, a primer annealing region, and an extension reaction region automatically. Machines specifically adapted for this purpose are commercially available.

In some embodiments, amplified sequences are also measured using invasive cleavage reactions such as the Invader® technology (Zou et al, 2010, Association of Clinical Chemistry (AACC) poster presentation on Jul. 28, 2010, "Sensitive Quantification of Methylated Markers with a Novel Methylation Specific Technology; and U.S. Pat. No. 7,011,944 (Prudent et al)).

Suitable next generation sequencing technologies are widely available. Examples include the 454 Life Sciences platform (Roche, Branford, Conn.) (Margulies et al. 2005 Nature, 437, 376-380); lllumina's Genome Analyzer, GoldenGate Methylation Assay, or Infinium Methylation Assays, i.e., Infinium HumanMethylation 27K BeadArray or VeraCode GoldenGate methylation array (Illumina, San Diego, Calif.; Bibkova et al, 2006, Genome Res. 16, 383-393; U.S. Pat. Nos. 6,306,597 and 7,598,035 (Macevicz); U.S. Pat. No. 7,232,656 (Balasubramanian et al.)); QX200™ Droplet Digital™ PCR System from Bio-Rad; or DNA Sequencing by Ligation, SOLiD System (Applied Biosystems/Life Technologies; U.S. Pat. Nos. 6,797,470, 7,083,917, 7,166,434, 7,320,865, 7,332,285, 7,364,858, and 7,429,453 (Barany et al); the Helicos True Single Molecule DNA sequencing technology (Harris et al, 2008 Science, 320, 106-109; U.S. Pat. Nos. 7,037,687 and 7,645,596 (Williams et al); U.S. Pat. No. 7,169,560 (Lapidus et al); U.S. Pat. No. 7,769,400 (Harris)), the single molecule, real-time (SMRT™) technology of Pacific Biosciences, and sequencing (Soni and Meller, 2007, Clin. Chem. 53, 1996-2001); semiconductor sequencing (Ion Torrent; Personal Genome Machine); DNA nanoball sequencing; sequencing using technology from Dover Systems (Polonator), and technologies that do not require amplification or otherwise transform native DNA prior to sequencing (e.g., Pacific Biosciences and Helicos), such as nanopore-based strategies (e.g., Oxford Nanopore, Genia Technologies, and Nabsys). These systems allow the sequencing of many nucleic acid molecules isolated from a specimen at high orders of multiplexing in a parallel fashion. Each of these platforms allow sequencing of clonally expanded or non-amplified single molecules of nucleic acid fragments. Certain platforms involve, for example, (i) sequencing by ligation of dye-modified probes (including cyclic ligation and cleavage), (ii) pyrosequencing, and (iii) single-molecule sequencing.

Pyrosequencing is a nucleic acid sequencing method based on sequencing by synthesis, which relies on detection of a pyrophosphate released on nucleotide incorporation. Generally, sequencing by synthesis involves synthesizing, one nucleotide at a time, a DNA strand complimentary to the strand whose sequence is being sought. Study nucleic acids may be immobilized to a solid support, hybridized with a sequencing primer, incubated with DNA polymerase, ATP sulfurylase, luciferase, apyrase, adenosine 5' phosphosulfate and luciferin. Nucleotide solutions are sequentially added and removed. Correct incorporation of a nucleotide releases a pyrophosphate, which interacts with ATP sulfurylase and produces ATP in the presence of adenosine 5' phosphosulfate, fueling the luciferin reaction, which produces a chemiluminescent signal allowing sequence determination. Machines for pyrosequencing and methylation specific reagents are available from Qiagen, Inc. (Valencia, Calif.). See also Tost and Gut, 2007, Nat. Prot. 2 2265-2275. An example of a system that can be used by a person of ordinary skill based on pyrosequencing generally involves the following steps: ligating an adaptor nucleic acid to a study nucleic acid and hybridizing the study nucleic acid to a bead; amplifying a nucleotide sequence in the study nucleic acid in an emulsion; sorting beads using a picoliter multiwell solid support; and sequencing amplified nucleotide sequences by pyrosequencing methodology (e.g., Nakano et al, 2003, J. Biotech. 102, 117-124). Such a system can be used to exponentially amplify amplification products generated by a process described herein, e.g., by ligating a heterologous nucleic acid to the first amplification product generated by a process described herein.

CpG Methylation Data Analysis Methods

In certain embodiments, the methylation values measured for biomarkers of a biomarker panel are mathematically combined and the combined value is correlated to the underlying diagnostic question. In some instances, methylated biomarker values are combined by any appropriate state of the art mathematical method. Well-known mathematical methods for correlating a biomarker combination to a disease status employ methods like discriminant analysis (DA) (e.g., linear-, quadratic-, regularized-DA), Discriminant Functional Analysis (DFA), Kernel Methods (e.g., SVM), Multidimensional Scaling (MDS), Nonparametric Methods (e.g., k-Nearest-Neighbor Classifiers), PLS (Partial Least Squares), Tree-Based Methods (e.g., Logic Regression, CART, Random Forest Methods, Boosting/Bagging Methods), Generalized Linear Models (e.g., Logistic Regression), Principal Components based Methods (e.g., SIMCA), Generalized Additive Models, Fuzzy Logic based Methods, Neural Networks and Genetic Algorithms based Methods. The skilled artisan will have no problem in selecting an appropriate method to evaluate an epigenetic marker or biomarker combination described herein. In one embodiment, the method used in a correlating methylation status of an epigenetic marker or biomarker combination, e.g. to diagnose liver cancer or a liver cancer subtype, is selected from DA (e.g., Linear-, Quadratic-, Regularized Discriminant Analysis), DFA, Kernel Methods (e.g., SVM), MDS, Nonparametric Methods (e.g., k-Nearest-Neighbor Classifiers), PLS (Partial Least Squares), Tree-Based Methods (e.g., Logic Regression, CART, Random Forest Methods, Boosting Methods), or Generalized Linear Models (e.g., Logistic Regression), and Principal Components Analysis. Details relating to these statistical methods are found in the following references: Ruczinski et al., 12 J. OF COMPUTATIONAL AND GRAPHICAL STATISTICS 475-511 (2003); Friedman, J. H., 84 J. OF THE AMERICAN STATISTICAL ASSOCIATION 165-75 (1989); Hastie, Trevor, Tibshirani, Robert, Friedman, Jerome, The Elements of Statistical Learning, Springer Series in Statistics (2001); Breiman, L., Friedman, J. H., Olshen, R. A., Stone, C. J. Classification and regression trees, California: Wadsworth (1984); Breiman, L., 45 MACHINE LEARNING 5-32 (2001); Pepe, M. S., The Statistical Evaluation of Medical Tests for Classification and Prediction, Oxford Statistical Science Series, 28 (2003); and Duda, R. O., Hart, P. E., Stork, D. O., Pattern Classification, Wiley Interscience, 2nd Edition (2001).

In one embodiment, the correlated results for each methylation panel are rated by their correlation to the disease or tumor type positive state, such as for example, by p-value test or t-value test or F-test. Rated (best first, i.e. low p- or t-value) biomarkers are then subsequently selected and added to the methylation panel until a certain diagnostic value is reached. Such methods include identification of methylation panels, or more broadly, genes that were differentially methylated among several classes using, for example, a random-variance t-test (Wright G. W. and Simon R, Bioinformatics 19:2448-2455, 2003). Other methods include the step of specifying a significance level to be used for determining the epigenetic markers that will be included in the biomarker panel. Epigenetic markers that are differentially methylated between the classes at a univariate parametric significance level less than the specified threshold are included in the panel. It doesn't matter whether the specified significance level is small enough to exclude enough false discoveries. In some problems better prediction is achieved by being more liberal about the biomarker panels used as features. In some cases, the panels are biologically interpretable and clinically applicable, however, if fewer markers are included. Similar to cross-validation, biomarker selection is repeated for each training set created in the cross-validation process. That is for the purpose of providing an unbiased estimate of prediction error. The methylation panel for use with new patient sample data is the one resulting from application of the methylation selection and classifier of the "known" methylation information, or control methylation panel.

Models for utilizing methylation profile to predict the class of future samples can also be used. These models may be based on the Compound Covariate Predictor (Radmacher et al. Journal of Computational Biology 9:505-511, 2002), Diagonal Linear Discriminant Analysis (Dudoit et al. Journal of the American Statistical Association 97:77-87, 2002), Nearest Neighbor Classification (also Dudoit et al.), and Support Vector Machines with linear kernel (Ramaswamy et al. PNAS USA 98:15149-54, 2001). The models incorporated markers that were differentially methylated at a given significance level (e.g. 0.01, 0.05 or 0.1) as assessed by the random variance t-test (Wright G. W. and Simon R. Bioinformatics 19:2448-2455, 2003). The prediction error of each model using cross validation, preferably leave-one-out cross-validation (Simon et al. Journal of the National Cancer Institute 95:14-18, 2003 can be estimated. For each leave-one-out cross-validation training set, the entire model building process is repeated, including the epigenetic marker selection process. In some instances, it is also evaluated in whether the cross-validated error rate estimate for a model is significantly less than one would expect from random prediction. In some cases, the class labels are randomly permuted and the entire leave-one-out cross-validation process is then repeated. The significance level is the proportion of the random permutations that gives a cross-validated error rate no greater than the cross-validated error rate obtained with the real methylation data.

Another classification method is the greedy-pairs method described by Bo and Jonassen (Genome Biology 3(4): research0017.1-0017.11, 2002). The greedy-pairs approach starts with ranking all markers based on their individual t-scores on the training set. This method attempts to select pairs of markers that work well together to discriminate the classes.

Furthermore, a binary tree classifier for utilizing methylation profile is optionally used to predict the class of future samples. The first node of the tree incorporated a binary classifier that distinguished two subsets of the total set of classes. The individual binary classifiers are based on the "Support Vector Machines" incorporating markers that were differentially expressed among markers at the significance level (e.g. 0.01, 0.05 or 0.1) as assessed by the random variance t-test (Wright G. W. and Simon R. Bioinformatics 19:2448-2455, 2003). Classifiers for all possible binary partitions are evaluated and the partition selected is that for which the cross-validated prediction error is minimum. The process is then repeated successively for the two subsets of classes determined by the previous binary split. The prediction error of the binary tree classifier can be estimated by cross-validating the entire tree building process. This overall cross-validation includes re-selection of the optimal partitions at each node and re-selection of the markers used for each cross-validated training set as described by Simon et al. (Simon et al. Journal of the National Cancer Institute 95:14-18, 2003). Several-fold cross validation in which a fraction of the samples is withheld, a binary tree developed on the remaining samples, and then class membership is predicted for the samples withheld. This is repeated several times, each time withholding a different percentage of the samples. The samples are randomly partitioned into fractional test sets (Simon R and Lam A. BRB-ArrayTools User Guide, version 3.2. Biometric Research Branch, National Cancer Institute).

Thus, in one embodiment, the correlated results for each marker b) are rated by their correct correlation to the disease, preferably by p-value test. It is also possible to include a step in that the markers are selected d) in order of their rating.

In additional embodiments, factors such as the value, level, feature, characteristic, property, etc. of a transcription rate, mRNA level, translation rate, protein level, biological activity, cellular characteristic or property, genotype, phenotype, etc. can be utilized in addition prior to, during, or after administering a therapy to a patient to enable further analysis of the patient's cancer status.

In some embodiments, a diagnostic test to correctly predict status is measured as the sensitivity of the assay, the specificity of the assay or the area under a receiver operated characteristic ("ROC") curve. In some instances, sensitivity is the percentage of true positives that are predicted by a test to be positive, while specificity is the percentage of true negatives that are predicted by a test to be negative. In some cases, an ROC curve provides the sensitivity of a test as a function of 1-specificity. The greater the area under the ROC curve, for example, the more accurate or powerful the predictive value of the test. Other useful measures of the utility of a test include positive predictive value and negative predictive value. Positive predictive value is the percentage of people who test positive that are actually positive. Negative predictive value is the percentage of people who test negative that are actually negative.

In some embodiments, one or more of the biomarkers disclosed herein show a statistical difference in different samples of at least $p<0.05$, $p<10^{-2}$, $p<10^{-3}$, $p<10^{-4}$ or $p<10^{-5}$. Diagnostic tests that use these biomarkers may show an ROC of at least 0.6, at least about 0.7, at least about 0.8, or at least about 0.9. In some instances, the biomarkers are differentially methylated in different subjects with or without liver cancer. In additional instances, the biomarkers for different subtypes of liver cancer are differentially methylated. In certain embodiments, the biomarkers are measured in a patient sample using the methods described herein and compared, for example, to predefined biomarker levels and are used to determine whether the patient has liver cancer, which liver cancer subtype does the patient have, and/or what is the prognosis of the patient having liver cancer. In other embodiments, the correlation of a combination of biomarkers in a patient sample is compared, for example, to a predefined set of biomarkers. In some embodiments, the measurement(s) is then compared with a relevant diagnostic amount(s), cut-off(s), or multivariate model scores that distinguish between the presence or absence of liver cancer, between liver cancer subtypes, and between a "good" or a "poor" prognosis. As is well understood in the art, by adjusting the particular diagnostic cut-off(s) used in an assay, one can increase sensitivity or specificity of the diagnostic assay depending on the preference of the diagnostician. In some embodiments, the particular diagnostic cut-off is determined, for example, by measuring the amount of biomarker hypermethylation or hypomethylation in a statistically significant number of samples from patients with or without liver cancer and from patients with different liver cancer subtypes, and drawing the cut-off to suit the desired levels of specificity and sensitivity.

Kits/Article of Manufacture

In some embodiments, provided herein include kits for detecting and/or characterizing the methylation profile of a biomarker described herein. In some instances, the kit comprises a plurality of primers or probes to detect or measure the methylation status/levels of one or more samples. Such kits comprise, in some instances, at least one polynucleotide that hybridizes to at least one of the methylation marker sequences described herein and at least one reagent for detection of gene methylation. Reagents for detection of methylation include, e.g., sodium bisulfate, polynucleotides designed to hybridize to sequence that is the product of a marker sequence if the marker sequence is not methylated (e.g., containing at least one C-U conversion), and/or a methylation-sensitive or methylation-dependent restriction enzyme. In some cases, the kits provide solid supports in the form of an assay apparatus that is adapted to use in the assay. In some instances, the kits further comprise detectable labels, optionally linked to a polynucleotide, e.g., a probe, in the kit.

In some embodiments, the kits comprise one or more (e.g., 1, 2, 3, 4, or more) different polynucleotides (e.g., primers and/or probes) capable of specifically amplifying at least a portion of a DNA region of a biomarker described herein. Optionally, one or more detectably-labeled polypeptides capable of hybridizing to the amplified portion are also included in the kit. In some embodiments, the kits comprise sufficient primers to amplify 2, 3, 4, 5, 6, 7, 8, 9, 10, or more different DNA regions or portions thereof, and optionally include detectably-labeled polynucleotides capable of hybridizing to each amplified DNA region or portion thereof. The kits further can comprise a methylation-dependent or methylation sensitive restriction enzyme and/or sodium bisulfite.

In some embodiments, the kits comprise sodium bisulfite, primers and adapters (e.g., oligonucleotides that can be ligated or otherwise linked to genomic fragments) for whole genome amplification, and polynucleotides (e.g., detectably-labeled polynucleotides) to quantify the presence of the converted methylated and or the converted unmethylated sequence of at least one cytosine from a DNA region of an epigenetic marker described herein.

In some embodiments, the kits comprise methylation sensing restriction enzymes (e.g., a methylation-dependent restriction enzyme and/or a methylation-sensitive restriction enzyme), primers and adapters for whole genome amplification, and polynucleotides to quantify the number of copies of at least a portion of a DNA region of an epigenetic marker described herein.

In some embodiments, the kits comprise a methylation binding moiety and one or more polynucleotides to quantify the number of copies of at least a portion of a DNA region of a marker described herein. A methylation binding moiety refers to a molecule (e.g., a polypeptide) that specifically binds to methyl-cytosine.

Examples include restriction enzymes or fragments thereof that lack DNA cutting activity but retain the ability to bind methylated DNA, antibodies that specifically bind to methylated DNA, etc.).

In some embodiments, the kit includes a packaging material. As used herein, the term "packaging material" can refer to a physical structure housing the components of the kit. In some instances, the packaging material maintains sterility of the kit components, and is made of material commonly used for such purposes (e.g., paper, corrugated fiber, glass, plastic, foil, ampules, etc.). Other materials useful in the performance of the assays are included in the kits, including test tubes, transfer pipettes, and the like. In some cases, the kits also include written instructions for the use of one or more of these reagents in any of the assays described herein.

In some embodiments, kits also include a buffering agent, a preservative, or a protein/nucleic acid stabilizing agent. In some cases, kits also include other components of a reaction mixture as described herein. For example, kits include one or more aliquots of thermostable DNA polymerase as described herein, and/or one or more aliquots of dNTPs. In some cases, kits also include control samples of known amounts of template DNA molecules harboring the individual alleles of a locus. In some embodiments, the kit includes a negative control sample, e.g., a sample that does not contain DNA molecules harboring the individual alleles of a locus. In some embodiments, the kit includes a positive control sample, e.g., a sample containing known amounts of one or more of the individual alleles of a locus.

Certain Terminology

Unless defined otherwise, all technical and scientific terms used herein have the same meaning as is commonly understood by one of skill in the art to which the claimed subject matter belongs. It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting.

As used herein, ranges and amounts can be expressed as "about" a particular value or range. About also includes the exact amount. Hence "about 5 µL" means "about 5 µL" and also "5 µL." Generally, the term "about" includes an amount that would be expected to be within experimental error.

The section headings used herein are for organizational purposes only and are not to be construed as limiting the subject matter described.

As used herein, the terms "individual(s)", "subject(s)" and "patient(s)" mean any mammal. In some embodiments, the mammal is a human. In some embodiments, the mammal is a non-human. None of the terms require or are limited to situations characterized by the supervision (e.g. constant or intermittent) of a health care worker (e.g. a doctor, a registered nurse, a nurse practitioner, a physician's assistant, an orderly or a hospice worker).

A "site" corresponds to a single site, which in some cases is a single base position or a group of correlated base positions, e.g., a CpG site. A "locus" corresponds to a region that includes multiple sites. In some instances, a locus includes one site.

EXAMPLES

These examples are provided for illustrative purposes only and not to limit the scope of the claims provided herein.

Example 1

Lung cancer (LUNC) and Hepatocellular carcinoma (HCC) are leading causes of cancer deaths worldwide. As with many cancers, LUNC and HCC found at an early stage carries much-improved prognosis compared to advanced stage disease, in part due to the relative efficacy of local treatments compared with systemic therapy. In some cases, early detection has the potential for reducing mortality.

DNA methylation is an epigenetic regulator of gene expression that usually results in gene silencing. In cancer, DNA methylation is typically increased in tumor suppressor genes and presents itself as one of the first neoplastic changes. Circulating tumor DNA (ctDNA) comprises of extracellular nucleic acid fragments shed into plasma via tumor cell necrosis, apoptosis, and active release of DNA. In some cases, ctDNA bearing cancer-specific methylation patterns is used as a biomarker in diagnosis of cancers.

Patient Data

Tissue DNA methylation data was obtained from The Cancer Genome Atlas (TCGA). Complete clinical, molecular, and histopathological datasets are available at the TCGA website. Individual institutions that contributed samples coordinated the consent process and obtained informed written consent from each patient in accordance to their respective institutional review boards.

A second independent Chinese cohort consisted of 654 LUNC and 654 HCC patients at the Sun Yat-sen University Cancer Center in Guangzhou, Xijing Hospital in Xi'an and the West China Hospital in Chengdu, China. Patients who presented with LUNC and HCC from stage I-IV were selected and enrolled in this study. Patient characteristics and tumor features are summarized in Table S1. The TNM staging classification for LUNC and HCC is according to the $7^{th}$ edition of the AJCC cancer staging manual (Edge, S. B., and Compton, C. C. (2010). The American Joint Committee on Cancer: the 7th edition of the AJCC cancer staging manual and the future of TNM. Annals of surgical oncology 17, 1471-1474). This project was approved by the IRBs of Sun Yat-sen University Cancer Center, Xijing Hospital, and West China Hospital. Informed consent was obtained from all patients. Tumor and normal tissues were obtained as clinically indicated for patient care and were retained for this study. Human blood samples were collected by venipuncture and plasma samples were obtained by taking supernatant after centrifugation and stored at −80° C. before cfDNA extraction.

Data Sources

DNA methylation data of 485,000 sites generated using the Infinium 450K Methylation Array were obtained from the TCGA and a dataset generated from the study Hannum, G., et al. (2013) Genome-wide methylation profiles reveal quantitative views of human aging rates, Mol Cell 49, 359-367 (GSE40279) in which DNA methylation profiles for HCC and blood were analyzed. IDAT format files of the methylation data were generated containing the ratio values of each scanned bead. Using the minfi package from Bioconductor, these data files were converted into a score, referred to as a Beta value. Methylation values of the Chinese cohort were obtained by targeted bisulfate sequencing using a molecular inversion probe and analyzed as described below.

Statistical Analysis

DNA Methylation Marker Pre-Selection for Diagnostic and Prognostic Analysis

Figure 1B:
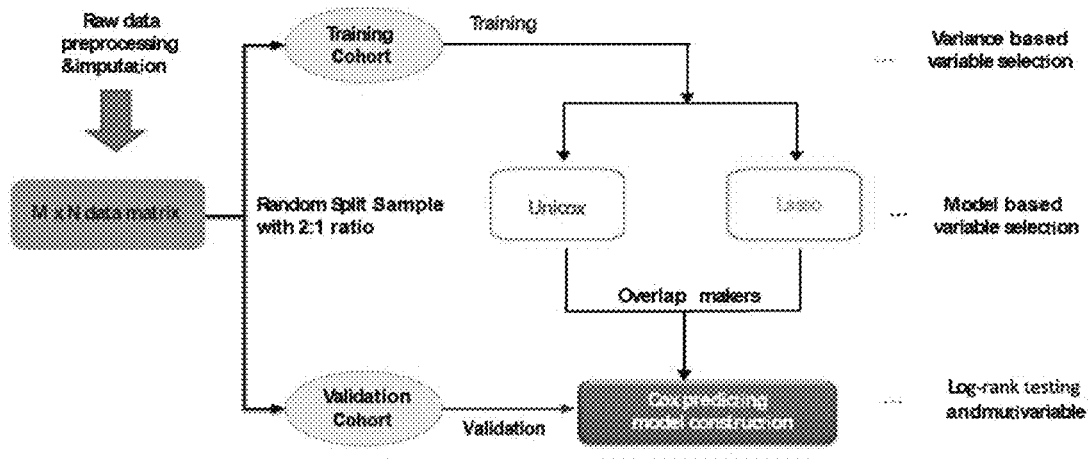

A differential methylation analysis on TCGA data was performed using a "moderated t-statistics shrinking" approach and the p-value for each marker was then corrected by multiple testing by the Benjamini-Hochberg procedure to control FDR at a significance level of 0.05. The list was ranked by adjusted p-value and selected the top 1000 markers for designing padlock probes for differentiating cancer (both LUNC and HCC) versus normal samples and a separate group of 1000 markers for differentiating LUNC versus HCC (FIG. 1). About 1673 padlock probes were obtained that gave positive and specific PCR amplification signals and they were therefore used as capture probes in the subsequent experiments in cfDNA samples. cfDNA samples with low quality or fewer than 30,000 reads per sample were also eliminated. About 2,173 cfDNA samples were included in our study (654 LUNC and 654 HCC blood samples and 865 normal blood samples). Methylated reads for each marker were defined as total unique methylated reads and methylation values for each marker were defined as the proportion of read counts with methylation divided by total read counts. For particular methylation markers with less than 20 unique reads, an imputed mean methylation value of HCC or normal healthy controls was used.

Building a Diagnostic Model cfDNA Feature Construction and MCB

Padlock probes were designed to encompass 2000 CpG methylation sites found to be differentially methylated in comparison between both LUNC and HCC versus blood, and between LUNC and HCC. Capture and sequencing were performed in bisulfate-converted cfDNA samples. The concept of MCBs was used to merge proximal CpG markers into a MCB, resulting in a total of 888 MCBs. For each MCB, the MCB-specific methylation value was quantified as log 10 (total methylated read count +1), using the log transform to reduce outlier effects.

cfDNA-Based Diagnostic Classifier Construction cfDNA sample data obtained from patients diagnosed with liver cancer (HCC), lung cancer (LUNC) and normal controls were divided into training and validation cohorts. Samples were excluded if they had less than 30,000 total unique reads. From the remaining samples with sufficient reads to ensure a good representation of MCBs, we selected 654 each of lung and liver cancer samples, and 865 healthy samples to ensure a balanced dataset. The full dataset was randomly split with a 2:1 ratio to form the training and validation cohorts.

MCBs that showed good methylation ranges across cfDNA samples were selected. Further, a two sample t-test was used to identify MCBs with the largest standardized absolute mean difference of methylated reads of an MCB between cancer samples (LUNC or HCC) versus normal controls samples. The top MCBs were chosen according to the ranked p-values that were still significant after correcting form multiple testing and constructed a diagnostic prediction model using top 100 markers. The panel of MCBs were aggregated into a composite score (cd-score) to perform a pairwise binary classification between LUNC and normal, HCC and normal, and LUNC and HCC. The composite score was generated from a multinomial logistic regression model using the top 50 MCBs per comparison.

The pre-treatment or initial methylation level was obtained at the initial diagnosis, and the post-treatment level was evaluated approximately 2 months after treatment, where the treatment referred to either chemotherapy or surgical resection of tumor. The primary endpoint (including response to treatment: progressive disease (PD), partial response (PR) and stable disease (SD)) were defined according to the RECIST guideline (Eisenhauer et al., 2009). For patients treated with surgical removal and no recurrence at time of evaluation, we assumed they had complete response (CR). The difference of cd-score distribution between clinical categories was examined by one-sided t-test as the cd-score was shown to be non-normally distributed using a Shapiro-Wilk Test.

Building a Predictive Model for Prognosis and Survival

The potential to use a combined prognosis score (cp-score) system was investigated based on total methylation reads in ctDNA for prediction of prognosis in LUNC and HCC in combination with clinical and demographic characteristics including age, gender, and AJCC stage. For each type of cancer, two thirds of the observations were randomly selected from the full dataset as the training cohort, and treated the rest as the validation cohort. Variable selection were conducted on the training cohort and built the composite score on the validation cohort. Within the training cohort, the "randomized lasso" scheme was adopted (Meinshausen, N., and Buihlmann, P. (2010) Stability selection. Journal of the Royal Statistical Society: Series B (Statistical Methodology) 72, 417-473) to reduce the sampling dependency to stabilize the variable selection in order to select biomarkers with a high confidence. The cohort with a 2:1 ratio was randomly divided. The variable selection procedure was initially conducted on the two-third of the training cohort and then used the remaining one-third cohort to conduct an internal validation test within the same training cohort. A variable selection procedure was conducted as following, First, a univariate Cox regression model was used to remove excessive noise and selected any biomarker with p-value less than or equal to 0.05 based on the Wald test. Second, LASSO was implemented with an optimal tuning parameter determined by either the expected generalization error from the 10-fold cross validation or the information based criteria AIC/BIC, whichever yielded the highest $\rho^2$ (the proportion of explained randomness) with the selected biomarkers. The discriminatory power in Cox regression of the selected biomarkers was further evaluated on the internal validation cohort using the concordance probability (also known as C-index). In HCC, both $\rho^2$ (Median 0.773; quartile: 0.722-0.838) and C-index (Median:0.768; quartile: 0.728-0.796) demonstrated the potential of biomarkers in an internal validation cohort. Similarly in LUNC, both $\rho^2$ (Median 0.737; quartile: 0.636-0.793) and C-index (0.614; quartile: 0.585-0.650) demonstrated potential clinical utility of biomarkers. The biomarkers presented in at least 30 out of 100 runs were aggregated, which resulted in 10 markers in HCC and 12 markers in LUNC (Table 3). To evaluate the predictability of each panel externally, a composite score was obtained for each patient in the validation cohort by multiplying the unbiased coefficient estimates from the Cox regression and the methylation reads. A Kaplan-Meier curve and log-rank test were generated using the dichotomized composite score, which formed a high-risk and low-risk group membership assignment according to its median. This segmentation was compatible with that formed by AJCC stage. Time-depended ROC was used to summarize the discrimination potential of the composite score, AJCC stage and the combination of two, with ROC curves varying as a function of time and accommodating censored data. Finally, a multivariate Cox regression model was fitted to assess the significance of potential risk factors. All hypothesis testing was two-sided with p-value <0.05 considered to be statistically significant. All the analysis was conducted in R version 3.2.3 with the following packages used: 'glmnet', 'pROC', 'limma', 'survival', 'survivalROC', 'survcomp'.

Tumor DNA Extraction

Genomic DNA extraction from freshly frozen healthy or cancer tissues was performed with QIAamp DNA Mini Kit (Qiagen) according to manufacturer's recommendations. Roughly 0.5 mg of tissue was used to obtain on average 5 µg of genomic DNA. DNA was stored at −20° C. and analyzed within one week of preparation.

DNA Extraction from FFPE Samples

Genomic DNA from frozen FFPE samples was extracted using QIAamp DNA FFPE Tissue Kit with several modifications. DNA samples were stored at −20° C. for further analysis.

Cell-Free DNA Extraction from Plasma Samples cfDNA extraction from 1.5 ml of plasma samples was performed with QIAamp cfDNA Kit (Qiagen) according to manufacturer's recommendations.

Bisulfite Conversion of Genomic DNA

About 10 ng of cfDNA was converted to bis-DNA using EZ DNA Methylation-Lightning™ Kit (Zymo Research) according to the manufacturer's protocol. Resulting bis-DNA had a size distribution of ~200-3000 bp, with a peak around ~500-1000 bp. The efficiency of bisulfite conversion was >99.8% as verified by deep-sequencing of bis-DNA and analyzing the ratio of C to T conversion of CH (non-CG) dinucleotides.

Determination of DNA Methylation Levels by Deep Sequencing of Bis-DNA Captured with Molecular-Inversion (Padlock) Probes CpG markers whose methylation levels significantly differed in any of the comparisons between any cancer tissue and normal blood were used to design padlock probes for capture and sequencing of cfDNA. Padlock-capture of bis-DNA was based on the technique on published methods with modifications (Deng, J., Shoemaker, R., Xie, B., Gore, A., LeProust, E. M., Antosiewicz-Bourget, J., Egli, D., Maherali, N., Park, I. H., Yu, J., et al. (2009). Targeted bisulfite sequencing reveals changes in DNA methylation associated with nuclear reprogramming. Nat Biotechnol 27, 353-360; Diep, D., Plongthongkum, N., Gore, A., Fung, H. L., Shoemaker, R., and Zhang, K. (2012). Library-free methylation sequencing with bisulfite padlock probes. Nat Methods 9, 270-272; Porreca, G. J., Zhang, K., Li, J. B., Xie, B., Austin, D., Vassallo, S. L., LeProust, E. M., Peck, B. J., Emig, C. J., Dahl, F., et al. (2007). Multiplex amplification of large sets of human exons. Nat Methods 4, 931-936).

Probe Design and Synthesis

Padlock probes were designed using the ppDesigner software. The average length of the captured region was 100 bp, with the CpG marker located in the central portion of the captured region. Linker sequence between arms contained binding sequences for amplification primers separated by a variable stretch of Cs to produced probes of equal length. A 6-bp unique molecular identifier (UMI) sequence was incorporated in probe design to allow for the identification of unique individual molecular capture events and accurate scoring of DNA methylation levels.

Probes were synthesized as separate oligonucleotides using standard commercial synthesis methods (ITD). For capture experiments, probes were mixed, in-vitro phosphorylated with T4 PNK (NEB) according to manufacturer's recommendations and purified using P-30 Micro Bio-Spin columns (Bio-Rad).

Bis-DNA Capture

About 10 ng of bisulfite-converted DNA was mixed with padlock probes in 20 µl reactions containing 1× Ampligase buffer (Epicentre). To anneal probes to DNA, 30 second denaturation at 95° C. was followed by a slow cooling to 55° C. at a rate of 0.02° C. per second. Hybridization was left to complete for 15 hrs at 55° C. To fill gaps between annealed arms, 5 µl of the following mixture was added to each reaction: 2U of PfuTurboCx polymerase (Agilent), 0.5U of Ampligase (Epicentre) and 250 pmol of each dNTP in 1× Ampligase buffer. After 5 hour incubation at 55° C., reactions were denatured for 2 minutes at 94° C. 5 µl of exonuclease mix (20U of Exo I and 100U of ExoIII, both from Epicentre) was added and single-stranded DNA degradation was carried out at 37° C. for 2 hours, followed by enzyme inactivation for 2 minutes at 94° C.

Circular products of site-specific capture were amplified by PCR with concomitant barcoding of separate samples. Amplification was carried out using primers specific to linker DNA within padlock probes, one of which contained specific 6 bp barcodes. Both primers contained Illumina next-generation sequencing adaptor sequences. PCR was done as follows: 1× Phusion Flash Master Mix, 3 µl of captured DNA and 200 nM primers, using the following cycle: 10s @ 98° C., 8× of (1 s @ 98° C., 5s @ 58° C., 10s @72° C.), 25× of (Is @ 98° C., 15s @ 72° C.), 60s @ 72° C. PCR reactions were mixed and the resulting library was size selected to include effective captures (~230 bp) and exclude "empty" captures (~150 bp) using Agencourt AMPure XP beads (Beckman Coulter). Purity of the libraries was verified by PCR using Illumina flowcell adaptor primers (P5 and P7) and the concentrations were determined using Qubit dsDNA HS assay (Thermo Fisher). Libraries we sequenced using MiSeq and HiSeq2500 systems (Illumina).

Optimization of Capture Coverage Uniformity

Deep sequencing of the original pilot capture experiments showed significant differences between number of reads captured by most efficient probes and non-efficient probes (60-65% of captured regions with coverage >0.2× of average). To ameliorate this, relative efficiencies were calculated from sequencing data and probes were mixed at adjusted molar ratios. This increased capture uniformity to 85% of regions at >0.2× of average coverage.

Sequencing Data Analysis

Mapping of sequencing reads was done using the software tool bisReadMapper with some modifications. First, UMI were extracted from each sequencing read and appended to read headers within FASTQ files using a custom script. Reads were on-the-fly converted as if all C were non-methylated and mapped to in-silico converted DNA strands of the human genome, also as if all C were non-methylated, using Bowtie2. Original reads were merged and filtered for single UMI, i.e. reads carrying the same UMI were discarded leaving a single, unique read. Methylation frequencies were calculated for all CpG dinucleotides contained within the regions captured by padlock probes by dividing the numbers of unique reads carrying a C at the interrogated position by the total number of reads covering the interrogated position.

Identification of Blocks of Correlated Methylation (BCM)

Pearson correlation coefficients between methylation frequencies of each pair of CpG markers separated by no more than 200 bp were calculated separately across 50 cfDNA samples from each of the two diagnostic categories, e.g. normal blood and HCC. A value of Pearson's r<0.5 was used to identify boundaries between adjacent markers with uncorrelated methylation. Markers not separated by a boundary were combined into Methylation Correlated Blocks (MCBs). This procedure identified a total of ~1550 BCMs in each diagnostic category within our padlock data, combining between 2 and 22 CpG positions in each block. Methylation frequencies for entire BCMs were calculated by summing up the numbers of Cs at all interrogated CpG positions within a BCM and dividing by the total number of C+Ts at those positions DNA Isolation and Digital Quantitative PCR Tumor and corresponding plasma samples were obtained from patients undergoing surgical tumor resection; samples were frozen and preserved in at −80° C. until use. Isolation of DNA and RNA from samples was performed using AllPrep DNA/RNA Mini kit and a cfDNA extraction kit, respectively (Qiagen, Valencia, Calif.).

Patient and Sample Characteristics

Clinical characteristics and molecular DNA methylation profiles were collected for 827 LUNC and 377 HCC tumor samples from The Cancer Genome Atlas (TCGA) and 754 normal samples from a dataset used in the methylation study on aging (GSE40279) (Hannum, G., et al. (2013). Genome-wide methylation profiles reveal quantitative views of human aging rates. Mol Cell 49, 359-367). Two cohorts of patients were studied. The first cohort was from solid tumors from TCGA and the second cohort was from cfDNA samples from China. To study ctDNA in LUNC and HCC, plasma samples were obtained from 2,173 Chinese patients with HCC or LUNC and randomly selected population matched healthy controls undergoing routine health care maintenance, resulting in a cohort of 654 LUNC and 654 HCC patients and 865 normal healthy controls. All participants provided written informed consent. Clinical characteristics of all patients and controls are listed in Table 4.

Identification of Methylation Markers Differentiating LUNC and HCC and Blood

Figure 6A:
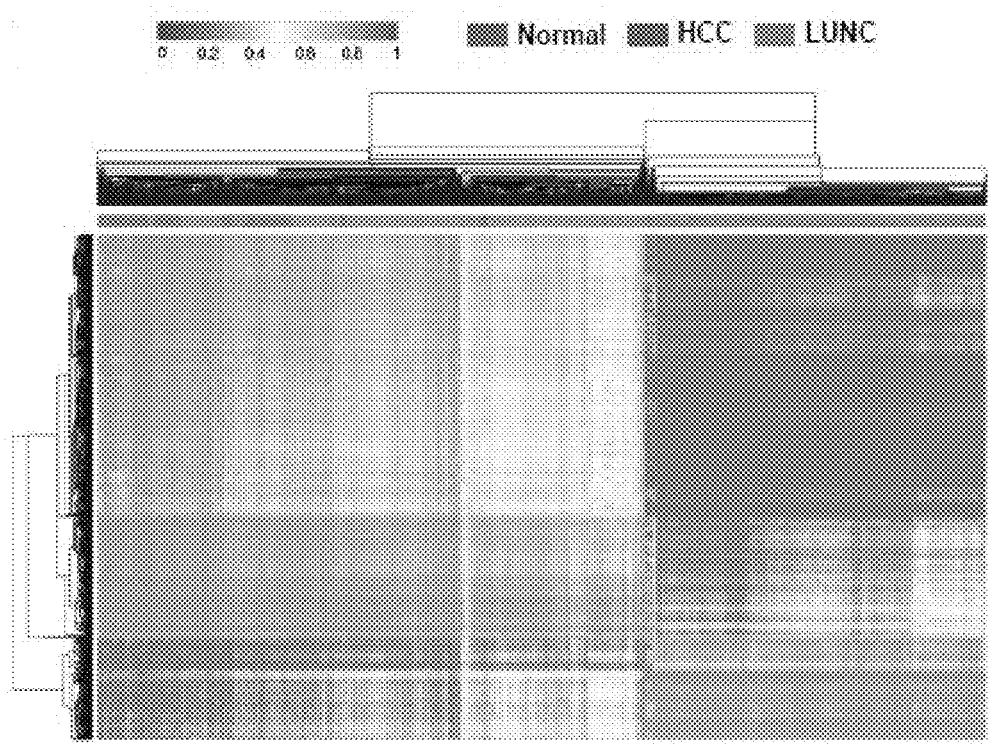
FIG. 6A shows unsupervised hierarchical clustering of top 1000 methylation markers differentially methylated in DNA in HCC and LUNC tissues versus normal blood.
Figure 6B:
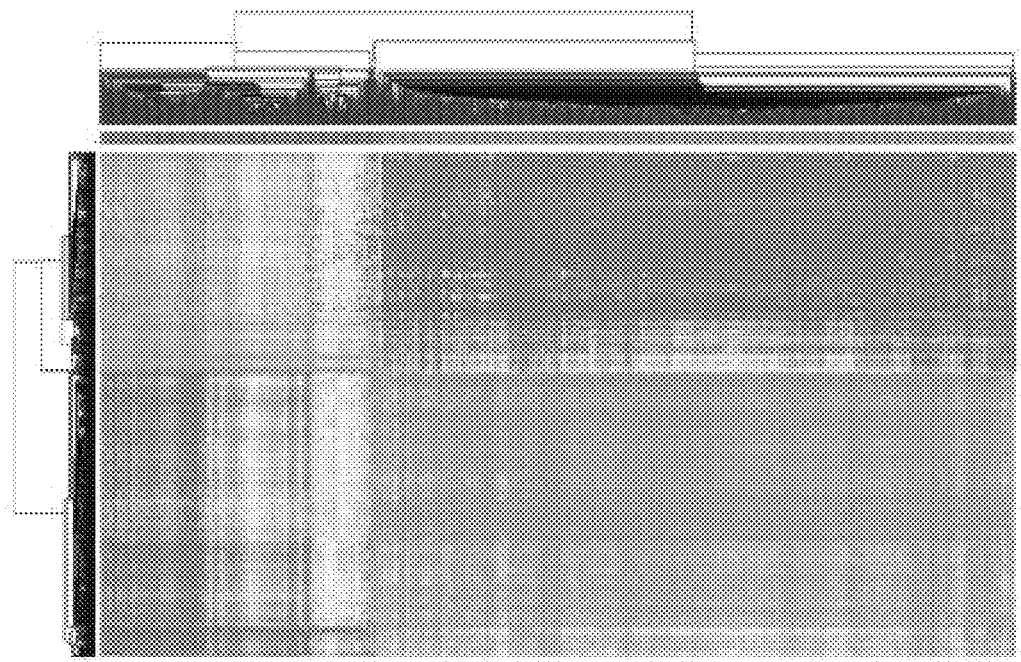
FIG. 6B shows unsupervised hierarchical clustering of the top 1000 methylation markers differentially methylated between HCC and LUNC tissue DNA. Each column represents an individual patient and each row represents a CpG marker.

It was hypothesized that since cfDNA originating from tumor cells is detected in a background of cfDNA predominantly released from leukocytes, CpG markers with a maximal difference in methylation values between LUNC or HCC versus normal leukocytes demonstrates detectable methylation differences in the cfDNA of HCC or LUNC patients when compared to that of normal controls. To identify putative markers, methylation data derived from cancer tissue DNA from the TCGA was compared with normal blood including 827 LUNC, 436 HCC, and 754 blood samples from healthy controls. In order to identify DNA sites with significantly different rates of methylation between LUNC or HCC and normal blood, a t-statistic with Empirical Bayes for shrinking the variance was used and top 1000 markers were selected, using the Benjamini-Hochberg procedure to control the FDR at a significance level of 0.05. Unsupervised hierarchical clustering of these top 1000 markers was able to distinguish between LUNC, HCC, and normal blood (FIG. 6). About 2,000 molecular inversion (padlock) probes corresponding to these 2000 markers for capture-sequencing cfDNA from plasma were designed.

Methylation Block Structure for Improved Allele Calling Accuracy

Figure 7A:
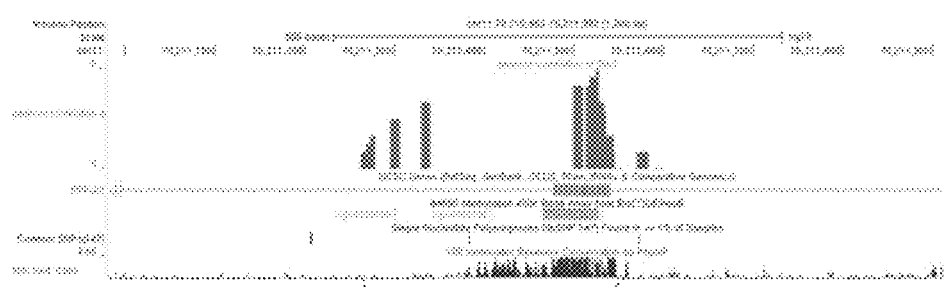
FIG. 7A-FIG. 7B show an illustrative region encompassing two Blocks of Correlated Methylation (BCM) in cfDNA samples of from LUNC and HCC patients and normal controls.
Figure 7B:
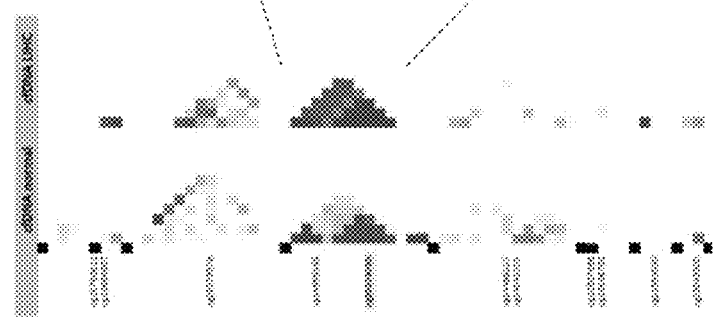

The well-established concept of genetic linkage disequilibrium (LD block) (Reich, D. E., et al., (2001) Linkage disequilibrium in the human genome. Nature 411, 199-204) was employed to study the degree of co-methylation among different DNA strands, with the underlying assumption is that DNA sites in close proximity are more likely to be co-methylated than distant sites. Paired-end Illumina sequencing reads were used to identify each individual methylation block (mBlock), and applied a Pearson correlation method to quantify co-methylation or mBlock. All common mBlocks of a region were compiled by calculating different mBlock fractions. The genome is partitioned into blocks of tightly co-methylated CpG sites that we termed methylation correlated blocks (MCBs), using an $r^2$ cutoff of 0.5, usually employed in a genetic linkage disequilibrium analysis. MCBs were surveyed in cfDNA of 500 normal samples and found that MCBs are highly consistent. Methylation levels within an MCB in cfDNA of 500 LUNC and 500 HCC samples were determined in addition to 500 normal samples. Similar to the case of a LD block, it was found that methylation pattern within an MCB was consistent when comparing normal versus HCC and LUNC cfDNA samples which significantly enhanced allele-calling accuracy (FIG. 7). Therefore, MCB values are used for all subsequent analyses. After filtering MCBs with a low dynamic methylation range to exclude non-informative MCBs (<5% in all cfDNA samples), 2000 differentially methylated CpG methylation sites were merged into 888 MCBs (FIG. 7). Also see Appendix A.

ctDNA Diagnostic Prediction Model for LUNC and HCC

Figure 2A:
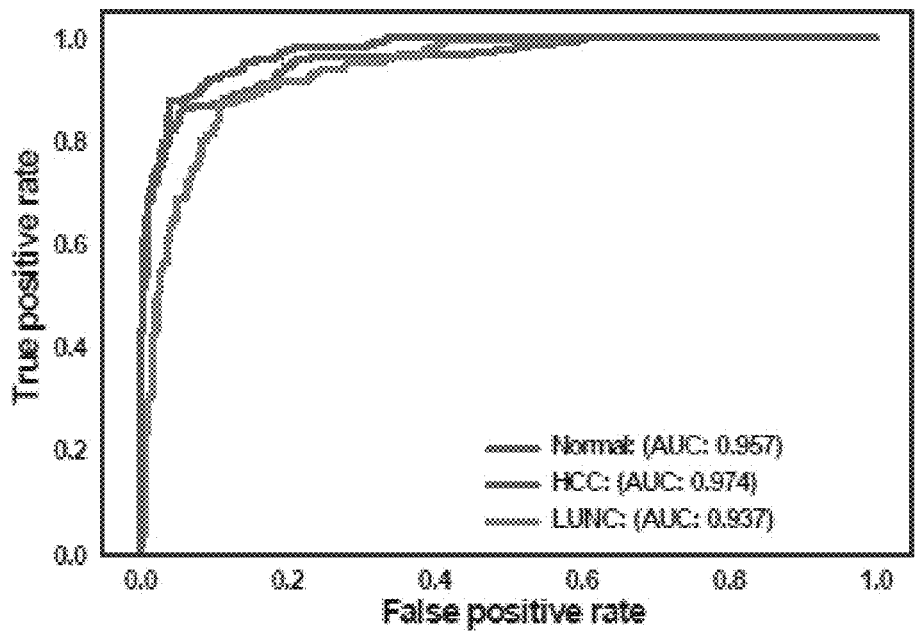
FIG. 2A-FIG. 2D illustrate cfDNA methylation analysis for diagnosis of LUNC and HCC.
Figure 2B:
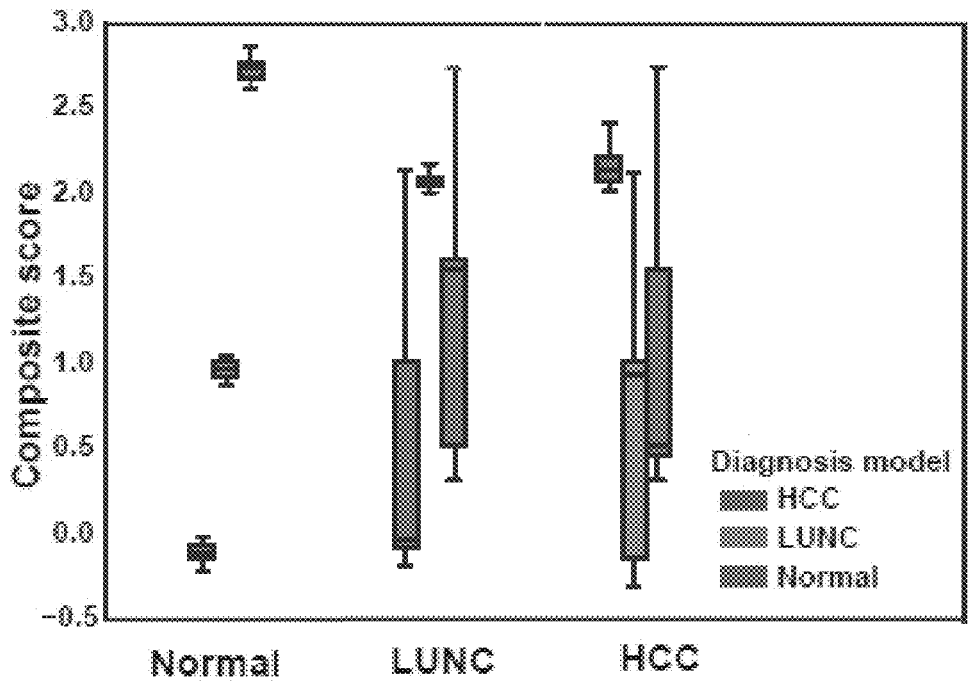
Figure 2C:
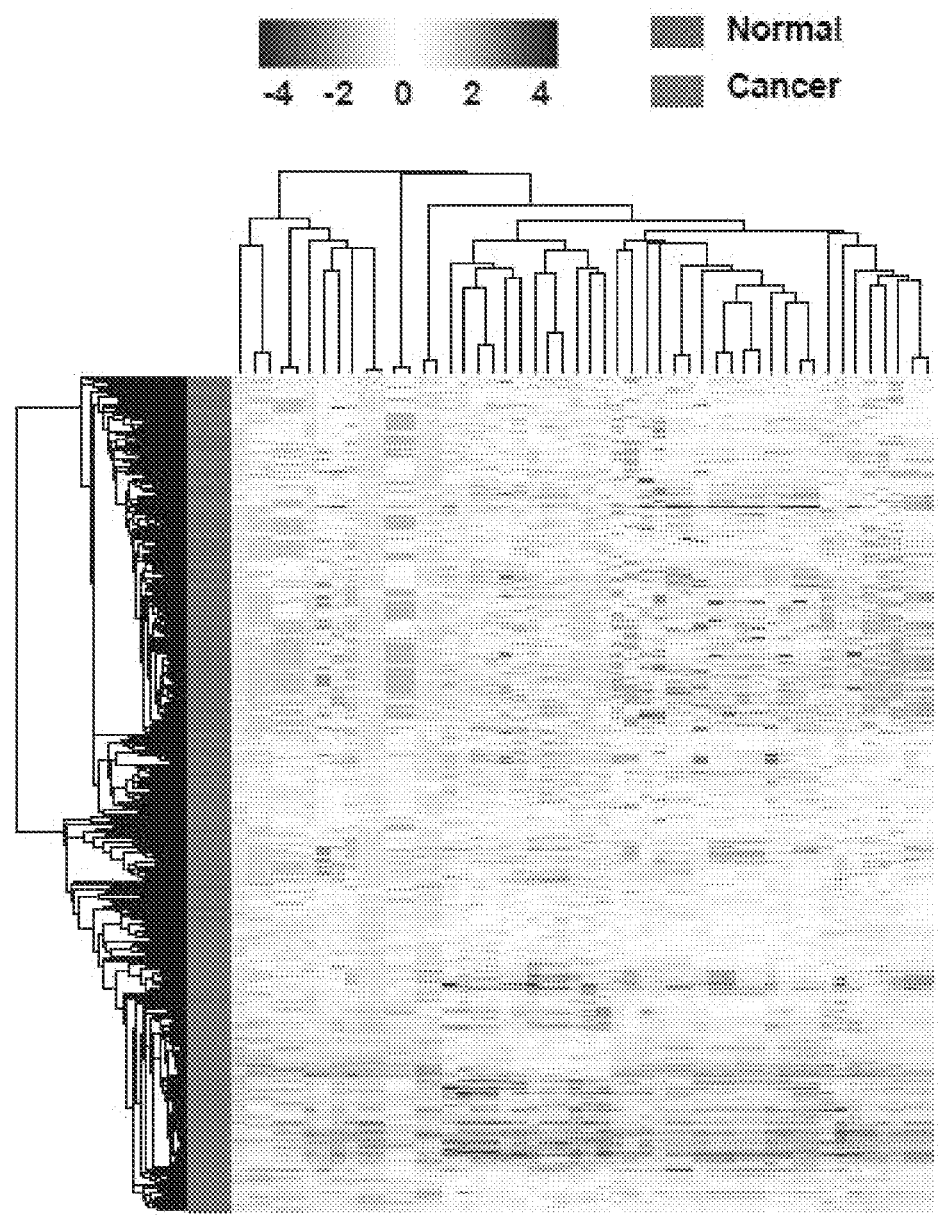
Figure 2D:
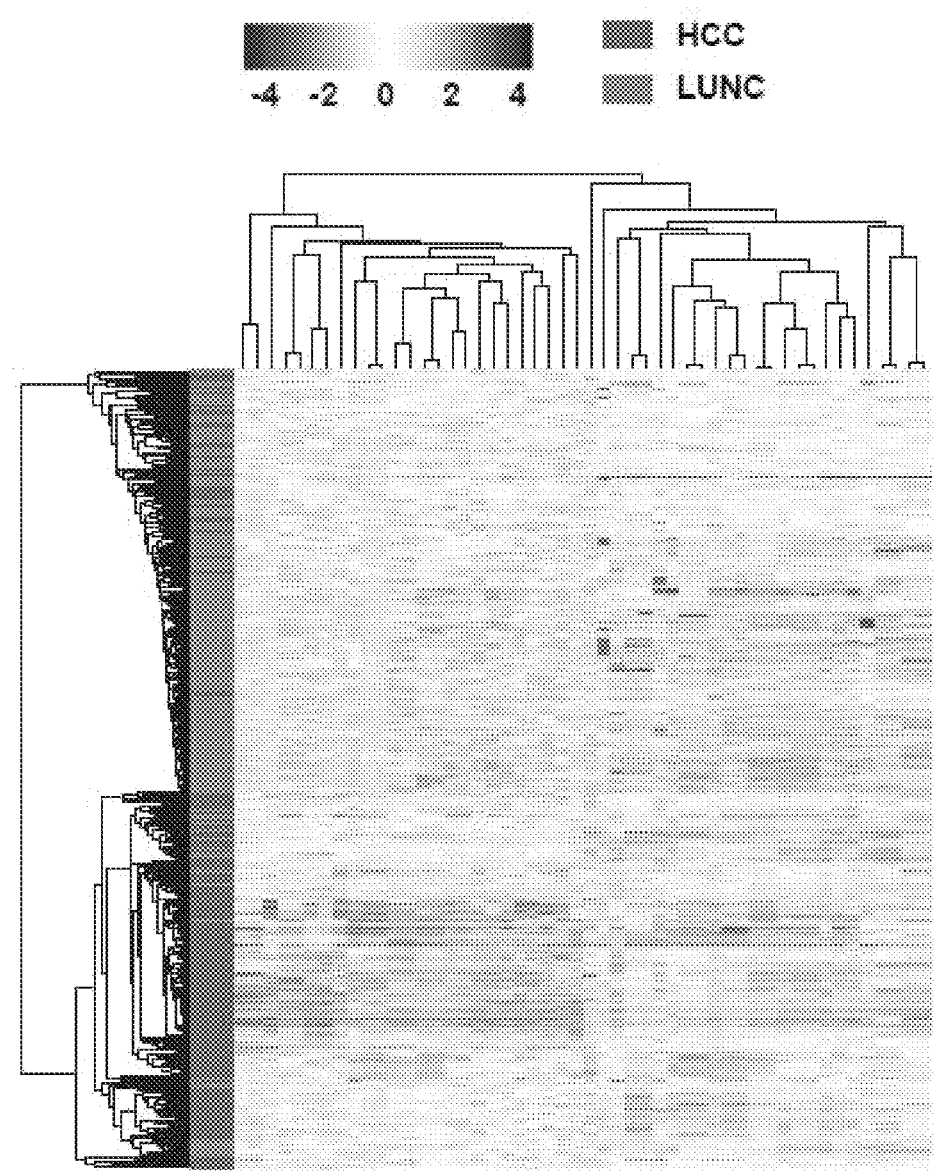
Figure 8A:
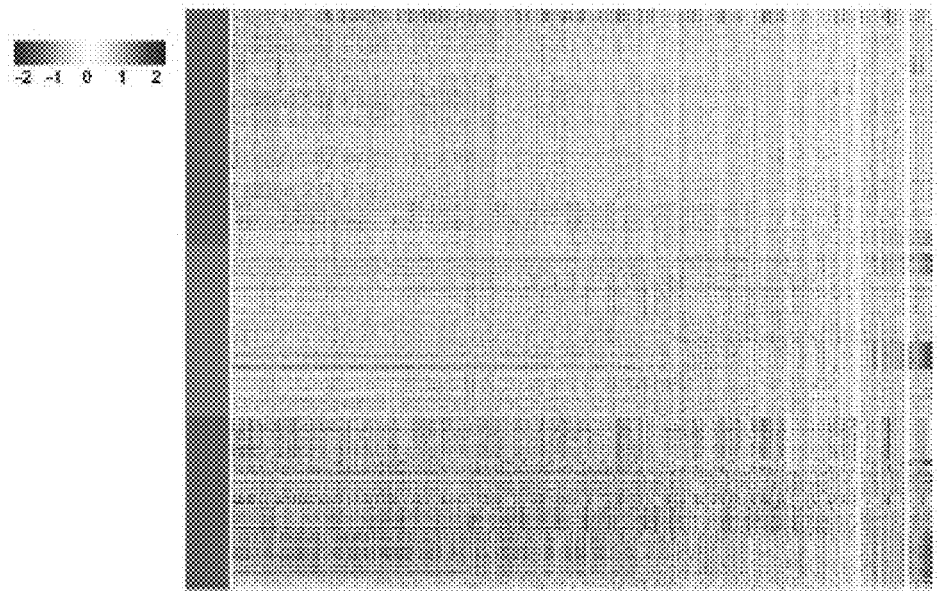
FIG. 8A shows unsupervised hierarchical clustering of 100 methylation markers selected for use in the diagnostic prediction model (cd-score) in the validation cohort.
Figure 8B:
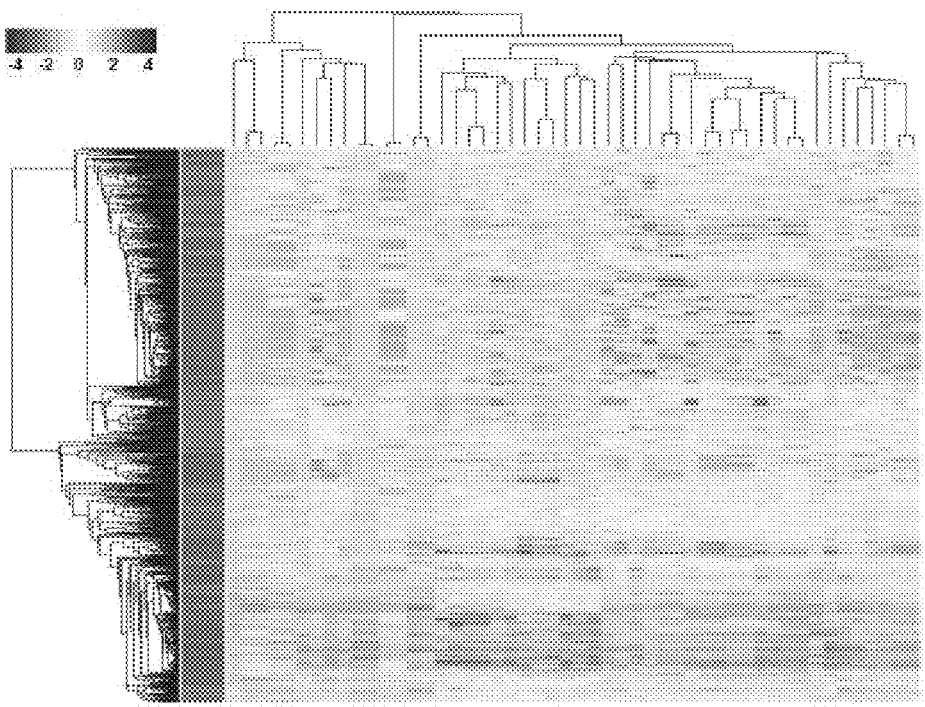
FIG. 8B shows global view of supervised hierarchical clustering of all MCBs in the entire cfDNA dataset.
Figure 9:
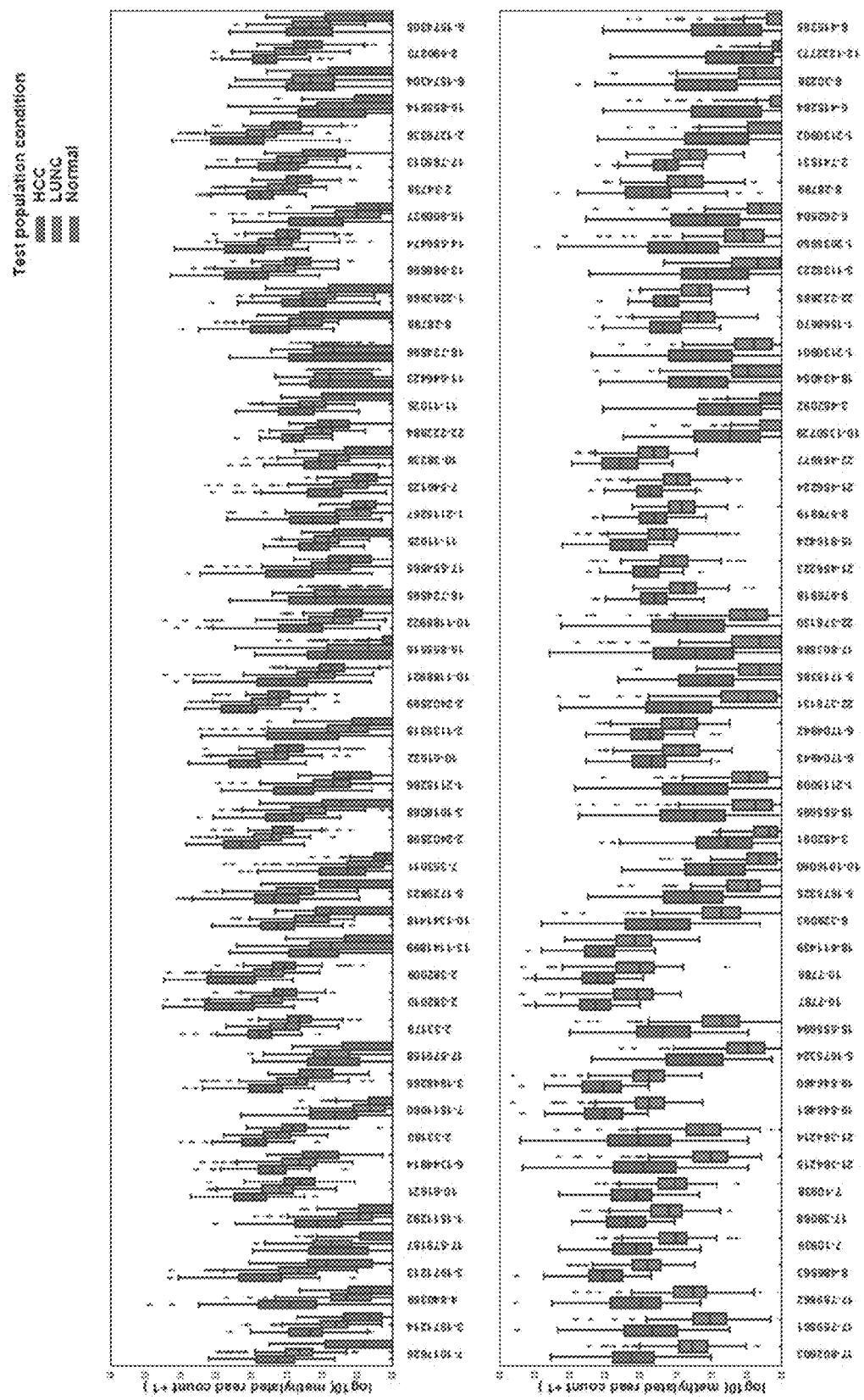
FIG. 9 shows boxplots showing the behavior of 100 MCBs in the validation cohorts. Top plot: MCB mean values and deviations in the healthy patients vs patients with HCC or LUNC; bottom plot: MCB mean values and deviations in patients with LUNC vs HCC.

The methylation values of the 888 selected MCBs that showed good methylation ranges in cfDNA samples (FIG. 7B) were analyzed by two-sample t-test to identify markers that gave the maximal standardized absolute mean difference of methylation reads for each marker between cancer samples (LUNC and HCC) versus normal controls samples. The top 100 most significant differentially methylated MCBs ranked by adjusted p-value after controlling the family-wise error rate were chosen to construct a diagnostic prediction model. Unsupervised hierarchical clustering of these MCBs by sample shown in FIG. 8A and methylated value of each selected MCB by tumor type shown in FIG. 9. For comparison, hierarchical clustering of all MCBs is shown in FIG. 8B. This panel of 100 MCB as used to generate a composite score (cd-score) in order to perform a pairwise binary classification between LUNC and normal, HCC and normal, and LUNC and HCC. The composite score was obtained from a multinomial logistic regression model using the top 50 MCBs per comparison. The full dataset was randomly split with a 2:1 ratio to form training and validation cohorts. The scoring system using 436 LUNC, 436 HCC and 576 normal control cfDNA samples were trained and then validated the score system in 218 LUNC, 218 HCC and 289 normal samples. Applying the model yielded a sensitivity of 85.8% for HCC and 80.3% for LUNC, and a specificity of 88.2% for in the validation dataset (Table 1 A). We also found that this model could successfully differentiate LUNC and HCC samples from normal controls in the validation cohort (AUC normal=0.957, AUC LUNC=0.937, AUC HCC=0.974) (FIG. 2A, Table 1B, Table 1C). Unsupervised hierarchical clustering of these 50 MCBs was able to distinguish HCC and LUNC from normal controls with high specificity and sensitivity (FIGS. 2C and 2D).

Figure 3A:
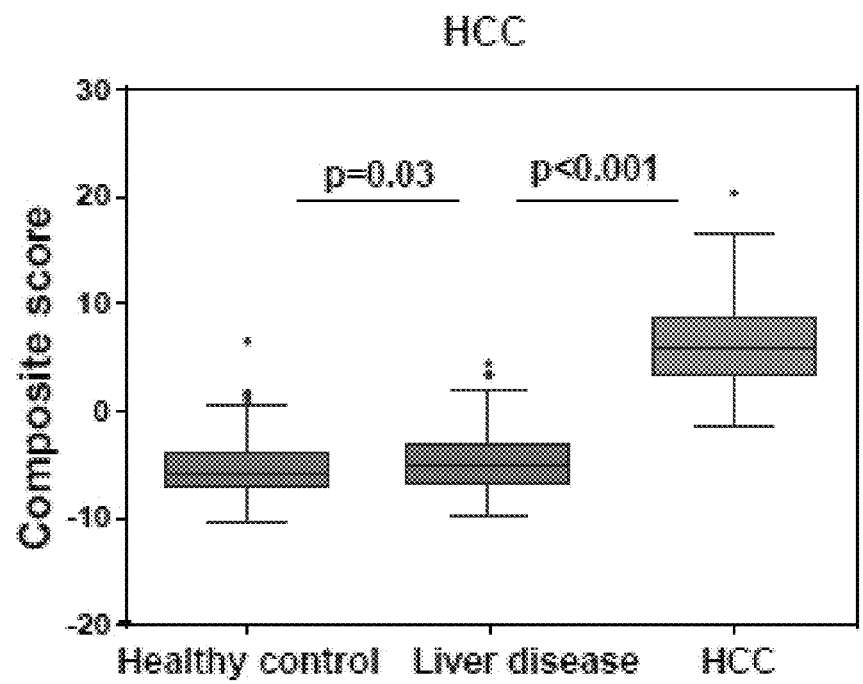
FIG. 3A-FIG. 3C shows methylation profiling in healthy control, high-risk patients and cancer patients.
Figure 3B:
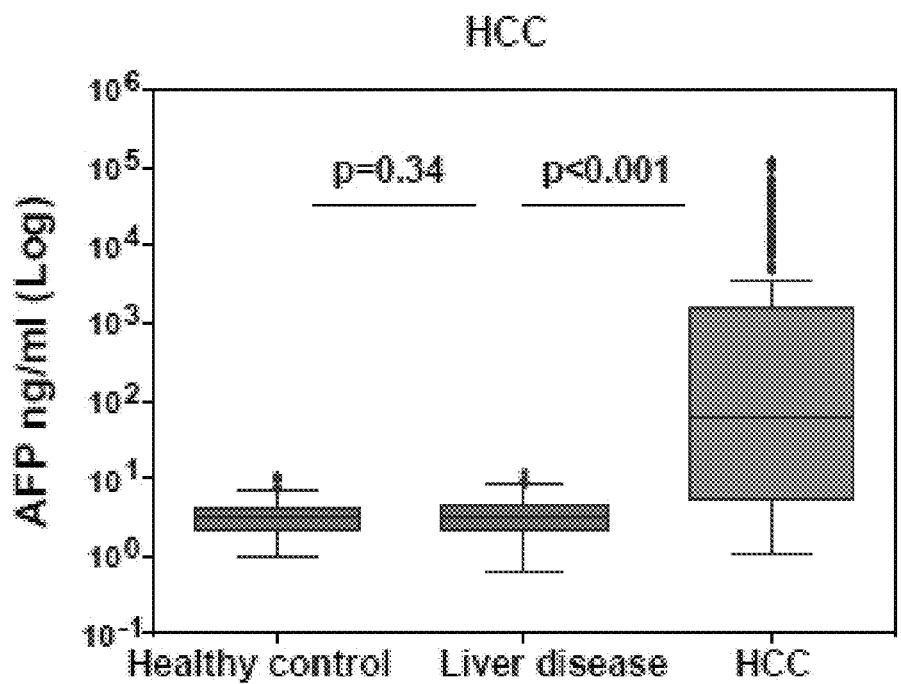
Figure 3C:
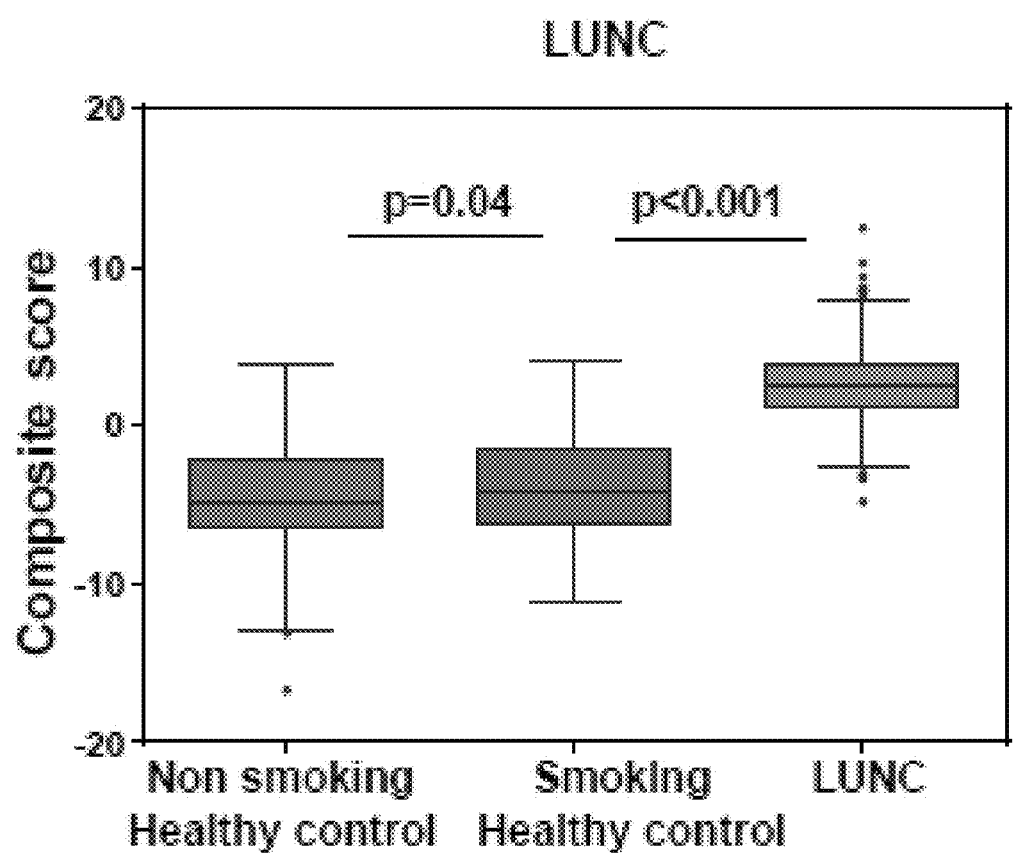

The cd-score of the model for differentiating between liver diseases (HBV/HCV infection, cirrhosis, and fatty liver) and HCC were assessed since these liver diseases are the known major risk factors for HCC. It was found that the cd-score was able to differentiate HCC patients from those with liver diseases or healthy controls (FIG. 3A). These results were consistent and comparable with those predicted by AFP levels in HCC (FIG. 3B). The composite diagnostic score could also differentiate between LUNC patients and non-LUNC patients with a smoking history (>1 pack/day for ten years) who were at an increased risk of LUNC (FIG. 3C).

Methylation Markers Predicted Tumor Burden Treatment Response and Staging

Figure 4E:
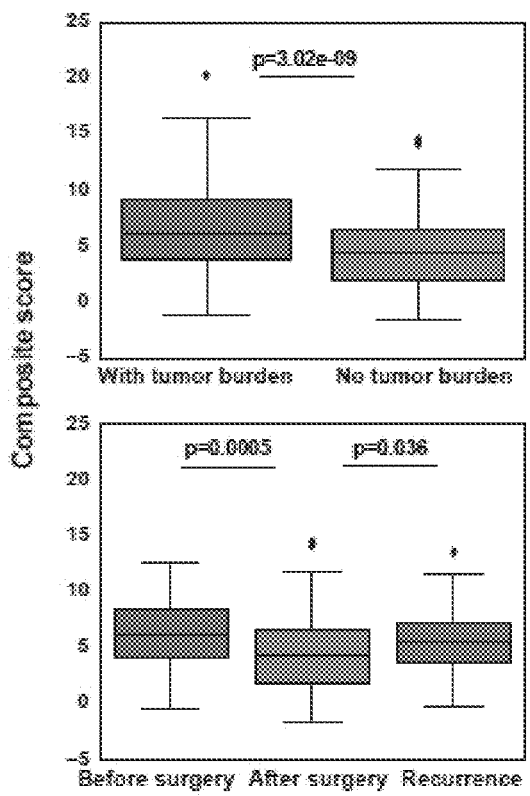
Figure 4E:
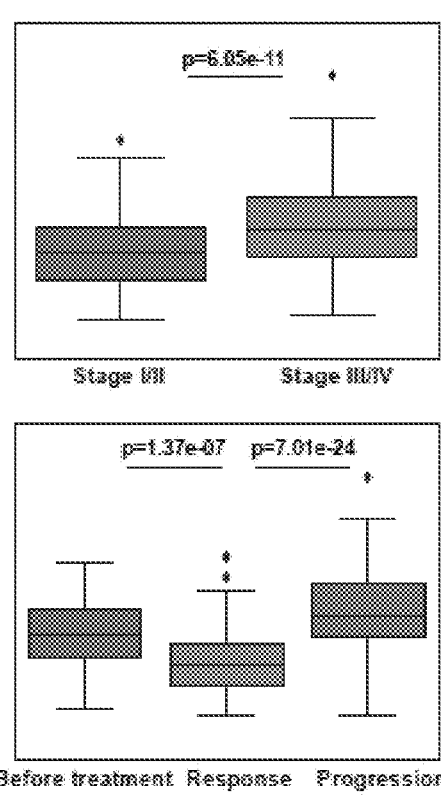
Figure 4G:
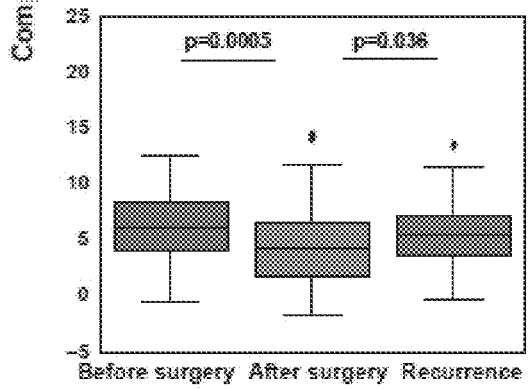
Figure 4H:
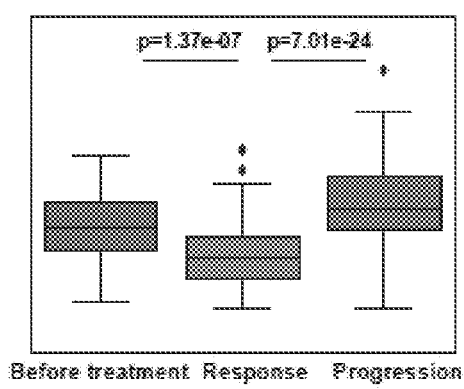
Figure 10A:
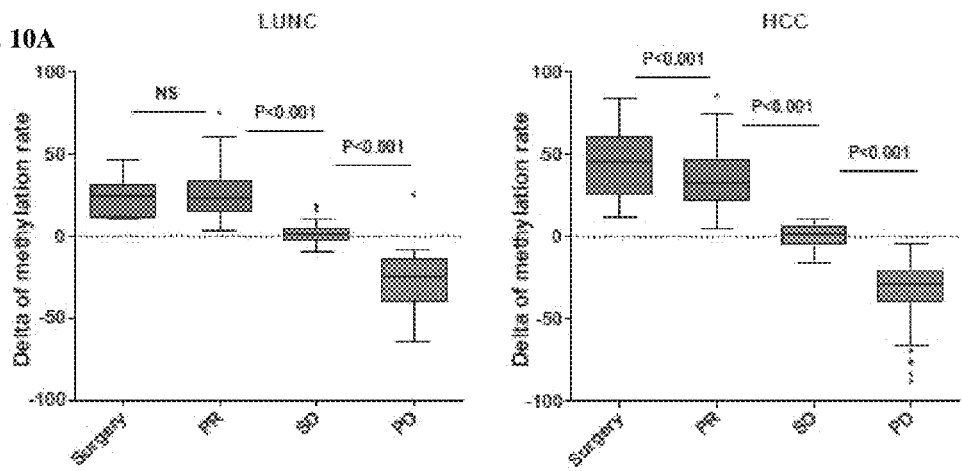
FIG. 10A-FIG. 10B show methylation values correlated with treatment outcomes in HCC and LUNC patients with serial plasma samples.
Figure 10B:
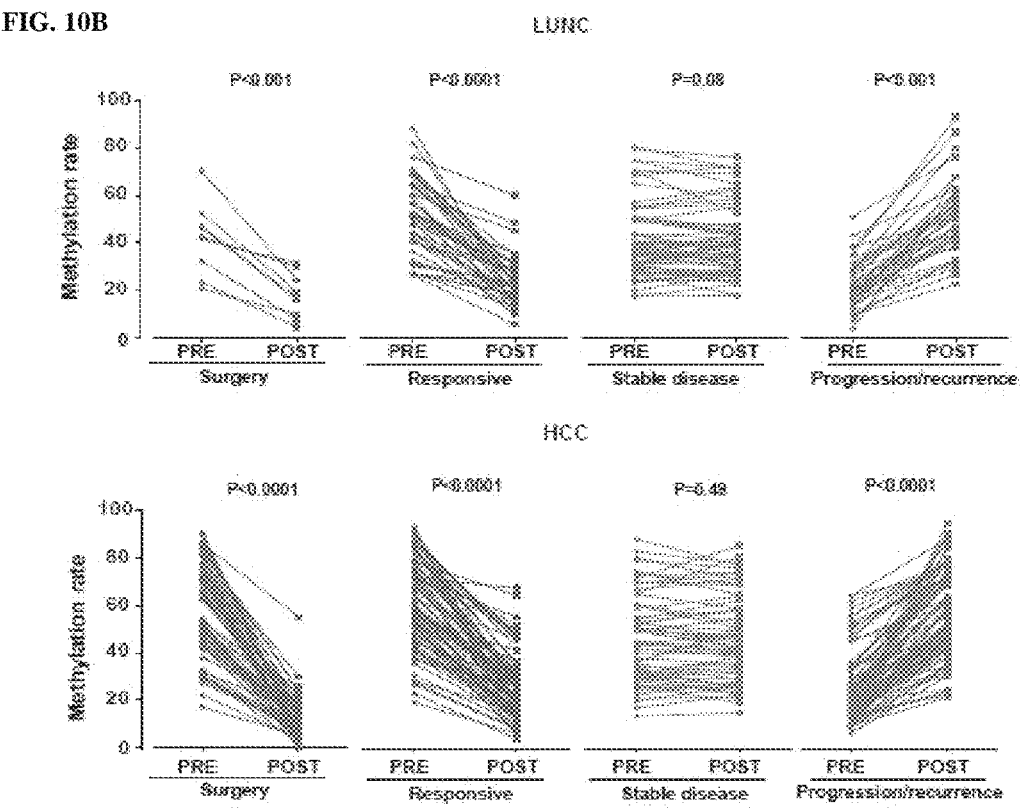
Figure 11A:
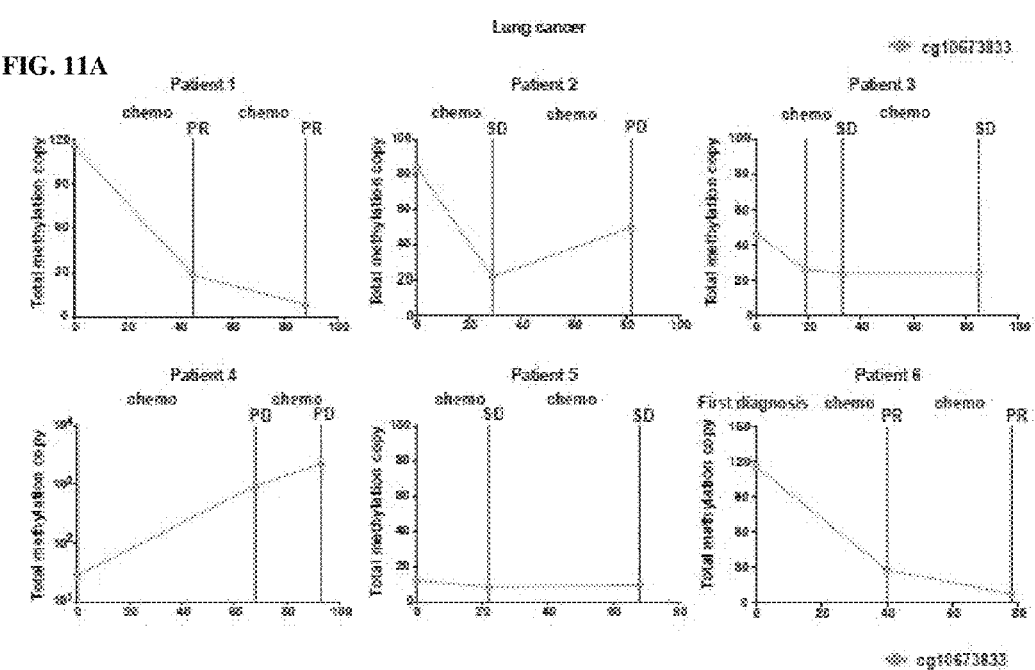
FIG. 11A shows dynamic monitoring of treatment outcomes using the total methylation copy numbers of an MCB in LUNC patients.
Figure 11B:
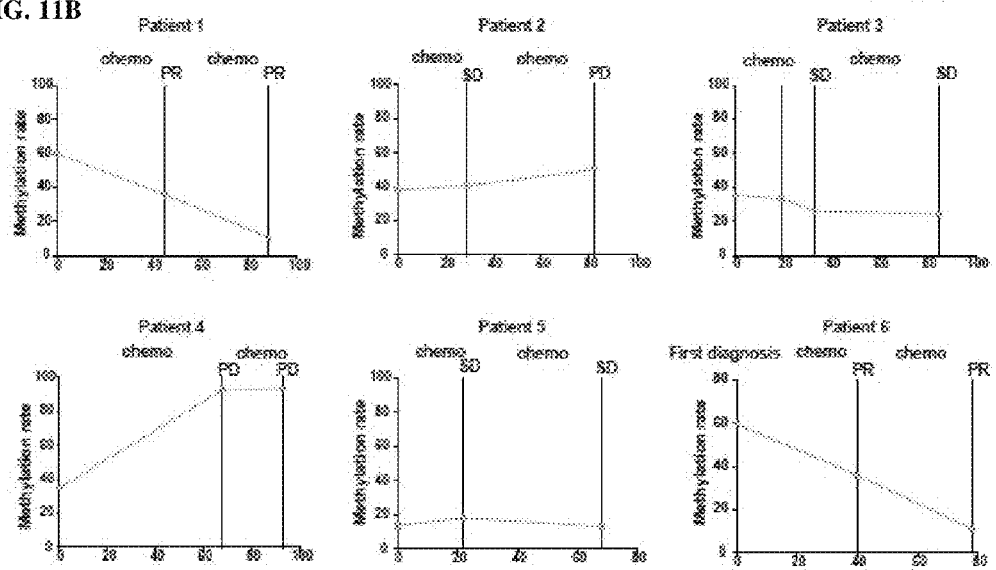
FIG. 11B shows dynamic monitoring of treatment outcomes with the methylation value of an MCB in LUNC patients. PD, progressive disease; PR partial response; SD, stable disease; chemo, chemotherapy.
Figure 12A:
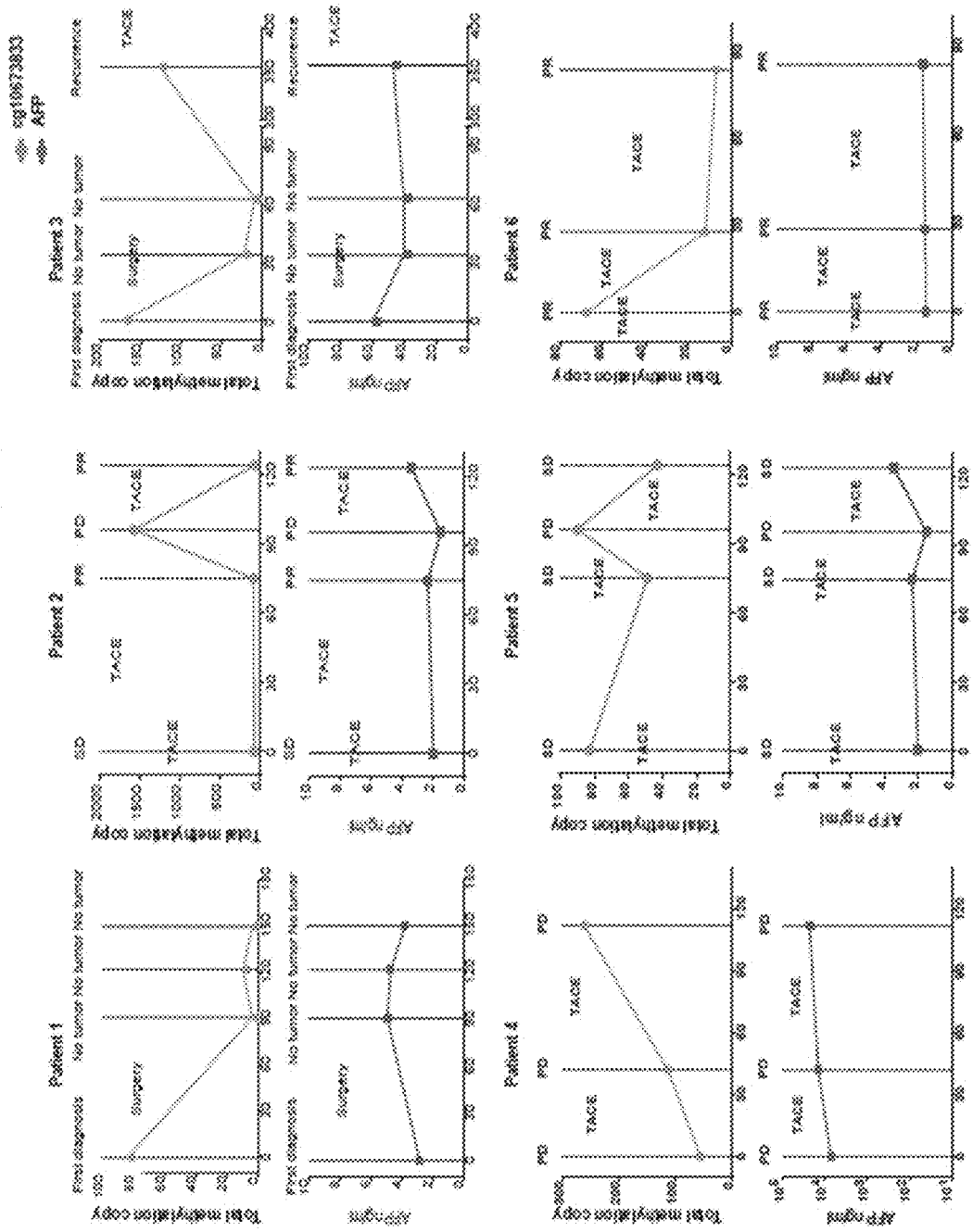
FIG. 12A shows dynamic monitoring of treatment outcomes using the total methylation copy numbers of an MCB and AFP in HCC patients.
Figure 12B:
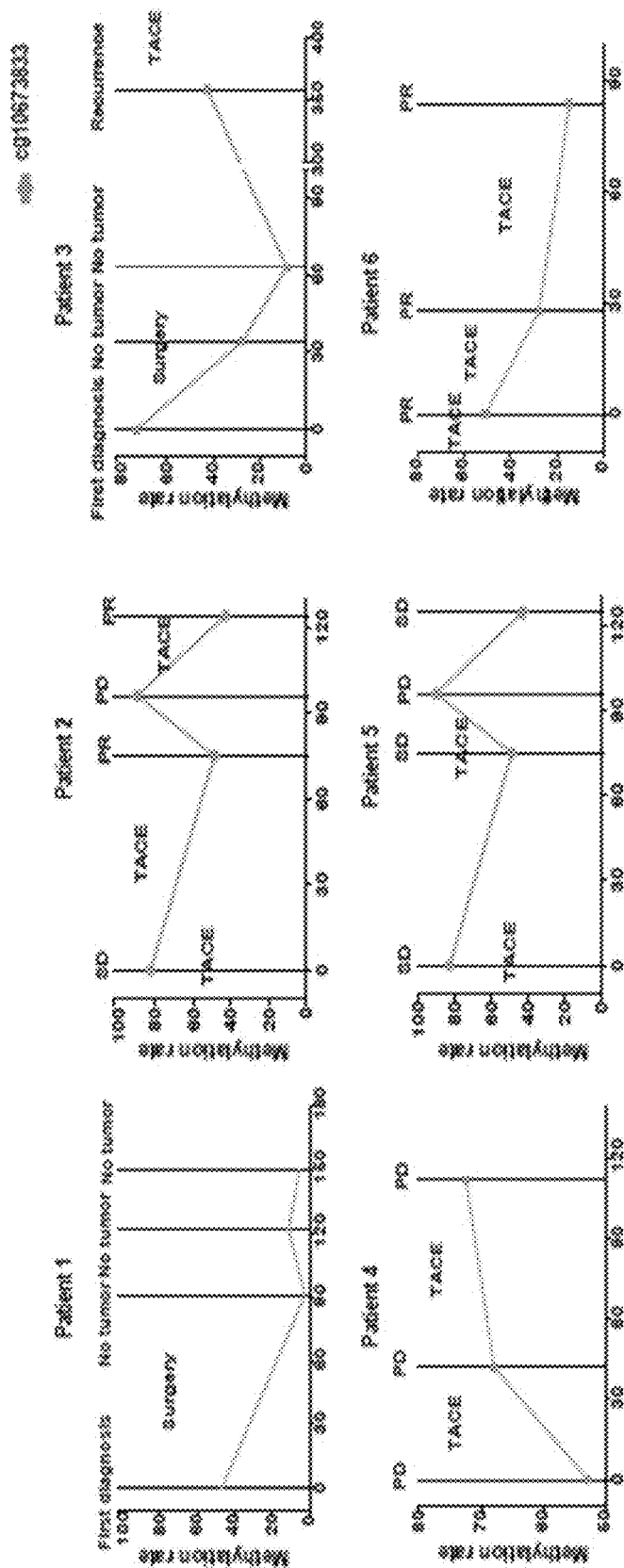
FIG. 12B shows dynamic monitoring of treatment outcomes with the methylation rate of an MCB in HCC patients. Dates of treatments are indicated in the figure. PD, progressive disease; PR partial response; SD, stable disease; chemo, chemotherapy, TACE, trans-catheter arterial chemoembolization.
Figure 13:
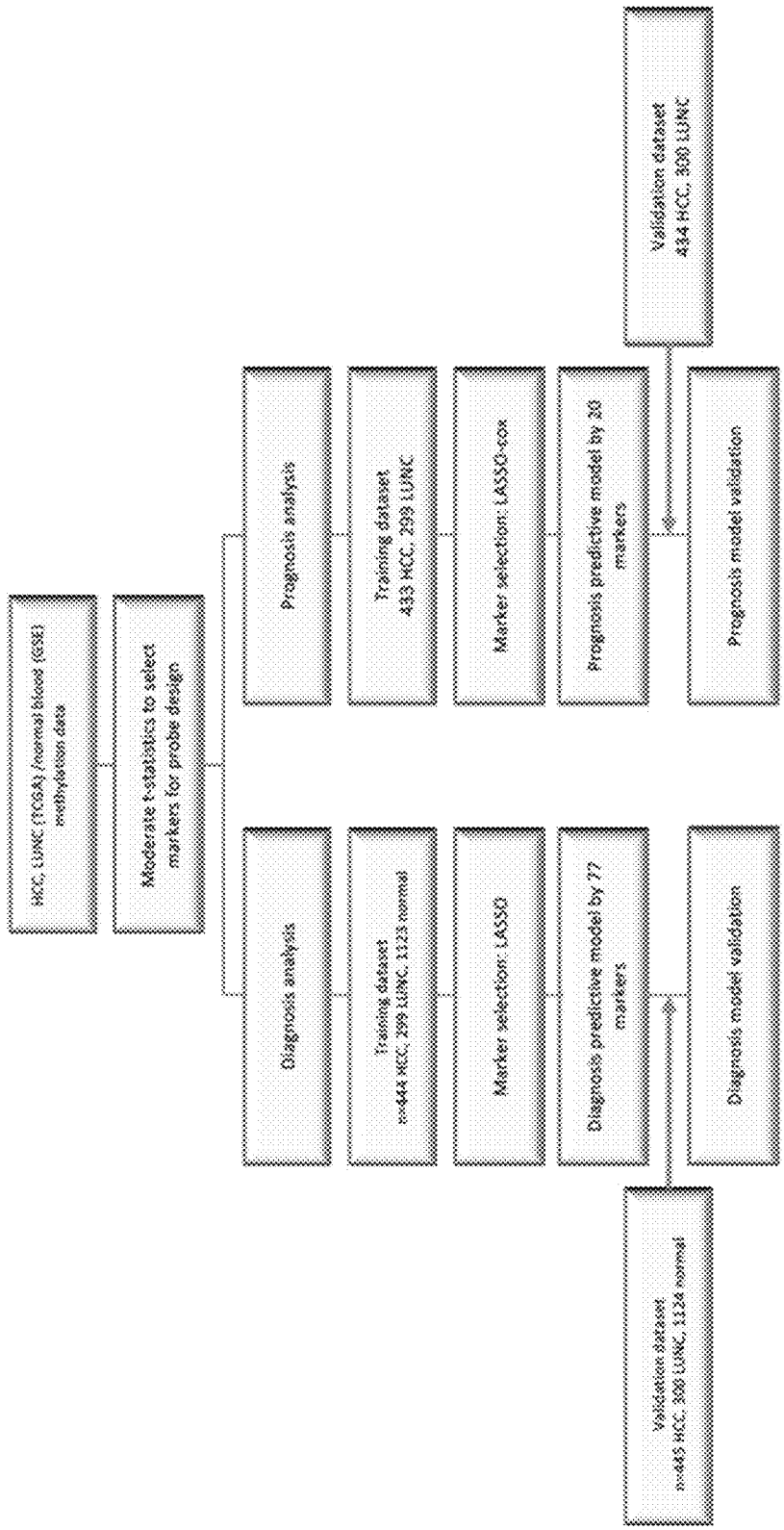
FIG. 13 illustrates a workflow for building the diagnostic and prognostic models. Whole genome methylation data on HCC, LUNC and normal blood were used to identify candidate markers for probe design. Left panel: diagnostic marker selection: LASSO analysis was applied to a training cohort of 444 HCC, 299 LUNC, and 1123 normal patients to identify a final selection of 77 markers. These 77 markers were applied to a validation cohort of 445 HCC, 300 LUNC, and 1124 normal patients. Right panel: prognostic marker selection: LASSO-Cox were applied to a training cohort of 433 HCC and 299 LUNC patients with survival data to identify a final selection of 20 markers. These 20 markers were applied to a validation cohort of 434 HCC and 300 LUNC with survival data.

The utility of the cd-score in assessing treatment response, the presence of residual tumor following treatment, and staging of LUNC and HCC were studied. In LUNC, The cd-scores of patients with detectable residual tumor following treatment (n=513) were significantly higher than those with no detectable tumor (n=126) (p=0.002, FIGS. 4A and 10B). Similarly, there was good correlation between the cd-scores and tumor stage. Patients with early stage disease (I, II) had substantially lower cd-scores compared to those with advanced stage disease (III, IV) (p=0.016, FIG. 4B). In addition, the cd-scores were significantly lower in patients with complete tumor resection after surgery (n=124) compared with those before surgery (n=59), yet became higher in patients with recurrence (n=48) (p<0.01, FIG. 3C). Furthermore, the cd-scores were significantly higher in patients before treatment (n=59) or with progression (n=120) compared to those with a positive treatment response (n=277) (p<0.001, FIG. 4D). In HCC, the cd-scores of patients with detectable residual tumor following treatment (n=495) were significantly higher than those with no detectable tumor (n=156) (p<0.0001, FIG. 4E). Similarly, there was a highly positive correlation between cd-scores and tumor stage. Patients with early stage disease (I, II) had substantially lower cd-scores compared to those with advanced stage disease (III, IV) (p<0.001, FIG. 3F). In addition, the cd-scores were significantly lower in patients with complete tumor resection after surgery (n=146) compared with those before surgery (n=72), yet became higher in patients with recurrence (n=72) (p=0.036, FIG. 3G). Furthermore, the cd-scores were significantly higher in patients before treatment (n=72) or with progression (n=245) compared to those with treatment response (n=105) (p<0.001, FIG. 4H). We were able to obtain serial longitudinal dynamic changes of methylation values in several individuals with LUNC or HCC patient in order to monitor treatment response and found there was a high correlation between methylation values and treatment outcomes (FIGS. 10, 11 and 12). Collectively, these results suggest that the cd-score (i.e., the amount of ctDNA in plasma) is highly correlated with tumor burden and may have utility for predicting tumor response and for surveillance to detect recurrence.

Utility of ctDNA Diagnostic Prediction Model and AFP.

Figure 4I:
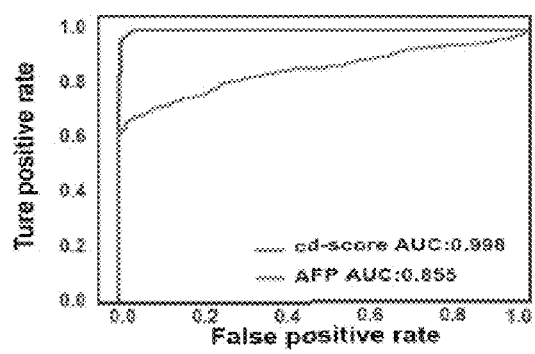
Figure 4J:
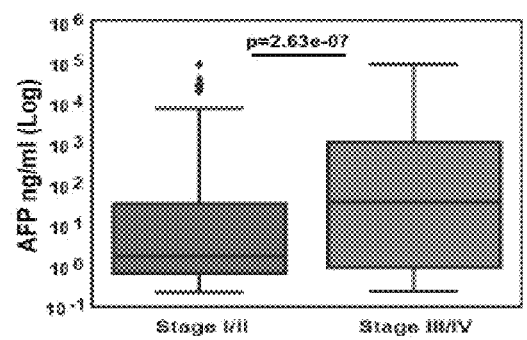
Figure 4K:
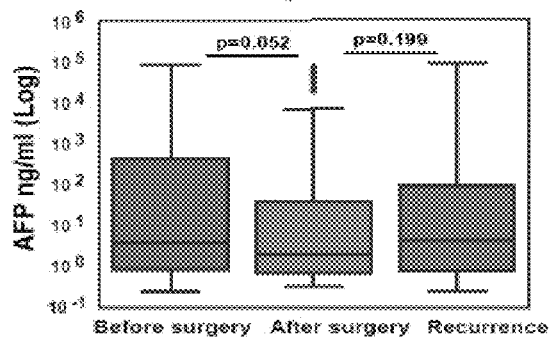
Figure 4L:
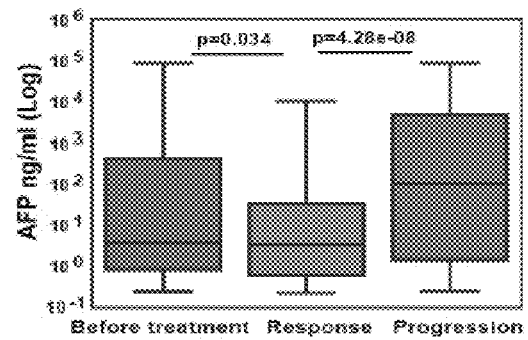

In some instances, the blood biomarker for risk assessment and surveillance of HCC is serum AFP levels. However, AFP has low sensitivity making it inadequate for detection of all patients that will develop HCC and severely limiting its clinical utility. In some cases, many cirrhotic patients develop HCC without any increase in AFP levels. For example, about 40% patients of the HCC study cohort have a normal AFP value (<25 ng/ml). In biopsy-proven HCC patients, the cd-score demonstrated superior sensitivity and specificity to AFP for HCC diagnosis (AUC 0.998 vs 0.855, FIG. 4I). Both cd-score and AFP values were highly correlated with tumor stage (FIGS. 4J and 4K). In patients with treatment response, tumor recurrence, or progression, cd-score showed more significant changes from initial diagnosis than that of AFP (FIGS. 4K and 4L). In patients with serial samples, those with a positive treatment response had a concomitant and significant decrease in cd-score compared to that prior to treatment, and there was an even further reduction in cd-score in patients after surgery. In contrast, patients with progressive or recurrent disease had an increase in methylation rate (FIG. 10). By comparison, AFP was less sensitive for assessing treatment efficacy in individual patients (FIG. 12).

ctDNA Prognostic Model for HCC and LUNC

Figure 5A:
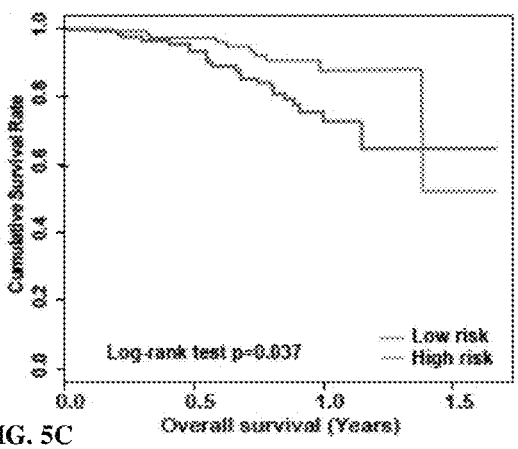
FIG. 5A-FIG. 5F show prognostic prediction in HCC and LUNC survival based on cfDNA methylation profiling.
Figure 5B:
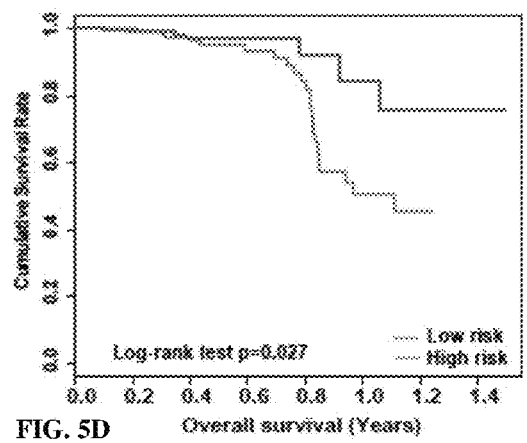

The potential to use a combined prognosis score (cp-score) based on cfDNA methylation analysis for prediction of prognosis in LUNC and HCC in combination with clinical and demographic characteristics including age, gender, AJCC stage, and AFP value was investigated. In the HCC cohort, the training dataset contained 764 observations with 69 events and the validation dataset contained 382 observations with 31 events. By using statistical learning methods, a predictive model using 10 CpG markers (Table 3) that can separate the HCC cohort into high and low risk groups was constructed, with median survival significantly greater in the low-risk group than in the high-risk group (log-rank test=4.884, df=1, p=0.027) (FIG. 5A). In the LUNC cohort, the training dataset contained 437 observations with 69 events and the validation dataset contained 220 observations with 33 events. A panel of 12 CpG markers (Table 3) was able to divide the LUNC cohort into high and low risk groups, with median survival significantly greater in the low-risk group than in the high-risk group (log-rank test=4.35, df=1, p=0.037) (FIG. 5B).

Figure 5C:
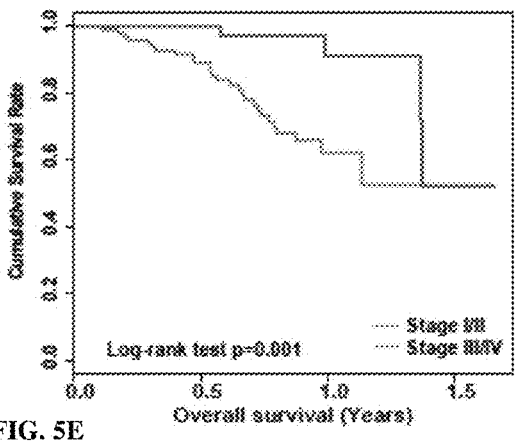
Figure 5D:
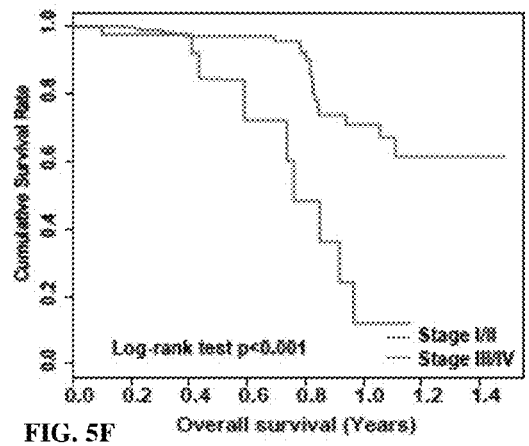
Figure 5E:
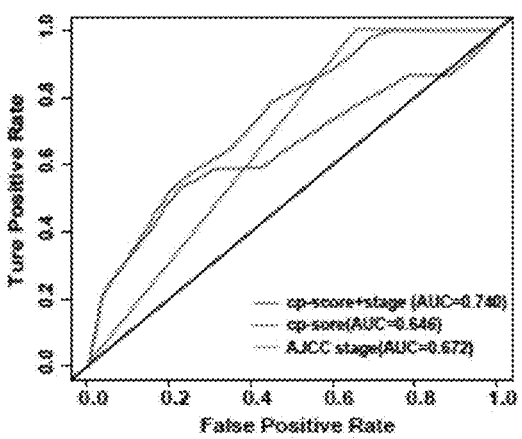
Figure 5F:
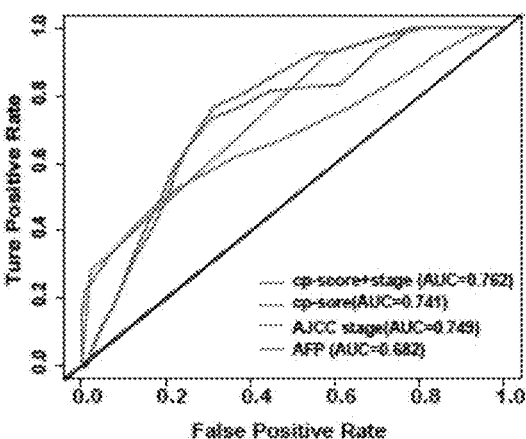

Multivariate Cox regression model showed that the cp-score was significantly correlated with incidence of mortality in both HCC and LUNC. The cp-score was an independent risk factor of survival both in HCC and LUNC validation cohorts (Coef 0.37; p=0.03 in HCC; Coef: 0.28; p=0.0017 in LUNC; Table S2). Interestingly, AFP was no longer significant as a risk factor when cp-score and other clinical characteristics were taken into account in HCC (Table 5). As expected, TNM stage (as defined by the AJCC guideline) predicted the prognosis of patients both in HCC and LUNC (FIGS. 5C and 5D). The combination of cp-score and TNM staging significantly improved our ability to predict prognosis in both HCC (AUC 0.762) and LUNC cohort (AUC 0.740) (FIGS. 5E and 5F).

Table 1A shows a confusion table of multi-classification predicted diagnosis in the validation cohort.

| VALIDATION COHORT | HCC | LUNC | NORMAL | Totals |
|---|---|---|---|---|
| HCC | 187 | 13 | 8 | |
| LUNC | 22 | 175 | 26 | |
| Normal | 9 | 30 | 255 | |
| Totals | 218 | 218 | 289 | 725 |
| Correct | 187 | 175 | 255 | 617 |
| Sensitivity (%) | 85.8 | 80.3 | | |
| Specificity (%) | | | 88.2 | 85.1 |

Table 1B shows a confusion table of binary classification predicted diagnosis between normal and HCC in the validation cohort.

| VALIDATION COHORT | HCC | NORMAL | Totals |
|---|---|---|---|
| HCC | 207 | 13 | |
| Normal | 11 | 276 | |
| Totals | 218 | 289 | 507 |
| Correct | 207 | 276 | 483 |
| Sensitivity (%) | 94.9 | | |
| Specificity (%) | | 95.5 | 95.3 |

Table 1C shows a confusion table of binary classification diagnosis between normal and LUNC in the validation cohort.

| VALIDATION COHORT | LUNC | NORMAL | Totals |
|---|---|---|---|
| LUNC | 189 | 26 | |
| Normal | 29 | 263 | |
| Totals | 218 | 289 | 507 |
| Correct | 189 | 263 | 452 |
| Sensitivity (%) | 86.7 | | |
| Specificity (%) | | 91.0 | 89.2 |

Table 1D shows a contingency table of binary classification diagnosis between LUNC and HCC in validation cohort.

| VALIDATION COHORT | HCC | LUNC | Totals |
|---|---|---|---|
| HCC | 196 | 14 | |
| LUNC | 22 | 204 | |
| Totals | 218 | 218 | 436 |
| Correct | 196 | 204 | 400 |
| Sensitivity (%) | 89.9 | | |
| Specificity (%) | | 93.6 | 91.7 |

Table 2 shows characteristics of 100 methylation markers and their coefficients in diagnosis.

| | diagnosis | Marker | feature selection: t-stat | logistic regression coef: lihc | logistic regression coef: normal | logistic regression coef: nsclc |
|---|---|---|---|---|---|---|
| 99 | caner vs cancer | 6-415285 | -17.61364538 | -0.236675214 | 0.010279099 | 0.023841014 |
| 10 | caner vs cancer | 17-39068 | -23.95893113 | -0.037590318 | -0.576572433 | -0.855315385 |
| 93 | caner vs cancer | 8-28799 | -18.05697716 | 0.216408897 | 0.192819267 | 0.366347583 |
| 3 | caner vs cancer | 17-759561 | -26.52474648 | -1.367721168 | -0.956150328 | -0.054902768 |
| 85 | caner vs cancer | 1-1568670 | -18.62705548 | 0.008670072 | 0.423911407 | 0.022632223 |
| 88 | caner vs cancer | 22-222885 | -18.57400396 | -0.326246574 | -0.198542802 | 0.43976473 |
| 89 | caner vs cancer | 3-1138223 | -18.55509702 | -0.393347975 | -1.396202888 | -1.807959073 |
| 90 | caner vs cancer | 1-2035950 | -18.51737266 | 0.115297952 | -0.4031146 | 0.0238655 |
| 4 | caner vs cancer | 17-759562 | -26.49964747 | -0.788704497 | -1.269985136 | 0.08324756 |
| 1 | caner vs cancer | 17-802603 | -27.95631084 | -0.044811111 | -0.439876458 | -0.823216834 |
| 83 | caner vs cancer | 1-2130901 | -18.64276869 | 0.432663118 | -0.629658794 | -0.417586625 |
| 82 | caner vs cancer | 18-434054 | -18.741526 | -0.401160179 | -0.515157305 | -0.804483279 |
| 92 | caner vs cancer | 6-262504 | -18.22430745 | -0.24712752 | -0.169911531 | 0.266218748 |
| 94 | caner vs cancer | 2-741531 | -17.86310499 | 0.356517591 | -0.15981238 | -0.35043126 |
| 79 | caner vs cancer | 3-452092 | -18.90554153 | -0.554783023 | -1.031814454 | -0.2629371 |
| 78 | caner vs cancer | 10-1350729 | -18.91807833 | -0.01273024 | -0.355980173 | -0.178555972 |
| 77 | caner vs cancer | 22-455977 | -18.94775481 | 1.345069788 | 0.266979058 | -2.312805466 |
| 76 | caner vs cancer | 21-456224 | -19.00487584 | 0.053035206 | -0.287082772 | -0.159022737 |
| 95 | caner vs cancer | 1-2130902 | -17.85100263 | -0.296114847 | -0.674120091 | 0.200710002 |
| 96 | caner vs cancer | 6-415284 | -17.82263372 | -0.145333786 | -0.004754725 | 0.161187342 |
| 97 | caner vs cancer | 6-30238 | -17.74738532 | 0.201307581 | -0.48399364 | -0.419071695 |

-continued

| | diagnosis | Marker | feature selection: t-stat | logistic regression coef: lihc | logistic regression coef: normal | logistic regression coef: nsclc |
|---|---|---|---|---|---|---|
| 8 | caner vs cancer | 8-486563 | −24.34195503 | −0.074149402 | 0.136565598 | −0.309646468 |
| 66 | caner vs cancer | 21-456223 | −19.41711427 | −0.169615641 | −0.422104365 | −0.147740017 |
| 68 | caner vs cancer | 9-976919 | −19.19924646 | 0.169754429 | −0.149870129 | 0.045179717 |
| 35 | caner vs cancer | 18-611439 | −20.84385078 | 0.659900298 | 1.179733872 | −1.28247216 |
| 36 | caner vs cancer | 6-329093 | −20.82914197 | 0.111947525 | −0.604232399 | −0.102113798 |
| 67 | caner vs cancer | 15-916424 | −19.20472322 | 1.098337579 | 0.123021312 | −0.425357804 |
| 14 | caner vs cancer | 21-364215 | −23.147695 | −0.349765433 | −0.333626994 | 0.209847484 |
| 63 | caner vs cancer | 9-976918 | −19.4484243 | −0.019813131 | −0.338493813 | −0.042379462 |
| 16 | caner vs cancer | 21-364214 | −23.01536252 | −0.053301516 | 0.028343845 | 0.177763167 |
| 61 | caner vs cancer | 22-378130 | −19.4880008 | 0.308365313 | 0.170565161 | 0.122550653 |
| 60 | caner vs cancer | 17-803588 | −19.49541887 | −0.292169228 | −0.024314234 | −0.368713245 |
| 59 | caner vs cancer | 5-1715385 | −19.5319759 | −0.249838093 | −0.956471176 | −0.071441678 |
| 18 | caner vs cancer | 19-546461 | −22.97080946 | −0.388273429 | −0.057401189 | 0.836969628 |
| 56 | caner vs cancer | 22-378131 | −19.72884156 | −0.284358361 | −0.110871059 | −0.131062087 |
| 19 | caner vs cancer | 19-546460 | −22.9605052 | −0.566211213 | 0.10298505 | 0.659746482 |
| 9 | caner vs cancer | 7-10939 | −24.19828156 | 0.007764618 | −0.684892994 | −0.760831017 |
| 53 | caner vs cancer | 6-1704942 | −19.84874402 | 0.378542639 | −0.542555509 | −0.957150419 |
| 11 | caner vs cancer | 7-10938 | −23.95579676 | 0.082561272 | −0.418722384 | −0.561011155 |
| 47 | caner vs cancer | 1-2115009 | −20.06586747 | −0.093577505 | 0.302518574 | 0.20564016 |
| 44 | caner vs cancer | 15-555695 | −20.15008607 | −0.803302241 | −0.382712364 | −0.30159139 |
| 43 | caner vs cancer | 3-452091 | −20.27929394 | −0.514707374 | 0.371259532 | −0.466839863 |
| 26 | caner vs cancer | 5-1675324 | −21.67048751 | −1.05021205 | −0.49235019 | 0.553850706 |
| 27 | caner vs cancer | 15-555694 | −21.57393773 | 0.023652533 | 0.240962939 | 0.232753361 |
| 40 | caner vs cancer | 10-1016060 | −20.46892585 | 0.029381721 | −0.426585276 | 0.033829985 |
| 39 | caner vs cancer | 5-1675325 | −20.59032645 | 0.480863067 | 0.275781467 | −0.402068556 |
| 28 | caner vs cancer | 10-7787 | −21.5431691 | 0.00598852 | −0.199608747 | −0.170189137 |
| 29 | caner vs cancer | 10-7786 | −21.47479725 | 0.038463232 | −0.220956901 | −0.015378708 |
| 48 | caner vs cancer | 6-1704943 | −20.04539412 | 0.115741682 | −0.518054639 | −0.856636887 |
| 98 | caner vs cancer | 12-1222773 | −17.72217416 | 0.16301047 | −1.858171112 | −1.216496148 |
| 0 | normal vs cancer vs cancer | 7-1017626 | −32.6798181 | −1.803275893 | 0.175153741 | 2.926283828 |
| 25 | normal vs cancer vs cancer | 2-382009 | −21.67679298 | −0.114868278 | 0.267337677 | 0.007397738 |
| 73 | normal vs cancer vs cancer | 14-556474 | −19.09929792 | 1.028802553 | 1.469882366 | 0.740193974 |
| 72 | normal vs cancer vs cancer | 13-988696 | −19.10886072 | 0.539713717 | −0.623018315 | −0.526201237 |
| 71 | normal vs cancer vs cancer | 1-2262968 | −19.11861008 | −0.639678522 | −0.087686268 | 0.512492514 |
| 70 | normal vs cancer vs cancer | 8-28798 | −19.14821227 | −0.650234953 | −0.804653337 | 0.150659271 |
| 69 | normal vs cancer vs cancer | 16-724596 | −19.17897078 | −0.181424125 | −0.144884684 | −0.006709982 |
| 65 | normal vs cancer vs cancer | 11-646423 | −19.42858974 | 0.137556127 | 0.769045641 | 1.010936575 |
| 64 | normal vs cancer vs cancer | 11-11026 | −19.42859291 | −0.384110053 | −0.360784146 | 0.149990972 |
| 62 | normal vs cancer vs cancer | 22-222884 | −19.47573625 | −0.639960957 | −0.778683987 | −0.556777877 |
| 58 | normal vs cancer vs cancer | 10-38238 | −19.67767651 | 0.765456023 | 1.021326356 | 0.391045996 |
| 57 | normal vs cancer vs cancer | 7-546123 | −19.69433464 | −0.558118495 | 0.714728365 | 1.200526621 |
| 55 | normal vs cancer vs cancer | 1-2115267 | −19.73690799 | −0.125706754 | 0.507930814 | −0.305947675 |
| 54 | normal vs cancer vs cancer | 11-11025 | −19.82113917 | −0.132624247 | −0.173316324 | 0.057514538 |

| | diagnosis | Marker | feature selection: t-stat | logistic regression coef: lihc | logistic regression coef: normal | logistic regression coef: nsclc |
|---|---|---|---|---|---|---|
| 52 | normal vs cancer vs cancer | 17-554565 | −19.87060257 | −0.001212871 | 0.035726276 | 0.060919648 |
| 51 | normal vs cancer vs cancer | 16-724595 | −19.87484907 | −0.698771621 | −0.122429418 | 0.213552543 |
| 50 | normal vs cancer vs cancer | 10-1188922 | −19.94415652 | 0.526723185 | 0.917937922 | −0.086531139 |
| 46 | normal vs cancer vs cancer | 10-1188921 | −20.0927365 | −0.078902836 | 0.164631916 | −0.387873458 |
| 45 | normal vs cancer vs cancer | 2-2402599 | −20.12830443 | 0.598962307 | 1.134520813 | 0.5877791 |
| 42 | normal vs cancer vs cancer | 2-1139315 | −20.3243112 | −0.633540516 | 0.613485917 | 1.167536542 |
| 41 | normal vs cancer vs cancer | 10-61622 | −20.42327924 | 0.005372067 | 0.196382224 | −0.085414271 |
| 38 | normal vs cancer vs cancer | 1-2115266 | −20.69111164 | −0.769131956 | 0.345916524 | 1.254836456 |
| 37 | normal vs cancer vs cancer | 3-1018088 | −20.80693297 | 0.609398167 | −0.090557439 | −0.766058116 |
| 74 | normal vs cancer vs cancer | 16-900927 | −19.08800159 | 0.912529483 | 0.453859311 | −0.179151851 |
| 30 | normal vs cancer vs cancer | 13-1141899 | −21.34469521 | −1.031186323 | −0.389204596 | 0.749708189 |
| 75 | normal vs cancer vs cancer | 2-34738 | −19.06924964 | 0.93625842 | 0.991715759 | −0.688867756 |
| 81 | normal vs cancer vs cancer | 2-1279336 | −18.75400747 | 0.26785859 | 0.679898396 | 1.980063473 |
| 21 | normal vs cancer vs cancer | 3-1948265 | −22.40390002 | −0.351581796 | 0.278320012 | 0.670590713 |
| 2 | normal vs cancer vs cancer | 3-1971214 | −26.9760943 | −1.096565994 | −1.140434035 | 0.235954502 |
| 23 | normal vs cancer vs cancer | 2-33179 | −21.87723261 | −0.367084719 | −0.982935256 | 0.385724888 |
| 22 | normal vs cancer vs cancer | 17-579158 | −22.35886206 | −0.855883545 | −0.643500898 | 0.371049084 |
| 12 | normal vs cancer vs cancer | 1-1511292 | −23.69581782 | −0.040188828 | 0.017871212 | 0.57857198 |
| 20 | normal vs cancer vs cancer | 7-1511060 | −22.42273418 | −0.344691441 | −0.52467607 | −0.001475964 |
| 5 | normal vs cancer vs cancer | 4-840359 | −25.59587088 | −0.908150793 | −0.023595253 | −0.493610136 |
| 17 | normal vs cancer vs cancer | 2-33180 | −22.98082672 | 0.031485683 | 0.578377676 | 0.561864702 |
| 6 | normal vs cancer vs cancer | 3-1971213 | −25.22834725 | 0.159158596 | −0.177874427 | −0.0415477 |
| 15 | normal vs cancer vs cancer | 6-1344914 | −23.0638498 | −0.765362602 | −0.056385391 | 0.371844191 |
| 7 | normal vs cancer vs cancer | 17-579157 | −24.69417969 | −1.836100826 | −0.49945522 | 1.378041275 |
| 32 | normal vs cancer vs cancer | 5-1729823 | −21.10727499 | 0.49063763 | 0.442695007 | 0.228719149 |

| | diagnosis | Marker | feature selection: t-stat | logistic regression coef: lihc | logistic regression coef: normal | logistic regression coef: nsclc |
|---|---|---|---|---|---|---|
| 13 | normal vs cancer vs cancer | 10-61621 | −23.33984193 | −0.732975123 | −0.170666754 | 0.853088439 |
| 31 | normal vs cancer vs cancer | 10-1341418 | −21.14588727 | −0.360228601 | −0.189755315 | 0.322305225 |
| 49 | normal vs cancer vs cancer | 16-855515 | −19.97033653 | −0.913916851 | 0.004403469 | 0.352850662 |
| 33 | normal vs cancer vs cancer | 7-353011 | −21.10478683 | 0.560990981 | 1.26871861 | 0.300870717 |
| 34 | normal vs cancer vs cancer | 2-2402598 | −20.95079767 | 0.560267322 | 0.568318096 | 0.352815469 |
| 91 | normal vs cancer vs cancer | 6-1574305 | −18.45922482 | 0.102685453 | 0.425266208 | −0.273613465 |
| 87 | normal vs cancer vs cancer | 2-690270 | −18.57780227 | 0.740025901 | −0.409429644 | −0.359030027 |
| 86 | normal vs cancer vs cancer | 6-1574304 | −18.58806884 | −0.095348947 | 0.333302114 | 0.04190651 |
| 84 | normal vs cancer vs cancer | 16-855514 | −18.62861605 | 0.020279096 | 0.051846711 | −0.155772388 |
| 80 | normal vs cancer vs cancer | 17-765013 | −18.86145879 | 0.791465144 | 0.476433898 | 0.192061881 |
| 24 | normal vs cancer vs cancer | 2-382010 | −21.732045 | −0.230367057 | 0.218145876 | −0.201298246 |

Table 3 shows Characteristics of 10 MCBs in HCC and 12 MCBs in LUNC for prediction of prognosis. Markers, MCB names; Target ID, initial cg markers used to perform targeted capture sequencing; Ref Gene, genes overlap with a MCB.

| Cancer type | Markes | Target ID | Ref Gene |
|---|---|---|---|
| HCC | X12.939663 | cg11225410 | SOCS2 |
| | X13.435663 | cg00338116 | EPSTI1 |
| | X2.704752 | cg00552226 | TIA1 |
| | X4.14001 | cg24496475 | CH4: |
| | X6.262503 | cg05414338 | CH6: |
| | X6.271255 | cg12041340 | CH6: |
| | X6.283040 | cg08343881 | ZNF323 |
| | X6.415284 | cg03431741 | FOXP4 |
| | X6.733300 | cg17126142 | CH6: |
| | X8.1025045 | cg18004756 | GRHL2 |
| LUNC | X8.538511 | cg26205771 | NPBWR1 |
| | X2.2355288 | cg08436738 | CH2: |
| | X2.698469 | cg01604601 | AAK1 |
| | X6.1009129 | cg27252696 | SIM1 |
| | X10.1205149 | cg24917945 | C10orf46 |
| | X17.803588 | cg11252953 | C17orf101 |
| | X22.321497 | cg03550506 | DEPDC5 |
| | X6.283041 | cg06903569 | ZNF323 |
| | X6.1009115 | cg12865837 | SIM1 |
| | X4.463914 | cg18440897 | GABRA2 |
| | X4.840359 | cg19255783 | PLAC8 |
| | X2.967814 | cg20634573 | ADRA2B |

Table 4 shows clinical characteristics of study cohort.

| Characteristic | TCGA HCC tissue | TCGA LUNC tissue | GSE Normal blood | HCC blood | LUNC blood | Normal blood |
|---|---|---|---|---|---|---|
| Total (n) | 377 | 827 | 754 | 654 | 654 | 865 |
| Gender | | | | | | |
| Female-no.(%) | 122(32.4) | 340(41.1) | 401(53.2) | 79(12.1) | 219(33.5) | 429(49.6) |
| Male-no.(%) | 255(67.6) | 487(58.9) | 353(46.8) | 548(83.8) | 415(63.4) | 418(48.3) |
| NA | 0 | 0 | 0 | 27(4.1) | 20(3.1) | 18(2.1) |
| Age (years) | | | | | | |
| Mean | 61 | 68 | 63 | 54 | 59 | 47 |
| Range | 16-90 | 33-90 | 19-101 | 15-84 | 28-85 | 19-90 |

-continued

| Characteristic | TCGA HCC tissue | TCGA LUNC tissue | GSE Normal blood | HCC blood | LUNC blood | Normal blood |
|---|---|---|---|---|---|---|
| Pathology | | | | | | |
| Hepatocellular carcinoma | 367(97.3) | 0 | NA | 654(100) | 0 | NA |
| Adenocarcinoma | 0 | 458(55.4) | NA | 0 | 338(51.7) | NA |
| Squamous cell carcinoma | 0 | 369(44.6) | NA | 0 | 229(35.0) | NA |
| Small Cell Lung Cancer | 0 | 0 | NA | 0 | 65(9.9) | NA |
| Others | 10(2.7) | 0 | NA | 0 | 22(3.4) | NA |
| Stage | | | | | | |
| I | 175(46.4) | 424(51.3) | NA | 96(14.7) | 49(7.5) | NA |
| II | 87(23.1) | 115(13.9) | NA | 101(15.4) | 42(6.4) | NA |
| III | 86(22.8) | 261(31.6) | NA | 342(52.3) | 126(19.3) | NA |
| IV | 6(1.6) | 25(3.0) | NA | 81(12.4) | 394(60.2) | NA |
| NA | 23(6.1) | 2(0.2) | NA | 34(5.2) | 43(6.6) | NA |
| Tumor burden | | | | | | |
| Tumor free | 236(62.6) | 503(60.8) | NA | 156(23.9) | 126(19.3) | NA |
| With tumor | 114(30.2) | 159(19.2) | NA | 495(75.7) | 513(78.4) | NA |
| NA | 27(7.2) | 165(20.0) | NA | 3(0.4) | 15(2.3) | NA |
| EGFR status | | | | | | |
| Wide type | NA | 400(48.4) | NA | NA | 90(13.7) | NA |
| Mutation | NA | 100(12.1) | NA | NA | 54(8.3) | NA |
| NA | NA | 327(39.5) | NA | NA | 510(78.0) | NA |
| Hepatic | | | | | | |
| Postive | 120(31.8) | NA | NA | 623(95.3) | NA | 346(40.0) |
| Negtive | 119(31.6) | NA | NA | 10(1.5) | NA | 505(58.4) |
| NA | 138(36.6) | NA | NA | 21(3.2) | NA | 14(1.6) |
| Smoking | | | | | | |
| Current smoker | NA | 725(87.7) | NA | NA | NA | 180(20.8) |
| Non-smoker | NA | 80(9.7) | NA | NA | NA | 671(77.6) |
| NA | NA | 22(2.6) | NA | NA | NA | 14(1.6) |

Table 5 shows multivariate survival analysis for HCC patients and LUNC patients with composite-score of methylation markers and relevant variables.

| Factor | Coef | Exp (coef) | Se (coef) | z | p |
|---|---|---|---|---|---|
| HCC | | | | | |
| cp-score | 0.37 | 1.45 | 0.169 | 2.20 | 0.03 |
| Gender | 1.04 | 2.83 | 0.76 | 1.36 | 0.17 |
| Age | −0.01 | 0.99 | 0.02 | −0.32 | 0.75 |
| Stage | 1.14 | 3.11 | 0.46 | 2.49 | 0.01 |
| AFP | 7.15e−6 | 1.00 | 5.11e−6 | 1.40 | 0.16 |

| Factor | Coef | Exp (coef) | Se (coef) | z | p |
|---|---|---|---|---|---|
| LUNC | | | | | |
| cp-score | 0.28 | 1.33 | 0.12 | 2.39 | 0.0017 |
| Gender | 0.66 | 1.93 | 0.44 | 1.50 | 0.13 |
| Age | 0.02 | 1.02 | 0.02 | 0.85 | 0.39 |
| Stage | 1.42 | 4.12 | 0.56 | 2.53 | 0.01 |
| AFP | NA | NA | NA | NA | NA |

Table 6 shows an illustrative list of 1000 markers (shown with cg identifier) described herein. In some instances, the markers are used in HCC vs. lung analysis.

| | | | | | | |
|---|---|---|---|---|---|---|
| cg20424833 | cg23993235 | cg08128768 | cg26954736 | cg02019444 | cg16243359 | cg19003412 |
| cg09363194 | cg07366553 | cg00177290 | cg18442524 | cg06615380 | cg14063008 | cg09555818 |
| cg06105778 | cg11818438 | cg03388786 | cg24864413 | cg07168204 | cg06197966 | cg12177087 |
| cg23693289 | cg22700686 | cg16038738 | cg07676920 | cg06387141 | cg27433062 | cg26734040 |
| cg24787470 | cg26453360 | cg26944011 | cg05894734 | cg15045356 | cg02149069 | cg27183818 |
| cg00177496 | cg19340420 | cg06302295 | cg16264966 | cg01428750 | cg17516247 | cg01053621 |
| cg20385508 | cg02395363 | cg27499925 | cg18901045 | cg00599393 | cg25060172 | cg22203219 |
| cg22356324 | cg06605158 | cg04359558 | cg03607648 | cg12092939 | cg23352146 | cg16962683 |
| cg02702614 | cg24860886 | cg10505610 | cg21487856 | cg25734035 | cg05590053 | cg21103992 |
| cg03422204 | cg22809315 | cg12269002 | cg20701182 | cg20986726 | cg08822227 | cg04113200 |
| cg07155478 | cg13747967 | cg20163796 | cg05673882 | cg09225388 | cg02734326 | cg22862526 |
| cg06815112 | cg07354371 | cg01994290 | cg01144225 | cg03399971 | cg10110271 | cg18899777 |
| cg12477903 | cg11828446 | cg06429887 | cg14596589 | cg13755546 | cg12332526 | cg24803202 |
| cg03038685 | cg03228760 | cg25096745 | cg18440692 | cg12433486 | cg26703661 | cg00983904 |
| cg07360250 | cg26996201 | cg07571734 | cg00899659 | cg16492597 | cg08110861 | cg18185189 |
| cg19418951 | cg14313833 | cg06601685 | cg00498089 | cg11225357 | cg02280309 | cg18811130 |
| cg04739306 | cg06235390 | cg02927327 | cg19616807 | cg20822579 | cg01855070 | cg18281418 |
| cg00456086 | cg16107172 | cg05583848 | cg20011134 | cg01289874 | cg00026222 | cg18560264 |

-continued

| | | | | | | |
|---|---|---|---|---|---|---|
| cg18234130 | cg03550864 | cg07823562 | cg21058973 | cg02633924 | cg00339769 | cg11083235 |
| cg24869195 | cg05597349 | cg02379560 | cg26313188 | cg12679230 | cg27650175 | cg04132540 |
| cg14221460 | cg05803361 | cg13788381 | cg03238516 | cg07054502 | cg13858803 | cg14480249 |
| cg01518459 | cg08597345 | cg11122795 | cg20365867 | cg13092487 | cg01145544 | cg11816229 |
| cg13197551 | cg00848594 | cg24461337 | cg19026124 | cg20926720 | cg18203965 | cg26536164 |
| cg23983315 | cg18668780 | cg27598168 | cg05020685 | cg24787755 | cg25962774 | cg19324462 |
| cg11743827 | cg01703291 | cg26173997 | cg02571470 | cg01224949 | cg03010018 | cg08521225 |
| cg03792768 | cg23646375 | cg12455762 | cg09437283 | cg08315613 | cg07000334 | cg26797073 |
| cg14463853 | cg07981910 | cg26318502 | cg26570844 | cg15882878 | cg14520423 | cg02852421 |
| cg01312997 | cg16689634 | cg15681358 | cg15903170 | cg07175582 | cg11962524 | cg02004979 |
| cg16326402 | cg21641834 | cg03971227 | cg13527922 | cg00211337 | cg20378628 | cg15425827 |
| cg19480965 | cg00363813 | cg13311607 | cg14031491 | cg05870586 | cg20852226 | cg01054402 |
| cg26386472 | cg01204911 | cg13039082 | cg20814312 | cg00150245 | cg25296314 | cg23241914 |
| cg01749347 | cg21303763 | cg15983520 | cg02831587 | cg14855292 | cg13324103 | cg00281551 |
| cg07819160 | cg07987843 | cg11857033 | cg11667117 | cg10075819 | cg08879470 | cg01566199 |
| cg26975459 | cg10201084 | cg04918831 | cg10097651 | cg01500055 | cg27075104 | cg22413603 |
| cg06400745 | cg25928199 | cg00586551 | cg06215107 | cg02796621 | cg24941681 | cg03661299 |
| cg23736307 | cg19786733 | cg21092551 | cg10881745 | cg11864490 | cg00590761 | cg03977657 |
| cg15264681 | cg01016592 | cg25302704 | cg17430228 | cg00803758 | cg26283127 | cg07560587 |
| cg17167468 | cg04919234 | cg26051755 | cg16508068 | cg14978242 | cg21663580 | cg07224221 |
| cg03743205 | cg17184704 | cg05283597 | cg25757470 | cg02787991 | cg14381919 | cg10550308 |
| cg21105227 | cg05772850 | cg06410591 | cg11154552 | cg20661695 | cg09866303 | cg19358738 |
| cg02488887 | cg14864022 | cg13860006 | cg26595520 | cg16782885 | cg09203199 | cg20038493 |
| cg21059834 | cg09004691 | cg08200419 | cg16814786 | cg26164269 | cg05299048 | cg25021247 |
| cg25686746 | cg20441502 | cg14804000 | cg15632164 | cg13583230 | cg02989244 | cg23400002 |
| cg09634469 | cg27079341 | cg02183564 | cg21380181 | cg23112360 | cg05143530 | cg21910390 |
| cg20024687 | cg05467676 | cg16619721 | cg20961591 | cg16674020 | cg10321723 | cg16608731 |
| cg14672128 | cg12797594 | cg03137177 | cg00788204 | cg27029623 | cg00571809 | cg09222367 |
| cg25934700 | cg19925558 | cg09147400 | cg05584597 | cg13081600 | cg15311822 | cg02179764 |
| cg00410895 | cg13502346 | cg11726288 | cg06098215 | cg21336594 | cg07359306 | cg09753772 |
| cg26259171 | cg11664818 | cg27094698 | cg00456593 | cg03710719 | cg20967139 | cg16414472 |
| cg08550839 | cg04213384 | cg17952661 | cg04520704 | cg00543474 | cg06625767 | cg20266715 |
| cg02954562 | cg10572969 | cg11233163 | cg19794481 | cg27083891 | cg19111459 | cg02622803 |
| cg07467716 | cg07054226 | cg03705926 | cg22501243 | cg06801028 | cg21195185 | cg18830083 |
| cg03781123 | cg26432459 | cg20227860 | cg07546508 | cg23065927 | cg07380907 | cg16129213 |
| cg14126493 | cg23953820 | cg06655216 | cg10581876 | cg16973107 | cg19898668 | cg08881019 |
| cg02363202 | cg26249100 | cg23404973 | cg08373169 | cg06573088 | cg02720618 | cg25573884 |
| cg22198044 | cg17198308 | cg20123637 | cg21487509 | cg17344048 | cg05718253 | cg21369890 |
| cg25479682 | cg09758490 | cg19324627 | cg06143864 | cg05142677 | cg02675308 | cg06250720 |
| cg23613051 | cg25781162 | cg11904686 | cg17001034 | cg01595997 | cg05159909 | cg10637370 |
| cg19580263 | cg27143326 | cg06828015 | cg19424265 | cg02580005 | cg24738592 | cg26530045 |
| cg26250609 | cg17927096 | cg07435445 | cg00949446 | cg00081919 | cg22747380 | cg04111789 |
| cg07216194 | cg21622186 | cg27436184 | cg19295951 | cg27264181 | cg11566244 | cg01959238 |
| cg21186296 | cg04355435 | cg03326059 | cg23982212 | cg05821186 | cg24239961 | cg02258444 |
| cg05876864 | cg06485940 | cg20205477 | cg05853772 | cg11254527 | cg03798986 | cg12544678 |
| cg02586182 | cg22056336 | cg25677092 | cg10494703 | cg14738670 | cg01979888 | cg11327659 |
| cg09747827 | cg14287403 | cg10543634 | cg01733599 | cg05095158 | cg18361815 | cg02288341 |
| cg16423337 | cg16919420 | cg02919168 | cg07839536 | cg09658645 | cg04221886 | cg18681028 |
| cg00264441 | cg19571617 | cg05845533 | cg08328777 | cg14052210 | cg24794433 | cg07681696 |
| cg19101893 | cg06498232 | cg09426825 | cg16560256 | cg27639142 | cg03123289 | cg03603211 |
| cg05967596 | cg13019092 | cg18229134 | cg26173847 | cg25391692 | cg13884295 | cg12296532 |
| cg15994519 | cg17792849 | cg26806924 | cg05450701 | cg14040358 | cg24412501 | cg05337743 |
| cg12074585 | cg04801085 | cg15485378 | cg15058210 | cg09868451 | cg08505222 | cg09036621 |
| cg18495118 | cg20358834 | cg17841421 | cg16809962 | cg13905586 | cg00237391 | cg22110888 |
| cg18263587 | cg16078836 | cg21798060 | cg08148261 | cg17582336 | cg21306329 | cg19975917 |
| cg04920951 | cg26585724 | cg10426084 | cg21361646 | cg18565268 | cg21306329 | cg07395439 |
| cg10704263 | cg00294025 | cg11970797 | cg10022788 | cg11493223 | cg25658385 | cg16983159 |
| cg09436823 | cg05891899 | cg09738156 | cg26080305 | cg15806880 | cg10064339 | cg18495710 |
| cg20315995 | cg11553755 | cg09218757 | cg02584377 | cg05314142 | cg07053546 | cg06703844 |
| cg20135243 | cg06230247 | cg24672271 | cg09050160 | cg13016732 | cg11856711 | cg19269520 |
| cg12137206 | cg21850578 | cg27619475 | cg16046444 | cg07818422 | cg01687401 | cg02153339 |
| cg00686694 | cg10910848 | cg00071950 | cg22972318 | cg04528038 | cg20588162 | cg10483825 |
| cg09038076 | cg03806087 | cg00589493 | cg13400249 | cg17297305 | cg14960043 | cg14582550 |
| cg05353659 | cg03794214 | cg01061553 | cg00920970 | cg18659483 | cg10418263 | cg07146773 |
| cg08498787 | cg18718410 | cg02243157 | cg09502149 | cg23315932 | cg21451309 | cg24782497 |
| cg10993460 | cg03355690 | cg09350274 | cg04450599 | cg05068848 | cg27308319 | cg20896113 |
| cg25264265 | cg07948194 | cg19777644 | cg18477949 | cg23511432 | cg04809136 | cg07541559 |
| cg13510651 | cg22076972 | cg25393009 | cg25746489 | cg12848457 | cg13972366 | cg01004382 |
| cg01614759 | cg10387890 | cg21861233 | cg04640684 | cg16865442 | cg21912556 | cg26192520 |
| cg19533443 | cg10394047 | cg04867634 | cg23973429 | cg01754009 | cg04674060 | cg12716083 |
| cg07991621 | cg15963326 | cg13263830 | cg07064544 | cg21101386 | cg00672333 | cg16738453 |
| cg16147221 | cg16311462 | cg08469255 | cg17468616 | cg09599740 | cg05684891 | cg17875935 |
| cg10745272 | cg21376120 | cg12353788 | cg07532183 | cg05382313 | cg10009801 | cg16362949 |
| cg03923535 | cg16367511 | cg20957796 | cg22094306 | cg01419582 | cg26661718 | cg03064642 |
| cg21766722 | cg12547516 | cg16430687 | cg12329933 | cg24390871 | cg26457013 | cg16895026 |
| cg17591574 | cg21561712 | cg22463097 | cg01250960 | cg25588844 | cg25865553 | cg27173151 |
| cg18482593 | cg18037808 | cg00394718 | cg24396400 | cg20482113 | cg22234930 | cg24220749 |
| cg17275162 | cg18309286 | cg02900995 | cg27297851 | cg13050240 | cg02579136 | cg20018469 |
| cg21574349 | cg20199333 | cg12022772 | cg12528056 | cg19243330 | cg13579752 | cg07076751 |

-continued

| | | | | | | |
|---|---|---|---|---|---|---|
| cg10356463 | cg12699648 | cg22310770 | cg11990902 | cg22885332 | cg06525453 | cg24327723 |
| cg12209075 | cg10230442 | cg17643864 | cg15111065 | cg13077930 | cg16789129 | cg10344081 |
| cg26099316 | cg05852537 | cg24036039 | cg27573591 | cg00299943 | cg26301689 | cg00001791 |
| cg02607544 | cg23278604 | cg19465165 | cg07054668 | cg23090870 | cg03023152 | cg25023684 |
| cg01710886 | cg17330652 | cg04437648 | cg15657641 | cg07891507 | cg22416916 | cg04060356 |
| cg02523400 | cg09858224 | cg12870750 | cg15851389 | cg04590184 | cg15978561 | cg15783800 |
| cg24441911 | cg25488206 | cg06370855 | cg26686009 | cg18964954 | cg12624523 | cg20267408 |
| cg08804892 | cg10056096 | cg11364420 | cg12191938 | cg12149319 | cg17252884 | cg01819912 |
| cg11614622 | cg13341720 | cg10195295 | cg08310176 | cg05132222 | cg27321913 | cg05799169 |
| cg13153661 | cg04581004 | cg15480897 | cg15889012 | cg19086110 | cg13255542 | cg14430591 |
| cg13863396 | cg25247596 | cg18966819 | cg02227867 | cg13984173 | cg05721858 | cg04394267 |
| cg08508763 | cg26940122 | cg21107197 | cg25210936 | cg07285675 | cg24965479 | cg02300825 |
| cg12332316 | cg06285337 | cg04917391 | cg01519063 | cg20218614 | cg19484481 | cg03930970 |
| cg24247370 | cg10599693 | cg03464224 | cg20381798 | cg00061039 | cg06076794 | cg08988797 |
| cg27255115 | cg10604002 | cg12817107 | cg18782488 | cg02466113 | cg19875375 | cg17218270 |
| cg14164596 | cg07046969 | cg14350120 | cg04508216 | cg00709775 | cg04431596 | cg09349409 |
| cg06271128 | cg16408565 | cg02647929 | cg02573551 | cg01770400 | cg20134984 | cg20594304 |
| cg26426488 | cg04849878 | cg00971369 | cg16178743 | cg17266515 | cg03723716 | cg24354101 |
| cg18563999 | cg22684041 | cg15310162 | cg02923485 | cg03284640 | cg00487187 | cg20381020 |
| cg12083852 | cg06594281 | cg12420472 | cg13184814 | cg01347228 | cg20250722 | cg10826043 |
| cg07946277 | cg15834395 | cg12180551 | cg19115272 | cg03771456 | cg02672397 | cg16452651 |
| cg05696406 | cg21987921 | cg00948524 | cg12301972 | cg03755115 | cg09146232 | cg00547530 |
| cg26619894 | cg25033767 | cg19784816 | cg10674105 | cg20253551 | cg20976787 | cg22709202 |
| cg22032528 | cg05005609 | cg07182753 | cg00004082 | cg19024980 | cg16364495 | cg26870803 |
| cg17557340 | cg00630164 | cg13060154 | cg25669504 | cg24938743 | cg14343701 | cg02465427 |
| cg00371195 | cg04682699 | cg16310003 | cg24105685 | cg11641102 | cg23613857 | cg24789424 |
| cg07297322 | cg13707645 | cg16581800 | cg25862768 | cg02206323 | cg24432073 | cg04413147 |
| cg10500733 | cg26166817 | cg20817175 | cg15202104 | cg00161955 | cg26288249 | cg16908948 |
| cg06120000 | cg16959747 | cg21225170 | cg19291696 | cg24877842 | cg09130035 | cg07061500 |
| cg05447556 | cg26859666 | cg23625458 | cg05903736 | cg23661013 | cg08643852 | cg21019174 |
| cg06228542 | cg06431702 | cg00238662 | cg16578104 | cg00428526 | cg12985235 | cg20059312 |
| cg26418880 | cg04208434 | cg24677674 | cg15451948 | cg17770034 | cg08688393 | cg11115622 |
| cg24980213 | cg23295181 | cg04195454 | cg26520930 | cg15951557 | cg25252585 | cg18660987 |
| cg16348316 | cg02535674 | cg20823137 | cg13187820 | cg15679052 | cg23718606 | cg23715029 |
| cg10899768 | cg04257163 | cg08875705 | cg01012445 | cg15741583 | cg19155007 | cg15352367 |
| cg19300937 | cg02380715 | cg05654197 | cg26474124 | cg00104348 | cg24928687 | cg09243454 |
| cg04667640 | cg16924822 | cg02374207 | cg07686392 | cg03168947 | cg09502865 | cg03315456 |
| cg22647018 | cg02066638 | cg18094261 | cg27021666 | cg24163360 | cg24319651 | cg16943019 |
| cg25957092 | cg00647246 | cg06743552 | cg23743114 | cg17578639 | cg07968770 | cg06945399 |
| cg17655624 | cg15468521 | cg25371267 | cg06391412 | cg20367521 | cg02119927 | cg12912920 |
| cg23041410 | cg00953211 | cg07960067 | cg13214149 | cg11972305 | cg09070316 | cg06237151 |
| cg19554037 | cg02285263 | cg07871590 | cg10426318 | cg10085305 | cg20834178 | cg19606103 |
| cg03946762 | cg01991967 | cg13159388 | cg08173959 | cg27061836 | cg13175850 | cg08457620 |
| cg11274314 | cg10008947 | cg22392666 | cg03228065 | cg18024037 | cg14003974 | cg23011886 |
| cg03367387 | cg17142134 | cg20970904 | cg20836156 | cg21874862 | cg10857558 | cg05009389 |
| cg27278017 | cg20314331 | cg07294541 | cg25938530 | cg19347790 | cg16032621 | |

Table 7 shows an illustrative list of 1000 markers (illustrated with cg identifier) described herein. In some cases, the markers are used in HCC-lung-blood analysis.

| | | | | | | |
|---|---|---|---|---|---|---|
| cg11252953 | cg14247287 | cg03684062 | cg04517263 | cg25671438 | cg12835012 | cg22008490 |
| cg25922751 | cg04411201 | cg25686087 | cg15136410 | cg11601297 | cg13017813 | cg03636488 |
| cg05614346 | cg00206490 | cg08430407 | cg16332159 | cg18317439 | cg15626285 | cg26363363 |
| cg02874908 | cg25739715 | cg13828227 | cg18440839 | cg01742370 | cg20855160 | cg00015530 |
| cg26769700 | cg06788514 | cg07222861 | cg22882523 | cg25006077 | cg25408950 | cg04466898 |
| cg09366118 | cg14430943 | cg16460342 | cg03593259 | cg08546016 | cg11677891 | cg23229016 |
| cg25490145 | cg06482498 | cg24100671 | cg22582875 | cg09254318 | cg09399878 | cg04314978 |
| cg17518965 | cg16927606 | cg00466334 | cg18493214 | cg04234016 | cg17745697 | cg17742416 |
| cg26668608 | cg17653203 | cg00903584 | cg26585899 | cg14386624 | cg02756056 | cg09097632 |
| cg08098128 | cg06039074 | cg24088438 | cg26955540 | cg15573664 | cg05693489 | cg05596756 |
| cg02053964 | cg14642045 | cg23545458 | cg08055663 | cg15728692 | cg11214001 | cg07579839 |
| cg11334870 | cg24706505 | cg04051365 | cg24605325 | cg18637383 | cg23807570 | cg12504877 |
| cg10542975 | cg18113826 | cg13415831 | cg18781835 | cg25023095 | cg07097098 | cg00302479 |
| cg00907272 | cg02871985 | cg06385449 | cg11884933 | cg07410339 | cg08433504 | cg20873136 |
| cg15698795 | cg11803771 | cg27309142 | cg21122474 | cg06230847 | cg04848682 | cg11791526 |
| cg18610205 | cg09414948 | cg09130535 | cg27360727 | cg10393744 | cg19047804 | cg14191688 |
| cg16622899 | cg18982286 | cg18128058 | cg09383860 | cg07924081 | cg15570035 | cg11779113 |
| cg18384097 | cg02286506 | cg19400179 | cg03094134 | cg16289449 | cg14654385 | cg27540367 |
| cg23130731 | cg27198931 | cg14134003 | cg13165140 | cg12900649 | cg08387014 | cg07860918 |
| cg19675731 | cg13925432 | cg03807883 | cg02673417 | cg21171858 | cg09031790 | cg19382157 |
| cg23612220 | cg07380021 | cg04523868 | cg23013029 | cg17809595 | cg21830050 | cg07884764 |
| cg07420137 | cg02798280 | cg25666403 | cg13085553 | cg03750478 | cg22566142 | cg26315985 |
| cg01903374 | cg21376733 | cg16649298 | cg19459094 | cg26681847 | cg02556655 | cg04490178 |
| cg01447914 | cg09335715 | cg27388962 | cg11217193 | cg25468516 | cg01440934 | cg03254137 |
| cg07644807 | cg20563971 | cg23677243 | cg26899651 | cg22331159 | cg02481714 | cg10511890 |

-continued

| | | | | | | |
|---|---|---|---|---|---|---|
| cg14519350 | cg00220455 | cg22742001 | cg27588321 | cg18571045 | cg07584494 | cg01765930 |
| cg19693177 | cg08715187 | cg08052292 | cg19619585 | cg06811300 | cg05959508 | cg17126555 |
| cg20136100 | cg02185248 | cg17984956 | cg01657186 | cg01314252 | cg07800907 | cg27405400 |
| cg20847580 | cg05304979 | cg21232937 | cg15128334 | cg13790288 | cg11685391 | cg20556803 |
| cg27125093 | cg06488150 | cg22935317 | cg27016579 | cg03964696 | cg01645955 | cg25953692 |
| cg11105292 | cg19300307 | cg01409343 | cg02367921 | cg19238349 | cg25210609 | cg10673833 |
| cg26680502 | cg01660934 | cg02844611 | cg17207512 | cg15309361 | cg26471058 | cg15095913 |
| cg16266227 | cg02522196 | cg02914427 | cg17697835 | cg15202213 | cg23128495 | cg20694619 |
| cg16061668 | cg20468939 | cg10351284 | cg21159568 | cg22216196 | cg04438229 | cg00045607 |
| cg01722297 | cg08632810 | cg16119522 | cg07915896 | cg26584120 | cg06908857 | cg06130354 |
| cg26112797 | cg25039325 | cg11753750 | cg27263049 | cg20720686 | cg08133848 | cg21293216 |
| cg15341833 | cg00933696 | cg13512830 | cg13612207 | cg06379589 | cg06901890 | cg19266387 |
| cg12737392 | cg06153925 | cg18281939 | cg12535569 | cg03109921 | cg20306863 | cg20781880 |
| cg03891050 | cg23093496 | cg01598009 | cg17013990 | cg21238234 | cg22550549 | cg20812370 |
| cg25954028 | cg01456691 | cg24686918 | cg26647135 | cg27366766 | cg09888229 | cg23742233 |
| cg24301930 | cg27262415 | cg22507723 | cg08144675 | cg16749930 | cg23281123 | cg13904214 |
| cg14083015 | cg13597051 | cg08574423 | cg27365208 | cg15059065 | cg16215084 | cg19923326 |
| cg22513455 | cg21604136 | cg18918538 | cg07041323 | cg00903825 | cg05369623 | cg07948875 |
| cg26769927 | cg02776283 | cg08781403 | cg14303478 | cg01603912 | cg01647936 | cg15759721 |
| cg13555415 | cg05798125 | cg08529481 | cg27182070 | cg01335087 | cg17936488 | cg11550234 |
| cg13395086 | cg27366280 | cg26696162 | cg17652424 | cg08120831 | cg20985399 | cg00032912 |
| cg20695297 | cg07589991 | cg15198736 | cg00058449 | cg12690996 | cg16802439 | cg05398700 |
| cg00055073 | cg15738800 | cg13695076 | cg09804858 | cg23547892 | cg25403205 | cg22552736 |
| cg03431741 | cg15139596 | cg05617650 | cg01921773 | cg26280326 | cg17705615 | cg05352688 |
| cg25432518 | cg02358862 | cg14088196 | cg26433975 | cg18973863 | cg12423658 | cg12360046 |
| cg27377213 | cg15902390 | cg25225070 | cg00282244 | cg03781748 | cg02565062 | cg26112909 |
| cg10590292 | cg15465439 | cg24742520 | cg24504194 | cg17750114 | cg14154456 | cg15704521 |
| cg12098228 | cg08224920 | cg25996077 | cg11143193 | cg06765217 | cg16274890 | cg20251225 |
| cg24166457 | cg04330884 | cg23254569 | cg20609302 | cg00024494 | cg11201532 | cg02041484 |
| cg06825448 | cg02512559 | cg01990910 | cg00447208 | cg06753787 | cg09972881 | cg06068897 |
| cg00558804 | cg26402555 | cg25338707 | cg16792302 | cg23764129 | cg07181702 | cg06787669 |
| cg01681367 | cg20784950 | cg01243072 | cg02331198 | cg25996553 | cg06449094 | cg05214235 |
| cg21004490 | cg11151942 | cg23663476 | cg04179740 | cg16044050 | cg13581832 | cg08330349 |
| cg25574765 | cg16782524 | cg23060513 | cg18183242 | cg11953794 | cg21584234 | |
| cg27141915 | cg12629796 | cg03654273 | cg13408086 | cg19005335 | cg17651972 | cg07939743 |
| cg25982880 | cg25765104 | cg08331345 | cg03234777 | cg12655137 | cg09169923 | cg13476072 |
| cg06380123 | cg03900314 | cg00188654 | cg07033722 | cg03308839 | cg03187073 | cg17974145 |
| cg06393830 | cg15172966 | cg15123730 | cg08352774 | cg18812353 | cg15878616 | cg06739107 |
| cg04514998 | cg03087897 | cg21208744 | cg27040700 | cg25739938 | cg21900653 | cg07701307 |
| cg03466198 | cg25946374 | cg21781157 | cg20432732 | cg07542476 | cg09731946 | cg24619378 |
| cg20046343 | cg06928952 | cg26691434 | cg11599269 | cg04273604 | cg13987606 | cg21282907 |
| cg08480068 | cg00037681 | cg16176600 | cg21133433 | cg21605283 | cg25499543 | cg01437204 |
| cg03549705 | cg03236137 | cg26488183 | cg19102955 | cg23554164 | cg16063587 | cg16863795 |
| cg09844573 | cg12970155 | cg20069407 | cg10045909 | cg15722438 | cg11051752 | cg07902156 |
| cg15046123 | cg23966363 | cg14584535 | cg22840361 | cg00287536 | cg24702826 | cg05997414 |
| cg24480810 | cg27025137 | cg25323554 | cg08947915 | cg00253248 | cg09153080 | cg07417146 |
| cg11436362 | cg21086153 | cg26306638 | cg12359001 | cg14145194 | cg10104480 | cg03128029 |
| cg14999168 | cg08097359 | cg18215449 | cg12005186 | cg27217214 | cg20389678 | cg20675040 |
| cg22589778 | cg18842353 | cg17910105 | cg19846295 | cg15921911 | cg01383911 | cg19663795 |
| cg12353452 | cg27219182 | cg13549444 | cg16659773 | cg10020520 | cg17920246 | cg18456508 |
| cg08912922 | cg06004454 | cg09684112 | cg02431531 | cg13693517 | cg27570661 | cg12242373 |
| cg06439655 | cg04936619 | cg02609337 | cg14858784 | cg15752436 | cg07380416 | cg07979757 |
| cg12967050 | cg26427090 | cg09638208 | cg20667480 | cg08905080 | cg16127573 | cg20107506 |
| cg00257775 | cg13832670 | cg17301248 | cg25913761 | cg26340050 | cg18854765 | cg07249939 |
| cg08075204 | cg05905531 | cg17009616 | cg24459792 | cg02189790 | cg11293275 | cg25598890 |
| cg11264392 | cg01647308 | cg05408317 | cg25451702 | cg00041666 | cg11612905 | cg19717347 |
| cg01797036 | cg16191087 | cg14539363 | cg24769398 | cg14677983 | cg05048927 | cg22662844 |
| cg05769344 | cg15797834 | cg15249357 | cg05387269 | cg24757533 | cg07052231 | cg07739604 |
| cg06064964 | cg26017930 | cg12617080 | cg03879823 | cg17080697 | cg22694271 | cg00501765 |
| cg15554421 | cg01760983 | cg13853198 | cg15724534 | cg03409108 | cg20030711 | cg07905808 |
| cg13924996 | cg21249754 | cg16302816 | cg23506842 | cg15240033 | cg10510259 | cg16824282 |
| cg13639901 | cg05878887 | cg05751148 | cg04515806 | cg13827209 | cg17395211 | cg15844596 |
| cg10530767 | cg03263730 | cg08253808 | cg24491784 | cg21757281 | cg10640333 | cg22143387 |
| cg24107852 | cg15334372 | cg05656900 | cg21792134 | cg25116200 | cg17583432 | cg16324409 |
| cg07641284 | cg11176159 | cg20971407 | cg14311559 | cg09006487 | cg01838544 | cg17911539 |
| cg18901104 | cg14345572 | cg01787084 | cg01016122 | cg03419014 | cg18071865 | cg07732037 |
| cg19704755 | cg24420089 | cg06119477 | cg00750430 | cg09152089 | cg25363807 | cg02597698 |
| cg26683005 | cg25384897 | cg08454507 | cg00442389 | cg13931640 | cg11744304 | cg12079904 |
| cg09866569 | cg18887230 | cg26038697 | cg08400494 | cg20366239 | cg00164997 | cg08859309 |
| cg26708220 | cg03187301 | cg20071624 | cg21524899 | cg10836110 | cg05344747 | cg06311355 |
| cg11600161 | cg23824762 | cg06620723 | cg03606269 | cg25774643 | cg25143508 | cg03396151 |
| cg09762242 | cg06340367 | cg02385661 | cg06405563 | cg01008602 | cg08176258 | cg10883375 |
| cg00816037 | cg08313420 | cg03569637 | cg17875657 | cg26094805 | cg17006136 | cg06087349 |
| cg04859102 | cg21455600 | cg15035143 | cg23128949 | cg17319795 | cg11796996 | cg19563932 |
| cg13912307 | cg07499032 | cg06173520 | cg12379383 | cg11080651 | cg03126713 | cg25440680 |
| cg07832674 | cg22190721 | cg02127509 | cg15625671 | cg24484352 | cg19797087 | cg17178291 |
| cg00759427 | cg00118342 | cg01382502 | cg05653018 | cg01923089 | cg00747922 | cg02646515 |
| cg24247537 | cg15046675 | cg09190408 | cg04655481 | cg15011899 | cg01554529 | cg15035133 |
| cg01620360 | cg05931497 | cg12401842 | cg06912814 | cg17346145 | cg09572125 | cg04567323 |

-continued

| | | | | | | |
|---|---|---|---|---|---|---|
| cg08858130 | cg16924010 | cg02744216 | cg19321684 | cg27226424 | cg10611016 | cg12686260 |
| cg00899907 | cg26118759 | cg08486903 | cg07786220 | cg02450981 | cg25251478 | cg26149678 |
| cg01604601 | cg17707057 | cg24835948 | cg07946977 | cg24202468 | cg20887442 | cg18457597 |
| cg18856478 | cg02233149 | cg17067993 | cg05711036 | cg12281620 | cg19747195 | cg15305732 |
| cg23589035 | cg11860434 | cg21108554 | cg04493247 | cg16107907 | cg17344770 | cg10186131 |
| cg08351710 | cg23021796 | cg03032552 | cg02042997 | cg13399952 | cg21426759 | cg07137244 |
| cg20336172 | cg26394055 | cg04531756 | cg10732611 | cg13616508 | cg11826104 | cg07428959 |
| cg23147227 | cg20685713 | cg08670658 | cg15027815 | cg12116137 | cg18696027 | cg00360761 |
| cg20826709 | cg19421584 | cg04990190 | cg14741474 | cg11094248 | cg16268734 | cg07116712 |
| cg07119472 | cg20610594 | cg21461981 | cg22258045 | cg22463795 | cg20300794 | cg00025044 |
| cg07573366 | cg09001226 | cg18002447 | cg08485187 | cg12192282 | cg05167561 | cg27023597 |
| cg00242035 | cg03603669 | cg20783697 | cg13561409 | cg13383814 | cg22980156 | cg03718241 |
| cg13911392 | cg04147906 | cg00407537 | cg00228142 | cg18960620 | cg14714629 | cg19192256 |
| cg16402452 | cg10491452 | cg01209642 | cg05287480 | cg27063969 | cg06576340 | cg10402417 |
| cg17122157 | cg07549381 | cg23797100 | cg03339537 | cg26808687 | cg01174743 | cg12269161 |
| cg14556909 | cg23950278 | cg16398761 | cg03956042 | cg01284289 | cg16389078 | cg03228145 |
| cg00916899 | cg03979258 | cg00997280 | cg14516183 | cg23304467 | cg25484252 | cg20411756 |
| cg21311067 | cg08161480 | cg15159247 | cg20485084 | cg04192740 | cg17309904 | cg05696678 |
| cg00862408 | cg20425130 | cg15678817 | cg01925950 | cg03758697 | cg22894329 | cg04784315 |
| cg03218479 | cg08132573 | cg09354037 | cg18966401 | cg27121758 | cg13468144 | cg14998613 |
| cg26836479 | cg18081760 | cg26133301 | cg20066792 | cg14282004 | cg19645616 | cg00878163 |
| cg07682037 | cg03762237 | cg07921503 | cg10456459 | cg16986578 | cg16590794 | cg16350446 |
| cg22460896 | cg01816936 | cg04858553 | cg05667818 | cg27307183 | cg24691453 | cg12067423 |
| cg19982684 | cg05979232 | cg22215508 | cg23549534 | cg26514623 | cg03297901 | cg13493526 |
| cg03331514 | cg23429794 | cg13487445 | cg03699843 | cg25662041 | cg02657012 | cg12042264 |
| cg23878564 | cg18942579 | cg20165946 | cg02145701 | cg14343513 | cg00048436 | cg08241318 |
| cg16509569 | cg26572452 | cg12033822 | cg27617225 | cg21452808 | cg23595413 | cg19021985 |
| cg12086464 | cg16260696 | cg21164509 | cg04726013 | cg08928675 | cg14315912 | cg24690709 |
| cg09419005 | cg19721787 | cg05177060 | cg12678686 | cg06508867 | cg24126180 | cg03089651 |
| cg02782634 | cg14564351 | cg05399244 | cg16958939 | cg01498832 | cg24032691 | cg24525952 |
| cg12192582 | cg09331545 | cg20510285 | cg08796391 | cg00327355 | cg19433118 | cg13857210 |
| cg01951274 | cg19193595 | cg18184218 | cg20181887 | cg03773413 | cg12436568 | cg02116768 |
| cg16911583 | cg10783294 | cg11410920 | cg18581405 | cg01765152 | cg15292446 | cg24948743 |
| cg13821008 | cg13464240 | cg15520845 | cg03649649 | cg26842815 | cg05938958 | cg01448132 |
| cg15569052 | cg05098343 | cg08357436 | cg11869499 | cg04992150 | cg24545967 | cg03275851 |
| cg10055231 | cg03190513 | cg20308351 | cg10001715 | cg03190661 | cg04690998 | cg00388871 |
| cg04441857 | cg12123728 | cg26077811 | cg02037425 | cg23184252 | cg23352695 | cg14788563 |
| cg19055828 | cg24234270 | cg24397241 | cg24668061 | cg20641026 | cg07938743 | cg04552555 |
| cg17285931 | cg22801913 | cg11888747 | cg03106245 | cg04943741 | cg17359629 | |

Example 2

Primary Tissue Patient Data

Both primary solid tissues from cancer patients and blood tissues from healthy donor were measured by Illumina 450k infimum bead chip. Primary tumor DNA methylation data of 485,000 sites was obtained from The Cancer Genome Atlas (TCGA). Complete clinical, molecular, and histopathological datasets are available at the TCGA website. Individual institutions that contributed samples coordinated the consent process and obtained informed written consent from each patient in accordance to their respective institutional review boards. Blood tissue DNA methylation data from healthy donor were obtained and generated based on study from Hannum et al., 2013, *Mol Cell* 49, 359-367 (GSE40279) in which DNA methylation profiles for HCC and blood were analyzed.

Serum Sample Patient Data

A second independent Chinese cohort consisted of LUNC and HCC patients at the Sun Yat-sen University Cancer Center in Guangzhou, Xijing Hospital in Xi'an, and the West China Hospital in Chengdu, China. Patients who presented with LUNC and HCC from stage I-IV were selected and enrolled in this study. Patient characteristics and tumor features are summarized in Table 11. The TNM staging classification for LUNC and HCC is according to the $7^{th}$ edition of the AJCC cancer staging manual. This project was approved by the IRBs of Sun Yat-sen University Cancer Center, Xijing Hospital, and West China Hospital. Informed consent was obtained from all patients. Two prospective trials on early detection of LUNC and HCC patients using methylation markers for predicting cancer occurrence in high-risk populations were conducted. In the first study, patients were recruited from a group of smokers that were undergoing CT scan-based lung cancer screening from December 2015 to December 2016. Patients presenting with lung nodules (<10 mm, n=232, Table 14) were selected to undergo methylation profiling at the time of screening and were subsequently followed through secondary testing to determine whether nodules were due to cancer or inflammatory or infectious conditions by tissue biopsy and pathology diagnosis verification. In the second trial, high risk patients with liver cirrhosis were enrolled (n=242).

Tumor and normal tissues were obtained as clinically indicated for patient care and were retained for this study. Human blood samples were collected by venipuncture, and plasma samples were obtained by taking the supernatant after centrifugation and stored at −80° C. before cfDNA extraction.

The pre-treatment serum samples were obtained at the initial diagnosis, and the post-treatment serum samples were evaluated approximately 2 months after treatment, where the treatment referred to either chemotherapy or surgical resection of tumor. The primary endpoint (including response to treatment: progressive disease (PD), partial response (PR) and stable disease (SD)) was defined according to the RECIST guideline. For patients treated with surgical removal and no recurrence at time of evaluation, we assumed they had complete response (CR).

Extraction of cfDNA from Plasma

It was determined that the minimal volume of plasma required to get consistent amounts of cfDNA for targeted sequencing. As a rough guide, it was aimed at ~20× coverage at 90% of markers covered by the padlock probe panel (see below). It was observed that 20,000 or more total unique reads per sample fulfilled this criterion. It was found that 1.5 ml or more plasma could reliably yield enough cfDNA to produce >20,000 unique reads. The relationship between amount of cfDNA in 1.5 ml plasma and detected copy numbers was further investigated using digital droplet PCR. It was found that 1.5 ml of plasma yielded >10 ng, what produced at least 140 copies of detected amplicons in each digital droplet PCR assay. It was therefore settled on using 15 ng/1.5 ml as a cutoff in all of our experiments to obtain consistent and reliable measurements of DNA methylation.

cfDNA from 1.5 ml of plasma was extracted using Elite-Health cfDNA extraction Kit (EliteHealth, Guangzhou Youze, China) according to manufacturer's recommendations.

Bisulfite Conversion of Genomic or cfDNA 10 ng of DNA was converted to bis-DNA using EZ DNA Methylation-Lightning™ Kit (Zymo Research) according to the manufacturer's protocol. Resulting bis-DNA had a size distribution of ~200-3000 bp, with a peak around ~500-1000 bp. The efficiency of bisulfite conversion was >99.8% as verified by deep-sequencing of bis-DNA and analyzing the ratio of C to T conversion of CH (non-CG) dinucleotides.

Marker Selection for Padlock Probe Panel Design

Figure 20A:
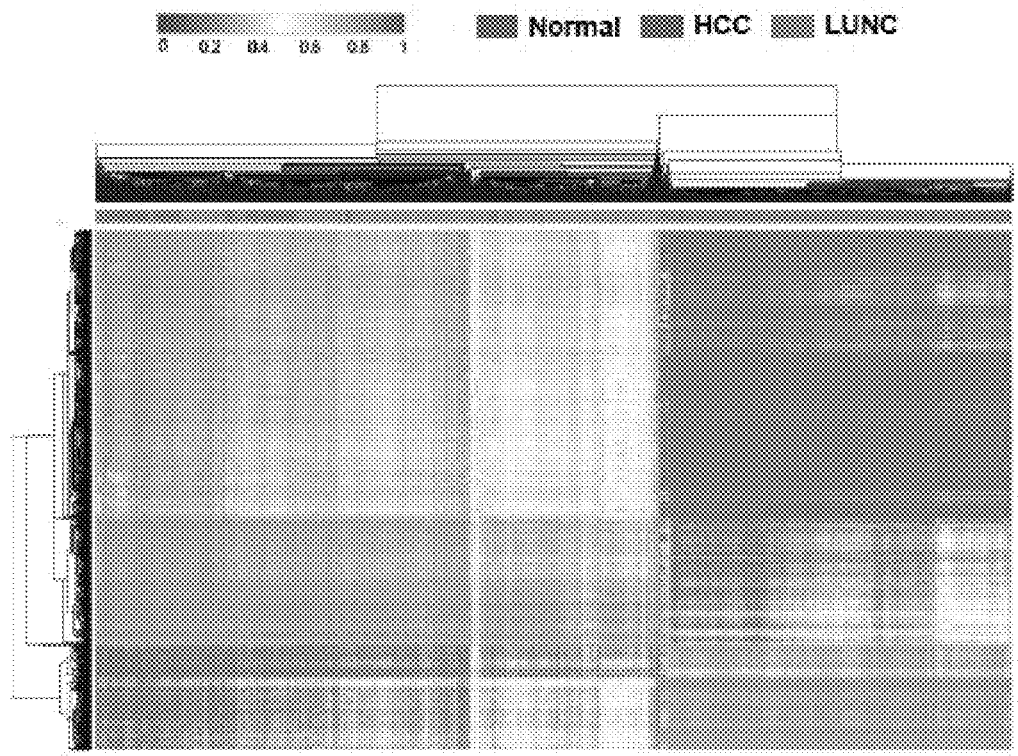
FIG. 20A illustrates unsupervised hierarchical clustering of top 1000 methylation markers differentially methylated in DNA in HCC and LUNC primary tissues versus normal blood.
Figure 20B:
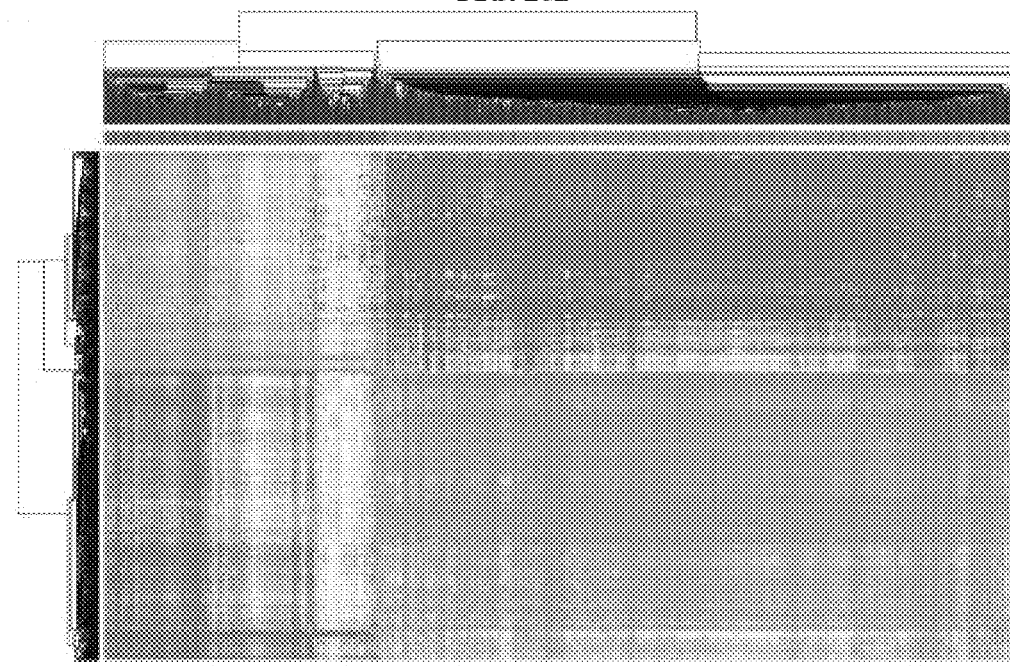
FIG. 20B shows unsupervised hierarchical clustering of the top 1000 methylation markers differentially methylated between HCC and LUNC tissue DNA. Each column represents an individual patient and each row represents a CpG marker.

To identify markers to differentiate HCC, LUNC and normal blood methylation signatures the "moderated t-statistics shrinking" approach on 450k methylation data with Benjamini-Hochberg procedure was employed to control FDR at a significance level of 0.05 using pairwise comparisons of 377 HCC samples and 827 LUNC samples (TCGA) and 754 normal blood samples (GSE40279, our previous study (HANNUM REF)). The lists was ranked by adjusted p-value and selected the top 1000 markers for designing padlock probes for differentiating cancer (both LUNC and HCC) versus normal samples and a separate group of 1000 markers for differentiating LUNC versus HCC (FIG. 20).

All 2000 markers were used to design padlock probes for capture and sequencing of cfDNA. Padlock-capture of bis-DNA was based on the technique on methods of Deng, et al., 2009, Nature Biotechnology 27, 353-360; Diep, et al., 2012, Nature Methods 9, 270-272; and Porreca, et al., 2007, Nature Methods 4, 931-936; and with further modifications. Because of a relatively modest total size of captured regions/cg markers, this approach offers much lower cost of sequencing than any current methods including whole methylome-wide sequencing, therefore enabling us to evaluate a large number of samples. Furthermore, the direct targeted sequencing approach offers digital readout, and requires much less starting cfDNA material (10-15 ng) than more traditional recent methods based on hybridization on a chip (eg. Infinium, Illumina) or target-enrichment by hybridization (eg. SureSelect, Agilent). This approach is also less sensitive to unequal amplification as it utilizes molecular identifiers (UMIs).

Padlock Probe Design, Synthesis and Validation

All probes were designed using the ppDesigner software. The average length of the captured region was 70 bp, with the CpG marker located in the central 80% of the captured region. A 6 bp 6-bp unique molecular identifier (UMI) flanked capture arms to aid in eliminating amplification bias in determination of DNA methylation frequencies. Linker sequence between arms contained binding sequences for amplification primers separated by a variable stretch of Cs to produce probes of equal length. Probes were synthesized as separate oligonucleotides (IDT). For capture experiments, probes were mixed in equimolar quantities and purified on Qiagen columns.

Deep sequencing of the original pilot capture experiments showed significant differences between number of reads captured by most efficient probes and non-efficient probes (60-65% of captured regions with coverage >0.2× of average). To ameliorate this, relative efficiencies were calculated from sequencing data and probes were mixed at adjusted molar ratios. This increased capture uniformity to 85% of regions at >0.5× of average coverage.

Targeted Methylation Sequencing Using Bis-DNA Padlock Probe Capture 10 ng of bisulfite-converted DNA was mixed with padlock probes in 20 µl reactions containing 1× Ampligase buffer (Epicentre). To anneal probes to DNA, 30 second denaturation at 95° C. was followed by a slow cooling to 55° C. at a rate of 0.02° C. per second and incubation for 15 hrs at 55° C. To fill gaps between annealed arms, 5 µl of the following mixture was added to each reaction: 2U of Pfu-TurboCx polymerase (Agilent), 0.5U of Ampligase (Epicentre) and 250 pmol of each dNTP in 1× Ampligase buffer. After 5-hour incubation at 55° C., reactions were denatured for 2 minutes at 94° C. 5 µl of exonuclease mix (20U of Exo I and 100U ExoIII of, Epicentre) was added and single-stranded DNA degradation was carried out at 37° C. for 2 hours, followed by enzyme inactivation for 2 minutes at 94° C.

Circular capture products were amplified by PCR using primers specific to linker DNA within padlock probes. Both primers contained 10 bp barcodes for unique dual-index multiplexing, and Illumina next-generation sequencing adaptor sequences. PCR was performed as follows: 1× Phusion Flash Master Mix, 3 µl of captured DNA and 200 nM primers, using the following cycle: 10s at 98° C., 8× of (1 s at 98° C., 5s at 58° C., 10s at 72° C.), 25× of (1 s at 98° C., 15s at 72° C.), 60s at 72° C. PCR reactions were mixed and the resulting library was size selected on 2.5% agarose gels to include effective captures (~230 bp) and exclude "empty" captures (~150 bp). Purity of the libraries was verified by TapeStation (Agilent) and PCR using Illumina flowcell adaptor primers (p5 and p7) and the concentrations were determined using Qubit dsDNA HS assay (Thermo Fisher). Libraries were sequenced on MiSeq and HiSeq2500 systems (Illumina) using PE100 reads. Median total reads for each sample was 500,000 and on-target mappability 25% (~125,000 on-target non-unique reads).

Optimization of Capture Coverage Uniformity

Deep sequencing of the original pilot capture experiments showed significant differences between number of reads captured by most efficient probes and non-efficient probes (60-65% of captured regions with coverage >0.2× of average). To ameliorate this, relative efficiencies were calculated from sequencing data and probes were mixed at adjusted molar ratios. This increased capture uniformity to 85% of regions at >0.5× of average coverage.

Sequencing Data Analysis

Mapping of sequencing reads was done using the software tool bisReadMapper with some modifications. First, UMI were extracted from each sequencing read and appended to read headers within FASTQ files using a custom script. Reads were on-the-fly converted as if all C were non-methylated and mapped to in-silico converted DNA strands of the human genome, also as if all C were non-methylated, using Bowtie2. Original reads were merged and filtered for single UMI, i.e. reads carrying the same UMI were discarded leaving a single, unique read. Methylation frequencies were calculated for all CpG dinucleotides contained within the regions captured by padlock probes by dividing the numbers of unique reads carrying a C at the interrogated position by the total number of reads covering the interrogated position.

DNA Isolation and Digital Quantitative PCR

Tumor and corresponding plasma samples were obtained from patients undergoing surgical tumor resection; samples were frozen and preserved in at −80° C. until use. Isolation of DNA and RNA from samples was performed using DNA/RNA MiniPrep kit and a cfDNA extraction kit, respectively (EliteHealth, Guangzhou Youze, China). To estimate tumor cfDNA fractions, we performed mixing experiments with various fractions of normal cfDNA and HCC tumor genomic DNA (gDNA) and assayed methylation values and copy numbers by dPCR (see next section for details). Digital droplet PCR (ddPCR) was performed according to the manufacturer's specifications (Bio-Rad, Hercules, Calif.). The following ddPCR assay was used in this study: cg10590292—forward primer 5'-TGTTAGTTTTTATG-GAAGTTT (SEQ ID NO: 19), reverse primer 5'-AAACIAACAAAATACTCAAA (SEQ IN NO: 20); fluorescent probe for methylated allele detection 5'/6-FAM/TGGGAGAGCGGGAGAT/BHQ1/-3' (SEQ ID NO: 21); probe for unmethylated allele detection, 5'/HEX/TTTGGGAGAGTGGGAGATTT/BHQ1/-3' (SEQ ID NO: 22). ddPCR was performed according to the manufacturer's specifications (Bio-Rad, Hercules, Calif.). using the following cycling conditions: 1× of 10 mins at 98° C., 40× of (30s at 98° C., 60s at 53° C.), 1× of 10 mins at 98° C.

Calculation of Tumor cfDNA Fraction

It was assumed that a particular methylation value observed for an HCC cfDNA sample results from the combined contribution of normal and tumor cfDNA. The fraction of cfDNA originating from the tumor was estimated using the following formula: fraction contributed from tumor DNA in sample i=[methylation value in HCC cfDNA in sample i−mean methylation value of normal cfDNA]/[mean methylation value of tumor DNA−mean methylation value of normal cfDNA]. Using this approach, it was estimated that on average the tumor fraction is around 23% in HCC cfDNA samples. Samples were then grouped according to factors that evaluate tumor load, such as an advanced stage and pre-treatment status, since these factors are expected to affect the tumor fraction in ctDNA. Indeed, it was observed that conditions associated with a higher tumor staging and severity also tended to have a larger tumor fraction. To further vet this approach, a mixing experiment with different fractions of normal cfDNA (0-100%) and tumor genomic DNA (0-100%) was performed and assayed methylation values using digital PCR. It was shown that incremental addition of tumor genomic DNA can increase methylation fraction percentage up to the values observed in the HCC patient samples. Specifically, addition of 10%, 20%, 40%, 60% or 100% fraction of tumor genomic DNA can be predicted by the above formula, when using methylation values obtained from the experiment.

Statistical Analysis

DNA Methylation Marker Selection for Diagnostic and Prognostic Analysis

Out of 2000 initially designed padlock probes, only 1673 were informative, i.e. able to give positive and specific PCR amplification signals, and thus were used as capture probes in the subsequent experiments in cfDNA samples. Sequencing depth was used as a sample inclusion criterion. Samples where less than 100 MCB (see below) showed 10× read coverage were excluded from further analysis. Since each MCB incorporated on average ~3 CG markers, the 10× coverage ensured at least 30 methylation measurements per MCB. Using these criteria, 73% of all samples with a median of 34K mapped reads per sample were included.

After having obtained DNA methylation data for 1673 CG markers, the concept of MCBs to merge proximal CpG markers into a MCB was used, resulting in a total of 888 MCBs. For each MCB, the MCB-specific methylation value was quantified with two numbers: log 10 (total methylated read count +1) and log 10 (total unmethylated read count +1), using the log transform to reduce outlier effects.

About 1673 informative padlock probes were obtained that were able to give positive and specific PCR amplification signals and they were used as capture probes in the subsequent experiments in cfDNA samples. cfDNA samples with less than 100 MCB of >30× coverage were also eliminated. Methylated reads for each marker were defined as total unique methylated reads and methylation values for each marker were defined as the proportion of read counts with methylation divided by total read counts.

cfDNA-Based Diagnostic Classifier Construction Using MCBs (Cd-Score)

cfDNA sample data obtained from patients diagnosed with liver cancer (HCC), lung cancer (LUNC) and normal controls were divided into training and validation cohorts. The full dataset was randomly split with a 1:1 ratio to form the training and validation cohorts.

Marker selections: Within the training cohort, the "randomized lasso" scheme was adopted to reduce the sampling dependency and stabilize variable selection in order to select biomarkers with high confidence. The training set was first randomly divided with 1:1 ratio. The variable selection procedure on two thirds of the samples was conducted and withheld a third of the samples for evaluating performance of the feature selection process. The feature selection process consisted of two steps repeated 50 times. MCBs were included for training the final model if they were selected in 40 out of 50 feature selection iteration. A multi-class prediction system based on Friedman et al., 2010, J Stat Softw 33, 1-22 was constructed to predict the group membership of samples in the test data using the panel of MCBs selected. A confusion matrix and ROC curves were also provided to evaluate sensitivity and specificity, in addition to prediction accuracy based on the held out partition of the training set.

Classification process: a two-step classification process was employed: cancer vs normal, LUNC vs HCC by building two binary multinomial logistic regression models. The multinomial logistic regression has the advantage where it can yield an intuitive probability score and allow for easier interpretation. For example, if the cancer-vs-normal model yield a probability score of 70% for a given methylation profile, it suggests that the patient has a 70% chance of having cancer. In order to minimize the number of false cancer predictions, we set the cancer prediction confidence threshold to 80%. For patients with at least 80% chance of cancer, we apply the cancer-vs-cancer regression model for classifying between LUNC and HCC, the classification model will decide only if the classified sample has a confidence of over 55%.

Building a Predictive Model for Prognosis and Survival

The potential to use a combined prognosis score (cp-score) system based on both methylation reads and non-methylated reads was investigated for each MCB in cfDNA for prediction of prognosis in LUNC and HCC in combination with clinical and demographic characteristics including age, gender, and AJCC stage. For each type of cancer, a cp-score model was build and validate it by randomly selecting half of the observations from the full dataset as the training cohort, and treated the rest as the validation cohort. Variable selection on the training cohort was conducted and built the composite score on the validation cohort. Within the training cohort, the "randomized lasso" scheme was adopted to reduce the sampling dependency to stabilize the variable selection in order to select biomarkers with a high confidence. The entire cohort was randomly divided with a 1:1 ratio. The variable selection procedure was conducted on two-thirds of the training cohort. LASSO was implemented with an optimal tuning parameter determined by either the expected generalization error from the 10-fold cross validation or the information based criteria AIC/BIC, whichever yielded the highest (the proportion of explained randomness) with the selected biomarkers. The 10 most recurring features from HCC and in LUNC (Table 10) was then aggregated. To evaluate the predictability of each panel externally, a composite score was obtained for each patient in the validation cohort by multiplying the unbiased coefficient estimates from the Cox regression and the methylation reads. A Kaplan-Meier curve and log-rank test were generated using the dichotomized composite score, which formed a high-risk and low-risk group membership assignment according to its median. This segmentation was compatible with that formed by AJCC stage. Time-dependent ROC was used to summarize the discrimination potential of the composite score, AJCC stage and the combination of two, with ROC curves varying as a function of time and accommodating censored data. Finally, we also fitted a multivariate Cox regression model to assess the significance of potential risk factors.

All the analysis was conducted in R (version 3.2.3) and python (version 2.7.13) with the following packages used: 'glmnet', 'limma', 'survival', 'sklearn', 'lifeline', 'survivalROC', 'survcomp'.

All hypothesis testing was done by two-sided with p-value <0.05 considered to be statistically significant unless specifically stated otherwise.

Patient and Sample Characteristics

Clinical characteristics and molecular DNA methylation profiles were collected for 827 LUNC and 377 HCC tumor samples from The Cancer Genome Atlas (TCGA) and 754 normal samples from a dataset used in our previous methylation study on aging (GSE40279) (Hannum et al., 2013). Two cohorts of patients were studied. The first cohort was from solid tumor samples from TCGA and the second cohort was from plasma samples from China. To study cfDNA in LUNC and HCC, plasma samples were obtained from 2,396 Chinese patients with HCC or LUNC, and from randomly selected, population-matched healthy controls undergoing routine health care maintenance, resulting in a cohort of 892 LUNC and 1504 HCC patients and 2247 normal healthy controls. Informed written consent was obtained from each study participant. Clinical characteristics of all patients and controls are listed in Table 11.

Identification of Methylation Markers Differentiating LUNC and HCC and Blood

Previous reports indicate that plasma contains DNA released from tissues within the body. It was hypothesized that because cfDNA originating from tumor cells can be detected in a background of cfDNA predominantly released from leukocytes, CpG markers with a maximal difference in methylation values between LUNC or HCC versus normal leukocytes would be most likely to demonstrate detectable methylation differences in the cfDNA of HCC or LUNC patients when compared to that of normal controls. To identify putative markers, methylation data derived from cancer tissue DNA from the TCGA and normal blood including 827 LUNC, 377 HCC, and 754 blood samples from healthy controls were compared. In order to identify DNA sites with significantly different rates of methylation between LUNC or HCC and normal blood, a t-statistic with Empirical Bayes was used for shrinking the variance and selected the top 1000 significant markers, using the Benjamini-Hochberg procedure to control the FDR at a significance level of 0.05. Unsupervised hierarchical clustering of these top 1000 markers was able to distinguish between LUNC, HCC, and normal blood, and between LUNC and HCC (FIG. 20). About 2,000 molecular inversion (padlock) probes corresponding to these 2000 markers for capture-sequencing cfDNA from plasma (1000 for cancer versus normal and 1000 for LUNC versus HCC) were then designed.

cfDNA Diagnostic Prediction Model for LUNC and HCC

Figure 14A:
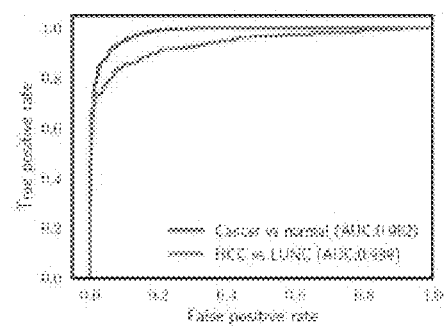
FIG. 14A-FIG. 14D illustrates cfDNA methylation analysis for diagnosis of LUNC and HCC.
Figure 14B:
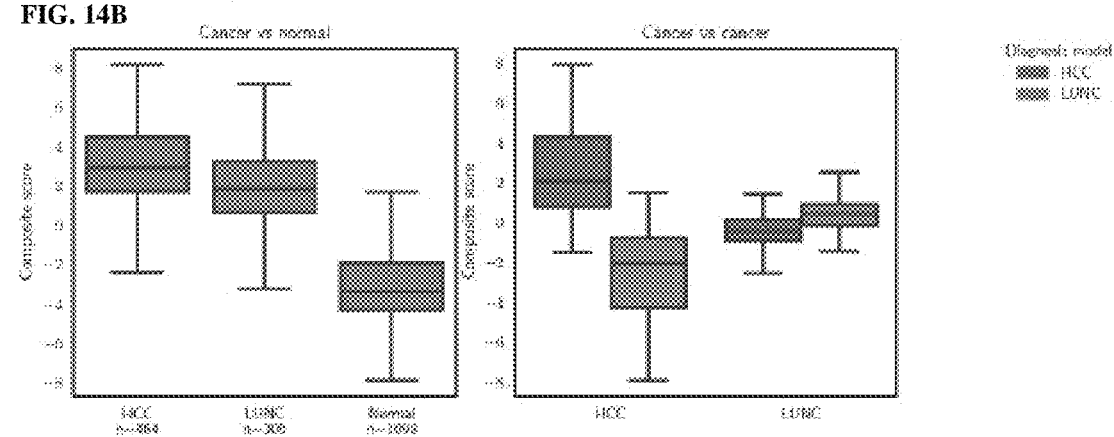
Figure 14C:
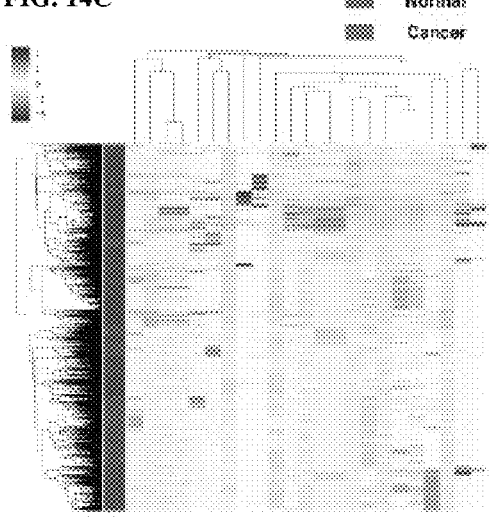
Figure 14D:
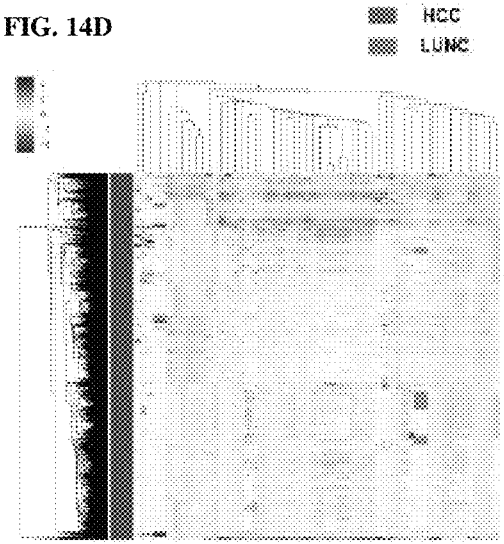
Figure 20C:
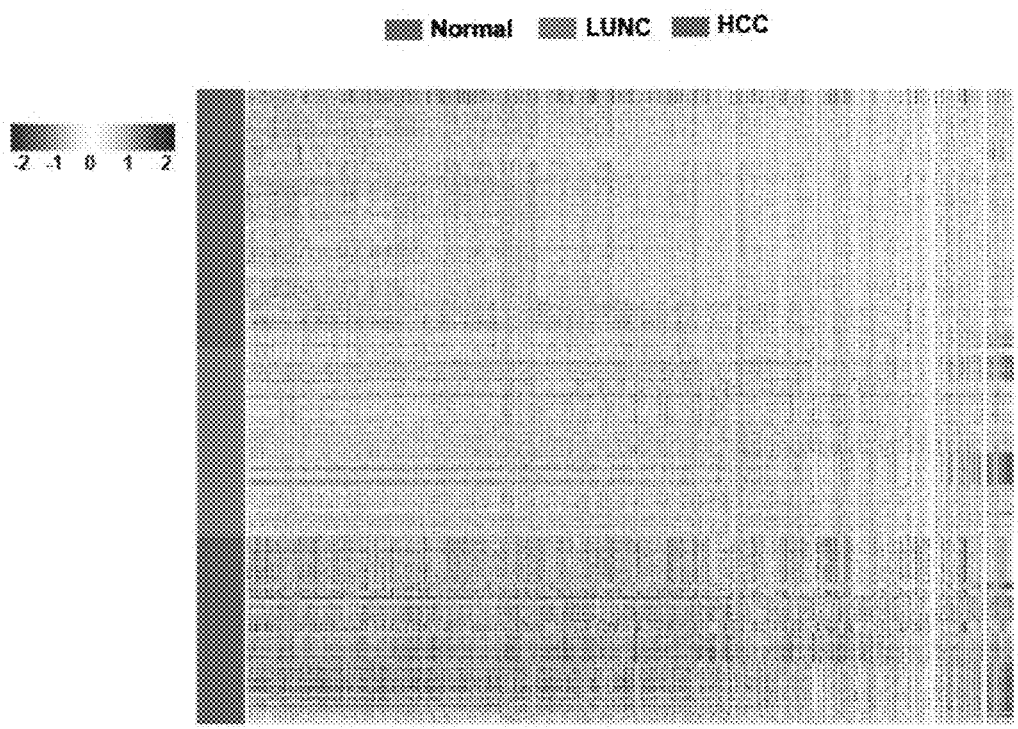
FIG. 20C illustrates a global view of supervised hierarchical clustering of all 888 MCBs in the entire cfDNA dataset.
Figure 21:
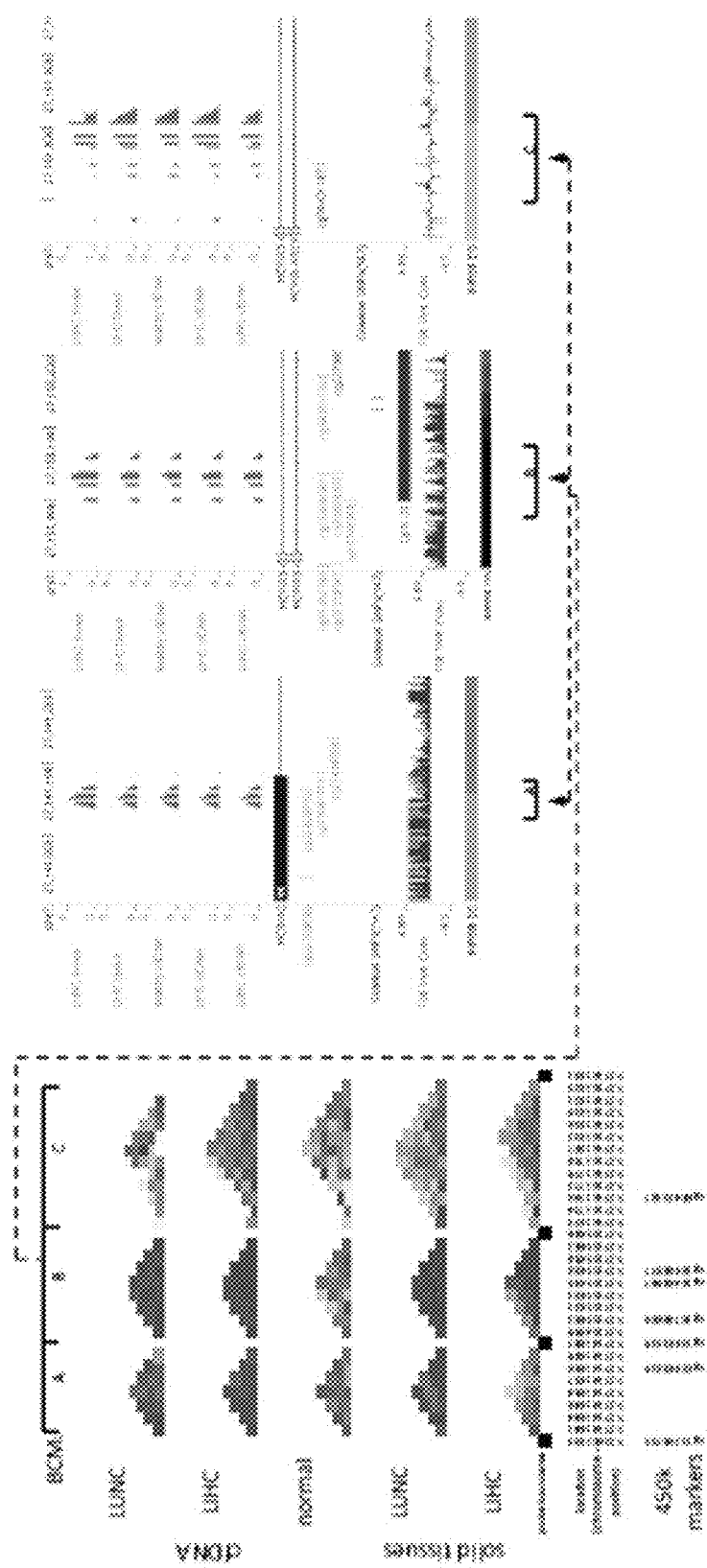
FIG. 21 illustrates Boxplots showing the features of MCBs in cohorts. Top plot: Mean values and deviations of Lasso MCBs in each one versus rest comparison.
Figure 22:
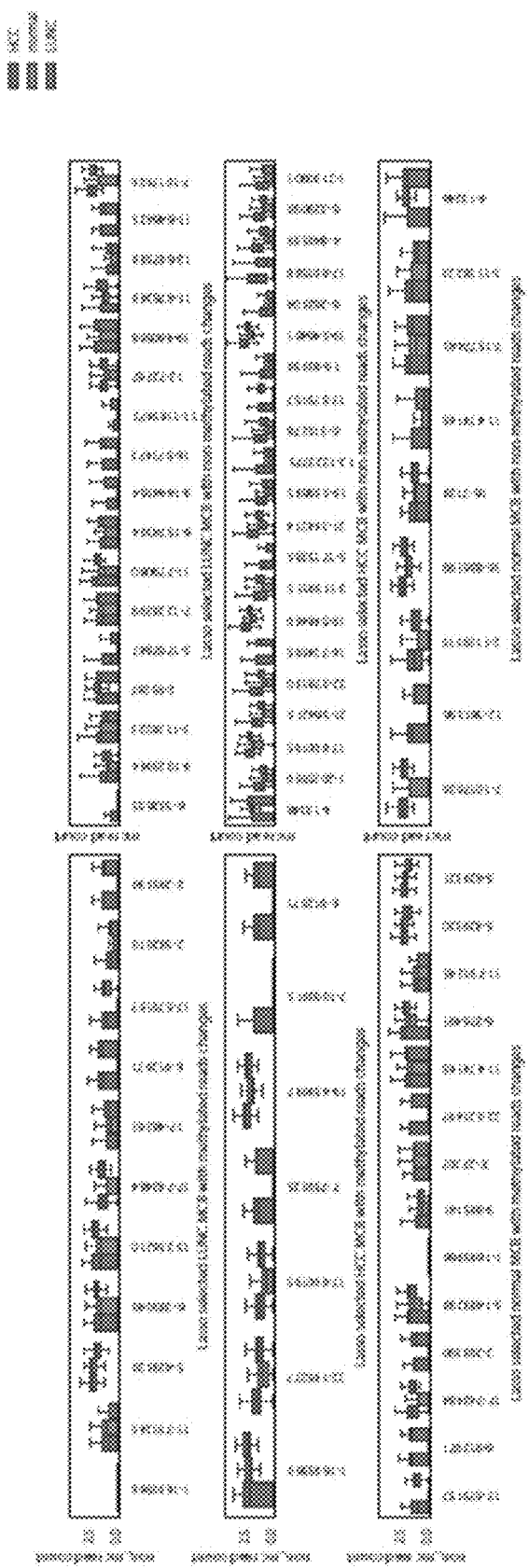
FIG. 22 illustrates methylation values correlated with treatment outcomes in HCC and LUNC patients with serial plasma samples. Summary graphs of change in methylation value comparing patients after surgery, with clinical response (Partial Remission (PR) or Stable Disease (SD), or with disease progression/recurrent (PD).

The methylation data of the 888 selected Methylation Correlated Blocks (MCB) that showed good methylation ranges in cfDNA samples were further analyzed to identify MCBs that showed significantly different methylation between cancer samples (LUNC and HCC) versus normal control samples. Unsupervised hierarchical clustering of these selected MCBs using methylated reads across samples is shown in FIG. 20C, and distributions of MCB methylated read values for normal, LUNC and HCC samples is shown in FIG. 21. The entire methylation dataset of 888 MCBs was therefore analyzed by Least Absolute Shrinkage and Selection Operator (LASSO) method and further reduced the number of MCBs. LASSO-based feature selection identified 28 MCBs for discriminating LUNC versus HCC and normal, 27 MCBs for discriminating of HCC versus LUNC and normal, 22 MCBs for discriminating of normal vs HCC and LUNC, resulting in 77 unique markers (5 MCBs overlap between models). This approach combined the information captured by the MCBs into a composite cfDNA-based score (composite diagnostic score: cd-score). The utility of this score was evaluated for predicting the presence of LUNC or HCC using a hold-out strategy where samples were randomly assigned to a training set and a validation set with a 1:1 ratio. The scoring system was trained using 229 LUNC, 444 HCC and 1123 normal control cfDNA samples and then validated on 300 LUNC, 445 HCC and 1124 normal samples. Applying the fitted model to the validation set samples yielded a sensitivity of 92.4% for HCC and 85.8% for LUNC, and a specificity of 99.0% for normal controls in a multi-classification scheme (Table 8A). It was found that this model could successfully differentiate LUNC and HCC samples from normal controls in the validation cohort (AUC cancer vs normal=0.979; AUC LUNC vs HCC=0.924; FIG. 14A, Table 8B, Table 8C). Unsupervised hierarchical clustering of the 77 MCBs was able to distinguish HCC and LUNC from normal controls with high specificity and sensitivity (FIG. 14C and FIG. 14D).

Figure 15B:
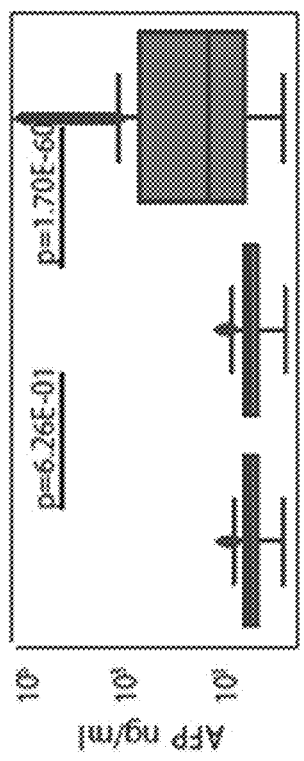
FIG. 15A-FIG. 15D illustrates methylation profiling in healthy control, high-risk patients and cancer patients.
Figure 15D:
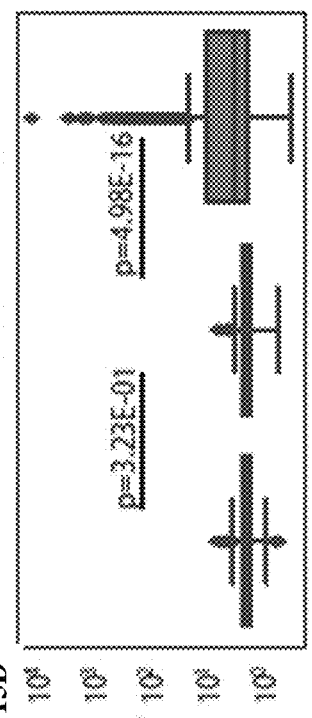
Figure 15A:
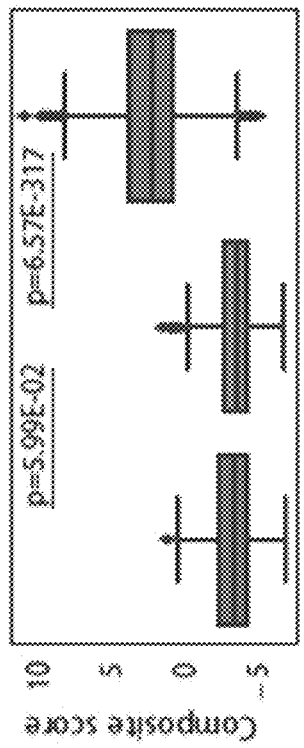
Figure 15C:
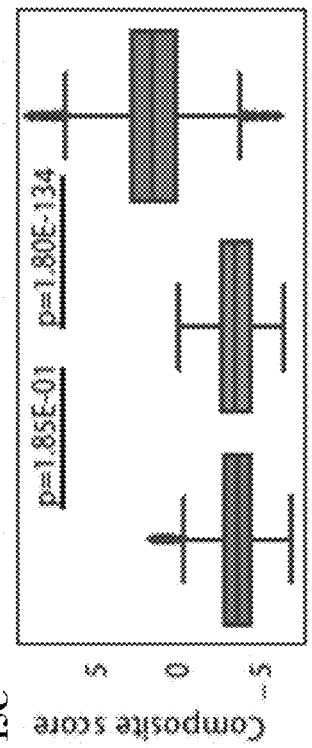

Liver diseases, such acirrhosis, and fatty liver, are major risk factors for HCC. Thus, the cd-score of the model was assessed for differentiating between liver diseases and. It was found that the cd-score was able to differentiate HCC patients from those with liver diseases or healthy controls (FIG. 15A). These results were consistent and comparable with those predicted by AFP levels in HCC (FIG. 15B). The cd-score could also differentiate between LUNC patients and non-LUNC patients with a smoking history (>1 pack/day for ten years) who were at an increased risk of LUNC (FIG. 15C). These results were consistent and comparable with those predicted by AFP levels in HCC (FIG. 15D).

Methylation Profiles Predicted Tumor Burden, Treatment Response and Staging

Figure 23A:
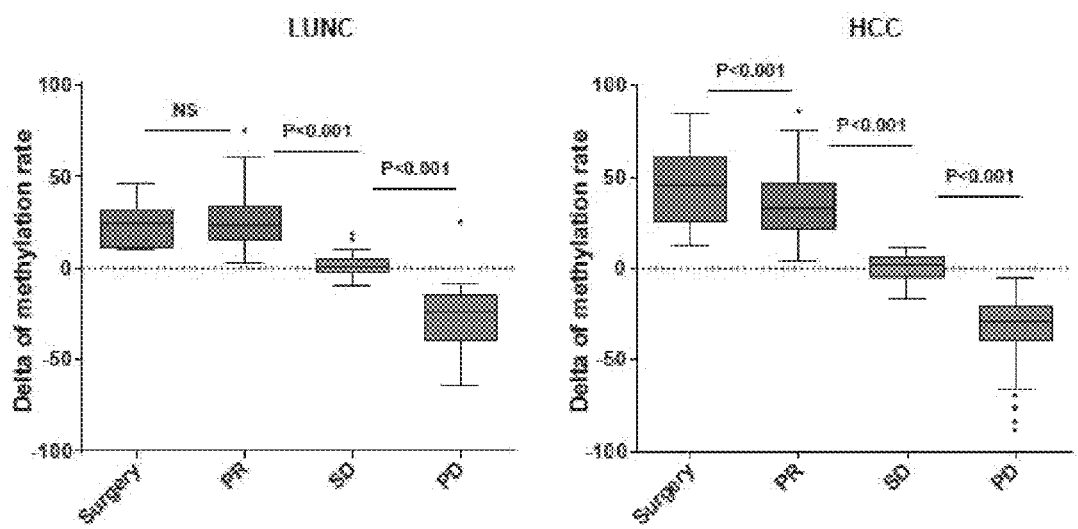
FIG. 23A shows dynamic monitoring of treatment outcomes using the total methylation copy numbers of an MCB in LUNC patients.
Figure 23B:
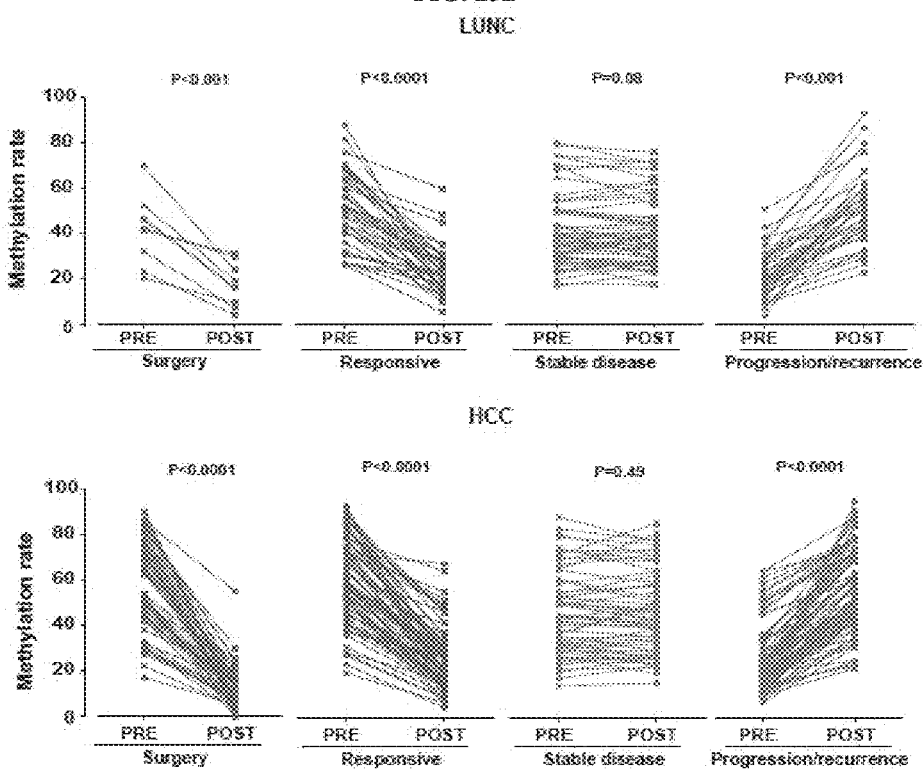
FIG. 23B shows dynamic monitoring of treatment outcomes with the methylation value of an MCB in LUNC patients. PD, progressive disease; PR partial response; SD, stable disease; chemo, chemotherapy.
Figure 24:
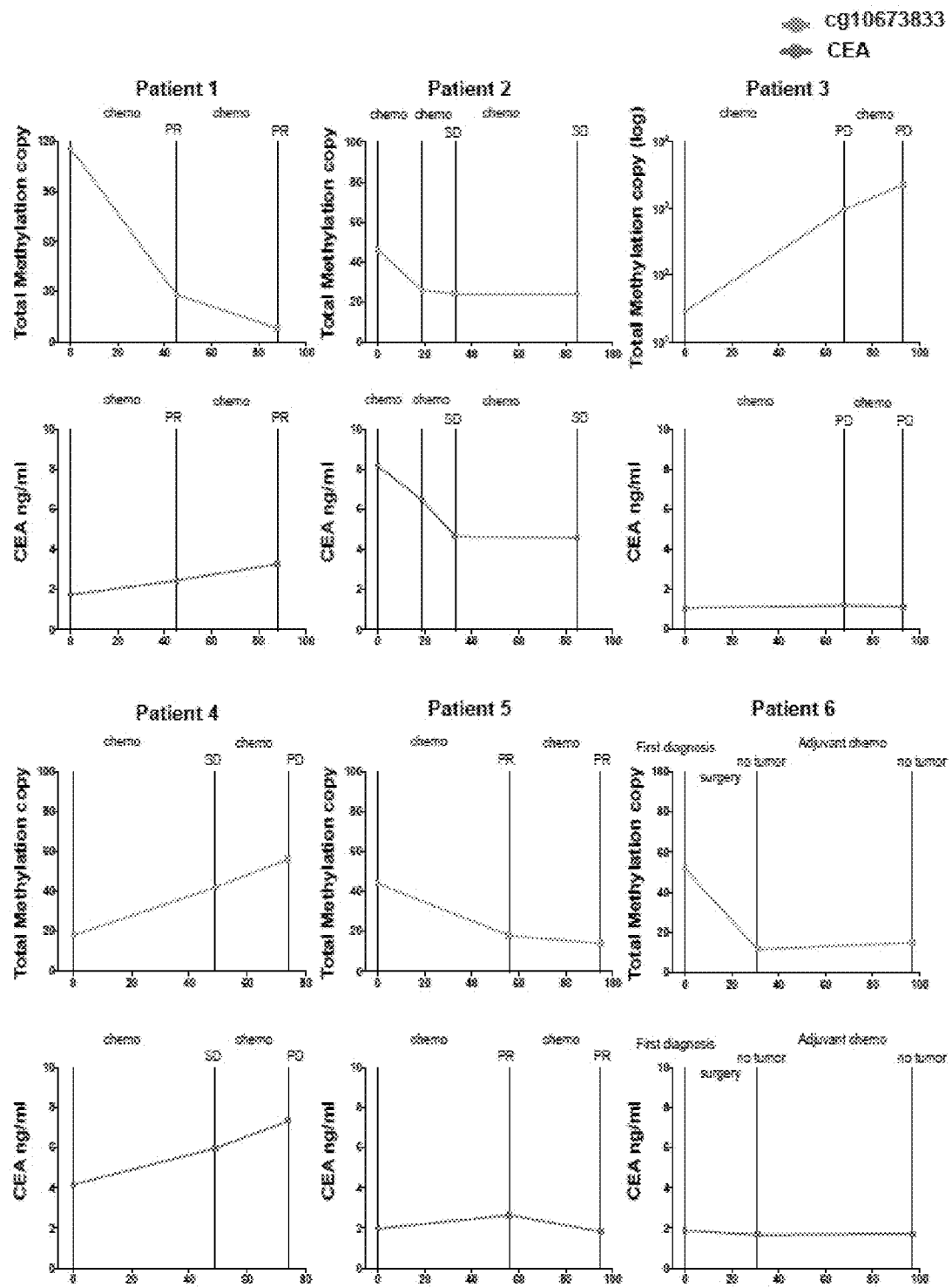
FIG. 24 illustrates dynamic monitoring of treatment outcomes using the total methylation copy numbers of an MCB and CEA in HCC patients.
Figure 25:
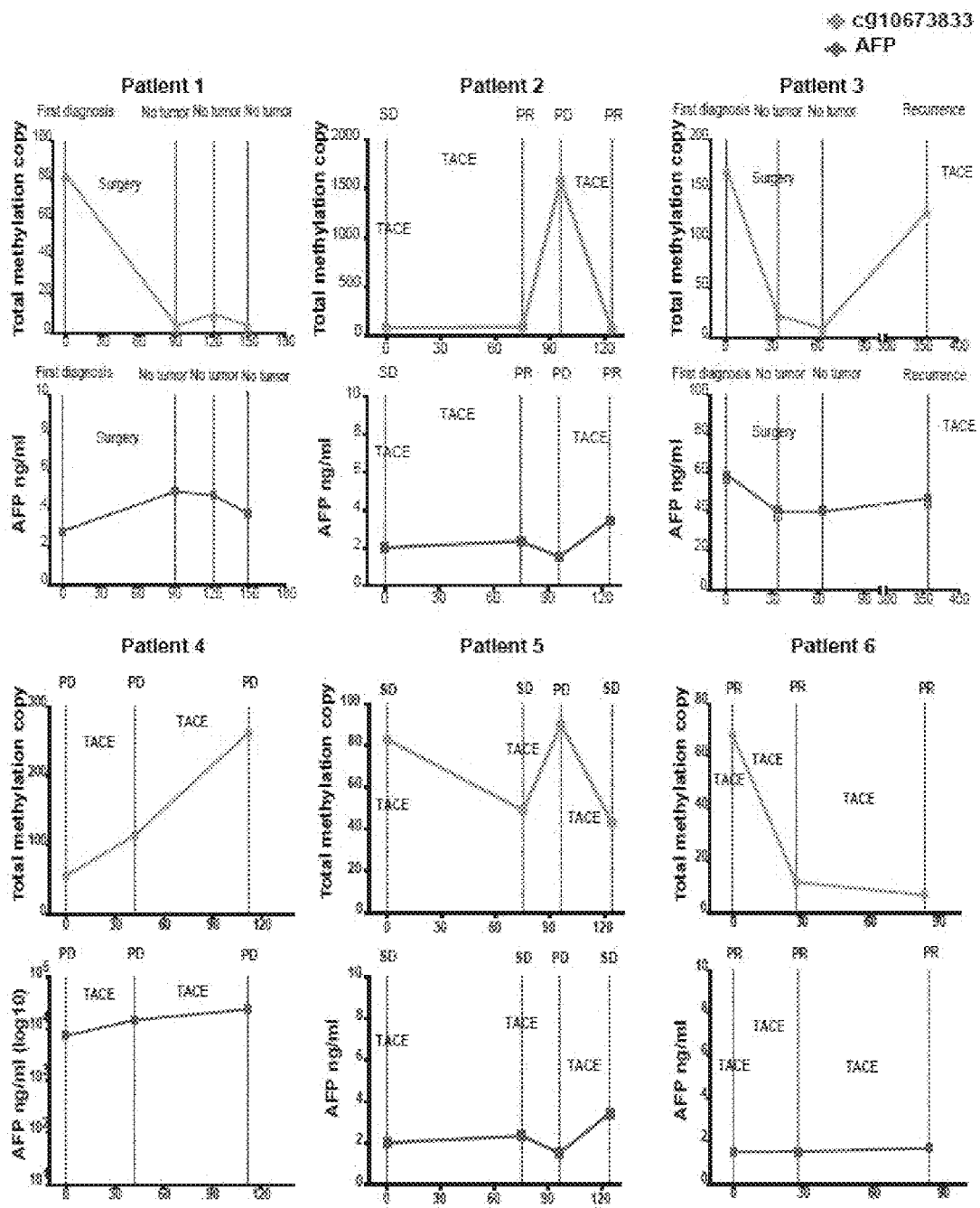
FIG. 25 shows dynamic monitoring of treatment outcomes with the methylation rate of an MCB in HCC patients. Dates of treatments are indicated in the figure. PD, progressive disease; PR partial response; SD, stable disease; chemo, chemotherapy, TACE, trans-catheter arterial chemo-embolization.

Next, the utility of the cd-score was studied in assessing treatment response, the presence of residual tumor following treatment, and staging of LUNC and HCC. In LUNC, the cd-scores of patients with detectable residual tumor following treatment (n=559) were significantly higher than those with no detectable tumor (n=160) (p<0.001, FIG. 16A). Similarly, there was good correlation between the cd-scores and tumor stage. Patients with early stage disease (I, II) had substantially lower cd-scores compared to those with advanced stage disease (III, IV) (p=<0.005, FIG. 16B). In addition, the cd-scores were significantly lower in patients with complete tumor resection after surgery (n=158) compared with those before surgery (n=67), yet became higher in patients with recurrence (n=56) (p<0.01, FIG. 16C). Furthermore, the cd-scores were significantly higher in patients before treatment (n=67) or with progression (n=136) compared to those with a positive treatment response (n=328) (p<0.001, FIG. 16D). In HCC, The cd-scores of patients with detectable residual tumor following treatment (n=889) were significantly higher than those with no detectable tumor (n=314) (p<0.0001, FIG. 16E). Similarly, there was a highly positive correlation between cd-scores and tumor stage. Patients with early stage disease (I, II) had substantially lower cd-scores compared to those with advanced stage disease (III, IV) (p<0.001, FIG. 16F). In addition, the cd-scores were significantly lower in patients with complete tumor resection after surgery (n=293) compared with those before intervention (n=109), yet became higher in patients with recurrence (n=155) (p<0.01, FIG. 16G). Furthermore, the cd-scores were significantly higher in patients before treatment (n=109) or with progression (n=381) compared to those with treatment response (n=249) (p<0.001, FIG. 16H). Serial longitudinal dynamic changes were obtained of methylation values of CpG site cg10673833 in several individuals with LUNC or HCC patient in order to monitor treatment response and found there was a high correlation between methylation values and treatment outcomes (FIG. 23, FIG. 24 and FIG. 25). Collectively, the results showed the significant correlation between he cd-score (i.e., the amount of cfDNA in plasma) and tumor burden, demonstrating its utility for the prediction of tumor response and for surveillance to detect recurrence.

Diagnostic Utility of cfDNA as Compared with AFP and CEA

Figure 16I:
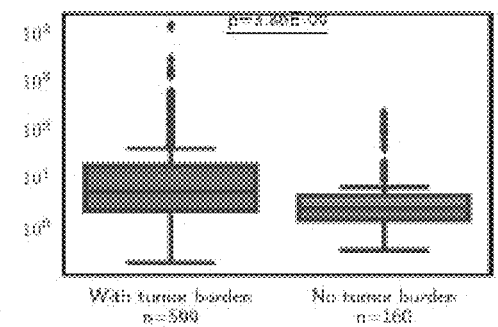
FIG. 16A-FIG. 16R illustrates cfDNA methylation analysis could predict tumor burden, staging, and treatment response using a composite diagnosis score in LUNC and HCC patients. cd-score in patients with and without detectable tumor burden in LUNC (FIG. 16A) when compared to CEA (FIG. 16I) and HCC (FIG. 16E) when compared to AFP (FIG. 16M); cd-score of patients with stage I/II and stage III/IV disease in LUNC (FIG. 16B) when compared to CEA (FIG. 16J) and HCC (FIG. 16F) patients when compared to AFP (FIG. 16N); cd-score in patients before intervention, after surgery, and with recurrence in LUNC (FIG. 16C) when compared to CEA (FIG. 16K) and HCC (FIG. 16G) when compared to AFP (FIG. 16O); cd-score in patients before intervention, with treatment response, and with worsening progression in LUNC (FIG. 16D) when compared to CEA (FIG. 16L) and HCC (FIG. 16H) when compared to AFP (FIG. 16P)
(FIG. 16Q) The ROC curve and the AUC of cd-score and AFP for LUNC diagnosis in the entire LUNC cohort.
Figure 16J:
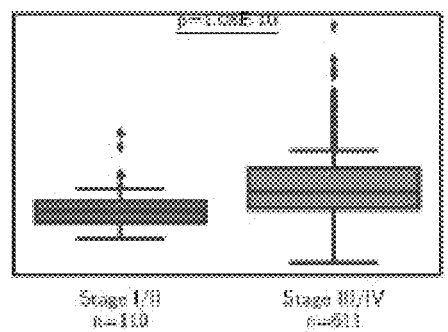
Figure 16K:
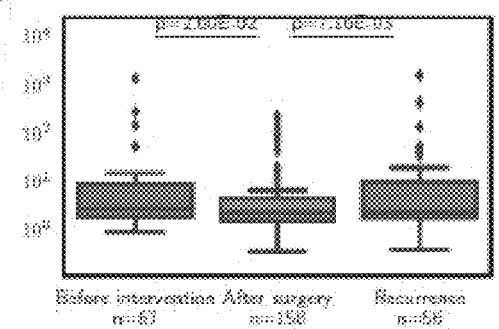
Figure 16L:
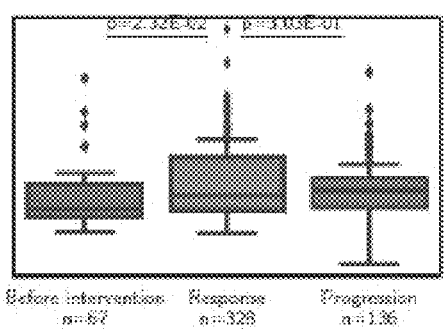
Figure 16M:
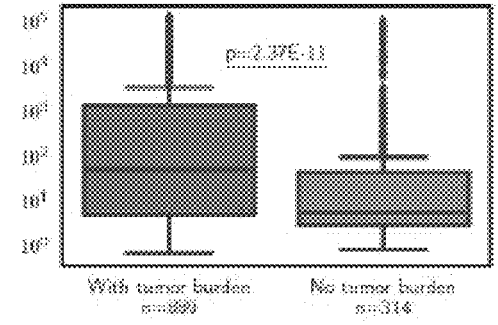
Figure 16N:
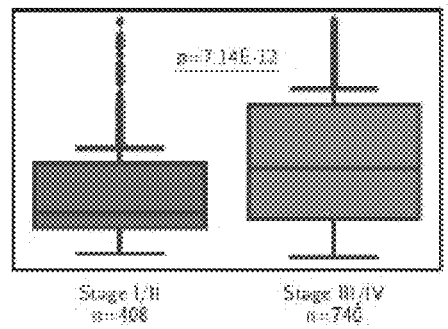
Figure 16O:
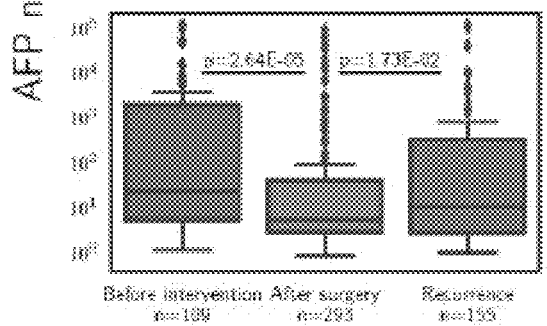
Figure 16P:
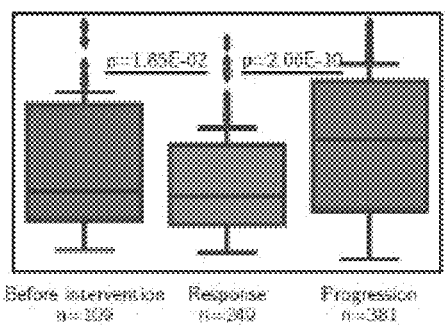
Figure 16Q:
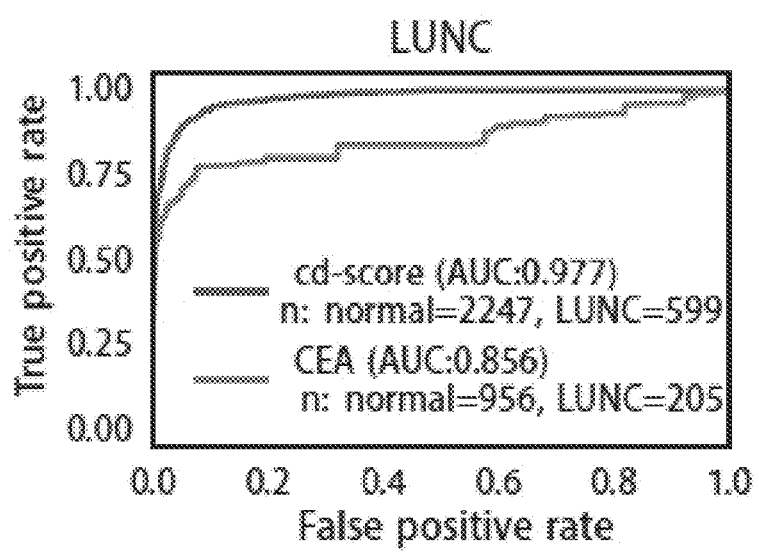
Figure 16R:
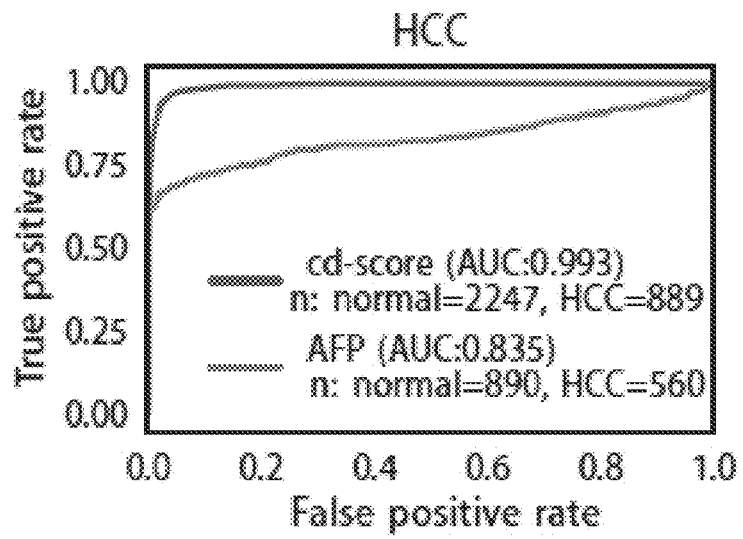

Despite enormous efforts, an effective noninvasive blood-based biomarker for surveillance and diagnosis of LUNC and HCC is still lacking. CEA (cancer embryonic antigen) and AFP have filled this role for lung cancer and HCC for decades, but its sensitivity and specificity are inadequate. Moreover, some patients with squamous cell carcinoma or small cell lung cancer will not have increased blood CEA levels. AFP has low sensitivity of 60%, making it inadequate for detection of all patients that will develop HCC and thus severely limiting its clinical utility. In fact, it is common for cirrhotic patients with HCC to show no increase in AFP levels. Strikingly, 30% patients of the HCC study cohort have a normal AFP value (<25 ng/ml). In biopsy-proven LUNC patients of the entire cohort, the cd-score demonstrated superior sensitivity and specificity to CEA for LUNC diagnosis (AUC 0.977 (cd-score) vs 0.856 (CEA), FIG. 16Q). Both cd-score and CEA values were highly correlated with tumor stage (FIG. 16J, FIG. 16B). On other hand, the cd-score demonstrated superior sensitivity and specificity to AFP for HCC diagnosis (AUC 0.993 vs 0.835, FIG. 4R) in biopsy-proven HCC patients. Both cd-score and AFP values were highly correlated with tumor stage (FIG. 16F and FIG. 16N). In patients with treatment response, tumor recurrence, or progression, the cd-score showed more changes from initial diagnosis than that of AFP (FIG. 16G and FIG. 16H, FIG. 16O and FIG. 16P). In LUNC patients with treatment response, tumor recurrence, or progression, the cd-score showed more significant changes from initial diagnosis than that of CEA (FIG. 16C and FIG. 16D, FIG. 16K and FIG. 16L). In LUNC and HCC patients with serial samples, there was a concomitant and significant decrease in cd-score in patients with a positive treatment response than in patients prior to treatment. There was an even further reduction in cd-score in patients after surgery. In contrast, there was an increase in methylation rate in patients with progressive or recurrent disease (FIG. 23). By comparison, CEA and AFP were less sensitive for assessing treatment efficacy in individual patients (FIG. 24 and FIG. 25).

cfDNA Prognostic Model for HCC and LUNC

The potential of using a combined prognosis score (cp-score) based on cfDNA methylation analysis for prediction of prognosis in LUNC and HCC in combination with clinical and demographic characteristics including age, gender, AJCC stage, and AFP value was investigated. Totally 599 LUNC patients and 867 HCC patients enrolled in prognosis analysis (patients without tumor burden are excluded from the analysis). The median follow up time was 9.5 months (rang 0.6-26 months) in LUNC cohort and 6.7 months (rang 1.2-21.0 months) in HCC cohort. In the HCC cohort, the training dataset contained 433 observations with 41 events and the validation dataset contained 434 observations with 58 events. By using statistical learning methods, a predictive model was constructed using 10 CpG MCBs (Table 10) that can separate the HCC cohort into high and low risk groups, with median survival significantly greater in the low-risk group than in the high-risk group (log-rank test=24.323, df=1, p<0.001) (FIG. 17A). In the LUNC cohort, the training dataset contained 299 observations with 61 events and the validation dataset contained 434 observations with 58 events. A panel of 10 CpG markers (Table 10) was able to divide the LUNC cohort into high and low risk groups, with median survival significantly greater in the low-risk group than in the high-risk group (log-rank test=6.697, df=1, p<0.001) (FIG. 17B).

Multivariate Cox regression model showed that the cp-score was significantly correlated with incidence of mortality in both HCC and LUNC. The cp-score was an independent risk factor of survival both in HCC and borderline in LUNC validation cohorts (hazard ratio=2.4881, p=0.000721 in HCC; hazard ratio=1.74, p=0.068 in LUNC; p=0.0017 in LUNC; Table 12). Interestingly, when cp-score and other clinical characteristics were taken into account in HCC, AFP was no longer significant as a risk factor (Table 13). As expected, TNM stage (as defined by AJCC guidelines) predicted the prognosis of patients both in HCC (FIG. 17C) and LUNC (FIG. 17D). The combination of cp-score and TNM staging improved our ability to predict prognosis in both HCC (AUC 0.867, FIG. 17E) and LUNC cohort (AUC 0.825, FIG. 17F).

Methylation Markers in Early Diagnosis of LUNC and HCC

Figures 18A, 18B:
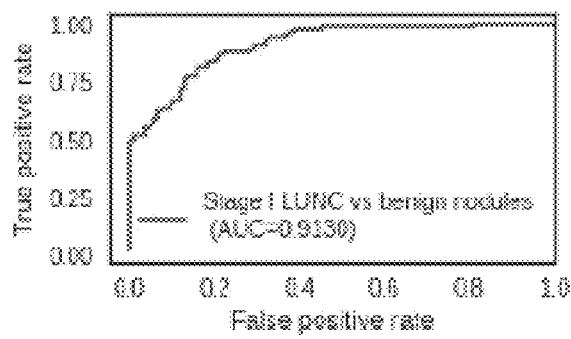
FIG. 18A-FIG. 18B illustrates early detection of LUNC using a cfDNA methylation panel. 208 smoker patients were enrolled with lung nodules between 10 mm and 30 mm in size in a prospective trial and measured a cfDNA LUNC methylation panel. Patients were divided into a training and a testing cohort (FIG. 18A); receiver operating characteristic (ROC) curves and the associated Area Under Curves (AUCs) of the prediction of Stage I LUNC versus benign lung nodules in the validation cohort with 91.4% accuracy (FIG. 18A); table showing prediction results between Stage I LUNC versus benign lung nodules showing high sensitivity and specificity in the validation cohort (FIG. 18B]).
Figures 19A, 19B, 19C, 19D:
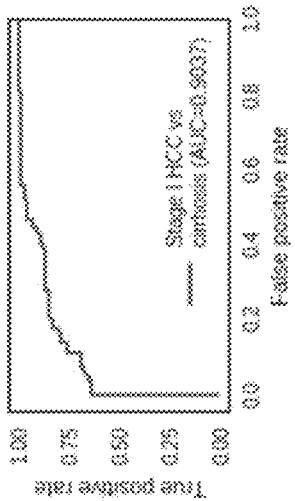
FIG. 19A-FIG. 19D illustrates methylation markers can differentiate between HCC and liver cirrhosis and Detect progression from liver cirrhosis to HCC. A prediction model was built using 217 HCC and 241 cirrhosis patients and divided patients into a training and a testing cohort (FIG. 19A); Receiver operating characteristic (ROC) curves and the associated Area Under Curves (AUCs) of the prediction of Stage I HCC versus liver cirrhosis in the validation cohort with 89.9% accuracy (FIG. 19B); table showing prediction results between Stage I HCC and liver cirrhosis in a validation cohort (FIG. 19C); table showing prediction results on progression from liver cirrhosis to stage 1HCC with high sensitivity (89.5%) and specificity (98%) (FIG. 19D).

Since LUNC and HCC are very aggressive cancers with poor prognosis and survival, and surgical removal of cancer at stage 1 carries a much more favorable prognosis, early detection becomes a key strategy in reducing morbidity and mortality. The method of using methylation markers for predicting cancer occurrence in high-risk populations was investigated in two prospective studies. In the first study, consecutive patients were recruited from a group of patients with solid lung nodules >10 mm identified on chest CT scans. These patients were enrolled in a study for early lung detection in smokers and underwent CT scan-based lung cancer screening. Patients presenting with a solid lung nodule (between 10 mm and 30 mm in size, n=208, Table 13) were selected to undergo methylation profiling at the time of screening. These patients were subsequently followed through secondary testing to determine whether nodules were due to LUNC or a benign condition due to inflammation or infection by tissue biopsy and pathology verification. The methylation profile was sufficient to differentiate patients with biopsy-proven stage 1 LUNC lesions compared to patients with benign nodules due to inflammatory or infectious conditions (FIG. 18, Table 14). Among the patients with at least 59% confidence for diagnosis, Positive predictive value (PPV) of stage I cancer was 95.9% and negative predictive value (NPV) was 97.4%. Similarly, we prospectively enrolled high risk HCC patients with liver cirrhosis (n=236, Table 13). The methylation profile was able to predict progression to stage 1 HCC with 89.5% sensitivity and 98.2% specificity (FIG. 19, Table 14) among the patients with at least 58% confidence for diagnosis. PPV was 80.9% and NPV was 99.1%.

In this study, differentially methylated CpG sites were first determined in LUNC and HCC tumor samples versus normal blood. Then, these markers were interrogated in the cfDNA of a large cohort of LUNC and HCC patients as well normal controls. A diagnostic model (cd-score) was developed using methylation of cfDNA to predict the presence of cancer, while at the same time differentiating between LUNC and HCC.

The cd-score discriminated patients with HCC from individuals with HBV/HCV infection, cirrhosis, and fatty liver disease as well as healthy controls. In some instances, it is important that a serum test reliably distinguish these disease states from HCC. According to the results, the sensitivity of the cd-score for HCC is comparable to liver ultrasound, the current standard for HCC screening. In addition, in some instances it is superior to AFP, the only clinically used biomarker for HCC, making cd-score a more cost-effective and less resource-intensive approach. Furthermore, by showing its high correlation with HCC tumor burden, treatment response, and stage, the cd-score of the model demonstrated superior performance than AFP in the instant cohort (AFP values were within a normal range for 40% of our HCC patients during the entire course of their disease). In some cases, the cd-score may be particularly useful for assessment of treatment response and surveillance for recurrence in HCC. Since nearly all of the HCC patients had hepatitis (most likely hepatitis B) in the study, 1HCC arising from other etiologies may have different cfDNA methylation patterns. Similar to HCC, screening for lung cancer has a high cost, involving CT imaging of the chest, which has an associated radiation exposure and a high false-positive rate. In some cases, the cd-score reliably distinguished smokers and patients with lung cancer and may also have utility in improving screening and surveillance.

Prognostic prediction models were also constructed for HCC and LUNC from the cp-score. The cp-score effectively distinguished HCC and LUNC patients with different prognosis and was validated as an independent prognostic risk factor in a multi-variable analysis in our cohorts. Of note, for predicting prognosis in HCC, cfDNA analysis was again superior to AFP. In some cases, this type of analysis is helpful for identification of patients for whom more or less aggressive treatment and surveillance is needed.

TABLE 8A

Contingency table of multi-classification diagnosis in validation cohort

| Prediction | HCC | LUNC | Normal |
|---|---|---|---|
| HCC | 329 | 19 | 6 |
| LUNC | 23 | 145 | 6 |
| Normal | 4 | 5 | 921 |
| Undecided | 89 | 131 | 191 |
| Totals | 354 | 174 | 930 |
| Correct | 329 | 145 | 921 |
| Sensitivity (%) | 92.4 | 85.8 | |
| Specificity (%) | | | 99.0 |

TABLE 8B

Contingency table of binary classification diagnosis between HCC and normal

| Prediction | HCC | Normal |
|---|---|---|
| cancer | 371 | 16 |
| normal | 4 | 921 |
| undecided | 70 | 187 |
| Totals | 375 | 937 |
| Correct | 371 | 921 |
| Sensitivity (%) | 98.9 | |
| Specificity (%) | | 98.3 |

TABLE 8C

Contingency table of binary classification diagnosis between LUNC and normal

| Prediction | LUNC | Normal |
|---|---|---|
| cancer | 188 | 16 |
| normal | 5 | 921 |
| undecided | 107 | 187 |
| Totals | 193 | 937 |
| Correct | 188 | 921 |
| Sensitivity (%) | 97.4 | |
| Specificity (%) | | 98.3 |

TABLE 9

List of MCBs selected by multi-class LASSO and used for cd-score generation. A, normal; B, LUNC; C, HCC.

| Diagnosis | MCBs | Read counts | Target ID | RefGene | Logistic regression coefficients | |
|---|---|---|---|---|---|---|
| | | | | | LUNC vs HCC | cancer vs normal |
| A, Normal | | | | | | |
| Normal | 1-1693966 | mc | cg00100121 | C1orf114 | 0.058289236 | −0.460201686 |
| | | non_mc | cg00100121 | C1orf114 | −0.264294546 | −0.362527983 |
| | 11-474165 | mc | cg13912307 | SLC39A13 | −0.019821436 | −0.342748675 |
| | | non_mc | cg13912307 | SLC39A13 | −0.119495297 | −0.097830945 |

TABLE 9-continued

List of MCBs selected by multi-class LASSO and used for cd-score generation. A, normal; B, LUNC; C, HCC.

| Diagnosis | MCBs | Read counts | Target ID | RefGene | Logistic regression coefficients | |
|---|---|---|---|---|---|---|
| | | | | | LUNC vs HCC | cancer vs normal |
| | 11-791245 | mc | cg08794954 | ODZ4 | −0.502459754 | −0.119001342 |
| | | non_mc | cg08794954 | ODZ4 | −0.050537884 | −0.237868292 |
| | 12-561356 | mc | cg00344358 | GDF11 | 0.013443025 | −0.152292508 |
| | | non_mc | cg00344358 | GDF11 | 0.210631385 | −0.24781796 |
| | 16-7128 | mc | cg05773599 | WDR90 | −0.220759943 | −0.438656833 |
| | | non_mc | cg05773599 | WDR90 | 0.123092944 | −0.14690629 |
| | 16-856199 | mc | cg10174683 | — | 0.05314766 | 0.335012824 |
| | | non_mc | cg10174683 | — | −0.182838798 | −0.279797616 |
| | 17-579157 | mc | cg12054453 | TMEM49 | 0.062499156 | −0.478242327 |
| | | non_mc | cg12054453 | TMEM49 | 0.549358501 | 0.925660526 |
| | 17-742484 | mc | cg24166450 | — | 0.240682421 | 0.067853997 |
| | | non_mc | cg24166450 | — | 0.443449771 | 0.566346654 |
| | 2-1139315 | mc | cg09366118 | PSD4 | 0.098868936 | 0.269196214 |
| | | non_mc | cg09366118 | PSD4 | 0.039975437 | −0.005683265 |
| | 2-293390 | mc | cg21972382 | CLIP4 | −0.099097051 | −0.61331161 |
| | | non_mc | cg21972382 | CLIP4 | 0.074745373 | 0.2650865 |
| | 22-321497 | mc | cg03550506 | DEPDC5 | −0.068645581 | −0.755902786 |
| | | non_mc | cg03550506 | DEPDC5 | −0.046222783 | −0.124629981 |
| | 3-1138223 | mc | cg06722069 | — | −0.427422216 | −0.26910555 |
| | | non_mc | cg06722069 | — | 0.089047399 | −0.071525276 |
| | 4-13248 | mc | cg07748255 | MAEA | 0.217866978 | −0.457591409 |
| | | non_mc | cg07748255 | MAEA | −0.011474644 | −0.340582424 |
| | 5-1489298 | mc | cg22928002 | CSNK1A1 | −0.19633718 | −0.006367323 |
| | | non_mc | cg22928002 | CSNK1A1 | −0.131881054 | 0.459975236 |
| | 5-429520 | mc | cg17757602 | — | 0.041309712 | 0.029262464 |
| | | non_mc | cg17757602 | — | −0.133713183 | −0.355503949 |
| | 5-429521 | mc | cg17757602 | — | 0.127773182 | 0.169659022 |
| | | non_mc | cg17757602 | — | −0.3026458 | −0.526377272 |
| | 6-276491 | mc | cg03161803 | — | −0.134554024 | 0.040255772 |
| | | non_mc | cg03161803 | — | −0.076945207 | −0.517353281 |
| | 6-912971 | mc | cg01087382 | MAP3K7 | 0.132083258 | −0.263202543 |
| | | non_mc | cg01087382 | MAP3K7 | 0.023651284 | 0.314783378 |
| | 7-1017626 | mc | cg06721601 | CUX1 | 0.305704307 | 0.347231675 |
| | | non_mc | cg06721601 | CUX1 | −0.061678409 | 0.340362292 |
| | 7-1577443 | mc | cg27104173 | PTPRN2 | 0.029132702 | −0.207025939 |
| | | non_mc | cg27104173 | PTPRN2 | 0.004420766 | −0.098341178 |
| | 9-885141 | mc | cg13740515 | — | 0.028390415 | −0.269846773 |
| | | non_mc | cg13740515 | — | −0.208939054 | −0.193859618 |
| | X-27307 | mc | cg13176022 | XG | 0.511857283 | 0.042177783 |
| | | non_mc | cg13176022 | XG | 0.048888339 | −0.232292001 |
| | | | | B: LUNC | | |
| LUNC | 1-1693966 | mc | cg00100121 | C1orf114 | 0.058289236 | −0.460201686 |
| | | non_mc | cg00100121 | C1orf114 | −0.264294546 | −0.362527983 |
| | 11-1169673 | mc | cg16858415 | SIK3 | 0.374145093 | 0.446746019 |
| | | non_mc | cg16858415 | SIK3 | 0.297361321 | 0.42281836 |
| | 11-476248 | mc | cg05585544 | — | 0.570677409 | 0.329004001 |
| | | non_mc | cg05585544 | — | 0.127193074 | −0.357434967 |
| | 11-646423 | mc | cg18518074 | EHD1 | 0.305179647 | 0.273679057 |
| | | non_mc | cg18518074 | EHD1 | −0.170377122 | −0.416439448 |
| | 11-779080 | mc | cg03423942 | USP35 | 0.049737225 | 0.05832888 |
| | | non_mc | cg03423942 | USP35 | −0.152714594 | 0.278866832 |
| | 11-791245 | mc | cg08794954 | ODZ4 | −0.502459754 | −0.119001342 |
| | | non_mc | cg08794954 | ODZ4 | −0.050537884 | −0.237868292 |
| | 12-687588 | mc | cg20323175 | — | 0.148739937 | 0.171957693 |
| | | non_mc | cg20323175 | — | −0.249738102 | 0.397951832 |
| | 12-72767 | mc | cg16959747 | RBP5 | 0.09713964 | −0.079430598 |
| | | non_mc | cg16959747 | RBP5 | 0.055654584 | 0.2763291 |
| | 13-256210 | mc | cg25366582 | — | 0.168798263 | −0.174946818 |
| | | non_mc | cg25366582 | — | 0.031754087 | 0.303827389 |
| | 16-571473 | mc | cg06880930 | CPNE2 | 0.235333764 | 0.168616245 |
| | | non_mc | cg06880930 | CPNE2 | −0.072680275 | −0.290080025 |
| | 17-48361 | mc | cg25526759 | GP1BA | −0.01244657 | 0.090902282 |
| | | non_mc | cg25526759 | GP1BA | 0.14744695 | 0.344718909 |
| | 17-579157 | mc | cg12054453 | TMEM49 | 0.062499156 | −0.478242327 |
| | | non_mc | cg12054453 | TMEM49 | 0.549358501 | 0.925660526 |
| | 17-742484 | mc | cg24166450 | — | 0.240682421 | 0.067853997 |
| | | non_mc | cg24166450 | — | 0.443449771 | 0.566346654 |
| | 19-460568 | mc | cg27391679 | OPA3 | 0.044319948 | 0.082373402 |
| | | non_mc | cg27391679 | OPA3 | −0.243746298 | −0.096052603 |
| | 2-293390 | mc | cg21972382 | CLIP4 | −0.099097051 | −0.61331161 |
| | | non_mc | cg21972382 | CLIP4 | 0.074745373 | 0.2650865 |

TABLE 9-continued

List of MCBs selected by multi-class LASSO and used for cd-score generation. A, normal; B, LUNC; C, HCC.

| Diagnosis | MCBs | Read counts | Target ID | RefGene | Logistic regression coefficients | |
|---|---|---|---|---|---|---|
| | | | | | LUNC vs HCC | cancer vs normal |
| | 2-382010 | mc | cg20626840 | FAM82A1 | 0.237250003 | 0.741677389 |
| | | non_mc | cg20626840 | FAM82A1 | 0.272198397 | 0.04877136 |
| | 2-95267 | mc | cg15545942 | ASAP2 | −0.557516889 | −0.185093352 |
| | | non_mc | cg15545942 | ASAP2 | −0.11738118 | −0.171014921 |
| | 3-1138223 | mc | cg06722069 | — | −0.427422216 | −0.26910555 |
| | | non_mc | cg06722069 | — | 0.089047399 | −0.071525276 |
| | 5-1767847 | mc | cg04466840 | RGS14 | −0.206022964 | −0.032074773 |
| | | non_mc | cg04466840 | RGS14 | −0.029935092 | 0.110871368 |
| | 5-429520 | mc | cg17757602 | — | 0.041309712 | 0.029262464 |
| | | non_mc | cg17757602 | — | −0.133713183 | −0.355503949 |
| | 6-1574304 | mc | cg17475813 | ARID1B | 0.129475454 | 0.045380298 |
| | | non_mc | cg17475813 | ARID1B | −0.398696708 | −0.14398793 |
| | 6-283040 | mc | cg08343881 | ZNF323 | 0.002401379 | 0.00651448 |
| | | non_mc | cg08343881 | ZNF323 | 0.255186684 | 0.345026825 |
| | 6-352655 | mc | cg02919168 | DEF6 | −0.372390965 | −0.054727228 |
| | | non_mc | cg02919168 | DEF6 | 0.070785826 | −0.098822441 |
| | 6-912971 | mc | cg01087382 | MAP3K7 | 0.132083258 | −0.263202543 |
| | | non_mc | cg01087382 | MAP3K7 | 0.023651284 | 0.314783378 |
| | 7-1017626 | mc | cg06721601 | CUX1 | 0.305704307 | 0.347231675 |
| | | non_mc | cg06721601 | CUX1 | −0.061678409 | 0.340362292 |
| | 7-1228399 | mc | cg22024657 | SLC13A1 | 0.013826947 | 0.222664259 |
| | | non_mc | cg22024657 | SLC13A1 | −0.056854833 | 0.037841165 |
| | 8-1025044 | mc | cg18004756 | GRHL2 | −0.293288901 | 0.034342458 |
| | | non_mc | cg18004756 | GRHL2 | −0.043777572 | −0.203017346 |
| | 8-1444164 | mc | cg12188860 | TOP1MT | 0.094522888 | −0.083700307 |
| | | non_mc | cg12188860 | TOP1MT | −0.083425117 | −0.026557506 |
| | | | | C: HCC | | |
| HCC | 1-1695560 | mc | cg16054275 | F5 | −0.214291458 | −0.606905543 |
| | | non_mc | cg16054275 | F5 | 0.524710881 | −0.648261504 |
| | 1-2035950 | mc | cg06637618 | ATP2B4 | −0.198233007 | −0.368854771 |
| | | non_mc | cg06637618 | ATP2B4 | 0.023774113 | 0.157886336 |
| | 1-2130901 | mc | cg04607844 | — | −0.293894301 | −0.012727778 |
| | | non_mc | cg04607844 | — | 0.119395918 | 0.246150856 |
| | 10-80958 | mc | cg18187680 | FLJ45983 | −0.028534778 | 0.369256194 |
| | | non_mc | cg18187680 | FLJ45983 | −0.130812947 | −0.247877838 |
| | 12-1222773 | mc | cg26386472 | HPD | −0.472436655 | 0.005424793 |
| | | non_mc | cg26386472 | HPD | 0.131065837 | −0.084249928 |
| | 15-555695 | mc | cg02712036 | RAB27A | −0.178526212 | 0.136059681 |
| | | non_mc | cg02712036 | RAB27A | −0.136916211 | 0.13904572 |
| | 16-724595 | mc | cg07864976 | — | 0.159138061 | 0.220936294 |
| | | non_mc | cg07864976 | — | −0.174358026 | 0.041182013 |
| | 17-579157 | mc | cg12054453 | TMEM49 | 0.062499156 | −0.478242327 |
| | | non_mc | cg12054453 | TMEM49 | 0.549358501 | 0.925660526 |
| | 17-800195 | mc | cg20651080 | DUS1L | 0.16564247 | 0.179098878 |
| | | non_mc | cg20651080 | DUS1L | −0.072821844 | 0.405200855 |
| | 17-803588 | mc | cg11252953 | C17orf101 | 0.009872935 | 0.197906181 |
| | | non_mc | cg11252953 | C17orf101 | −0.088619833 | −0.047902639 |
| | 19-459097 | mc | cg06663668 | CD3EAP | 0.026258194 | 0.077247979 |
| | | non_mc | cg06663668 | CD3EAP | −0.209537326 | 0.55413999 |
| | 19-546460 | mc | cg11441617 | CNOT3 | −0.272150647 | 0.31583956 |
| | | non_mc | cg11441617 | CNOT3 | −0.485831577 | 0.011388271 |
| | 19-546461 | mc | cg11441617 | CNOT3 | 0.345456601 | 0.601027916 |
| | | non_mc | cg11441617 | CNOT3 | 0.252775143 | 0.151478291 |
| | 2-1139315 | mc | cg09366118 | PSD4 | 0.098868936 | 0.269196214 |
| | | non_mc | cg09366118 | PSD4 | 0.039975437 | −0.005683265 |
| | 21-364214 | mc | cg01519261 | RUNX1 | 0.350276252 | 0.086780025 |
| | | non_mc | cg01519261 | RUNX1 | 0.205448988 | −0.230292808 |
| | 21-364215 | mc | cg01519261 | RUNX1 | −0.068910744 | 0.175787941 |
| | | non_mc | cg01519261 | RUNX1 | −0.470630509 | −0.686309747 |
| | 22-185277 | mc | cg02415779 | — | 0.056697461 | 0.313717112 |
| | | non_mc | cg02415779 | — | 0.122239689 | −0.243806777 |
| | 22-378130 | mc | cg00107982 | ELFN2 | −0.03021978 | 0.143360514 |
| | | non_mc | cg00107982 | ELFN2 | −0.063348947 | 0.490504707 |
| | 4-13248 | mc | cg07748255 | MAEA | 0.217866978 | −0.457591409 |
| | | non_mc | cg07748255 | MAEA | −0.011474644 | −0.340582424 |
| | 4-840359 | mc | cg19255783 | PLAC8 | 0.024851345 | 0.211399591 |
| | | non_mc | cg19255783 | PLAC8 | −0.154998544 | −0.217029094 |
| | 5-17153 85 | mc | cg25650256 | STK10 | −0.296078256 | 0.069437129 |
| | | non_mc | cg25650256 | STK10 | −0.134013643 | 0.178025221 |
| | 6-262504 | mc | cg05414338 | HIST1H3F | −0.291906307 | 0.385669376 |
| | | non_mc | cg05414338 | HIST1H3F | −0.188285503 | 0.279553121 |

TABLE 9-continued

List of MCBs selected by multi-class LASSO and used for cd-score generation. A, normal; B, LUNC; C, HCC.

| Diagnosis | MCBs | Read counts | Target ID | RefGene | Logistic regression coefficients LUNC vs HCC | cancer vs normal |
|---|---|---|---|---|---|---|
| | 6-315278 | mc | cg06393830 | NFKBIL1 | 0.120351939 | 0.122094253 |
| | | non_mc | cg06393830 | NFKBIL1 | 0.206309569 | −0.082505936 |
| | 6-329093 | mc | cg00862588 | HLA-DMB | −0.322857861 | 0.005678509 |
| | | non_mc | cg00862588 | HLA-DMB | 0.382920486 | −0.054366936 |
| | 6-912971 | mc | cg01087382 | MAP3K7 | 0.132083258 | −0.263202543 |
| | | non_mc | cg01087382 | MAP3K7 | 0.023651284 | 0.314783378 |
| | 7-1000913 | mc | cg03113878 | C7orf51 | −0.173651065 | −0.291203774 |
| | | non_mc | cg03113878 | C7orf51 | −0.009576582 | 0.090427416 |
| | 7-759325 | mc | cg21217886 | HSPB1 | −0.135144273 | −0.558395663 |
| | | non_mc | cg21217886 | HSPB1 | −0.163997602 | −0.133445148 |

TABLE 10

Characteristics of 10 MCBs in LUNC prognosis prediction and 10 MCBs in HCC prognosis prediction

| | Features | Target ID | RefGene |
|---|---|---|---|
| LUNC | mc_17-742484 | cg24166450 | — |
| | non_mc_2-741532 | cg02478828 | DGUOK |
| | mc_2-2355288 | cg08436738 | — |
| | mc_1-295863 | cg04933208 | PTPRU |
| | non_mc_22-358223 | cg20146967 | MCM5 |
| | non_mc_16-900927 | cg07860918 | GAS8 |
| | mc_20-374337 | cg16119522 | PPP1R16B |
| | non_mc_3-1960650 | cg05556202 | TM4SF19 |
| | mc_12-687588 | cg20323175 | — |
| | non_mc_10-299484 | cg13324103 | SVIL |
| HCC | mc_6-262503 | cg05414338 | HIST1H3F |
| | mc_6-733300 | cg17126142 | KCNQ5 |
| | non_mc_7-450187 | cg06787669 | MYO1G |
| | mc_19-185898 | cg06747543 | ELL |
| | mc_12-1222773 | cg26386472 | HPD |
| | non_mc_1-20665 | cg00866690 | PRKCZ |
| | mc_12-939663 | cg11225410 | SOCS2 |
| | mc_7-450187 | cg06787669 | MYO1G |
| | mc_6-283040 | cg08343881 | ZNF323 |
| | mc_6-733299 | cg17126142 | KCNQ5 |

TABLE 11

Clinical characteristics of study cohort

| Characteristic | TCGA HCC tissue | TCGA LUNC tissue | GSE Normal | HCC blood | LUNC blood | Normal blood |
|---|---|---|---|---|---|---|
| Total (n) | 377 | 827 | 754 | 1504 | 892 | 2247 |
| Gender | | | | | | |
| Female-no. (%) | 122(32.4) | 340(41.1) | 401(53.2) | 146(9.7) | 263(29.5) | 507(22.6) |
| Male-no. (%) | 255(67.6) | 487(58.9) | 353(46.8) | 991(65.9) | 487(54.6) | 480(21.4) |
| NA | 0 | 0 | 0 | 367(24.4) | 142(15.9) | 1260(56.1) |
| Age (years) | | | | | | |
| Mean | 61 | 68 | 63 | 54 | 58 | 48 |
| Range | 16-90 | 33-90 | 19-101 | 11-85 | 19-85 | 19-90 |
| Pathology | | | | | | |
| Hepatocellular carcinoma(%) | 367(97.3) | 0 | NA | 1504(100) | 0 | NA |
| Adenocarcinoma(%) | 0 | 458(55.4) | NA | 0 | 402(45.1) | NA |
| Squamous cell carcinoma(%) | 0 | 369(44.6) | NA | 0 | 138(15.5) | NA |
| Small Cell Lung Cancer(%) | 0 | 0 | NA | 0 | 79(8.9) | NA |
| Others(%) | 10(2.7) | 0 | NA | 0 | 273(30.6) | NA |
| Stage | | | | | | |
| I (%) | 175(46.4) | 424(51.3) | NA | 206(13.7) | 58(6.5) | NA |
| II (%) | 87(23.1) | 115(13.9) | NA | 202(13.4) | 52(5.8) | NA |
| III (%) | 86(22.8) | 261(31.6) | NA | 612(40.7) | 148(16.6) | NA |
| IV(%) | 6(1.6) | 25(3.0) | NA | 134(8.9) | 463(51.9) | NA |
| NA (%) | 23(6.1) | 2(0.2) | NA | 350(23.3) | 171(19.2) | NA |

TABLE 11-continued

Clinical characteristics of study cohort

| Characteristic | TCGA HCC tissue | TCGA LUNC tissue | GSE Normal | HCC blood | LUNC blood | Normal blood |
|---|---|---|---|---|---|---|
| Tumor burden | | | | | | |
| Tumor free (%) | 236(62.6) | 503(60.8) | NA | 314(20.9) | 160(17.9) | NA |
| With tumor (%) | 114(30.2) | 159(19.2) | NA | 889(59.1) | 599(67.2) | NA |
| NA (%) | 27(7.2) | 165(20.0) | NA | 301(20.0) | 133(14.9) | NA |
| EGFR status | | | | | | |
| Wide type (%) | NA | 400(48.4) | NA | NA | 102(11.4) | NA |
| Mutation (%) | NA | 100(12.1) | NA | NA | 69(7.7) | NA |
| NA (%) | NA | 327(39.5) | NA | NA | 721(80.8) | NA |
| Hepatitis | | | | | | |
| Positive (%) | 120(31.8) | NA | NA | 623(95.3) | NA | 379(16.9) |
| Negative (%) | 119(31.6) | NA | NA | 10(1.5) | NA | 571(25.4) |
| NA (%) | 138(36.6) | NA | NA | 21(3.2) | NA | 1297(57.7) |
| Smoking (%) | | | | | | |
| Current smoker (%) | NA | 725(87.7) | NA | NA | NA | 192(8.5) |
| Non-smoker (%) | NA | 80(9.7) | NA | NA | NA | 670(29.8) |
| NA (%) | NA | 22(2.6) | NA | NA | NA | 1385(61.6) |

TABLE 12

Multivariate survival analysis for HCC patients and LUNC patients with composite-score of methylation markers (cp-score) and relevant variables in validation cohorts

| | coef | exp(coef) | se(coef) | z | p | lower 0.95 | upper 0.95 |
|---|---|---|---|---|---|---|---|
| HCC | | | | | | | |
| cp-score | 0.9115 | 2.4881 | 0.2696 | 3.3813 | 0.0007 | 0.3830 | 1.4400 |
| stage | 0.3336 | 1.3960 | 0.3034 | 1.0995 | 0.2715 | −0.2612 | 0.9284 |
| AFP | −0.0861 | 0.9175 | 0.2115 | −0.4069 | 0.6841 | −0.5008 | 0.3286 |
| age | −330.8028 | 0.0000 | 75.7050 | −4.3696 | 0.0000 | −479.2145 | −182.3911 |
| Gender | −0.0885 | 0.9153 | 0.2361 | −0.3748 | 0.7078 | −0.5512 | 0.3743 |
| LUNC | | | | | | | |
| cp-score | 0.5577 | 1.7467 | 0.3056 | 1.8249 | 0.0680 | −0.0414 | 1.1569 |
| stage | 0.4647 | 1.5916 | 0.8422 | 0.5518 | 0.5811 | −1.1863 | 2.1157 |
| CEA | 0.2695 | 1.3093 | 0.6035 | 0.4466 | 0.6552 | −0.9135 | 1.4525 |
| age | −321.0835 | 0.0000 | 94.6796 | −3.3913 | 0.0007 | −506.6928 | −135.4742 |
| Gender | 0.0897 | 1.0938 | 0.3858 | 0.2325 | 0.8162 | −0.6666 | 0.8460 |

TABLE 13

Clinical characteristics and sensitivity/specificity for detection of stage I LUNC and benign lung nodules
Sensitivity and Specificity for the Detection of Lung Cancer

| Characteristic | Stage I lung cancer N = 116 | Benign nodules N = 116 |
|---|---|---|
| Age-yr | | |
| Median | 61 | 52 |
| Range | 29-83 | 26-86 |
| Gender | | |
| Female | 80 | 53 |
| male | 36 | 63 |
| Pathology | | |
| Adenocarcinoma | 100 | NA |
| Squamous cell carcinoma | 6 | NA |
| Small Cell Lung Cancer | 0 | NA |
| Others | 0 | NA |
| Nodule size-mm | | |
| Mean | 14.6 ± 6.1 | 7.2 ± 2.1 |
| Median | 15.0 | 6.4 |
| Range | 3-58 | 2.7-18.2 |
| Stage | | |
| AIS | 7 | NA |
| MIA | 8 | NA |
| IA | 78 | NA |
| IB | 13 | NA |
| Sensitivity - % (95% CI) | 77.8 | |
| Specificity - % (95% CI) | 85.3 | |
| Positive predictive value - % (95% CI) | 81.0 | |

TABLE 13-continued

Clinical characteristics and sensitivity/specificity
for detection of stage I LUNC and benign lung nodules
Sensitivity and Specificity for the Detection of Lung Cancer

| Characteristic | Stage I lung cancer<br>N = 116 | Benign nodules<br>N = 116 |
|---|---|---|
| Negative predictive value - % (95% CI) | 84.1 | |

TABLE 14

Clinical characteristics and sensitivity/specificity for
detection of progression to stage I HCC from liver cirrhosis
Sensitivity and Specificity for the Detection of Liver Cancer

| Characteristic | Stage I liver cancer<br>N = 204 | Cirrhosis<br>N = 242 |
|---|---|---|
| Age-yr | | |
| Median | 62 | 52 |
| Range | 21-81 | 25-82 |
| Gender | | |
| Female | 32 | 47 |
| Male | 172 | 195 |
| Hepatitis B | | |
| Positive | 198 | 193 |
| Negative | 4 | 13 |
| NA | 2 | 36 |
| AFP | | |
| <25 ng/ml | 113 | 196 |
| >25 | 43 | 29 |
| NA | 48 | 17 |
| Sensitivity - % (95% CI) | 94.9 | |
| Specificity - % (95% CI) | 92.6 | |
| Positive predictive value - % (95% CI) | 94.9 | |
| Negative predictive value - % (95% CI) | 92.8 | |

Example 3

Hepatocellular carcinoma (HCC) is a leading cause of cancer deaths worldwide. As with many cancers, HCC found at an early stage carries much-improved prognosis compared to advanced stage disease, in part due to the relative efficacy of local treatments compared with systemic therapy. In some cases, early detection has a potential for reducing the mortality of HCC. In some instances, alpha fetal protein (AFP) is used for detection and surveillance of HCC. However, it some cases its clinical utility is limited by low sensitivity.

DNA methylation is an epigenetic regulator of gene expression that usually results in gene silencing. In cancer, DNA methylation is typically increased in tumor suppressor genes and presents itself as one of the first neoplastic changes. Circulating tumor DNA (ctDNA) comprises of extracellular nucleic acid fragments shed into plasma via tumor cell necrosis, apoptosis, and active release of DNA. In some cases, ctDNA bearing cancer-specific methylation patterns is used as a biomarker in diagnosis of cancers.

Patient Data

Tissue DNA methylation data was obtained from The Cancer Genome Atlas (TCGA). Complete clinical, molecular, and histopathological datasets are available at the TCGA website. Individual institutions that contributed samples coordinated the consent process and obtained informed written consent from each patient in accordance to their respective institutional review boards.

A second independent Chinese cohort consisted of HCC patients at the Sun Yat-sen University Cancer Center in Guangzhou, Xijing Hospital in Xi'an and the West China Hospital in Chengdu, China. Those who presented with HCC from stage I-IV were selected and enrolled in this study. Patient characteristics and tumor features are summarized in Table 17. The TNM staging classification for HCC is according to the NCCN Hepatobiliary Cancers Clinical Practice Guidelines (Benson III A B, Abrams T A, Ben-Josef E et al. Hepatobiliary Cancers: Clinical Practice Guidelines in Oncology. Journal of the National Comprehensive Cancer Network: JNCCN 2009; 7: 350). This project was approved by the IRBs of Sun Yat-sen University Cancer Center, Xijing Hospital, and West China Hospital. Informed consent was obtained from all patients. Tumor and normal tissues were obtained as clinically indicated for patient care and were retained for this study. Human blood samples were collected by venipuncture and plasma samples were obtained by taking supernatant after centrifugation and stored at −80° C. before cfDNA extraction.

Data Sources

DNA methylation data of 485,000 sites generated using the Infinium 450K Methylation Array were obtained from the TCGA and dataset generated from the previous study (GSE40279) in which DNA methylation profiles for HCC and blood were analyzed. IDAT format files of the methylation data were generated containing the ratio values of each scanned bead. Using the minfi package from Bioconductor, these data files were converted into a score, referred to as a Beta value. Methylation values of the Chinese cohort were obtained by targeted bisulfate sequencing using a molecular inversion probe and analyzed as described below.

Figure 26:
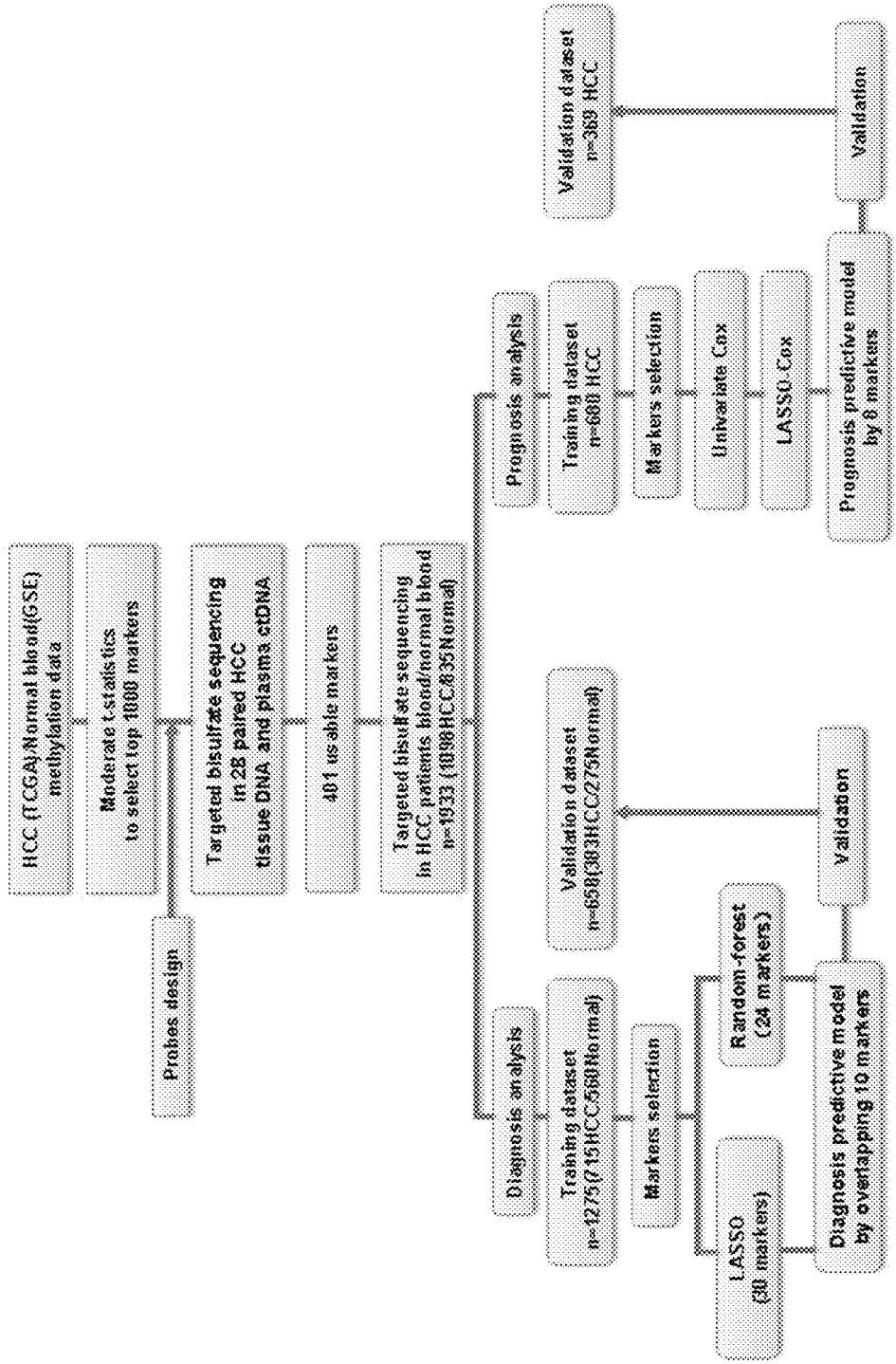
FIG. 26 illustrates an exemplary workflow chart of data generation and analysis described herein.
Figure 27A:
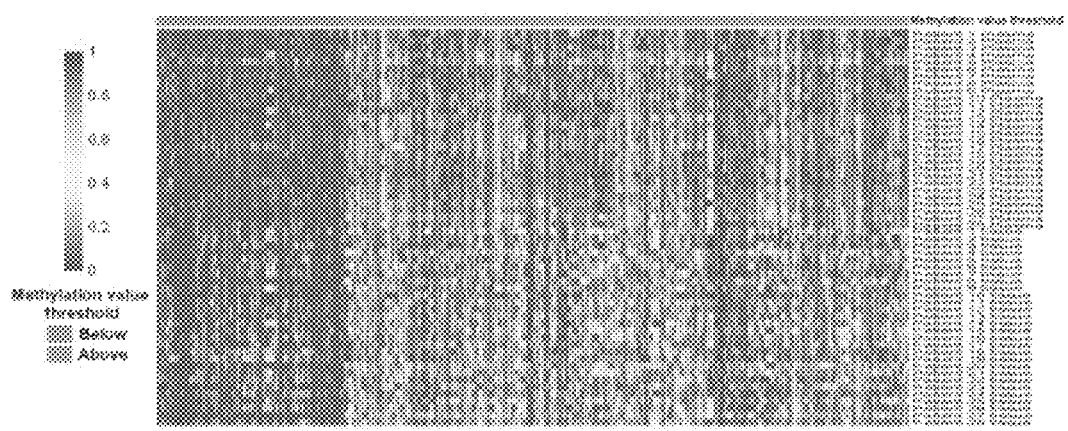
Figure 27B:
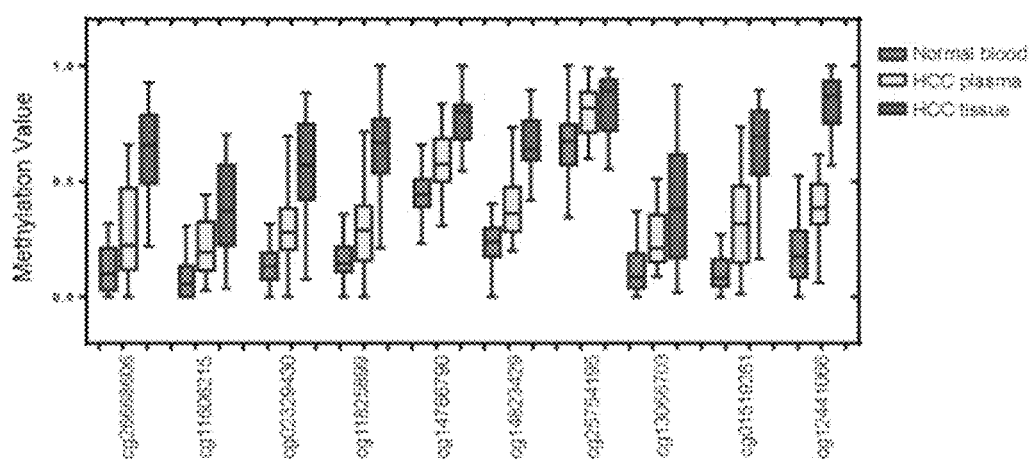

Statistical Analysis—DNA Methylation Marker Pre-Selection for Diagnostic and Prognostic Analysis A differential methylation analysis on TCGA data using a "moderated t-statistics shrinking" approach was first performed and the P-value for each marker was then corrected by multiple testing by the Benjamini-Hochberg procedure to control FDR at a significance level of 0.05. The list was ranked by adjusted P-value and selected the top 1000 markers for designing padlock probes (FIG. 26). About 682 padlock probes were obtained that gave positive and specific PCR amplification signals and were used as capture probes in the subsequent experiments in cfDNA samples (FIG. 27A-FIG. 27H). cfDNA samples with low quality or fewer than 20,000 reads per sample were also eliminated. About 1933 cfDNA samples were included in the study (1098 HCC blood samples and 835 normal blood samples). Methylation values for each marker were defined as the proportion of read counts with methylation divided by total read counts. Of the 682 padlock probes, about 401 markers were retained for further analysis after eliminating methylation markers with a range of methylation values less than 0.1 in matched tumor tissue and tumor blood samples (FIG. 27A). For a particular methylation markers with less than 20 unique reads, an imputed mean methylation value of HCC or normal healthy controls were used.

Building a Diagnostic Model

The full cfDNA dataset (1098 HCC blood samples and 835 normal blood samples) was randomly split into training and validation cohorts with a 2:1 ratio, corresponding to 1275 and 658 total samples, respectively. Two variable selection methods suitable for high-dimensionality on the prescreened training dataset were applied: Least Absolute Shrinkage and Selection Operator (LASSO) and Random Forest based variable selection method using OOB error. As results can depend strongly on the arbitrary choice of a random sample split for sparse high-dimensional data, an analysis of the "multi-split" method were adopted, which improves variable selection consistency while controlling finite sample error. For LASSO selection operator, 75 percent of the dataset was subsampled without replacement 500 times and selected the markers with repeat occurrence frequency more than 450. The tuning parameters was determined according to the expected generalization error estimated from 10-fold cross-validation and information-based criteria AIC/BIC, and we adopted the largest value of lambda such that the error was within one standard error of the minimum, known as "1-se" lambda. For the random forest analysis, using the OOB error as a minimization criterion, variable elimination from the random forest was carried out by setting variable a dropping fraction of each iteration at 0.3. Ten overlapping methylation markers were chosen by the two methods for model building a binary prediction. A logistic regression model was fitted using these 10 markers as the covariates and obtained a combined diagnosis score (designated as cd-score) by multiplying the unbiased coefficient estimates and the marker methylation value matrix in both the training and validation datasets. The predictability of the model was evaluated by area under ROC (AUC, also known as C-index), which calculated the proportions of concordant pairs among all pairs of observations with 1.0 indicating a perfect prediction accuracy. Confusion tables were generated using an optimized cd-score cutoff with a maximum Youden's index.

The pre-treatment or initial methylation level was evaluated at baseline, and the post-methylation level was evaluated approximately 2 months after treatment, where the treatment referred to either chemotherapy or surgical resection of tumor. The primary endpoint (including response to treatment: progressive disease (PD), partial response (PR) and stable disease (SD)) were defined according to the RECIST guideline. For patients treated with surgical removal and no recurrence at time of evaluation, it was assumed that they had complete response (CR). The difference of cd-score distribution between clinical categories was examined by Wilcoxon Rank Sum test as cd-score was tested to be non-normally distributed using a Shapiro-Wilk Test.

Building a Predictive Model for Prognosis and Survival

The HCC cohort was split into a training dataset and a validation dataset and explored building a predictive model for prognosis and survival. About 680 cases were used for training and 369 cases for validation. Next, in the training dataset, a sequential model-based variable selection strategy was applied to screen markers for predicting survival outcome. A univariate pre-screening procedure was first performed to remove excessive noise to facilitate the computational analysis, which is generally recommended prior to applying any variable selection method. For each methylation marker, a univariate Cox proportional hazards model was fit by using each marker as the covariate. A marker with p-value <0.05 from the Wald statistic was retained in the dataset. Second, a similar subsampling strategy was used in a diagnosis marker selecting process based on LASSO-cox method to shrink the marker numbers to a reasonable range (less than events). Slightly different from the binary classifier, subsampling in the training dataset with replacement in case that the event proportion was too low for a model construction. The frequency cutoff was set as 50 to retain approximately 1/10th of total events. The above analysis generated 8 final markers to construct a prognostic signature. By fitting a multi-variable Cox proportional hazards model on these 8 markers, the coefficients of each marker was determined and a combined prognostic score (designated as cp-score) was obtained for each individual. To validate the predictive model, a cp-score was calculated for each patient in the validation dataset using coefficient estimates from the training dataset. By dividing the cp-score according to its median, high and low cp-score groups were formed with a roughly equal number of observations. It was investigated if the median survival time was significantly different between these two groups using a Kaplan-Meier estimator and log-rank test.

Using cp-score and clinical information as covariates, multi-variable Cox proportional hazards models were fitted separately in the training and validation dataset to infer weather the cp-score is an independent predictive factor when compared to AFP, stage, sex and age for HCC prognosis.

All the hypothesis testing is two-sided with p-value <0.05 considered to be statistically significant. All the analysis was conducted in R version 3.2.3 with the following packages used: 'glmnet', 'rms', 'pROC', 'limma', 'ROCR', ' varSelRF', 'survival'.

Tumor DNA Extraction

Genomic DNA extraction from freshly frozen healthy or cancer tissues was performed with QIAamp DNA Mini Kit (Qiagen) according to manufacturer's recommendations. Roughly 0.5 mg of tissue was used to obtain on average 5 µg of genomic DNA. DNA was stored at −20° C. and analyzed within one week of preparation.

DNA Extraction from FFPE Samples

Genomic DNA from frozen FFPE samples was extracted using QIAamp DNA FFPE Tissue Kit with several modifications. DNA were stored at −20° C. for further analysis.

Cell-Free DNA Extraction from Plasma Samples cfDNA extraction from 1.5 ml of plasma samples was performed with QIAamp cfDNA Kit (Qiagen) according to manufacturer's recommendations.

The minimal volume of plasma that will give a consistent cfDNA recovery and reliable sequencing coverage defined as more than 20 reads for a target cg marker was investigated. It was shown that a requirement of at least 20,000 total reads per sample corresponded to 20 or more reads per cg marker for ~90% of markers in a sample and was accurate to make a good prediction of the beta value of the corresponding cg marker. It was found that 1.5 ml or more plasma can give 20 or more reads per cg marker for ~90% of markers in a sample. The relationship between amount of cfDNA in 1.5 ml plasma and copy numbers was further investigated using digital droplet PCR. It was found that DNA quantity of 15 ng gave good copy numbers as defined by >140 total copies of detected amplicons in each digital droplet PCR assay (FIG. 39B) and a minimal 1.5 ml plasma volume gave a cfDNA yield of 15 ng. About 15 ng/1.5 ml as a cutoff was used in the experiments to obtain consistent and reliable measurements of DNA quantity and good recovery. cfDNA yield was also compared by several commercial cfDNA extraction kits (EliteHealth, Qiagen and Thermo Fisher). It was found that EliteHealth or Qiagen cfDNA extraction kits yielded the highest cfDNA quantities in a highly consistent manner [~10 ng+/−3 ng/per 1 ml plasma, FIG. 39C].

Bisulfite Conversion of Genomic DNA

About 10-15 ng of cf DNA was converted to bis-DNA using EZ DNA Methylation-Lightning™ Kit (Zymo Research) according to the manufacturer's protocol. Resulting bis-DNA had a size distribution of ~200-3000 bp, with a peak around ~500-1000 bp. The efficiency of bisulfite conversion was >99.8% as verified by deep-sequencing of bis-DNA and analyzing the ratio of C to T conversion of CH (non-CG) dinucleotides.

Determination of DNA Methylation Levels by Deep Sequencing of Bis-DNA Captured with Molecular-Inversion (Padlock) Probes CpG markers whose methylation levels significantly differed in any of the comparisons between any cancer tissue and any normal tissue were used to design padlock probes for capture and sequencing of cfDNA. Padlock-capture of bis-DNA was based on the technique on published methods with modifications.

Probe Design and Synthesis

Padlock probes were designed using the ppDesigner software. The average length of the captured region was 100 bp, with the CpG marker located in the central portion of the captured region. Linker sequence between arms contained binding sequences for amplification primers separated by a variable stretch of Cs to produced probes of equal length. A 6-bp unique molecular identifier (UMI) sequence was incorporated into the probe design to allow for the identification of unique individual molecular capture events and accurate scoring of DNA methylation levels. See Table 19.

Probes were synthesized as separate oligonucleotides using standard commercial synthesis methods (ITD). For capture experiments, probes were mixed, in-vitro phosphorylated with T4 PNK (NEB) according to manufacturer's recommendations and purified using P-30 Micro Bio-Spin columns (Bio-Rad).

Bis-DNA Capture

About 10 ng of bisulfite-converted DNA was mixed with padlock probes in 20 µl reactions containing 1× Ampligase buffer (Epicentre). To anneal probes to DNA, 30 second denaturation at 95° C. was followed by a slow cooling to 55° C. at a rate of 0.02° C. per second. Hybridization was left to complete for 15 hrs at 55° C. To fill gaps between annealed arms, 5 µl of the following mixture was added to each reaction: 2U of PfuTurboCx polymerase (Agilent), 0.5U of Ampligase (Epicentre) and 250 pmol of each dNTP in 1× Ampligase buffer. After 5 hour incubation at 55° C., reactions were denatured for 2 minutes at 94° C. 5 µl of exonuclease mix (20U of Exo I and 100U of ExoIII, both from Epicentre) was added and single-stranded DNA degradation was carried out at 37° C. for 2 hours, followed by enzyme inactivation for 2 minutes at 94° C.

Circular products of site-specific capture were amplified by PCR with concomitant barcoding of separate samples. Amplification was carried out using primers specific to linker DNA within padlock probes, one of which contained specific 6 bp barcodes. Both primers contained Illumina next-generation sequencing adaptor sequences. PCR was done as follows: 1× Phusion Flash Master Mix, 3 µl of captured DNA and 200 nM primers, using the following cycle: 10s at 98° C., 8× of (1 s at 98° C., 5s at 58° C., 10s at 72° C.), 25× of (1 s at 98° C., 15s at 72° C.), 60s at 72° C. PCR reactions were mixed and the resulting library was size selected to include effective captures (~230 bp) and exclude "empty" captures (~150 bp) using Agencourt AMPure XP beads (Beckman Coulter). Purity of the libraries was verified by PCR using Illumina flowcell adaptor primers (P5 and P7) and the concentrations were determined using Qubit dsDNA HS assay (Thermo Fisher). Libraries we sequenced using MiSeq and HiSeq2500 systems (Illumina).

Optimization of Capture Coverage Uniformity

Deep sequencing of the original pilot capture experiments showed significant differences between number of reads captured by most efficient probes and non-efficient probes (60-65% of captured regions with coverage >0.2× of average). To ameliorate this, relative efficiencies were calculated from sequencing data and probes were mixed at adjusted molar ratios. This increased capture uniformity to 85% of regions at >0.2× of average coverage.

Sequencing Data Analysis

Mapping of sequencing reads was done using the software tool bisReadMapper with some modifications. First, UMI were extracted from each sequencing read and appended to read headers within FASTQ files using a custom script. Reads were on-the-fly converted as if all C were non-methylated and mapped to in-silico converted DNA strands of the human genome, also as if all C were non-methylated, using Bowtie2. Original reads were merged and filtered for single UMI, i.e. reads carrying the same UMI were discarded leaving a single, unique read. Methylation frequencies were calculated for all CpG dinucleotides contained within the regions captured by padlock probes by dividing the numbers of unique reads carrying a C at the interrogated position by the total number of reads covering the interrogated position.

Identification of Blocks of Correlated Methylation (BCM)

Pearson correlation coefficients between methylation frequencies of each pair of CpG markers separated by no more than 200 bp were calculated separately across 50 cfDNA samples from each of the two diagnostic categories, ie normal health blood and HCC. A value of Pearson's r<0.5 was used to identify transition spots (boundaries) between any two adjacent markers indicating uncorrelated methylation. Markers not separated by a boundary were combined into Blocks of Correlated Methylation (BCM). This procedure identified a total of ~1550 BCM in each diagnostic category within our padlock data, combining between 2 and 22 CpG positions in each block. Methylation frequencies for entire BCMs were calculated by summing up the numbers of Cs at all interrogated CpG positions within a BCM and dividing by the total number of C+Ts at those positions DNA Isolation and Digital Quantitative PCR Tumor and corresponding plasma samples were obtained from patients undergoing surgical tumor resection; samples were frozen and preserved in at −80° C. until use. Isolation of DNA and RNA from samples was performed using AllPrep DNA/RNA Mini kit and a cfDNA extraction kit, respectively (Qiagen, Valencia, Calif.).

To estimate tumor cfDNA fractions, mixing experiments with various fractions of normal cfDNA and HCC tumor genomic DNA (gDNA) were performed and methylation values and copy numbers were assayed by digital droplet PCR (ddPCR, see next section for details). ddPCR was performed according to the manufacturer's specifications (Bio-Rad, Hercules, Calif.). ddPCR was set up as following: amplification primer pair, cg10590292-Forward 5'-TGT-TAGTTTTTATGGAAGTTT (SEQ ID NO: 19), cg10-590292-Reverse 5'-AAACIAACAAAATACTCAAA (SEQ ID NO: 20); fluorescent probe for methylated allele detection, cg10590292-M 5'/6-FAM/TGGGAGAGCGGGAGAT/BHQ1/-3' (SEQ ID NO: 21); probe for unmethylated allele detection, cg10590292-NM 5'/HEX/TTTGGGAGAGT-GGGAGATTT/BHQ1/-3' (SEQ ID NO: 22). Cycling condition: 1× of 10 mins at 98° C., 40× of (30s at 98° C., 60s at 53° C.), 1× of 10 mins at 98° C.

Calculation of Tumor cfDNA Fraction

Figure 38A:
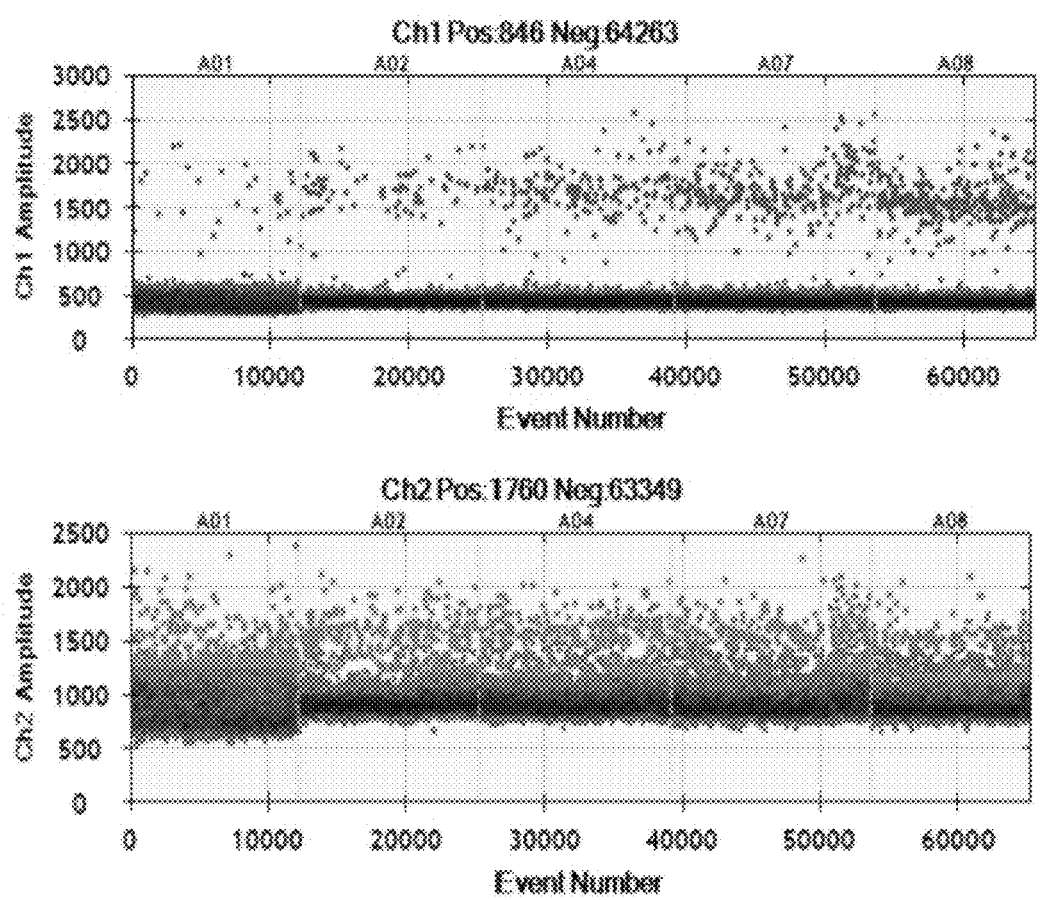
Figure 38C:
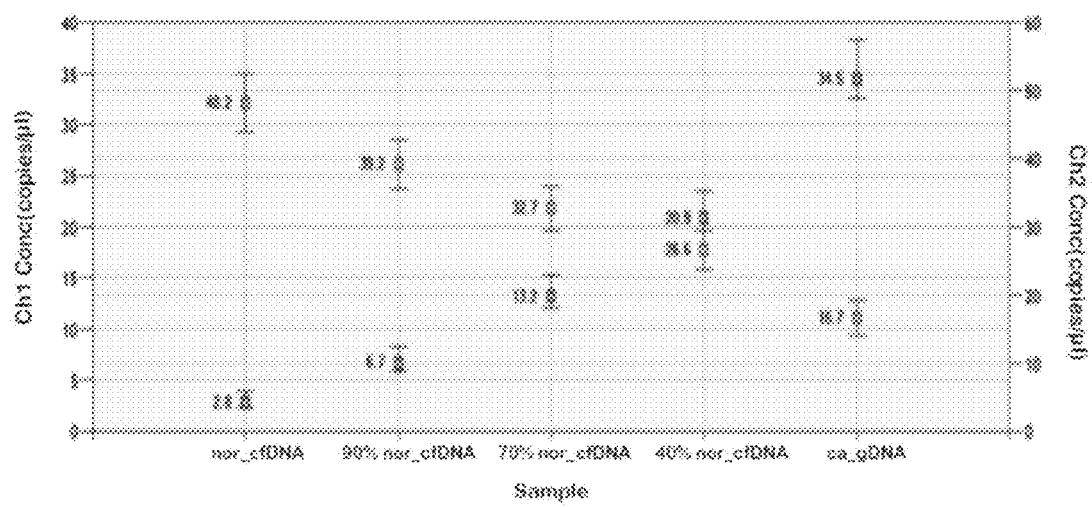
Figure 39A:
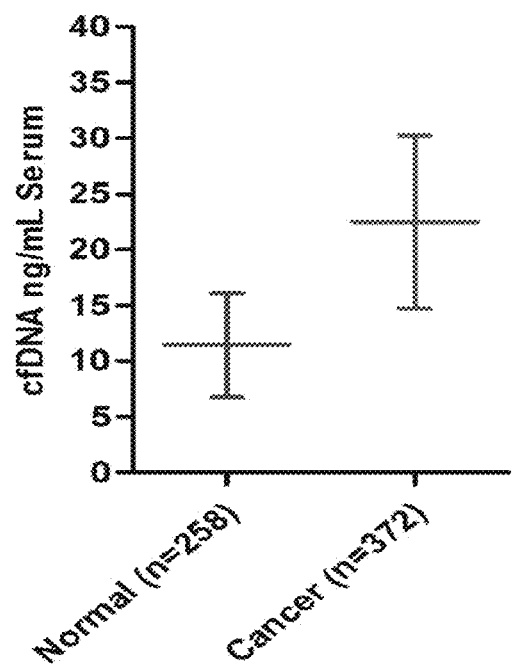
FIG. 39A-FIG. 39C show measurements of cfDNA concentrations in normal and HCC plasma samples.
Figure 39B:
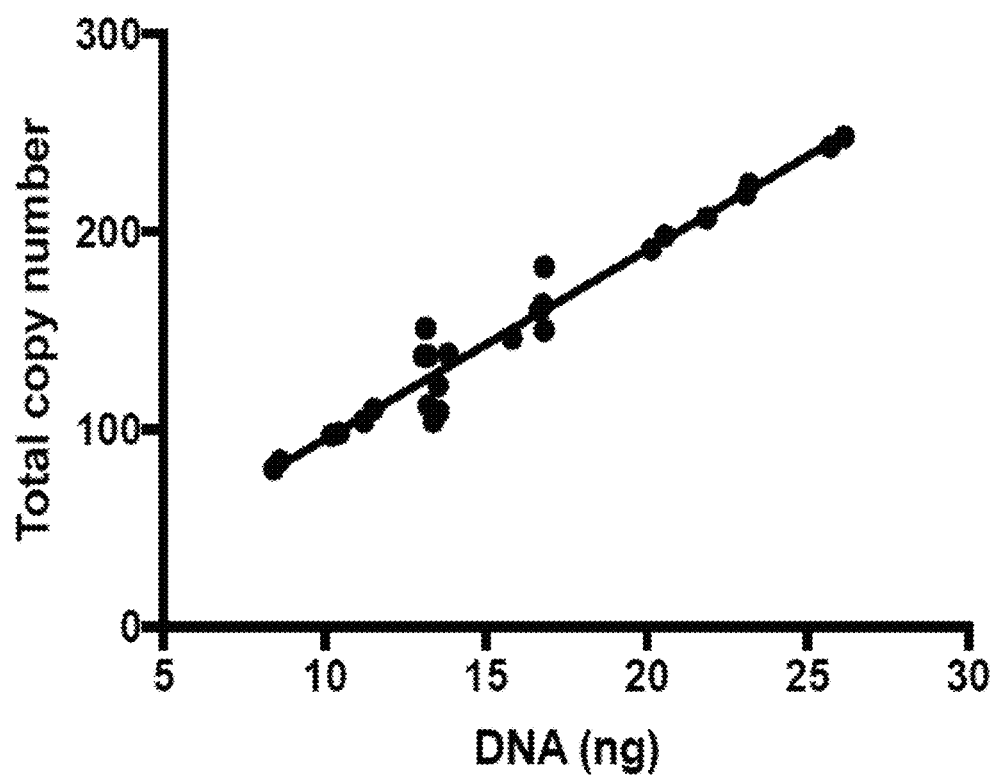
Figure 39C:
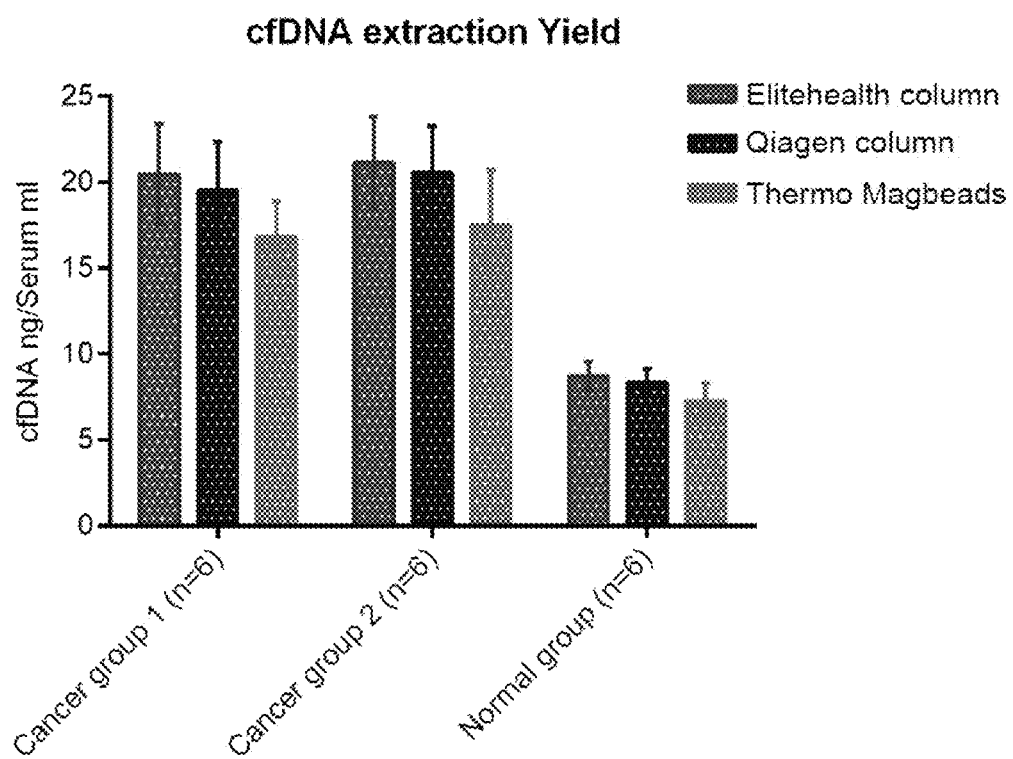

It was assumed that a particular methylation value observed for an HCC cfDNA sample resulted from the combined contribution of normal and tumor cfDNA. The fraction of cfDNA originating from the tumor was estimated using the following formula: fraction contributed from tumor DNA in sample i=[methylation value in HCC cfDNA in sample i−mean methylation value of normal cfDNA]/[mean methylation value of tumor DNA−mean methylation value of normal cfDNA]. Using this approach, it was estimated that on average the tumor fraction was about 23% in HCC cfDNA samples. Samples were then grouped according to factors that evaluate tumor load, such as an advanced stage and pre-treatment status, since these factors were expected to affect the tumor fraction in ctDNA (Table 20). Indeed, it was observed that conditions associated with a higher tumor staging and severity also tended to have a larger tumor fraction (Table 20). To further vet this approach, a mixing experiment was performed with different fractions of normal cfDNA (0-100%) and tumor genomic DNA (0-100%) and assayed methylation values using digital PCR. It was shown that incremental addition of tumor genomic DNA could increase methylation fraction percentage up to the values observed in the HCC patient samples (FIG. 38A-FIG. 38C). Specifically, addition of 10%, 20%, 40%, 60% or 100% fraction of tumor genomic DNA could be predicted by the above formula, when using methylation values obtained from the experiment.

cfDNA concentration was measured in normal and HCC plasma samples using a Qubit® fluorescent dye method 10. 1 ul out of 20 ul of cfDNA extracted from a 1.5 mL plasma sample was diluted in 199 ul Qubit® working solution containing Qubit® dsDNA HS Reagent. It was found that on average, there are about 11 ng cfDNA in 1 mL of normal plasma and 22 ng cfDNA in 1 mL of HCC plasma (FIG. 39A).

Patient and Sample Characteristics

Clinical characteristics and molecular profiling including methylation data for comparison between HCC and blood lymphocytes including 377 HCC tumor samples from The Cancer Genome Atlas (TCGA) and 754 normal samples from a dataset used in a methylation study on aging (GSE40279). To study ctDNA in HCC, plasma samples were obtained from Chinese patients with HCC and randomly selected healthy controls undergoing routine health care maintenance, resulting in a training cohort of 715 HCC patients and 560 normal healthy controls and a validation cohort of 383 HCC patients and 275 healthy controls. All participants provided written informed consent. Clinical characteristics of all patients and controls are listed in Table 17.

Identification of Methylation Markers Differentiating HCC and Blood

Figure 30:
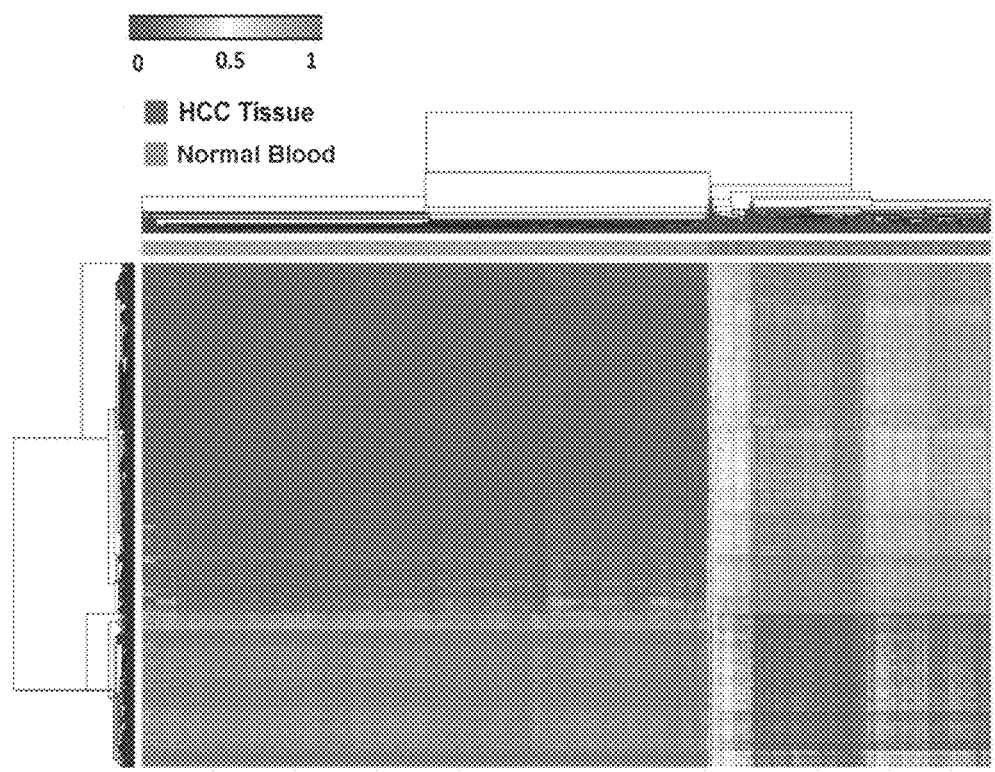
FIG. 30 illustrates an unsupervised hierarchical clustering of top 1000 methylation markers differentially methylated between HCC tumor DNA and normal blood. Each column represents an individual patient and each row represents a CpG marker.

It is hypothesized that CpG markers with a maximal difference in methylation between HCC and normal blood is likely to demonstrate detectable methylation differences in the cfDNA of HCC patients when compared to that of normal controls. The "moderate t-statistics" method with Empirical Bayes for shrinking the variance was used, and Benjamini-Hochberg procedure was used to control the FDR at a significance level of 0.05 to get top 1000 markers with the lowest P values, identifying the most significantly different rates of methylation between HCC and blood (FIG. 26). Unsupervised hierarchical clustering of these top 1000 markers was able to distinguished between HCC and normal blood (FIG. 30). Molecular inversion (padlock) probes corresponding to these 1000 markers were designed and tested in 28 pairs of HCC tissue DNA and matched plasma ctDNA within the same patient. The methylation profiles in HCC tumor DNA and matched plasma ctDNA were highly consistent, giving them potential as sensitive diagnostic markers (FIG. 27A, FIG. 27B, FIG. 34A, and FIG. 34B). 401 markers demonstrated a good amplification profile and dynamic methylation value and were therefore selected as good candidates for further analysis.

Methylation Block Structure for Improved Allele Calling Accuracy

Figure 31A:
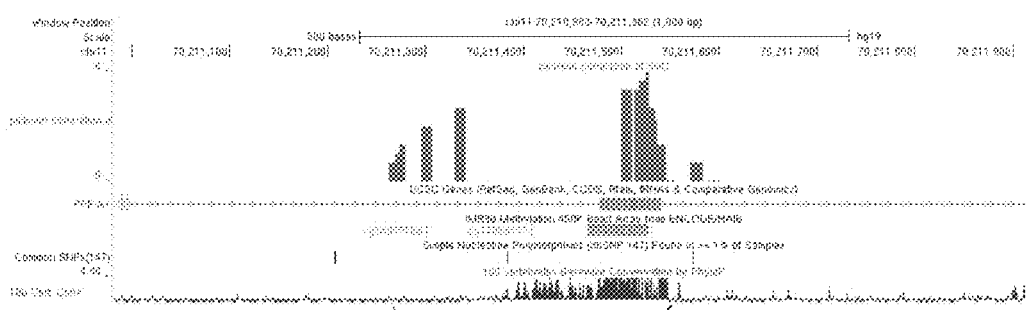
FIG. 31A-FIG. 31B illustrate an exemplary region encompassing two Blocks of Correlated Methylation (BCM) in cfDNA samples of from HCC and normal controls.
Figure 31B:
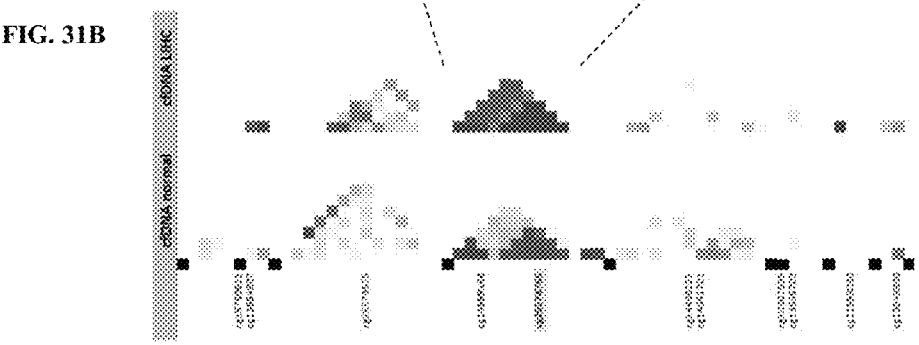

The concept of genetic linkage disequilibrium (LD block) was used to study the degree of co-methylation among different DNA stands. Paired-end Illumina sequencing reads were used to identify each individual methylation block (mBlock). A Pearson correlation method was applied to quantify co-methylation or mBlock. All common mBlocks of a region were compiled by calculating different mBlock fractions. Next, the genome was partitioned into blocks of tightly co-methylated CpG sites termed methylation correlated block (MCB), using an $r^2$ cutoff of 0.5. MCBs were surveyed in cfDNA of 500 normal samples and it was found that MCBs are consistent. Methylation levels within an MCB in cfDNA in 500 HCC samples were then determined. It was found that an MCB has a consistent methylation pattern when comparing normal versus HCC cfDNA samples (FIG. 31A-FIG. 31B).

ctDNA Diagnostic Prediction Model for HCC

Figure 27E:
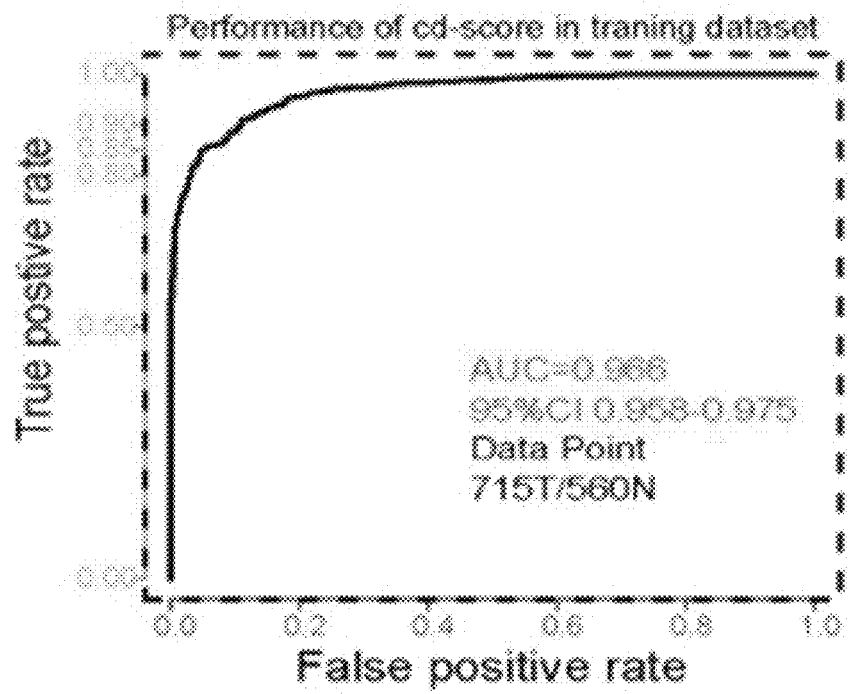
Figure 27F:
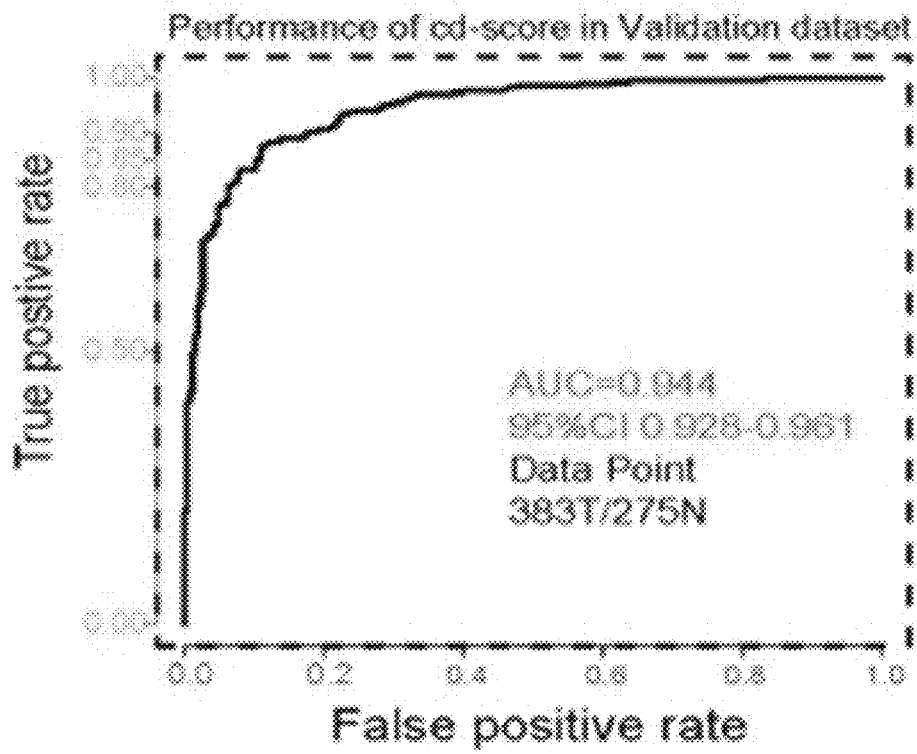
Figure 27G:
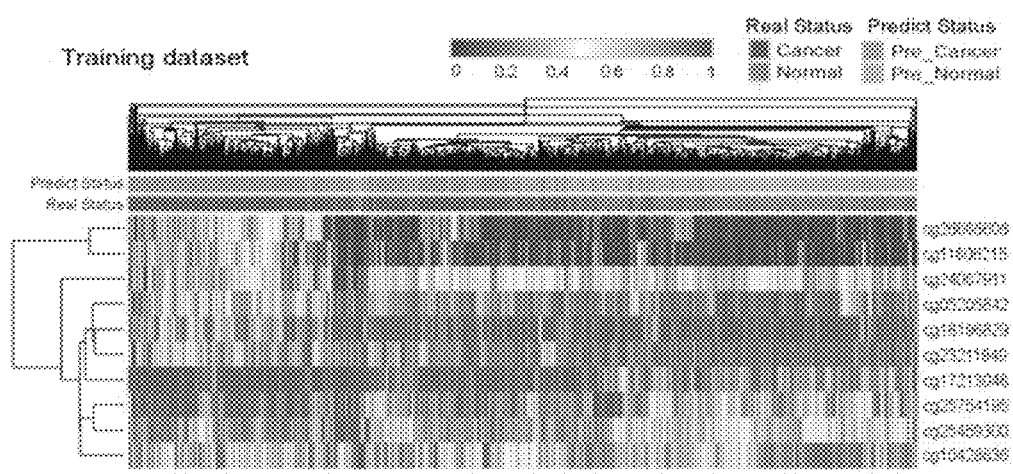
Figure 27H:
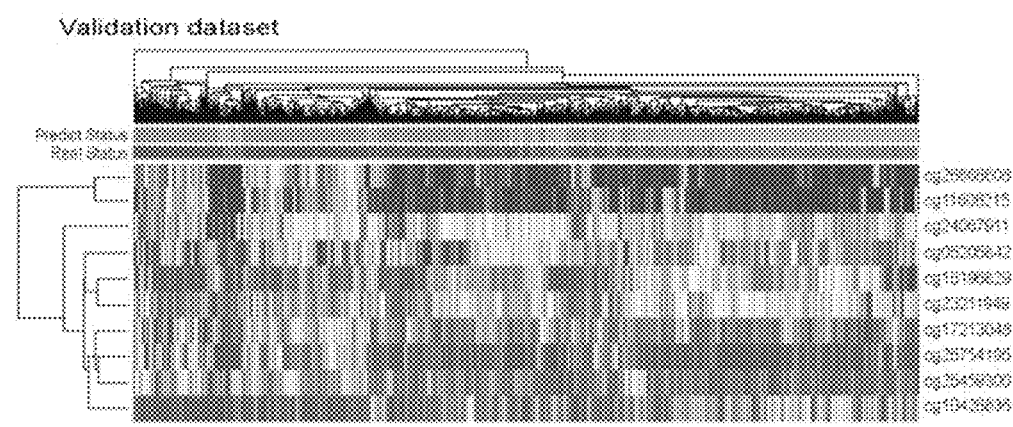
Figure 35:
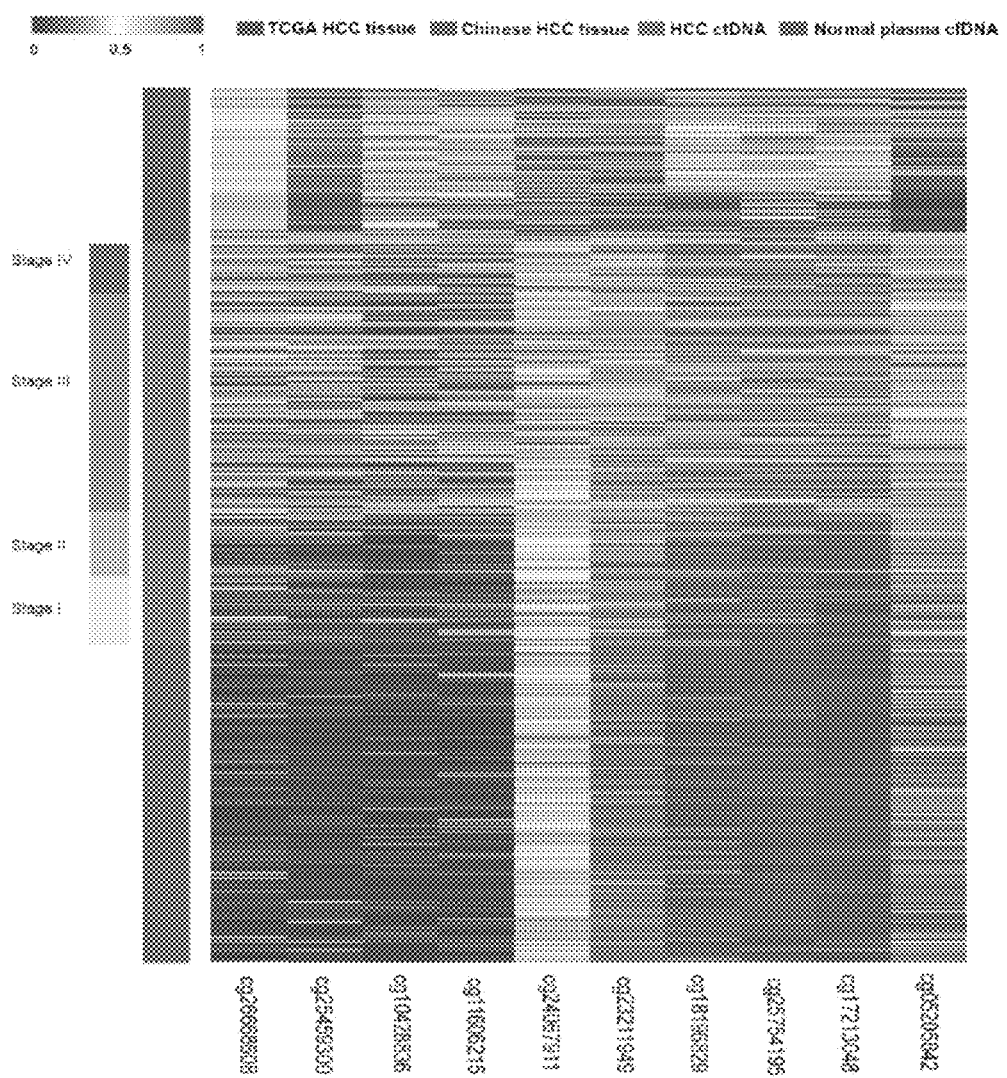
FIG. 35 illustrates hierarchical clustering of 10 diagnostic markers in TCGA HCC tissue DNA, Chinese HCC tissue DNA, HCC ctDNA and normal plasma cfDNA. Each column represents an individual patient and each row represents a CpG marker. Clustering within groups shows that beta values follow a gradient between primary HCC tissue and normal cfDNA, with tumor cfDNA showing intermediate beta values. cfDNA of samples with higher stage tumors have beta values approaching primary HCC tissue samples.

The methylation values of the 401 selected markers that showed good methylation ranges in cfDNA samples were analyzed by Random Forest and Least Absolute Shrinkage and Selection Operator (LASSO) methods to further reduce the number of markers by modeling them in 715 HCC ctDNA and 560 normal cfDNA samples (FIG. 26). About 24 markers were obtained using the Random Forest analysis. 30 markers were obtained using a LASSO analysis in which it was required that selected markers were to appear over 450 times out of a total of 500 repetitions. There were 10 overlapping markers between these two methods (Table 15). Using a logistic regression method, a diagnostic prediction model was constructed with these 10 markers. Applying the model yielded a sensitivity of 85.7% and specificity of 94.3% for HCC in the training dataset of 715 HCC and 560 normal samples (FIG. 27C) and a sensitivity of 83.2% and specificity of 90.5% in the validation dataset of 383 HCC and 275 normal samples (FIG. 27D). In some cases, this model further differentiate HCC from normal controls both in the training dataset (AUC=0.966) and the validation dataset (AUC=0.944) (FIG. 27E and FIG. 27F). Unsupervised hierarchical clustering of these 10 markers was able to distinguish HCC from normal controls with high specificity and sensitivity (FIG. 27G, FIG. 27H, and FIG. 35).

Figure 28A:
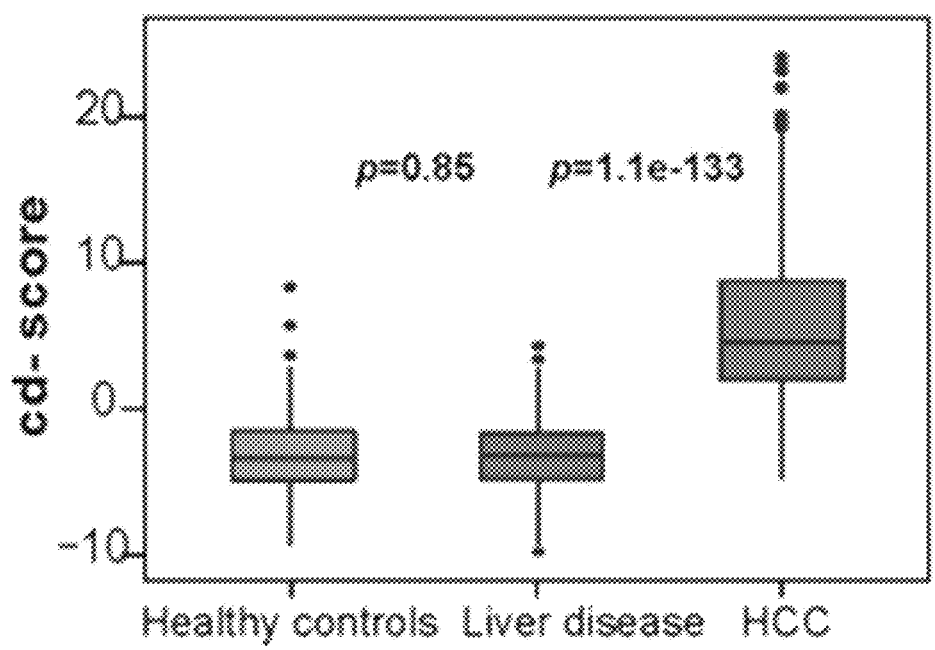
FIG. 28A-FIG. 28K shows cfDNA methylation analysis and tumor burden, treatment response, and staging.
Figure 28B:
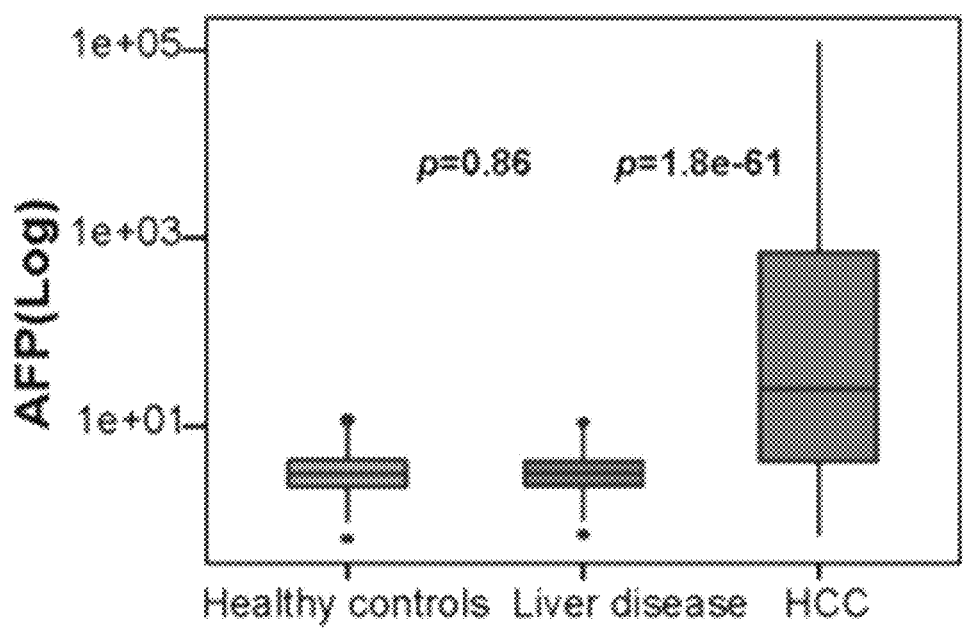

A combined diagnostic score (cd-score) of the model was assessed for differentiating between liver diseases (e.g., HBV/HCV infection, cirrhosis, and fatty liver) and HCC since these liver diseases are known risk factors for HCC. It was found that the cd-score was able to differentiate HCC patients as compared to those with liver diseases or healthy controls (FIG. 28A). These results were consistent and comparable with those predicted by AFP levels (FIG. 28B).

Methylation Markers Predicted Tumor Load, Treatment Response and Staging

Figure 28C:
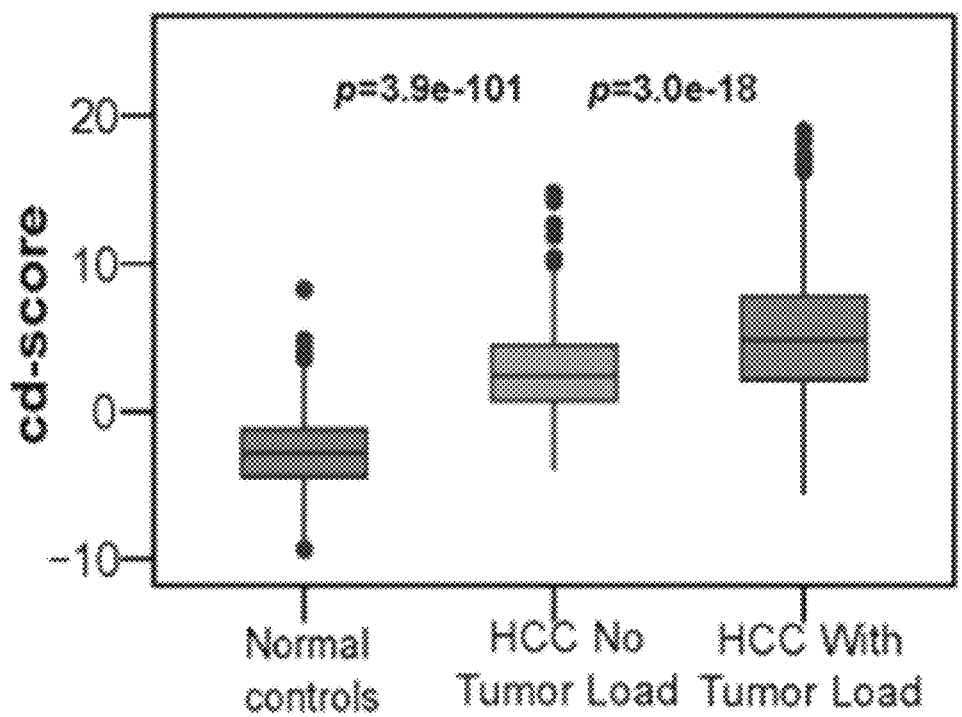
Figure 28D:
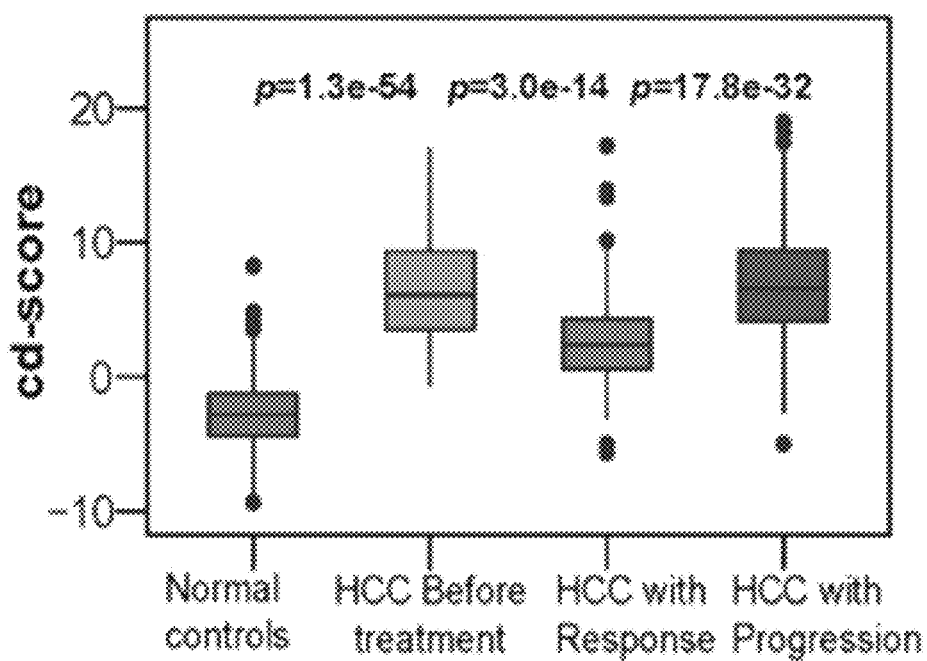
Figure 28E:
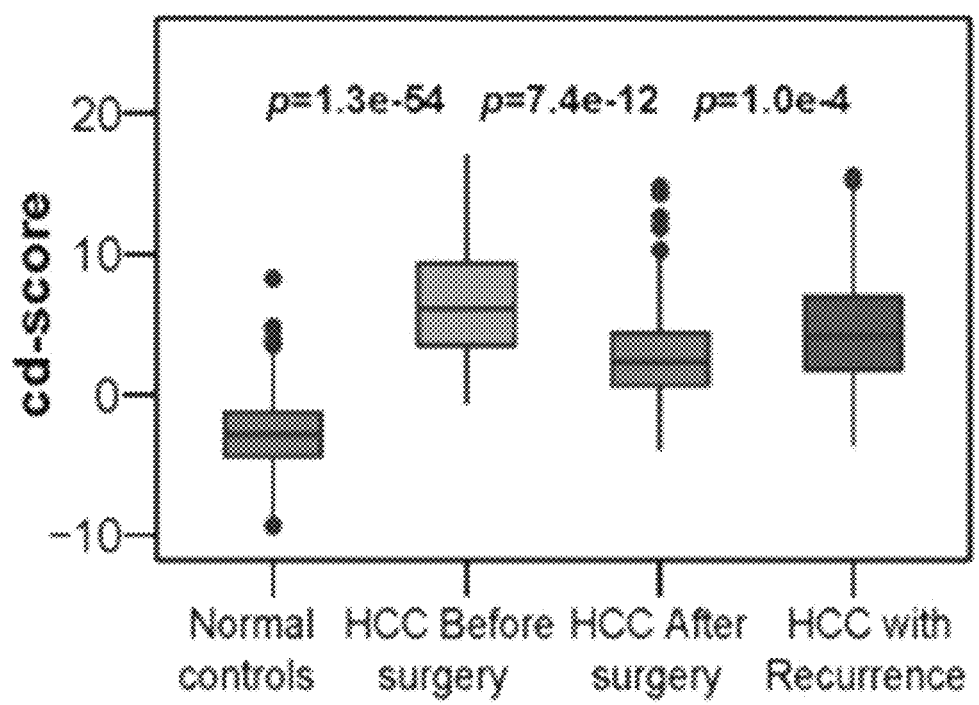
Figure 28F:
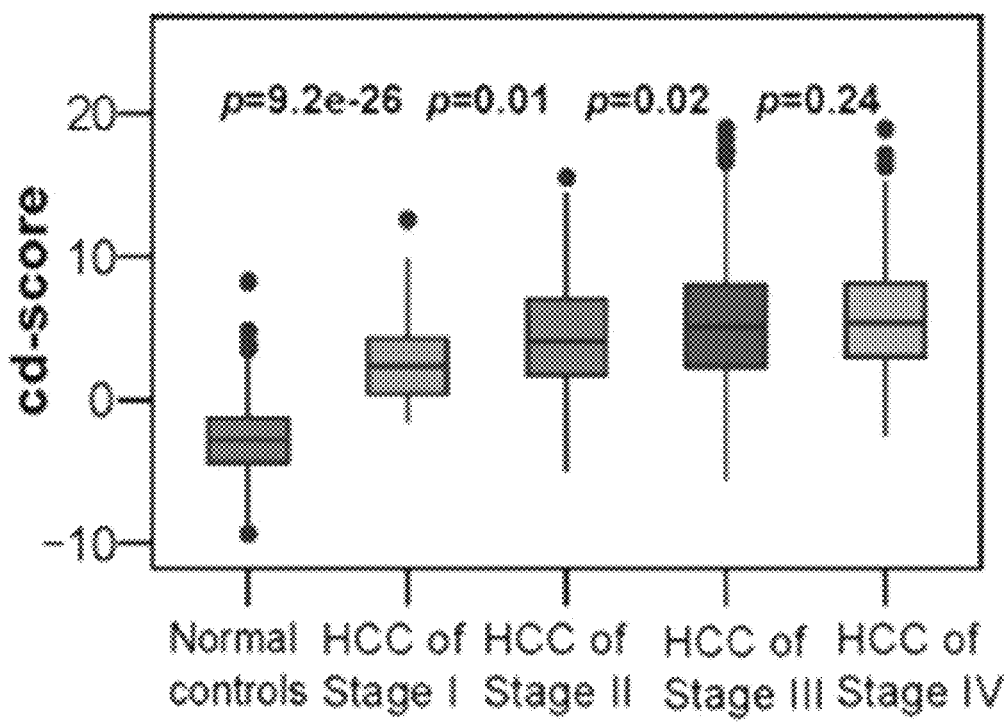

The utility of the cd-score in assessing treatment response, the presence of residual tumor following treatment, and staging of HCC was further studied. Clinical and demographic characteristics, such as age, gender, race, and AJCC stage were included in the analysis. The cd-scores of patients with detectable residual tumor following treatment (n=828) were significantly higher than those with no detectable tumor (n=270), and both were significantly greater than normal controls (n=835) (p<0.0001, FIG. 28C). Similarly, the cd-scores were significantly higher in patients before treatment (n=109) or with progression (n=381) compared to those with treatment response (n=248) (p<0.0001, FIG. 28D). In addition, the cd-scores were significantly lower in patients with complete tumor resection after surgery (n=170) compared with those before surgery (n=109), yet became higher in patients with recurrence (n=155) (p<0.0001, FIG. 28E). Furthermore, there is good correlation between the cd-scores and tumor stage. Patients with early stage disease (I, II) had substantially lower cd-scores compared to those with advanced stage disease (III, IV) (p<0.05, FIG. 28F). Collectively, these results suggest that the cd-score (i.e., the amount of ctDNA in plasma) correlates well with tumor burden and may have utility in predicting tumor response and surveillance for recurrence.

Utility of ctDNA Diagnostic Prediction Model and AFP

In some instances, the blood biomarker for risk assessment and surveillance of HCC is serum AFP levels. However, its low sensitivity makes it inadequate to detect all patients that will develop HCC and severely limits its clinical utility. In some cases, many cirrhotic patients develop HCC without any increase in AFP levels. In additional cases, 40% patients of the HCC study cohort have a normal AFP value (<25 ng/ml).

Figure 28G:
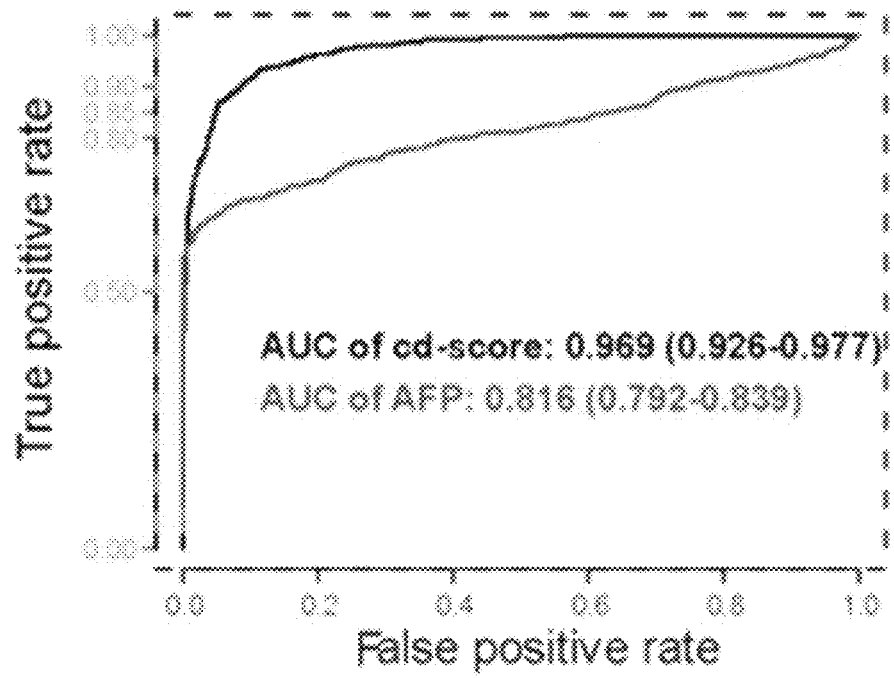
Figure 28H:
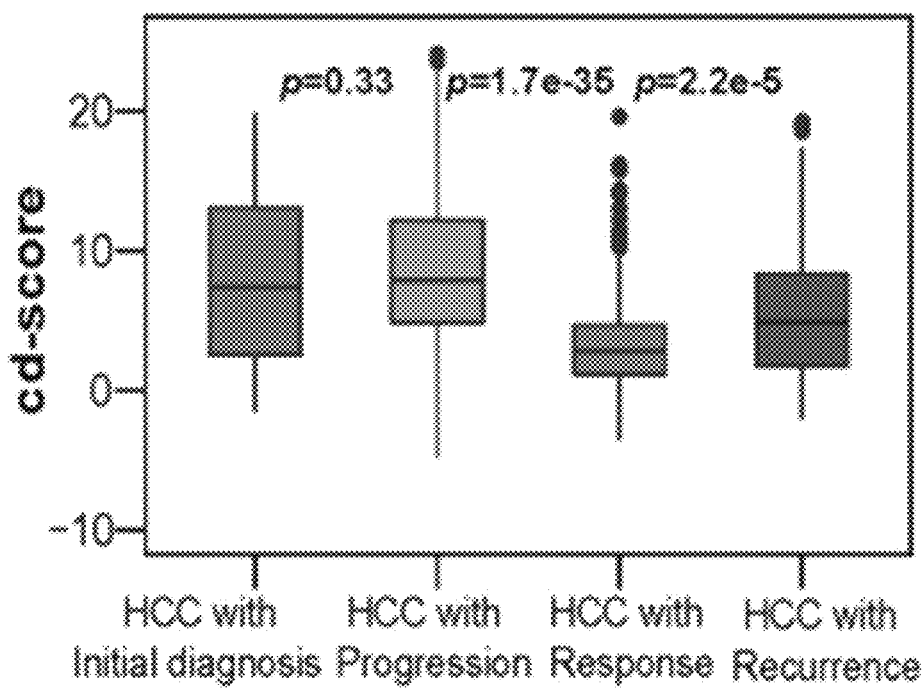
Figure 28I:
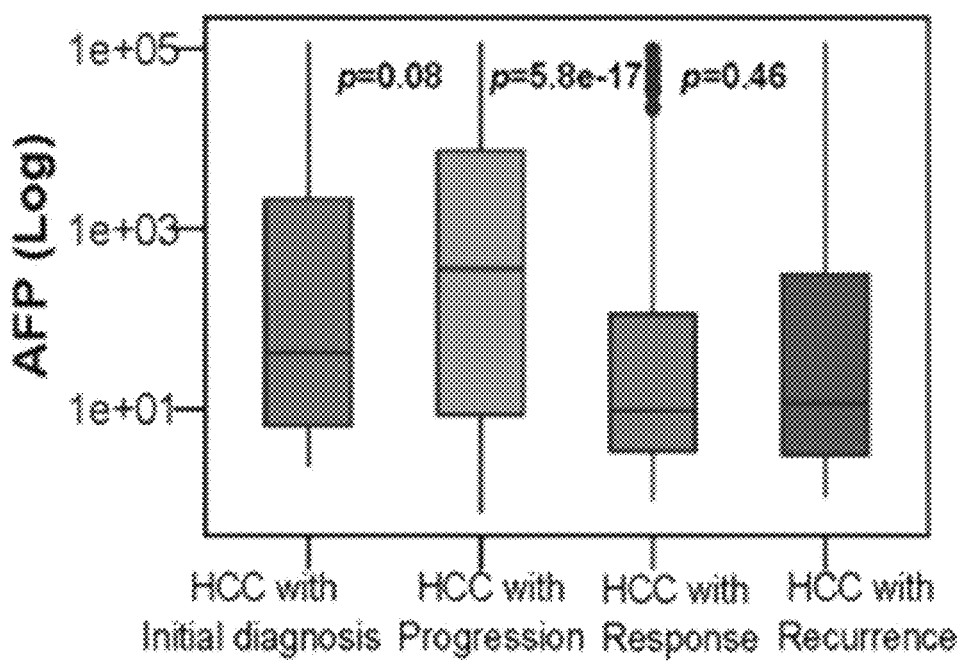
Figure 32A:
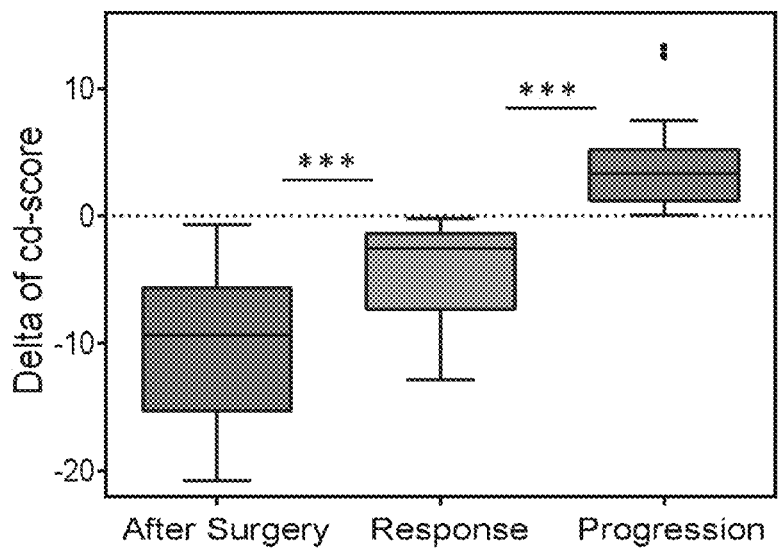
FIG. 32A-FIG. 32B show methylation values correlated with treatment outcomes in HCC patients with serial plasma samples.
Figure 32B:
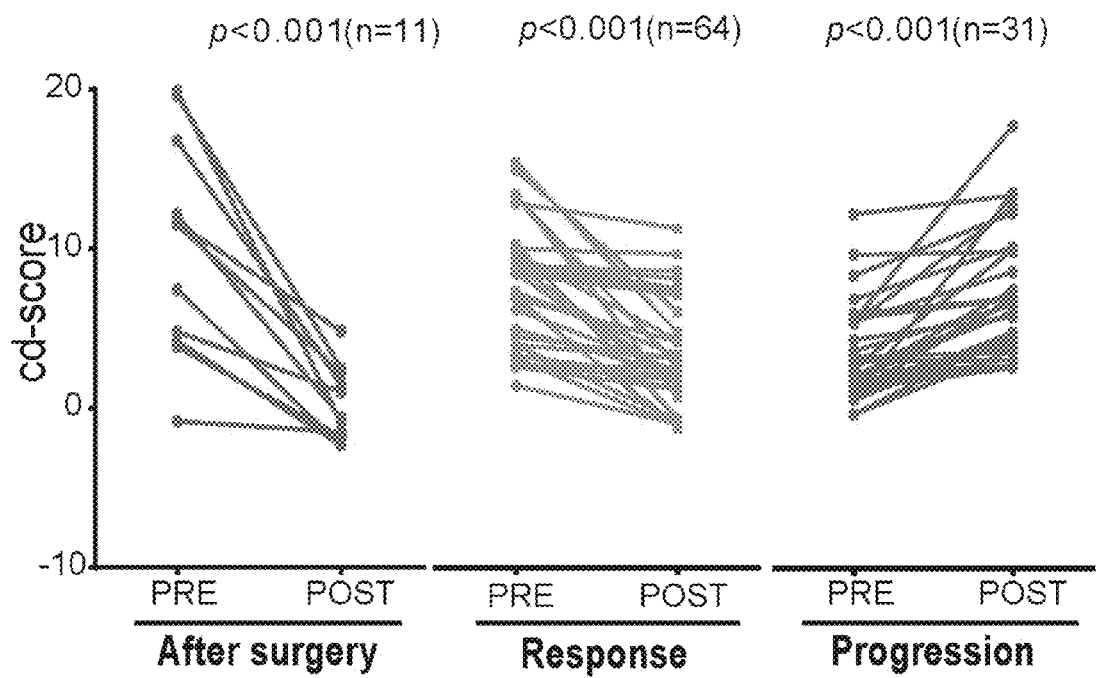
Figure 33:
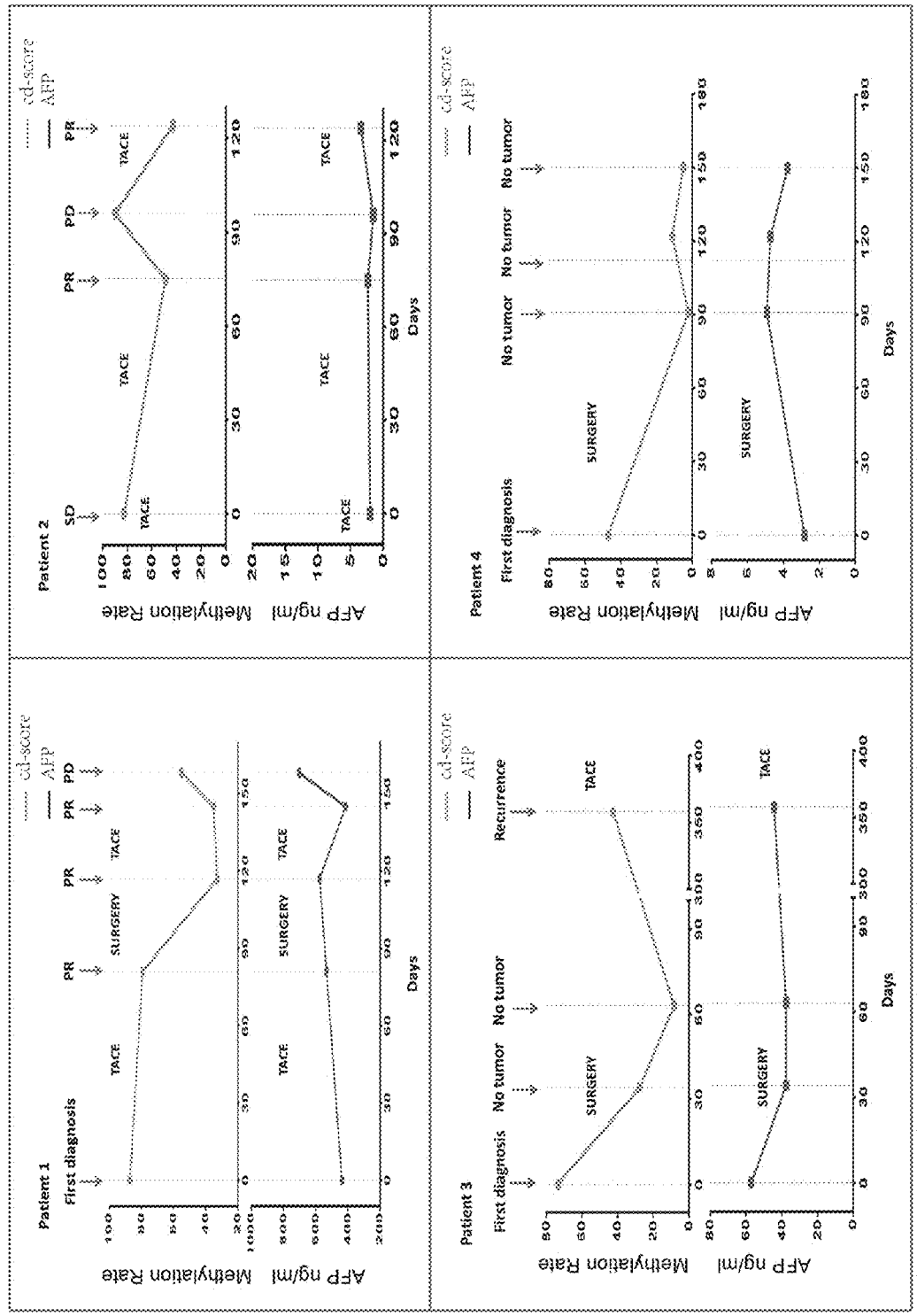
FIG. 33 illustrates a dynamic monitoring of treatment outcomes in individual patients with cd-score and AFP. Dates of treatments are indicated by vertical blue arrows. PD, progressive disease; PR partial response; SD, stable disease; TACE, trans-catheter arterial chemoembolization.
Figure 34A:
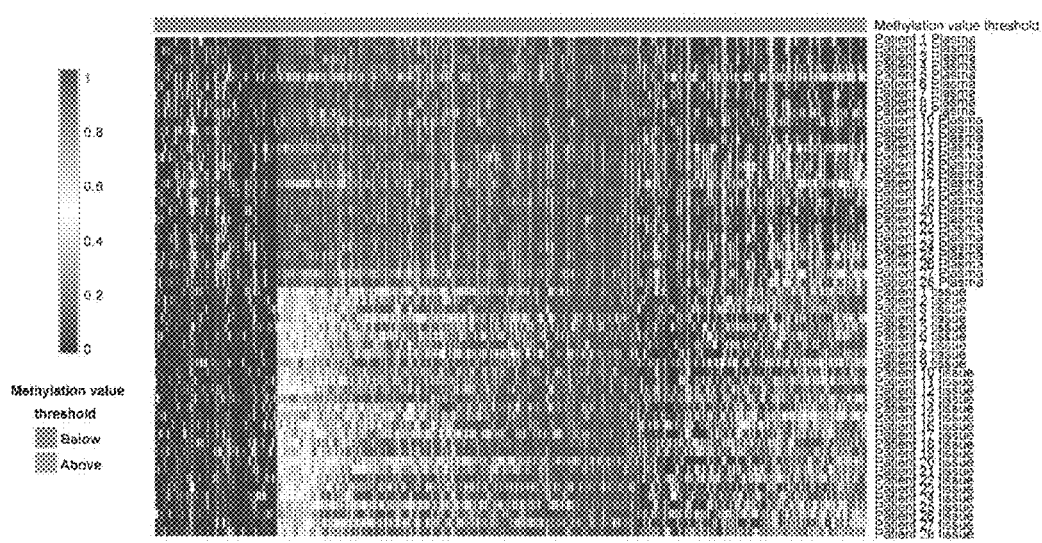
FIG. 34A-FIG. 34B illustrate cfDNA methylation analysis of HCC diagnosis.
Figure 34B:
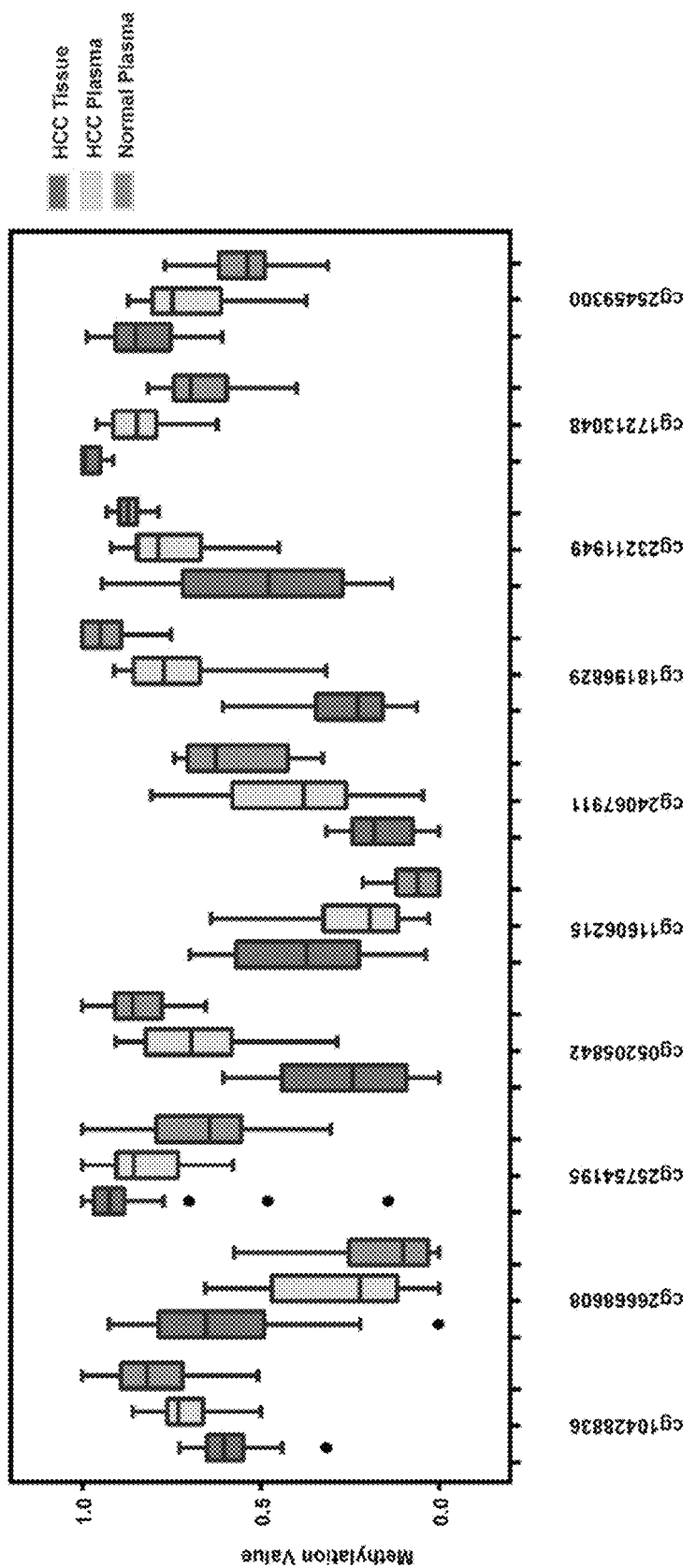
Figure 36:
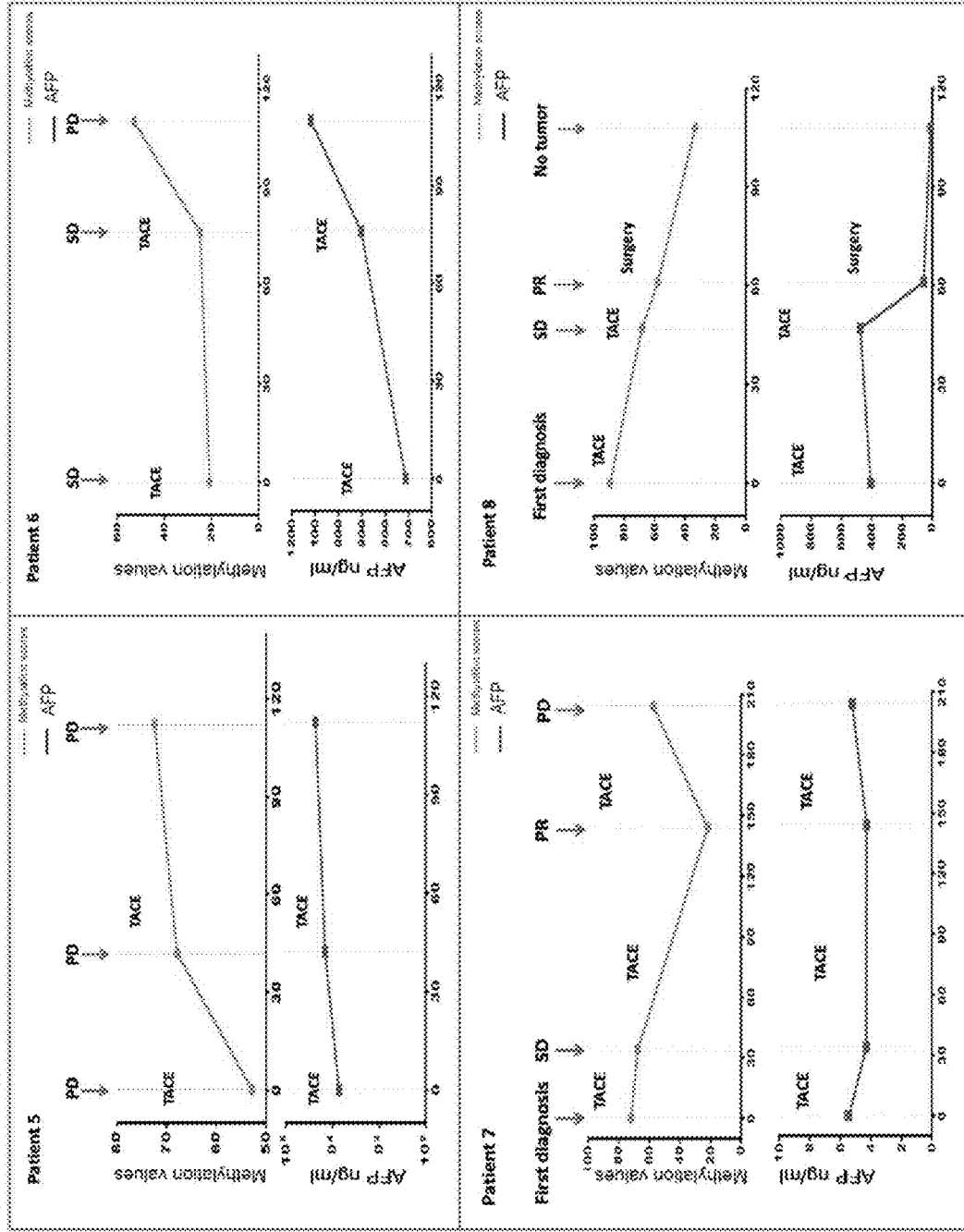
FIG. 36 shows dynamic monitoring of treatment outcomes in individual patients with methylation composite values and AFP. Dates of treatments are indicated by vertical blue arrows. PD, progressive disease; PR partial response; SD, stable disease; TACE, trans-catheter arterial chemoembolization.
Figure 37A:
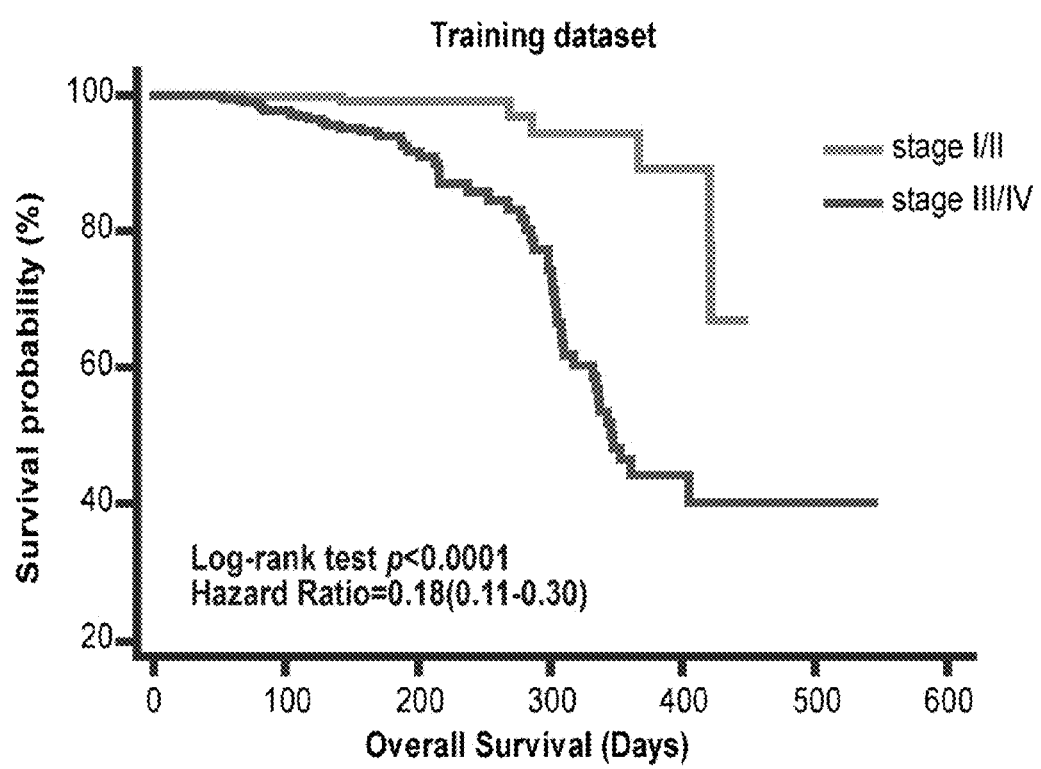
FIG. 37A-FIG. 37B show TNM stage for prognostic prediction HCC survival, Survival curves of HCC patients with stage I/II and stage III/IV in the training (FIG. 37A) and validation datasets (FIG. 37B).
Figure 37B:
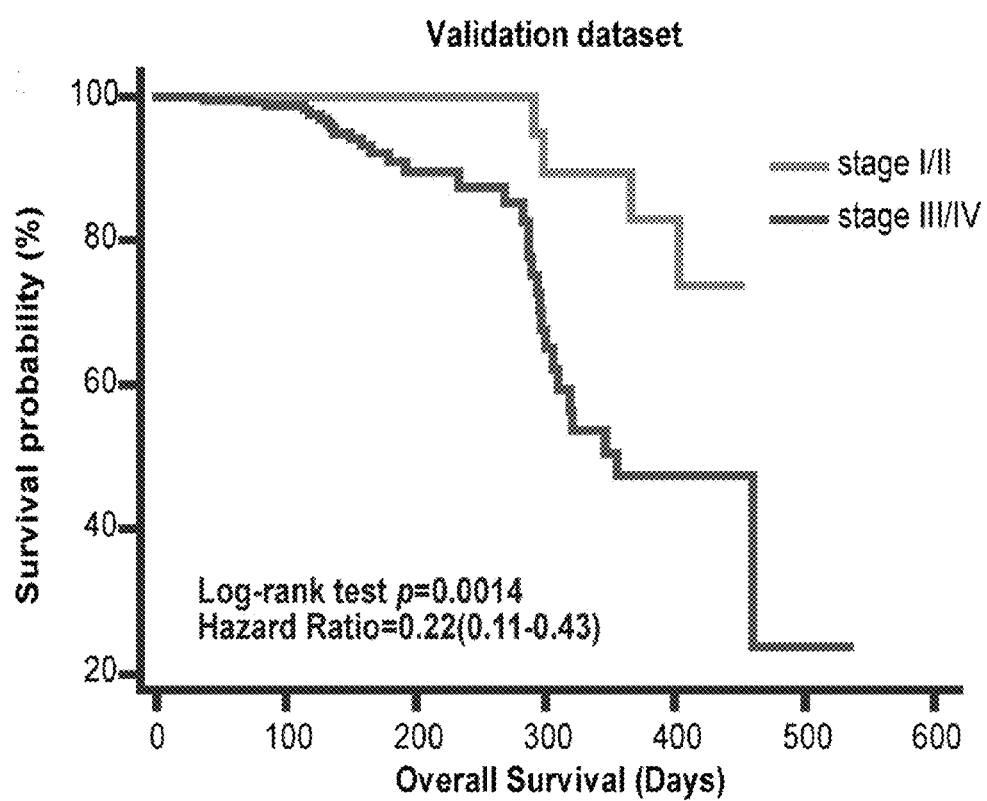

In biopsy-proven HCC patients, the cd-score demonstrated superior sensitivity and specificity than AFP for HCC diagnosis (AUC 0.969 vs 0.816, FIG. 28G). In patients with treatment response, tumor recurrence, or progression, cd-score showed more significant changes compared to testing at initial diagnosis than AFP (FIG. 28H and FIG. 28I). In patients with serial samples, those with a positive treatment response had a concomitant significant decrease in cd-score compared to that prior to treatment, and there was an even further reduction in patients after surgery. In contrast, the patients with progressive or recurrent disease all had an increase in cd-score (FIG. 32A-FIG. 32B). By comparison, AFP is less sensitive for assessing treatment efficacy in individual patients (FIG. 33 and FIG. 36).

Figure 28J:
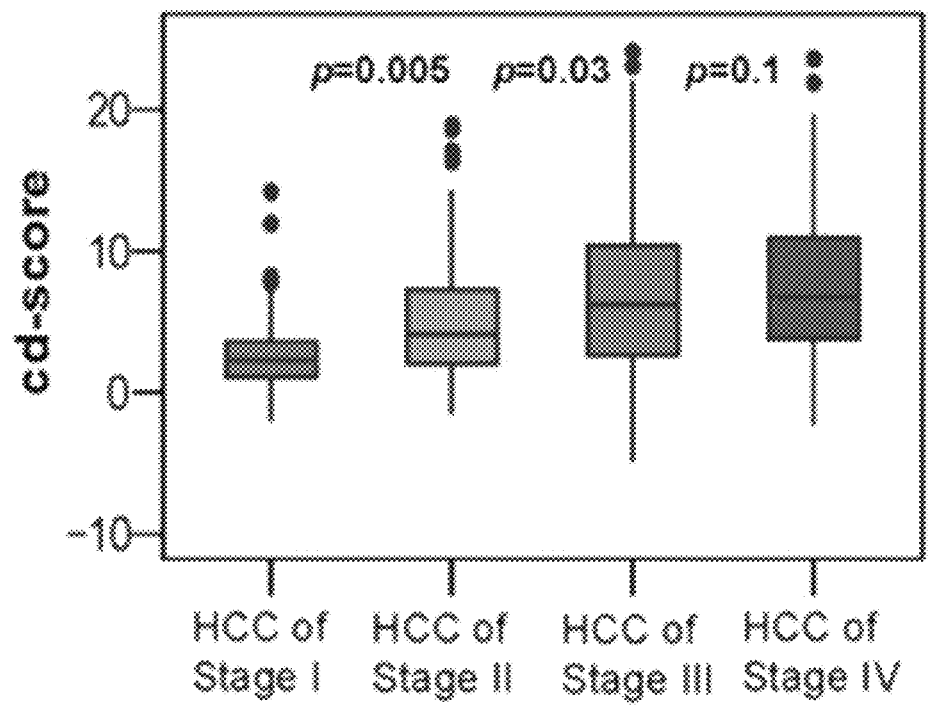
Figure 28K:
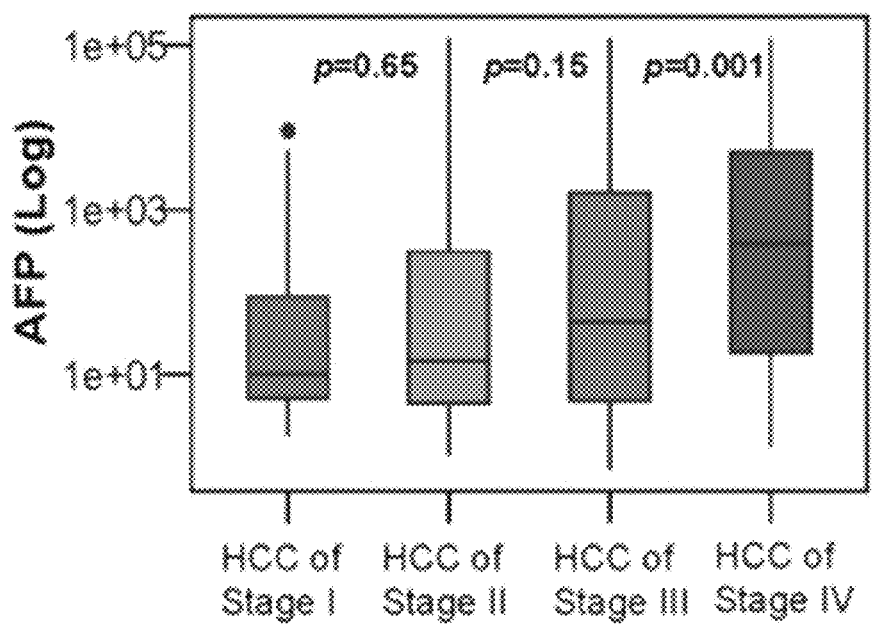

In addition, cd-score correlated well with tumor stage (FIG. 28J), particularly among patients with stage I, II and III, whereas there was not significant different AFP values in patients with different stages except between patients with stage III and IV (FIG. 28K), indicating an advantage of cd-score over AFP in differentiation of early stage HCC.

ctDNA Prognostic Prediction Model for HCC

Figure 29A:
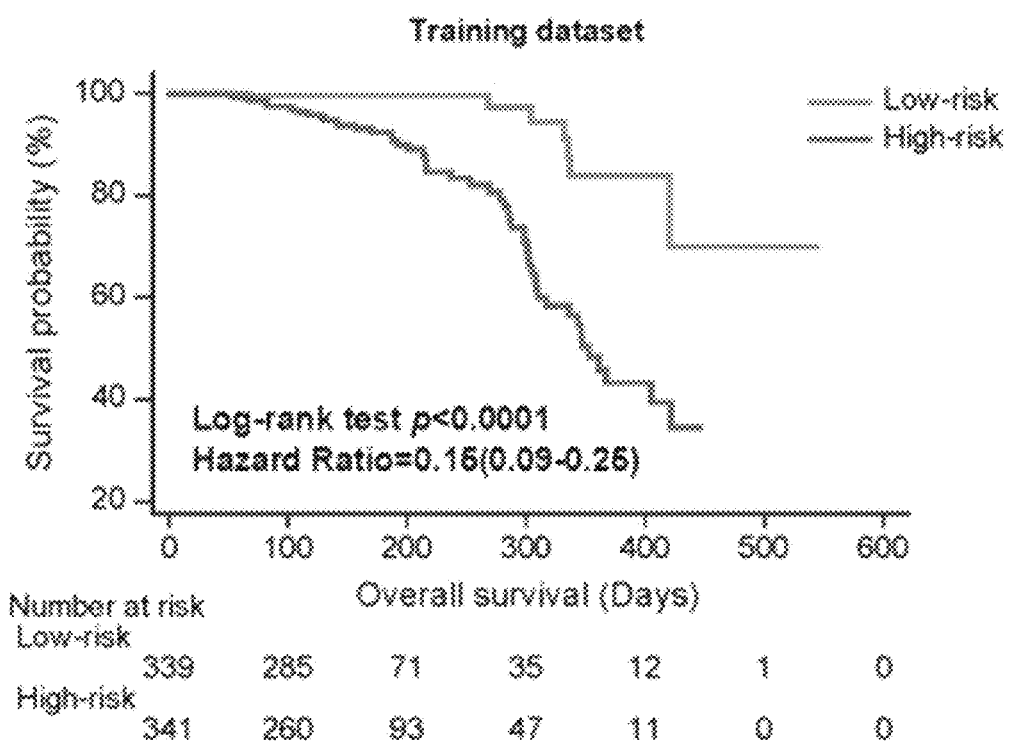
Figure 29C:
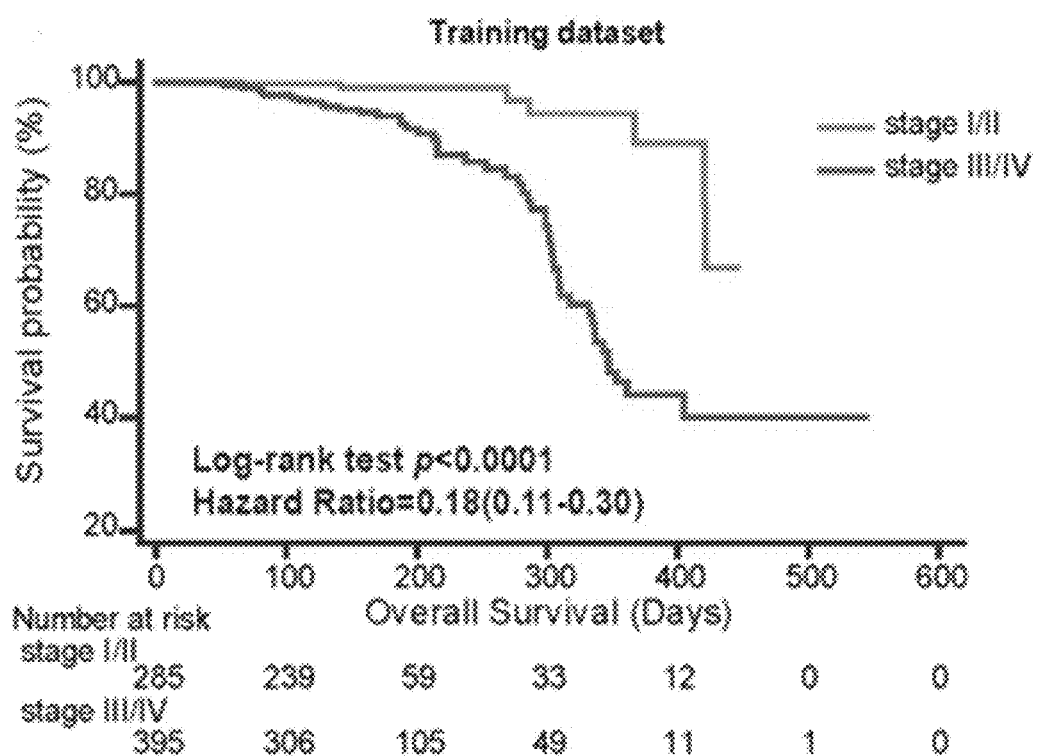
Figure 29E:
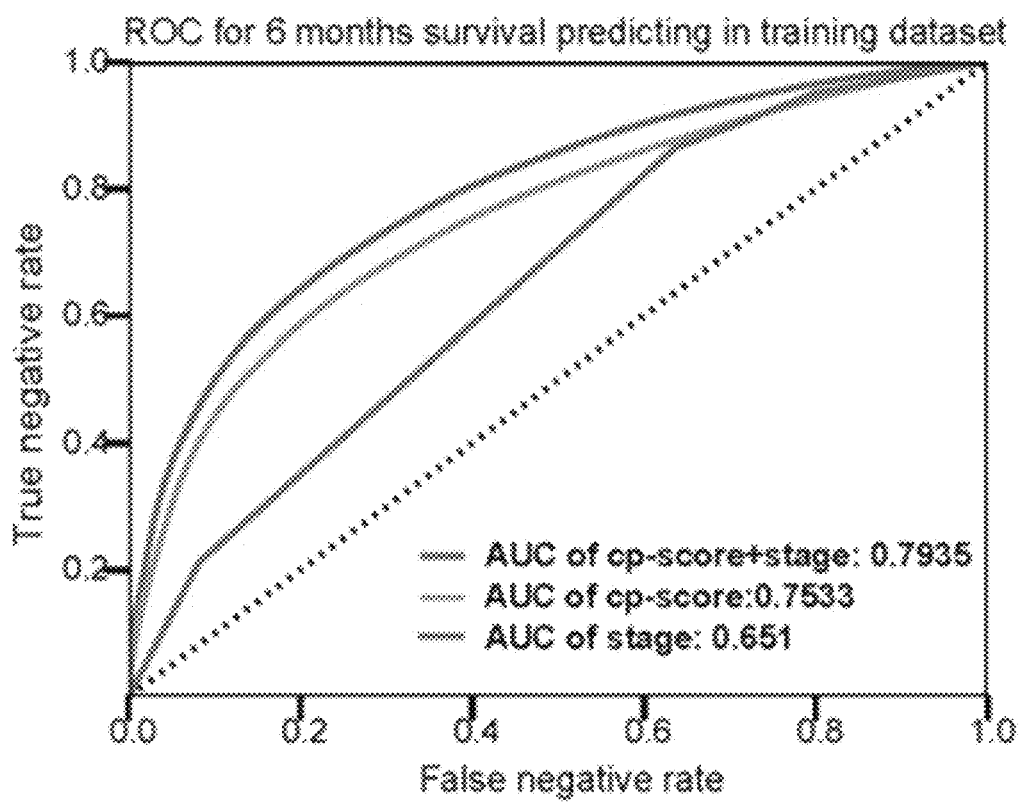
Figure 29F:
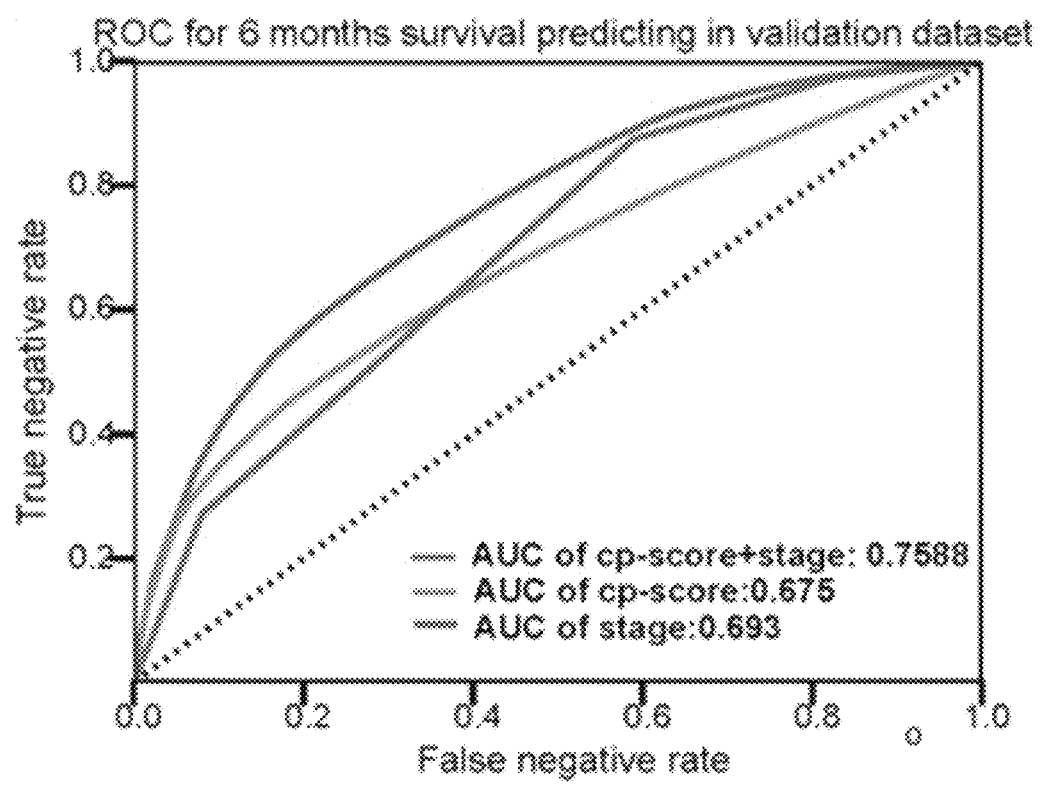

The potential to use methylation markers in ctDNA for prediction of prognosis in HCC in combination with clinical and demographic characteristics including age, gender, race, and AJCC stage was investigated. The 1049 HCC patients with complete survival information was randomly split into training and validation datasets with allocation of 2:1. The Unicox and LASSO-cox methods were implemented to reduce the dimensionality and constructed a cox-model to predict prognosis with an 8-marker panel (Table 16). Kaplan-Meier curves were generated in training and validation datasets using a combined prognosis score (cp-score) with these markers. The high-risk group (cp-score >−0.24) has 341 observations with 53 events in training dataset and 197 observations with 26 events in validation dataset; and the low-risk group (cp-score ≤−0.24) has 339 observations with 7 events in training dataset and 172 observations with 9 events in validation dataset. Median survival was significantly different in both the training set (p<0.0001) and the validation set (p=0.0014) by log-rank test (FIG. 29A and FIG. 29B).

Multivariate variable analysis showed that the cp-score significantly correlated with risk of death both in the training and validation dataset, and that the cp-score was an independent risk factor of survival (hazard ratio [HR]: 2.512; 95% confidence interval [CI]: 1.966-3.210; p<0.001 in training set; HR: 1.553, CI: 1.240-1.944; p<0.001 in validation set, Table 18). Interestingly, AFP was no longer significant as a risk factor when cp-score and other clinical characteristics were taken in to account (Table 18).

TNM stage predicted the prognosis of patients in the training and validation dataset (FIG. 29C, FIG. 29D, FIG. 37A, and FIG. 37B). However, the combination of cp-score and TNM staging improved the ability to predict prognosis in both the training (AUC 0.7935) and validation datasets (AUC 0.7586). Kaplan-Meier curves also showed that patients separated by both cp-score and staging have significantly different prognosis (p<0.0001, FIG. 29G).

Table 15 illustrates characteristics often methylation markers and their coefficients in HCC diagnosis.

| Markers | Ref Gene | Coefficients | SE | z value | p value |
|---|---|---|---|---|---|
|  |  | 15.595 | 2.395 | 6.513 | <0.001 |
| cg10428836 | BMPR1A | 11.543 | 0.885 | −13.040 | <0.001 |
| cg26668608 | PSD | 4.557 | 0.889 | 5.129 | <0.001 |
| cg25754195 | ARHGAP25 | 2.519 | 0.722 | 3.487 | <0.001 |
| cg05205842 | KLF3 | −3.612 | 0.954 | −3.785 | <0.001 |
| cg11606215 | PLAC8 | 6.865 | 1.095 | 6.271 | <0.001 |
| cg24067911 | ATXN1 | −5.439 | 0.868 | −6.265 | <0.001 |
| cg18196829 | Chr 6:170 | −9.078 | 1.355 | −6.698 | <0.001 |
| cg23211949 | Chr 6:3 | −5.209 | 1.081 | −4.819 | <0.001 |
| cg17213048 | ATAD2 | 6.660 | 1.422 | 4.683 | <0.001 |
| cg25459300 | Chr 8:20 | 1.994 | 1.029 | 1.938 | <0.053 |

SE: standard errors of coefficients;
z value: Wald z-static value

Table 16 illustrates the characteristics of eight methylation markers and their coefficients in HCC prognosis prediction.

| Markers | Ref Gene | Coefficients | HR | CI | SE | z value | p value |
|---|---|---|---|---|---|---|---|
| cg23461741 | SH3PXD2A | −1.264 | 0.282 | 0.024-3.340 | 1.2604 | −1.003 | 0.316 |
| cg06482904 | C11orf9 | −0.247 | 0.781 | 0.067-9.100 | 1.2530 | −0.197 | 0.844 |
| cg25574765 | PPFIA1 | 1.026 | 2.790 | 0.488-15.900 | 0.8894 | 1.153 | 0.249 |
| cg07459019 | Chr 17:78 | −8.156 | 0.000 | 0.000-0.012 | 1.9112 | −4.267 | <0.001 |
| cg20490031 | SERPINB5 | 6.082 | 438.000 | 13.200-14600.000 | 1.7885 | 3.400 | 0.001 |
| cg01643250 | NOTCH3 | −5.368 | 0.005 | 0.000-0.140 | 1.7357 | −3.093 | 0.002 |
| cg11397370 | GRHL2 | 1.497 | 4.470 | 1.030-19.400 | 0.7506 | 1.994 | 0.046 |
| cg11825899 | TMEM8B | 2.094 | 8.120 | 0.957-68.900 | 1.0909 | 1.920 | 0.055 |

HR: Hazard Ratio;
CI: 95% confidence interval;
SE: standard errors of coefficients;
z value: Wald z-static value Table 17 shows the clinical characteristics of study cohort.

| Characteristic | HCC Tissue (TCGA) | Normal blood (GSE) | Study HCC cohort | Study normal cohort |
|---|---|---|---|---|
| Total (n) | 377 | 754 | 1098 | 835 |
| Gender | | | | |
| Female-no.(%) | 123(32.6) | 401(53.2) | 130(11.8) | 407(48.7) |
| Male-no.(%) | 254(67.4) | 353(46.8) | 905(82.4) | 417(49.9) |
| NA | 0 | | 61(5.7) | 11(1.4) |
| Age (years) | | | | |
| Mean | 61 | 63 | 55 | 47 |
| Range | 16-90 | 19-101 | 15-81 | 19-90 |
| AFP value | | | | |
| >25 ng/ml.(%) | 122(32.4) | NA | 350(31.9) | 1(0.1) |
| <25 ng/ml.(%) | 163(43.0) | NA | 352(32.1) | 784(93.9) |
| NA | 93(24.6) | | 387(36.0) | 51(6.0) |
| Stage | | | | |
| I | 175(46.4) | IA | 176(16.0) | IA |
| II | 87(23.1) | IA | 170(15.5) | IA |
| III | 86(22.8) | IA | 572(52.1) | IA |
| IV | 6(1.6) | IA | 132(12.0) | IA |
| NA | 23(6.1) | IA | 46(0.4) | IA |
| Tumor Load | | | | |
| No Tumor Load | 236(62.6) | IA | 270(24.6) | LA |
| With Tumor Load | 114(30.2) | IA | 825(75.4) | IA |
| NA | 27(7.2) | IA | 0 | IA |
| Hepatic | | | | |
| Postive | 120(31.8) | NA | 1043(95.0) | 343(41.1) |
| Negtive | 119(31.6) | NA | 10(0.9) | 483(51.8) |
| NA | 138(36.6) | NA | 45(4.1) | 9(1.1) |

NA, not available;
IA, inapplicable

Table 18 shows the Multivariate survival analysis for HCC patients with cp-score of methylation markers and relevant variables.

| Factor | Coefficients | | HR | | CI | | SE | | z value | | p value | |
|---|---|---|---|---|---|---|---|---|---|---|---|---|
| | Training | Validation | Training | Validation | Training | Validation | Training | Validation | Training | Validation | Training | Validation |
| cp-score | 0.921 | 0.440 | 2.512 | 1.553 | 1.966-3.210 | 1.240-1.944 | 0.125 | 0.115 | 7.360 | 3.836 | <0.001 | <0.001 |
| AFP | 0.000 | 0.000 | 1.000 | 1.000 | 1.000-1.000 | 1.000-1.000 | 0.000 | 0.000 | 0.936 | 2.229 | 0.349 | 0.026 |
| Stage | 0.498 | 0.832 | 1.646 | 2.298 | 1.157-2.341 | 1.365-3.868 | 0.180 | 0.266 | 2.772 | 3.130 | 0.006 | 0.002 |
| Gender | 0.077 | 0.799 | 0.926 | 2.224 | 0.427-2.088 | 0.505-9.801 | 0.395 | 0.757 | −0.195 | 1.056 | 0.845 | 0.291 |
| Age | 0.015 | 0.011 | 0.985 | 1.011 | 0.962-1.009 | 0.981-1.042 | 0.012 | 0.015 | 1.237 | 0.733 | 0.216 | 0.463 |

HR: Hazard Ratio;
CI: 95.0% confidence interval;
SE: standard errors of coefficients;
z value: Wald z-statistic value Table 19 illustrates exemplary padlock sequences described herein.

| Marker | Gene | Sequence | SEQ ID NO: |
|---|---|---|---|
| cg10428836 | BMPR1A | ACAATATCCCAAACACATCATCATCTGTCTCTTATACACATCTCCGAGCCCACGAGACCCCCCCCCCCCCCCCCTCGTCGGCAGCGTCAGATGTGTATAAGAGACAGNNNNNNAAATTATTTTCTTCTAATTCAAAT | 1 |
| cg26668608 | PSD | ACAACCACATTCACTAAACACTGTCTCTTATACACATCTCCGAGCCCACGAGACCCCCCCCCCCCCCCTCGTCGGCAGCGTCAGATGTGTATAAGAGACAGNNNNNNAAATATAAAATATTAAACAACTAAAAA | 2 |
| cg25754195 | ARHGAP25 | ACCCTCTTCTCTCACTTCCACTGTCTCTTATACACATCTCCGAGCCCACGAGACCCCCCCCCCCCCCCCCTCGTCGGCAGCGTCAGATGTGTATAAGAGACAGNNNNNNACATCCTAAAAATATAAAACATA | 3 |
| cg05205842 | KLF3 | ACCCTACTACCCACCCTATCTCCTGTCTCTTATACACATCTCCGAGCCCACGAGACCCCCCCCCCCCCCCTCGTCGGCAGCGTCAGATGTGTATAAGAGACAGNNNNNNACCAACAATAAATACATAATAATAAT | 4 |

-continued

| Marker | Gene | Sequence | SEQ ID NO: |
|---|---|---|---|
| cg11606215 | PLAC8 | ACACAATTACCTCTCCCCTTCTGTCTCTT ATACACATCTCCGAGCCCACGAGACCCC CCCCCCCCCCCCTCGTCGGCAGCGTCAGA TGTGTATAAGAGACAGNNNNNNAAAAATA TATTCATTCTCCAAATAAAAA | 5 |
| cg24067911 | ATXN1 | TCTTTACTCTCTCAATCCAACCCTGTCTC TTATACACATCTCCGAGCCCACGAGACCC CCCCCCCCCCCCCCCTCGTCGGCAGCGT CAGATGTGTATAAGAGACAGNNNNNNNAAA TCCCAAATACAATTTCAAAAT | 6 |
| cg18196829 | Chr 6:170 | CCCTTAAACACCAATCTTCCAACCCTGTC TCTTATACACATCTCCGAGCCCACGAGAC CCCCCCCCCCCCCCCCCTCGTCGGCAGC GTCAGATGTGTATAAGAGACAGNNNNNNA ATAAAACAAAAATAACCCCAA | 7 |
| cg23211949 | Chr 6:3 | ATCTTCCCAACACTCAAAACAATACCCTG TCTCTTATACACATCTCCGAGCCCACGAG ACCCCCCCCCCCTCGTCGGCAGCGTCAGA TGTGTATAAGAGACAGNNNNNNATCCCAT ACATTCCTAACTCCTTTAAAT | 8 |
| cg17213048 | ATAD2 | TCTTAAACCACTTCTAACTACACCACAAT CTGTCTCTTATACACATCTCCGAGCCCAC GAGACCCCCCCCCCTCGTCGGCAGCGTCA GATGTGTATAAGAGACAGNNNNNNAACCA TTATATCCTTCCCATCTTTTT | 9 |
| cg25459300 | Chr 8:20 | CTCCTCCTCTTACCACACCCTTTTCCTAA ACACTGTCTCTTATACACATCTCCGAGCC CACGAGACCCCCCCCTCGTCGGCAGCGTC AGATGTGTATAAGAGACAGNNNNNNNTAAA TCCCCATATATCTTTTCTTCA | 10 |
| cg23461741 | SH3PXD2A | ATAAAAACACTAAAACCCTAAAACACTGT CTCTTATACACATCTCCGAGCCCACGAGA CCCCCCCCCCCCCCCCCTCGTCGGCAGC GTCAGATGTGTATAAGAGACAGNNNNNNA ATACCCTCTTTAATACAAAAA | 11 |
| cg06482904 | C11orf9 | ATACAACCTAAATACAAACTTCCCACTGT CTCTTATACACATCTCCGAGCCCACGAGA CCCCCCCCCCCCTCGTCGGCAGCGTCAGA TGTGTATAAGAGACAGNNNNNNAAAAACC TAACCCTACCTTCTAAACAAAT | 12 |
| cg25574765 | PPFIA1 | CACAACCTACACTCCTCCCAACCTGTCTC TTATACACATCTCCGAGCCCACGAGACCC CCCCCCCCCCCCCTCGTCGGCAGCGTCA GATGTGTATAAGAGACAGNNNNNNNTTCCC TTACCCTAAATATAATTAATA | 13 |
| cg07459019 | Chr 17:78 | TCATTTCCCCCAACAAATTCTTTTTCTTC TCCTGTCTCTTATACACATCTCCGAGCCC ACGAGACCCCCCCCCCCCTCGTCGGCAGC GTCAGATGTGTATAAGAGACAGNNNNNNT ACCAAAACCTTTATATTCTAA | 14 |
| cg20490031 | SERPINB5 | ACATATAACTCACAACCCCTTCCTACCCC TGTCTCTTATACACATCTCCGAGCCCACG AGACCCCCCCCCCTCGTCGGCAGCGTCA GATGTGTATAAGAGACAGNNNNNNAAAAA TTTATAATATTACTATCATCA | 15 |
| cg01643250 | NOTCH3 | ACTCAAACACTCATCCACATCCTGTCTCT TATACACATCTCCGAGCCCACGAGACCCC CCCCCCCCCCCCCCCCCTCGTCGGC AGCGTCAGATGTGTATAAGAGACAGNNNN NNCCCACCTAAAACTACAATC | 16 |

| Marker | Gene | Sequence | SEQ ID NO: |
|---|---|---|---|
| cg11397370 | GRHL2 | ACCAATAACAACTCACCTAAACTGTCTCT TATACACATCTCCGAGCCCACGAGACCCC CCCCCCCCCCCCCTCGTCGGCAGCGTCAG ATGTGTATAAGAGACAGNNNNNNAAAACT AACCCTCAACTCTCACAAACT | 17 |
| cg11825899 | TMEM8B | CTCCCCTTAAATCAAAAACTAAACATTTA AATCTGTCTCTTATACACATCTCCGAGCC CACGAGACCCCTCGTCGGCAGCGTCAGA TGTGTATAAGAGACAGNNNNNNATTTACA TTCCATCCATCTACATTCTAT | 18 |

Table 20 illustrates fraction of HCC cfDNA derived from tumor stratified according to tumor staging and treatment status. HCC patients with an advanced tumor stage and before treatment had higher tumor cfDNA fractions.

| | Tumor cfDNA fraction ± STDEV |
|---|---|
| Tumor Stage Status | |
| 1 | 0.098 ± 0.020 |
| 2 | 0.161 ± 0.146 |
| 3 | 0.301 ± 0.273 |
| 4 | 0.389 ± 0.178 |
| Treatment Status | |
| Before treatment * | 0.389 ± 0.148 |
| After treatment * | 0.109 ± 0.085 |

* Before treatment cohort included patients prior to any treatment (surgery or chemotherapy). After treatment included patients with a positive response to surgery or chemotherapy and reduction of tumor load.

Embodiment 1 recites a method of detecting the methylation status of one or more genes of a gene panel in a subject, comprising: (a) processing a biological sample obtained from the subject with a deaminating agent to generate treated DNA comprising deaminated nucleotides; and (b) detecting the methylation status in a gene selected from the gene panel consisting of BMPR1A, PSD, ARHGAP25, KLF3, PLAC8, ATXN1, Chromosome 6:170, Chromosome 6:3, ATAD2, Chromosome 8:20, SH3PXD2A, C11orf9, PPFIA1, Chromosome 17:78, SERPINB5, NOTCH3, GRHL2, and TMEM8B by (i) contacting the treated DNA with a probe that hybridizes under high stringency conditions to a target sequence of the gene to generate an amplified product; and (ii) analyzing the amplified product to determine the methylation status of the gene.

Embodiment 2: the method of embodiment 1, wherein the probe comprises about 80%, 85%, 90%, 95%, or 99% sequence identity to a probe selected from SEQ ID NOs: 1-18.

Embodiment 3: the method of embodiment 1, wherein the probe is a padlock probe selected from SEQ ID NOs: 1-18.

Embodiment 4: the method of embodiment 1, wherein the gene is selected from BMPR1A, PSD, ARHGAP25, KLF3, PLAC8, ATXN1, Chromosome 6:170, Chromosome 6:3, ATAD2, and Chromosome 8:20.

Embodiment 5: the method of embodiment 1, wherein the gene is selected from SH3PXD2A, C11orf9, PPFIA1, Chromosome 17:78, SERPINB5, NOTCH3, GRHL2, and TMEM8B.

Embodiment 6: the method of embodiment 1, further comprising detecting the methylations status of two or more genes from the gene panel consisting of BMPR1A, PSD, ARHGAP25, KLF3, PLAC8, ATXN1, Chromosome 6:170, Chromosome 6:3, ATAD2, Chromosome 8:20, SH3PXD2A, C11orf9, PPFIA1, Chromosome 17:78, SERPINB5, NOTCH3, GRHL2, and TMEM8B.

Embodiment 7: the method of embodiment 6, wherein the detecting comprises hybridizing under high stringency conditions with a set of probes, wherein the set of probes hybridizes up to 18 and no more than 18 genes from the gene panel.

Embodiment 8: the method of embodiment 1, further comprising determining a combined diagnostic score (cd-score) or a combined prognostic score (cp-score) based on the methylation status of the one or more genes, wherein the cd-score and the cp-score each independently correlates to an amount of circulating tumor DNA (ctDNA) present in the biological sample.

Embodiment 9: the method of embodiment 8, wherein the cd-score and the cp-score is each independently determined utilizing an algorithm selected from one or more of the following: a principal component analysis, a logistic regression analysis, a nearest neighbor analysis, a support vector machine, and a neural network model.

Embodiment 10: the method of embodiment 1, wherein the biological sample is treated with a deaminating agent to generated the treated DNA.

Embodiment 11: the method of embodiment 1, wherein the subject is suspected of having hepatocellular carcinoma (HCC).

Embodiment 12: the method of embodiment 1, wherein the subject has a stage I, stage II, stage III, or stage IV HCC.

Embodiment 13: the method of embodiment 1, wherein the subject is further treated with an effective amount of a therapeutic agent.

Embodiment 14: the method of embodiment 13, wherein the treatment comprises: (a) transcatheter arterial chemoembolization, radiofrequency ablation, or brachytherapy; (b) a chemotherapeutic agent or an agent for a targeted therapy; or (c) surgery.

Embodiment 15: the method of embodiment 14, wherein the chemotherapeutic agent comprises cisplatin, doxorubicin, fluoropyrimidine, gemcitabine, irinotecan, mitoxantrone, oxaliplatin, thalidomide, or a combination thereof.

Embodiment 16: the method of embodiment 14, wherein the agent for the targeted therapy comprises axitinib, bevacizumab, cetuximab, erlotinib, ramucirumab, regorafenib, sorafenib, sunitinib, a thymidine kinase (TK) inhibitor, or a combination thereof.

Embodiment 17: the method of embodiment 1, wherein the biological sample comprises a blood sample, a tissue biopsy sample, or circulating tumor cells.

Embodiment 18 recites a method of selecting a subject suspected of having hepatocellular carcinoma (HCC) for treatment, comprising: (a) contacting treated DNA with a probe that hybridizes under high stringency conditions to a target sequence of a gene selected from a gene panel consisting of BMPR1A, PSD, ARHGAP25, KLF3, PLAC8, ATXN1, Chromosome 6:170, Chromosome 6:3, ATAD2, and Chromosome 8:20 to generate an amplified product, wherein the treated DNA is processed from a biological sample obtained from the subject; analyzing the amplified product to generate a methylation profile of the gene; (b) applying the methylation profile to a model relating methylation profiles of genes from the gene panel to the presence to HCC; (c) evaluating an output from the model to determine whether the subject has HCC; and (d) administering an effective amount of a therapeutic agent to the subject if the subject is determined to have HCC.

Embodiment 19: the method of embodiment 18, wherein the probe comprises about 80%, 85%, 90%, 95%, or 99% sequence identity to a probe selected from SEQ ID NOs: 1-10.

Embodiment 20: the method of embodiment 18, further comprising contacting the treated DNA with at least an additional probe that hybridizes under high stringency conditions to a target sequence of an additional gene selected from the gene panel to generated an additional amplified product, and analyze the additional amplified product to generate a methylation profile of the additional gene, thereby determining the presence of HCC in the subject.

Embodiment 21: the method of embodiment 18, wherein the contacting comprises hybridizing under high stringency conditions with a set of probes, wherein the set of probes hybridizes up to ten and no more than ten genes from the gene panel.

Embodiment 22: the method of embodiment 18, wherein the biological sample is treated with a deaminating agent to generated the treated DNA.

Embodiment 23: the method of embodiment 18, wherein the model comprises methylation profiles of genes from the gene panel generated from an HCC positive sample.

Embodiment 24: the method of embodiment 23, wherein the HCC positive sample comprises cells from a metastatic HCC.

Embodiment 25: the method of embodiment 18 or 23, wherein the model further comprises methylation profiles of genes from the gene panel generated from a normal sample.

Embodiment 26: the method of any one of the embodiments 18 or 23-25, wherein the model is developed based on the methylation profiles of biomarkers from Table 15 or Table 16.

Embodiment 27: the method of any one of the embodiments 18 or 23-26, wherein the model is developed using an algorithm selected from one or more of the following: a principal component analysis, a logistic regression analysis, a nearest neighbor analysis, a support vector machine, and a neural network model.

Embodiment 28: the method of embodiment 18, further comprising determining the HCC as Stage I, Stage II, Stage III, or Stage IV.

Embodiment 29 recites a method selecting a subject suspected of having hepatocellular carcinoma (HCC) or lung cancer for treatment, comprising (a) contacting treated DNA with a probe that hybridizes under high stringency conditions to a target sequence of a gene selected from Tables 2, 6, 7, 9, or 10 to generate an amplified product, wherein the treated DNA is processed from a biological sample obtained from the subject; (b) analyzing the amplified product to generate a methylation profile of the gene; (c) applying the methylation profile to a model relating methylation profiles of genes from the gene panel to the presence to HCC or lung cancer; (d) evaluating an output from the model to determine whether the subject has HCC or lung cancer; and (e) administering an effective amount of a therapeutic agent to the subject if the subject is determined to have HCC or lung cancer.

Embodiment 30: the method of embodiment 29, further comprising contacting the treated DNA with at least an additional probe that hybridizes under high stringency conditions to a target sequence of an additional gene selected from the gene panel to generated an additional amplified product, and analyze the additional amplified product to generate a methylation profile of the additional gene, thereby determining the presence of HCC or lung cancer in the subject.

Embodiment 31: the method of embodiment 29, wherein the probe is a padlock probe.

Embodiment 32: the method of embodiment 29, wherein the biological sample is treated with a deaminating agent to generated the treated DNA.

Embodiment 33: the method of embodiment 29, wherein the model comprises methylation profiles of genes from the gene panel generated from an HCC positive sample or a lung cancer positive sample.

Embodiment 34: the method of embodiment 33, wherein the HCC positive sample comprises cells from a metastatic HCC.

Embodiment 35: the method of embodiment 33, wherein the lung cancer positive sample comprises cells from metastatic lung cancer.

Embodiment 36: the method of any one of the embodiments 29 or 33-35, wherein the model further comprises methylation profiles of genes from the gene panel generated from a normal sample.

Embodiment 37: the method of any one of the embodiments 29 or 33-36, wherein the model is developed based on the methylation profiles of biomarkers from Tables 3, 6, 7, 9, or 10.

Embodiment 38: the method of any one of the embodiments 29 or 33-37, wherein the model is developed using an algorithm selected from one or more of the following: a principal component analysis, a logistic regression analysis, a nearest neighbor analysis, a support vector machine, and a neural network model.

Embodiment 39: the method of embodiment 29, further comprising distinguishing between HCC and lung cancer.

Embodiment 40: the method of embodiment 18 or 29, wherein the treatment comprises: (a) transcatheter arterial chemoembolization, radiofrequency ablation, or brachytherapy; (b) a chemotherapeutic agent or an agent for a targeted therapy; or (c) surgery.

Embodiment 41 recites a method of determining the prognosis of a subject having hepatocellular carcinoma (HCC) or monitoring the progression of HCC in the subject, comprising: (a) processing a biological sample obtained from the subject with a deaminating agent to generate treated DNA comprising deaminated nucleotides; (b) generating a methylation profile comprising one or more genes selected from SH3PXD2A, C11orf9, PPFIA1, Chromosome 17:78, SERPINB5, NOTCH3, GRHL2, and TMEM8B from the treated DNA; (c) obtaining a methylation score based on the methylation profile of the one or more genes; and (d) based on the methylation score, initiate a first treatment, decrease a dosage of a first therapeutic agent if the subject has experienced a remission, initiate a second treatment if the subject has experienced a relapse, or switch to a second therapeutic agent if the subject becomes refractory to the first therapeutic agent.

Embodiment 42: the method of embodiment 41, wherein the methylation score correlates to survival for at least 6 months, 1 year, 1.5 years, 2 years, 2.5 years, 3 years, 4 years, 5 years, or more.

Embodiment 43: the method of embodiment 41, wherein the methylation score is calculated based on Cox proportional hazards (PH) regression analysis.

Embodiment 44: the method of embodiment 41, wherein the generating in step b) further comprises contacting treated DNA with a probe that hybridizes under high stringency conditions to a target sequence of a gene selected from SH3PXD2A, C11orf9, PPFIA1, Chromosome 17:78, SERPINB5, NOTCH3, GRHL2, and TMEM8B.

Embodiment 45: the method of embodiment 41, wherein the probe comprises about 80%, 85%, 90%, 95%, or 99% sequence identity to a probe selected from SEQ ID NOs: 11-18.

Embodiment 46: the method of embodiment 41, wherein the generating comprises hybridizing under high stringency conditions with a set of probes, wherein the set of probes hybridizes up to eight and no more than eight genes from the gene panel.

Embodiment 47 recites a method of determining the prognosis of a subject having hepatocellular carcinoma (HCC) or monitoring the progression of HCC in the subject, comprising: (a) processing a biological sample obtained from the subject with a deaminating agent to generate treated DNA comprising deaminated nucleotides; (b) generating a methylation profile comprising one or more genes selected from SOCS2, EPSTI1, TIA1, Chromosome 4, Chromosome 6, ZNF323, FOXP4, and GRHL2 from the treated DNA; (c) obtaining a methylation score based on the methylation profile of the one or more genes; and (d) based on the methylation score, initiate a first treatment, decrease a dosage of a first therapeutic agent if the subject has experienced a remission, initiate a second treatment if the subject has experienced a relapse, or switch to a second therapeutic agent if the subject becomes refractory to the first therapeutic agent.

Embodiment 48 recites a method of determining the prognosis of a subject having lung cancer or monitoring the progression of lung cancer in the subject, comprising: (a) processing a biological sample obtained from the subject with a deaminating agent to generate treated DNA comprising deaminated nucleotides; (b) generating a methylation profile comprising one or more genes selected from NPBWR1, Chromosome 2, AAK1, SIM1, C10orf46, C17orf101, DEPDC5, ZNF323, GABRA2, PLAC8 and ADRA2B from the treated DNA; (c) obtaining a methylation score based on the methylation profile of the one or more genes; and (d) based on the methylation score, initiate a first treatment, decrease a dosage of a first therapeutic agent if the subject has experienced a remission, initiate a second treatment if the subject has experienced a relapse, or switch to a second therapeutic agent if the subject becomes refractory to the first therapeutic agent.

Embodiment 49: the method of embodiment 47 or 48, wherein the methylation score correlates to survival for at least 6 months, 1 year, 1.5 years, 2 years, 2.5 years, 3 years, 4 years, 5 years, or more.

Embodiment 50: the method of embodiment 47 or 48, wherein the methylation score is calculated based on Cox proportional hazards (PH) regression analysis.

Embodiment 51: the method of any one of the embodiments 41, 47, or 48, wherein the first treatment comprises: (a) transcatheter arterial chemoembolization, radiofrequency ablation, or brachytherapy; (b) a chemotherapeutic agent or an agent for a targeted therapy; or (c) surgery.

Embodiment 52: the method of any one of the embodiments 41, 47, or 48, wherein the second treatment comprises: (a) transcatheter arterial chemoembolization, radiofrequency ablation, or brachytherapy; (b) a chemotherapeutic agent or an agent for a targeted therapy; or (c) surgery.

Embodiment 53: the method of any one of the preceding embodiments, wherein the chemotherapeutic agent comprises cisplatin, doxorubicin, fluoropyrimidine, gemcitabine, irinotecan, mitoxantrone, oxaliplatin, thalidomide, or a combination thereof.

Embodiment 54: the method of any one of the preceding embodiments, wherein the agent for the targeted therapy comprises axitinib, bevacizumab, cetuximab, erlotinib, ramucirumab, regorafenib, sorafenib, sunitinib, a thymidine kinase (TK) inhibitor, or a combination thereof.

Embodiment 55: the method of any one of the preceding embodiments, wherein the biological sample comprises a blood sample, a tissue biopsy sample, or circulating tumor cells.

Embodiment 56: the method of any one of the preceding embodiments, wherein the subject is a human.

Embodiment 57 recites a method of diagnosing hepatocellular carcinoma (HCC) in a subject, comprising: (a) obtaining treated DNA from a blood sample from the subject; (b) contacting the treated DNA with a probe that hybridizes under high stringency conditions to a target sequence of a gene selected from a gene panel consisting of BMPR1A, PSD, ARHGAP25, KLF3, PLAC8, ATXN1, Chromosome 6:170, Chromosome 6:3, ATAD2, and Chromosome 8:20 to generate an amplified product; (c) analyzing the amplified product to determine a combined diagnostic score (cd-score), wherein the cd-score correlates to an amount of circulating tumor DNA (ctDNA) present in the blood sample; and (d) diagnosing the subject with HCC when the cd-score is elevated relative to a cd-score obtained from a blood sample of a healthy subject.

Embodiment 58: the method of embodiment 57, wherein the probe comprises about 80%, 85%, 90%, 95%, or 99% sequence identity to a probe selected from SEQ ID NOs: 1-10.

Embodiment 59: the method of embodiment 57, wherein the probe comprises about 100% sequence identity to a probe selected from SEQ ID NOs: 1-10 or consists of a probe selected from SEQ ID NOs: 1-10.

Embodiment 60: the method of embodiment 57, further comprising contacting the treated DNA with at least an additional probe that hybridizes under high stringency conditions to a target sequence of an additional gene selected from the gene panel to generate an additional amplified product, and analyze the additional amplified product to generate an additional cd-score.

Embodiment 61: the method of embodiment 57, wherein the contacting comprises hybridizing under high stringency conditions with a set of probes, wherein the set of probes hybridizes up to ten and no more than ten genes from the gene panel.

Embodiment 62: the method of embodiment 57, wherein the blood sample is treated with a deaminating agent to generated the treated DNA.

Embodiment 63: the method of embodiment 57, further comprising determining the HCC as Stage I, Stage II, Stage III, or Stage IV.

Embodiment 64: the method of embodiment 57, wherein the subject is further treated with an effective amount of a therapeutic agent.

Embodiment 65: the method of embodiment 64, wherein the treatment comprises: (a) transcatheter arterial chemoembolization, radiofrequency ablation, or brachytherapy; (b) a chemotherapeutic agent or an agent for a targeted therapy; or (c) surgery.

Embodiment 66: the method of any one of the embodiments 57-65, wherein the chemotherapeutic agent comprises cisplatin, doxorubicin, fluoropyrimidine, gemcitabine, irinotecan, mitoxantrone, oxaliplatin, thalidomide, or a combination thereof.

Embodiment 67: the method of any one of the embodiments 57-65, wherein the agent for the targeted therapy comprises axitinib, bevacizumab, cetuximab, erlotinib, ramucirumab, regorafenib, sorafenib, sunitinib, a thymidine kinase (TK) inhibitor, or a combination thereof.

Embodiment 68: the method of embodiment 57, wherein the cd-score is elevated by about 2-fold, 3-fold, 4-fold, 5-fold, 6-fold, 7-fold, 8-fold, 9-fold, 10-fold, or more relative to the cd-score obtained from a blood sample of a healthy subject.

Embodiment 69: the method of embodiment 57, wherein the cd-score is elevated by about 5%, 10%, 15%, 20%, 30%, 40%, 50%, 60%, 70%, 80%, 90%, 100%, or more relative to the cd-score obtained from a blood sample of a healthy subject.

Embodiment 70: the method of embodiment 57, wherein the cd-score is based on the methylation status of the one or more genes from the gene panel.

Embodiment 71: the method of embodiment 57, wherein the cd-score is determined utilizing an algorithm selected from one or more of the following: a principal component analysis, a logistic regression analysis, a nearest neighbor analysis, a support vector machine, and a neural network model.

Embodiment 72 recites a method of determining the prognosis of a subject having hepatocellular carcinoma (HCC), comprising: (a) obtaining treated DNA from a blood sample from the subject; (b) contacting the treated DNA with a probe that hybridizes under high stringency conditions to a target sequence of a gene selected from a gene panel consisting of SH3PXD2A, C11orf9, PPFIA1, Chromosome 17:78, SERPINB5, NOTCH3, GRHL2, and TMEM8B to generate an amplified product; (c) analyzing the amplified product to determine a combined prognosis score (cp-score), wherein the cp-score correlates to an amount of circulating tumor DNA (ctDNA) present in the blood sample; and (d) determining the prognosis of the subject with HCC when the cp-score is elevated relative to a cp-score obtained from a blood sample of a healthy subject.

Embodiment 73: the method of embodiment 72, wherein the probe comprises about 80%, 85%, 90%, 95%, or 99% sequence identity to a probe selected from SEQ ID NOs: 11-18.

Embodiment 74: the method of embodiment 72, wherein the probe comprises about 100% sequence identity to a probe selected from SEQ ID NOs: 11-18 or consists of a probe selected from SEQ ID NOs: 11-18.

Embodiment 75: the method of embodiment 72, wherein the cp-score correlates to survival for at least 6 months, 1 year, 1.5 years, 2 years, 2.5 years, 3 years, 4 years, 5 years, or more.

Embodiment 76: the method of embodiment 72, further comprising contacting the treated DNA with at least an additional probe that hybridizes under high stringency conditions to a target sequence of an additional gene selected from the gene panel to generate an additional amplified product, and analyze the additional amplified product to generate an additional cp-score.

Embodiment 77: the method of embodiment 72, wherein the generating comprises hybridizing under high stringency conditions with a set of probes, wherein the set of probes hybridizes up to eight and no more than eight genes from the gene panel.

Embodiment 78: the method of embodiment 72, wherein the cp-score is elevated by about 2-fold, 3-fold, 4-fold, 5-fold, 6-fold, 7-fold, 8-fold, 9-fold, 10-fold, or more relative to the cd-score obtained from a blood sample of a healthy subject.

Embodiment 79: the method of embodiment 72, wherein the cp-score is elevated by about 5%, 10%, 15%, 20%, 30%, 40%, 50%, 60%, 70%, 80%, 90%, 100%, or more relative to the cd-score obtained from a blood sample of a healthy subject.

Embodiment 80: the method of embodiment 72, wherein the cp-score is based on the methylation status of the one or more genes from the gene panel.

Embodiment 81: the method of embodiment 72, wherein the cp-score is determined utilizing an algorithm selected from one or more of the following: a principal component analysis, a logistic regression analysis, a nearest neighbor analysis, a support vector machine, and a neural network model.

Embodiment 82: the method of embodiment 72, wherein the subject is treated with a therapeutic agent for HCC prior to determining the prognosis of the subject.

Embodiment 83: the method of embodiment 72, wherein the subject is a naïve subject or a subject that has not been treated with a therapeutic agent for HCC.

Embodiment 84: the method of any one of the preceding embodiments, wherein the subject is a human.

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure. It is intended that the following claims define the scope of the disclosure and that methods and structures within the scope of these claims and their equivalents be covered thereby.

What is claimed is:

1. A method of detecting the methylation pattern of a plurality of markers in a human subject suspected of having hepatocellular carcinoma (HCC), comprising:
   a) processing a biological sample obtained from the human subject with a deaminating agent to generate treated DNA comprising deaminated nucleotides; and
   b) detecting the methylation pattern of cg26668608, cg11606215, cg18196829, cg25459300, cg25574765, cg11397370, and cg11825899, and one or more markers selected from the group consisting of cg10428836, cg25754195, cg05205842, cg24067911, cg24067911, cg23211949, cg17213048, cg23461741, cg06482904, cg07459019, cg20490031, and cg01643250, by
      i) contacting the treated DNA with a first set and a second set of nucleic acid probes, wherein the first set of nucleic acid probes hybridizes to seven markers and no more than seven markers, wherein the markers are cg26668608, cg11606215, cg18196829, cg25459300, cg25574765, cg11397370, and cg11825899, and wherein the second set of nucleic acid probes hybridizes to at least one but no more than 11 markers selected from the group consisting of cg10428836, cg25754195, cg05205842, cg24067911, cg24067911, cg23211949, cg17213048, cg23461741, cg06482904, cg07459019, cg20490031, and cg01643250, and combinations thereof; and
      ii) performing a DNA sequencing analysis to determine the methylation pattern of the plurality of markers.

2. The method of claim 1, wherein the method comprises detecting the methylation pattern of cg10428836, cg26668608, cg25754195, cg05205842, cg11606215, cg24067911, cg18196829, cg23211949, cg17213048, cg25459300, cg23461741, cg06482904, cg25574765, cg07459019, cg20490031, cg01643250, cg11397370, and cg11825899.

3. The method of claim 1, wherein the human subject has a stage I, stage II, stage III, or stage IV hepatocellular carcinoma (HCC).

4. The method of claim 1, wherein the biological sample comprises a blood sample, a tissue biopsy sample, or circulating tumor cells.

5. The method of claim 1, wherein the probe is a padlock probe.

6. The method of claim 1, wherein the DNA sequencing analysis comprises a digital droplet PCR analysis.

7. A method of detecting the methylation pattern of a plurality of markers in a human subject suspected of having hepatocellular carcinoma (HCC), the method comprising:
   (a) processing a biological sample obtained from the human subject with a deaminating agent to generate treated DNA comprising deaminated nucleotides; and
   (b) detecting the methylation pattern of cg26668608, cg11606215, cg18196829, cg25459300, cg25574765, cg11397370, and cg11825899, by
      (i) contacting the treated DNA with a set of nucleic acid probes that hybridizes to seven markers and no more than seven markers, and wherein the markers are cg26668608, cg11606215, cg18196829, cg25459300, cg25574765, cg11397370, and cg11825899; and
      (ii) performing a DNA sequencing analysis to determine the methylation pattern of the plurality of markers.

8. The method of claim 7, wherein the probe is a padlock probe.

9. The method of claim 7, wherein the DNA sequencing analysis comprises a digital droplet PCR analysis.

10. The method of claim 7, wherein the human subject has a stage I, stage II, stage III, or stage IV HCC.

11. The method of claim 7, wherein the biological sample comprises a blood sample, a tissue biopsy sample, or circulating tumor cells.

\* \* \* \* \*